(12) United States Patent
Xu

(10) Patent No.: US 10,456,424 B2
(45) Date of Patent: *Oct. 29, 2019

(54) PANCREATIC ENDOCRINE CELLS AND METHODS THEREOF

(71) Applicant: Janssen Biotech, Inc., Horsham, PA (US)

(72) Inventor: Jean Xu, Raritan, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/660,885

(22) Filed: Jul. 26, 2017

(65) Prior Publication Data

US 2017/0354690 A1   Dec. 14, 2017

Related U.S. Application Data

(60) Continuation of application No. 14/751,416, filed on Jun. 26, 2015, now Pat. No. 9,744,195, which is a division of application No. 12/183,656, filed on Jul. 31, 2008, now Pat. No. 9,096,832.

(60) Provisional application No. 60/953,178, filed on Jul. 31, 2007.

(51) Int. Cl.
*C12N 5/071* (2010.01)
*A61K 35/39* (2015.01)

(52) U.S. Cl.
CPC ............ *A61K 35/39* (2013.01); *C12N 5/0676* (2013.01); *C12N 2500/34* (2013.01); *C12N 2501/115* (2013.01); *C12N 2501/12* (2013.01); *C12N 2501/155* (2013.01); *C12N 2501/16* (2013.01); *C12N 2501/21* (2013.01); *C12N 2501/23* (2013.01); *C12N 2501/335* (2013.01); *C12N 2501/385* (2013.01); *C12N 2501/40* (2013.01); *C12N 2501/415* (2013.01); *C12N 2501/42* (2013.01); *C12N 2501/70* (2013.01); *C12N 2501/999* (2013.01); *C12N 2506/02* (2013.01); *C12N 2533/90* (2013.01)

(58) Field of Classification Search
CPC .................................................. C12N 5/0676
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,762 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

D'Amour et al. (2006, Nature Biotechnology, vol. 24(11), pp. 1392-1401). (Year: 2006).*

(Continued)

*Primary Examiner* — Thaian N Ton
*Assistant Examiner* — David A. Montanari
(74) *Attorney, Agent, or Firm* — Klarquist Sparkman, LLP

(57) ABSTRACT

The present invention provides methods to promote the differentiation of pluripotent stem cells. In particular, the present invention provides an improved method for the formation of pancreatic endoderm, pancreatic hormone expressing cells and pancreatic hormone secreting cells. The present invention also provides methods to promote the differentiation of pluripotent stem cells without the use of a feeder cell layer.

15 Claims, 58 Drawing Sheets

Specification includes a Sequence Listing.

(56) References Cited

U.S. PATENT DOCUMENTS

| | | |
|---|---|---|
| 6,703,017 B1 | 3/2004 | Peck et al. |
| 6,713,446 B2 | 3/2004 | Gupta |
| 6,793,945 B2 | 9/2004 | Bathurst et al. |
| 6,800,460 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 9,528,090 B2 | 12/2016 | Rezania |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003313 A1 | 1/2006 | D'Amour et al. |
| 2006/0003446 A1 | 1/2006 | Keller et al. |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania et al. |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |
| 2014/0186953 A1 | 7/2014 | Rezania |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2005537803 | 12/2005 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 1767433 A1 | 10/1992 |
| RU | 2342427 | 12/2008 |
| RU | 2359030 C1 | 6/2009 |
| RU | 2359671 C2 | 6/2009 |
| WO | WO199219759 A2 | 2/1992 |
| WO | 1996040172 A1 | 12/1996 |
| WO | 199830679 A1 | 7/1998 |

(56) References Cited

FOREIGN PATENT DOCUMENTS

| | | |
|---|---|---|
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO200305049 A1 | 6/2003 |
| WO | 2002086107 A3 | 7/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | 2006088867 A2 | 2/2006 |
| WO | WO2006016999 A1 | 2/2006 |
| WO | 2006026473 A2 | 3/2006 |
| WO | 2006029197 A1 | 3/2006 |
| WO | 2006036925 A1 | 4/2006 |
| WO | 2006073911 A1 | 7/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A1 | 3/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007136673 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015418 A2 | 2/2008 |
| WO | 2008015682 A2 | 2/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096049 A1 | 8/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011096223 A1 | 8/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Balajthy, et al., Molecular therapies., Chapter 8, Embryonic and Adult Stem Cells in Regenerative Medicine, 2011, pp. 1-6.

Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.

Brimble, S., et al., The Cell Surface Glycosphingolipis SSEA-3 and SSEA-4 Are Not Essential for Human ESC Pluripotency, Stem Cells, Jan. 2007, pp. 54-62, vol. 25, MX.

Buta, et al., Reconsidering pluripotency tests: Do we still need teratoma assays?, Stem Cell Research, Mar. 26, 2013, pp. 552-562, vol. 11.

Chen, et al., Retinoic acid signaling is essential for pancreas development and promotes endocrine at the expense of exocrine cell differentiation in Xenopus; Developmental Biology, May 4, 2004, pp. 144-160, vol. 271.

Chen, et al., Scalable GMP Compliant Suspension Culture System for Human ES Cells, Stem Cell Research, 2012, pp. 388-402, vol. 8.

Choi, et al., Effect of ascorbic acid on bone marrow-derived rnesenchyrnal stern cell proliferation and differentiation, J Biosci Bioeng, Jun. 2008, pp. 586-594, vol. 105 Issue 6.

Cirulli, et al., Netrins: beyond the brain, Molecular Cell Biology, Apr. 2007, pp. 296-306, vol. 8.

(56) References Cited

OTHER PUBLICATIONS

Cohick, et al., The Insulin-Like Growth Factors, Annual Reviews Physiol, 1993, pp. 131-153, vol. 55, Annual Reviews Inc.

Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.

Daheron, et al., LIF/STAT3 Signaling Fails to Maintain Self-Renewal of Human Embryonic Stern Cells, Stem Cells, 2004, pp. 770-778, vol. 22.

Findikli, et al., Establishment and characterization of new human embryonic stem cell lines, Reproductive BioMedicine Online, Mar. 3, 2005, pp. 617-627, vol. 10 Issue 5.

Foster, et al., Differentiation of Transplanted Microencapsulated Fetal Pancreatic Cells, Transpiantation, Jun. 15, 2007, pp. 1440-1448, vol. 83 issue 11.

Furue, et al., Heparin propotes the growth of human embryonic stem cells in a defined serum-free medium, PNAS, Sep. 9, 2008, pp. 13409-13414, vol. 105 Issue 36.

Gibco, Insulin-Transferin-Selenium-X 100X, Invitrogen Cell Culture, Apr. 2005, pp. 1, Form No. 3032.

Gomez, et al., Derivation of cat embryonic stem-like cells from in vitro-produced blastocysts on homologous and heterologous feeder cells, Theriogenology, May 11, 2010, pp. 498-515, vol. 74.

Gordon Weir.; Do stem cells hold the key to a future cure for diabetes?, DiabetesVoice, Jun. 2008, pp. 29-31, vol. 53 Issue 2.

Guillemain, et al., Glucose Is Necessary for Embryonic Pancreatic Endocrine Cell Differentiation, The Journal of Biological Chemistry, May 18, 2007, pp. 15228-15237, vol. 282 Issue 20.

Guo, et al., Efficient differentiation of insulin-producing cells from skin-derived stem cells, Cell Proliferation, 2009, pp. 49-62, vol. 42.

Hebrok, et al., Notochord repression of endodermal Sonic hedgehog permits pancreas development, Genes & Development, Apr. 2, 1998, pp. 1705-1713, vol. 12 , Issue 11, Cold Spring Harbor Laboratory Press.

Hiemisch, H., et al., Transcriptional Regulation in Endoderm Develoment: Characterization of an Enhancer Controlling Hnf3g Expression by Transgenesis and Targeted Mutagenesis, The EMBO Journal, 1997, 3995-4006, vol. 16(13), MX.

Jaenisch, et al., Stem Cells, The Molecular Circuitry of Pluripotency and Nuclear Reprogramming, cell, Feb. 22, 2008, pp. 567-582, vol. 132, Elsevier Inc.

Jean, et al., Pluripotent genes in avian stem cells, Development Growth & Differentitalon, 2013, pp. 41-51, vol. 55.

Kang, et al., Plasma treatment of textiles—Synthetic Polymer-Based Textiles, AATCC Review, 2004, pp. 29-33, Page number.

Kehoe, et al., Scalable Stirred-Suspension Bioreactor Culture of Human Pluripotent Stem Cells, Tissue Eng Part A, 2010, pp. 405-421, vol. 16 Issue 2.

Kim, et al., Reprogrammed Pluripotent Stem Cells from Somatic Cells, International Journal of Stem Cells, 2011 , pp. 1-8, vol. 4 Issue 1.

Klajnert, et al., Fluorescence studies on PAMAM dendrimers interactions with bovine serum albumin, Bioelectrochemistry, 2002, pp. 33-35, vol. 55.

Kubota,et al., Growth factors essential for self-renewal and expansion of mouse spermatogonial stem cells, cell Biology, Nov. 23, 2004, pp. 16489-16494, vol. 101 , Issue 47.

Kunisada, et al., Small molecules induce efficient differentiation into insulin-producing cells from human induced pluripotent stem cells, Stem Cell Research, Oct. 11, 2011, pp. 274-284, vol. 8.

Lavial, etal., Chicken Embryonic Stem Cells as a Non-Mammalian Ebryonic Stem Cell Model, Development Growh Differentiation, Jan. 2010, pp. 101-114, vol. 52(1).

Lee, et al., Available human feeder cells for the maintance of human embryonic stem cells, Reproduction, 2004, pp. 727-735, vol. 128.

Lin, C., et al., Coagulation Dysregulatin as a Barrier to Xenotransplantation n the Primate, Transplant Immunology, 2009, pp. 75-80, vol. 21, MX.

Ludwig, et al., Defind, Feeder-Independent Medium for human Embryonic Stem Cell Culture, Current Protocols in Stem Cell Biology, 2007, pp. 1C.2.1-1C.2.16, vol. 1, John Wiley & Sons, Inc.

Maimets, et al., Activation of p53 by nutlin leads to rapid differentiation of human embryonic stem cells, Oncogene, Jun. 2, 2008, pp. 5277-5287, vol. 27.

Maria-Jesus Obregon, Thyroid hormone and adipocyte differentiation, Thyroid, 2008, pp. 185-195, vol. 18 Issue 2.

McMahon, et al., Noggin-mediated antagonsim of BMP signaling is required for growth and patterning of the neural tube and somite, Genes & Development, Mar. 16, 1998, pp. 1438-1452, vol. 12.

Micallef, et al., Pancreas Differentiation of Mouse ES Cells, Current Protocols in Stem Cell Biology, 2007, pp. 1-8, Supplementary 2, John Wiley & Sons, Inc.

Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204

Nakanishi, et al., Pancreatic tissue formation from murine embryonic stem cells in vitro, Differentiation, 2007, pp. 1-11, vol. 75.

Nakase, et al., Myeliod Antigen, CD13, CD14, and/ or CD33 Expression Is Restricted to Certain Lymphiod Neoplasms, Hematopathology, Jun. 1996, pp. 761-768, vol. 105 Issue 6.

Narang, A., et al., Biological and Biomaterial Approaches for Improved Islet Transplantation, Pharmacological Review, Jun. 2006, pp. 194-243, vol. 58(2), MX.

Nekrasov, et al., Induced pluripotent stem cells as a model for studying human diseases, Cellular Transplantology and Tissue Engineering, 2011, pp. 32-37, vol. 6 Issue 2.

Olmer, et al., Long Term Expansion of Undifferentiated Human iPS and ES Cells in Suspension Culture Using Defined Medium, Stem Cell Research, 2010, pp. 51-64, vol. 5.

Osafune, et al., Marked differences in differentiation propensity among human embryonic stern cell lines, Nature Biotechnology, Feb. 17, 2008, pp. 313-315, vol. 26 Issue 3.

Ouziel-Yahalom, et al., Expansion and redifferentiation of adult human pancreatic islet cells, Biochemical and Biophysical Research Communications, Jan. 19, 2006, pp. 291-298, vol. 341.

Petitte, J., et al., Avian Plluripotent Stem Cells, Mechanisms of Development, 2004, pp. 1159-1168, Volme 121, MX.

Ramiya, et al., Reversal of insulin-dependent diabetes using islets generated in vitro from pancreatic stem cells, Nature Medicine, Mar. 2000, pp. 278-282, vol. 6 Issue 3.

Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34 , Issue 4.

Rother, et al., Challenges facing islet transplantation for the treatment of type 1 diabetes mellitus, The Journal of Clinical Investigation, 2004, pp. 877-883, vol. 114 Issue 7.

Rowely, et al., Meeting Lot-size Challenges of Manufacturing Adherent Cells for Therapy, Bio Process International, Mar. 2012, pp. 16-22, vol. 10 Issue 3.

Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182 , Issue 2.

Sigma-Aldrich, Sigma-Aldrich Inc., MCDB 131 Medium, Product Sheet, 2007, pp. 1-2.

Sjogren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.

Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.

Suzuken., Differentiation of Multifunctional Stem Cells Using Human Feeder Cells, Research Papers of the Suzuken Memorial Foundation, 2007, pp. 193-197, vol. 2.

Thomson, Bioprocessing of Embryonic Stem Cells for Drug Disvoery, Trends in Biotechnology, 2007, pp. 224-230, vol. 25, No. 5.

(56) References Cited

OTHER PUBLICATIONS

Verkhovskaya, et al., Effect of alkoxy-substituted of glycerin on the morphofunctional properties of continuous cell culture, Cryobiology, 1990, pp. 30-33, vol. 1.
Wang, et al., Cultivation and identification of pancreatic endocrine progenitor cells, National Medical Journal of China, 2006, pp. 1850-1853, vol. 86 Issue 26.
Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.
Yadlin, et al., Small-molecule inducers of insulin expression in pancreatic α-cells, PNAS, Aug. 24, 2010, pp. 15099-15104, vol. 107 Issue 34.
Yang JW, et al., Evaluation of human MSCs cell cycle, viability and differentiation in micromass culture, Bioheology, 2006, pp. 1-2, vol. 43 Issue (3-4).
Yim,et al., Proliferation and differentiation of human embryonic germ cell derivatives in bioactive polymeric fibrous scaffold, J.Biomater. Sci.Polymer Edn,, Jan. 19, 2005, pp. 1193-1217, vol. 16 Issue 10.
Zhu, et al., A Small Molecule Primes Embryonic Stem Cells for Differentiation, Cell Stem Cell, May 8, 2009, pp. 416-426, vol. 4.
Zulewski, et al., Multipotentital Nestin-Positive Stem Cells lasolated From Adult Pancreatic Islets Differentiate Ex Vivo Into Pancreatic Endocrine, Exocrine, and Hepatic Phenotypes, Diabetes, 2001, pp. 521-533, vol. 50.
Abe, et al., Evidence That P13K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, et al., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Ali, et al., Exploitation of Protein Kinase C: A Useful Target for Cancer Therapy, Cancer Treatment Reviews, 2009, pp. 1-8, vol. 35.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11
Assady, et al., Insulin Production by Human Embryonic Stem Cells, Diabetes, 2001, pp. 1691-1697, vol. 50.
Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2
Balsam, et al., Haematopoeitic Stem Cells Adopt Mature Haeatopoietic Fates in Ischaemic Myocardium, Nature, Apr. 8, 2004, pp. 668-673, ?, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Beltrami, et al., Adult Cardiac Stem Cells are Multipotent and Support Myocardial Regeneration, Cell, Sep. 19, 2003, pp. 763-776, vol. 114, Cell Press.
Best, et al., Embryonic Stem Cells to Beta-Cells by Understanding Pancreas Development, Molecular and Cellular Endorinology, 2008, pp. 86-94, vol. 288.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bo, et al., Research Progress of Pancreatic Islet Development and Pancreatic Stem Cells, Journal of Clinical Surgery, 2009, pp. 208-210, vol. 17, No. 3.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., in vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence intensity of Surface Marker.. Blood, Jun. 1, 1997, 3960-3966, 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brambrink, et al., Sequential Expression of Pluripotency Markers During Direct Reprogramming of Mouse Somatic Cells, Cell Stem Cell, 2008, pp. 151-159, vol. 2.

(56) References Cited

OTHER PUBLICATIONS

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini et al, "Embryonic Stem Cells in Domestic Animals, No Shortcuts to Pig Embryonic Stem Cells" Theriogenology, 2010, pp. 544-550, vol. 74.
Bross, et al., Approval Summary for Bortezomib for Injection in the Treatment of Multiple Myeloma, Clinical Cancer Research, Jun. 15, 2004, pp. 3954-3964, vol. 10.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature Biotechnology, Apr. 1, 2004, 381-382, 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesencymai Stem Cells in Pancreatic Islet Beta-Cells, World Journal of Gastroenterology, Oct. 15, 2004, 3016-3020, 10.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.
Cheon, et al., Defined Feeder-Free Culture System of Human Embryonic Stem Cells, Biol Reprod, 2005, 105.046870, DOI10/1095.
Chetty, et al., A Simple Tool ti improve Pluripotent Stem Cell Differentiation, Nature Methods, 2013, pp. 553-558, vol. 10, No. 6.
Chu, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330
Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1968, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al, "Production of pancreatic hormone-expressing endocrine cells from human embryonic stem cells" Nature Biotechnology 24, 1392-1401 (2006).
D'Amour et al., Efficient differentiation of human embryonic stem cells to definitive endoderm; Nature Biotechnology, Oct. 28, 2005, 1-6, :W.1038/nbt1163, Nature Publishing Group.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, John Wiley & Sons, Chichester, 1995, pp. 1-3, page number, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331 XP002699177, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.

(56) References Cited

OTHER PUBLICATIONS

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44 No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low O2 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Frandsen et al., Activin B mediated induction of Pdx1 in human embryonic sterncell derived ernbryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Rag, et al., The Effect of Medical Therapy and Islet Cell Transplantation on Diabetic Nephropathy: An Interim Report, Transplantation, Jul. 15, 2007, pp. 17-22, vol. 84, No. 1.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Gibco, Solutions for Life Science Research and Drug Discovery, Catalogue Cell Culture Products, 2004-2005, pp. 1-4E 281406 26 5 27.
Giltaire, et al., The CYP26 inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.
Gittes, Developmental Biology of the Pancreas: A comprehensive Review, Developmental Bioiogy, 2009, pp. 4-35 XP025995041, vol. 326, No. 1.
Gordon Weir, Do stem cells hold the key to creation of a cure for diabetes?, Diabetes Voice, 2008, pp. 29-31, Edition 53, No. 2.
Gosden, et al., Amniotic Fluid Cell Types and Culture, British Medical Bulletin, 1963, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Gregg Duester, Retionoic Acid Synthesis and Signaling During Early Organogenesis, Cell, 2008, pp. 921-931, vol. 134.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hainsworth, et al., Retinal Capillar Basement Membrane Thickening in a Porcine Model of Diabetes Mellitus, Comp Med, 2002, pp. 523-529, vol. 52.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell integrity of Self-Renewing Pluripotent Stem Cells, Plos One, 2008, Article e3001, XP002530386, vol. 3, Issue 8.
Harmon, et al., GDF11 Modulates NGN3+ Islet Progenitor Cell Number and Promotes B-Cell Differentiation in Pancreas Development, Development, 2004, pp. 6163-6174, vol. 131.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45 Issue 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Hay, et al., Highly Efflicient Differentiation of hESCs to Functional Hepatic Endoderm Requires ActivinA and Wnt3a Signaling, PNAS, 2008, pp. 12301-12306, vol. 105, No. 34.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Helena Edlund., Pancreatic Organogenisis—Pancreatic Mechanisirns and Implications for Therapy, Nature, Jul. 1, 2002, pp. 524-532, vol. 3, Nature Publishing Group, US.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

(56) References Cited

OTHER PUBLICATIONS

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322 XP001004766, vol. 127, No. 11.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp 763-770, vol. 21, No. 7.
Ho, et al., Animal Cell Bioreactors, Animal Cell Bioreactors, 1991, pp. 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.
Hosoya, et al., Induction of Differentiation of Undifferentiated Cells into Pancreatic Beta-Cells in Vertebrates, Int. J. Dev. Biol., 2012, pp. 313-323, vol. 16.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al, Generation of Insulin-Producing Islet-Like Clusters from Human Embryonic Stem Cells, Stem Cells, 2007, pp. 1940-1953, vol. 25, Issue 8.
Jiang, et al., In Vitro Derivation of Functional Insulin-Producing Cells from Human Embryonic Stem Cells, Cell Research, 2007, pp. 333-344, vol. 17.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.

Karvonen, et al., Incidene of Childhood Type 1 Diabetes Worldwide, Diabetes Care, 2000, pp. 1516-1526, vol. 23, No. 10.
Kelly, et al., Cell-Surface Markers for the Isolation of Pancreatic Cell Types Derived from Human Embryonic Stem Cells, Nature Biotechnology, 2011, pp. 750-756, vol. 29, Issue 6.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
King, et al., Bioreactor development for stem cell expansion and controlled differentiation, Current Opinion in Chemical Biology, Jul. 25, 2007, pp. 394-398, vol. 11, Elsevier Ltd.
Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, 312-318, 25, American Chemical Society.
Klimanskaya, et al., Human Embryonic Stern Cells Derived without Feeder Cells, Lancet, May 2005, pp. 1636-1641, vol. 365, No. 9471.
Koblas, et al., Differentiation of CD133-Positive Pancreatic Cells Into Insulin-Producing islet-Like Cell Clusters, Transplantation Proceedings, 2008, pp. 415-418, vol. 40.
Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova_et_al_2007, EphA-Ephrin-A-Mediated Beta Cell Communication Regulates Insulin Secretion from Pancreatic Islets, Cell, Apr. 20, 2007, pp. 359-370, vol. 129.
Koyangi et al., Inhibitio nof the Rho/ROCK Pathway Reduces Apoptosis During Transpiantatation of Embryonic Stem Cell-Derived Neural Precursors, Journal of Neuroscine Research, Sep. 7, 2007, 270-280, 66, Wiley-Liss, Inc.
Kozikowski, et al., New Amide-Bearing Benzolactarn-Based Protein Kinase C Modulators induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine immune Cell Surface Markers and Intracellular Phosphoproteins by Flow Cytometry, Journal of Immunology, May 30, 2005, 2357-2365, 175, American Association of Immunologists, Inc., US.
Ku et al., Committing Embryonic Stem Cells to Early Endocrine Pancreas In Vitro, Stem Cells, 2004, 1205-1217, 22, AlphaMed Press.
Kubo et al., Development of definitive endoderm from embryonic stem cells in culture, Development, 2004, 1651-1662, 131, The Company of Biologists.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

(56) References Cited

OTHER PUBLICATIONS

Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stern Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Larsen, et al., Use of the Gottingen Minipig as a Model of Diabetes, with Special Focus on Type 1 Diabetes Research, ILAR Journal, 2004, pp. 303-313, vol. 45, No. 3.
Avon et al., the Effect of Overexpression of Pdx1 and Foxa2 on the Differentiation of Human Embryonic Stem Cells into Pancreatic Cells, Stem Cells, 2006, 1923-1930, 24, Alpha Med Press, IL.
Le Blanc, et al., Mesenchyrnal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., PKC—Inhibitors Sustain Self-Renewal of Mouse Embryonic Stem Cells Under Hypoxia in Vitro, Experimental and Molecular Medicine, Apr. 2010, pp. 294-301, vol. 42, No. 4.
Lee, et al., Protein Kinase A- and C- Induced Insulin Release from Ca2+-insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.
Levenstein et al., Basic Fibroblast Growth Factor Support of Human Embryonic Stem Cell Self-Renewal, Stem Cells, Nov. 10, 2005, 568-574, 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Li, et al., Pluripotency Can be Rapidly and Efficiently Induced in Human Amniotic Fluid-Derived Cells, Human Moiecular Genetics, 2009, pp. 4340-4349, vol. 18, No. 22.
Lilja et al., Cyclin-dependent Kinase 5 Promotes insulin Exocytosis, Journal of Biological Chemistry, Jul. 6, 2001, 34199-34205, 36-7, JBC Papers in Press.
Lim, et al., Proteome Analysis of Conditioned Medium from Mouse Embryonic Fibroblast Feeder Layers which Support the Growth of Human Embryonic Stern Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Loh, et al., Genomic Approaches to Deconstruct Puripotency, Annu Rev Genomics Hum Genet, 2011, pp. 165-185, vol. 12.

Ludwig, et al., Defined Culture Media for Human Embryonic Stem Cells, Embryonic Stem Cells, 2007, pp. 1-16, XP009185398, Springer.
Ludwig, et al., Derivation of Human Embryonic Stern Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, 1389-1394, 292, HighWire Press.
Lund, et al., Cell Transplantation as a Treatment for Retinal Disease, Progress in Retinal and Eye Research, 2001, pp. 415-449, vol. 20, No. 4. Elsevier Science Ltd.
Lund, et al., Retinal Transplantation: Progress and Problems in Clinical Application, J. Lsukoc. Biol, Aug. 2003, pp. 151-160, vol. 74.
Lyttle, et al., Transcription Factor Expression in the Developing Human Fetal Endocrine Pancreas, Diabetologica, 2008, pp. 1169-1180, vol. 51, Spring-Verlag.
MacFarlane, et al., Glucose Stimulates Translocation of the Horneodornain Transcription Factor PDX1 from the Cytoplasm to the Nucleus in Pancreatic B-Cells, The Journal of Biological Chemistry, 1999, pp. 1011-1016, vol. 274, No. 2.
Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.
Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.
Marshall, et al., Early Micro-and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
Mathis, et al., B-Cell Death During Progression to Diabetes, Nature, 2001, pp. 792-798, vol. 414.
Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.
McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.

(56) References Cited

OTHER PUBLICATIONS

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Veithoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, an Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Generation of Induced Pluripotent Stern Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, pp. S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nie, et al., Scalable Passaging of Adherent Human Pluripotent Stem Cells, PLOS One, 2014, pp. 1-9, vol. 9, Issue 1.
Nishimura, et al., Expression of MafA in Pancreatic Progenitors is Detrimental for Pancreatic Development, Developmental Biology, 2009, pp. 108-120, vol. 333.
Nostro, et al., Generation of Beta Cells from Human Pluripotent Stem Cells: Potential for Regenerative Medicine, Seminars in Cell & Developmental Biology, 2012, pp. 701-710, vol. 23.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.

Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current ideas on the Pathogenesis and the Role of Neuroprotection in Glaucomatous Optic Neuropathy, European Journal of Ophthalmology, 2003, pp. S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Ouziel-Yahalom, et al., Expansion and Redifferentiation of Adult Human Pancreatic islet Cells, Biochemical and Biophysical Research Communications, 2006, pp. 291-298, vol. 341.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al, The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report, XP002530385.
Paris, et al, Equine Embryos and Embryonic Stem Ceils: Defining Reliable Markers of Pluripotency, Theriogeneology, 2010, pp. 516-524, vol. 74.
Park, et al., Effects of Activin A on Pancreatic Ductal Cells in Streptozotocin-inducted Diabetic Rats, Experimental Transplantation, 2007, pp. 925-930, vol. 83.
Peerani, et al., Niche-Mediated Control of Human Embryonic Stem Cell Self-Renewal and Differentiation, The EMBO Journal, 2007, pp. 4744-4755, vol. 26.
Perrier, et al., Derivation of Midbrain Dopamine Neurons from Human Embryonic Stem Cells, PNAS, Aug. 24, 2004, pp. 12543-12548, vol. 101, No. 34.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578 XP009090566, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28. No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout (dated May 31, 2013).

(56) References Cited

OTHER PUBLICATIONS

R&D Systems, Pancreatic Endoderm, Pancreatic Endoderm, Jun. 24, 2013, http://www.rndsystems.com/molecule_group.aspx?g=801 &r, 1 page web printout.

Rajagopal, et al., Insulin Staining of ES Cell Progeny from Insulin Uptake, Science, Jan. 17, 2003, pp. 363, vol. 299.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Ramiya, et al., Reversal of Insulin-Dependent Diabetes Using Islets Generated in vitro from Pancreatic Stem Cells, Nature Medicine, 2000, pp. 278-281, vol. 6.

Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.

Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.

Rebollar, et al., Proliferation of Aligned Mammalian Cells on Laser-Nanostructured Polystyrene, Biomaterials, 2008, pp. 1796-1806, vol. 29.

Reisner, Growing Organs for Transplantation form Embryonic Precursor Tissues, Immunol. Res., 2007, pp. 261-273, vol. 38.

Reubinoff et al., Embryonic stem cell lines from human blastocysts: somatic differentiation in vitro, Nature Biotech, Apr. 18, 2000, 399-404, 18, Nature America Inc.

Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Rezania, et al., Enrichman of Human Embryonic Stern Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.

Rezania, et al., Reversal of Diabetes with Insulin-Producing Cells Derived in vitro from Human Pluripotent Stem Cells, Nature Biotechnology, 2014, pp. 1121-1133, vol. 32, No. 11.

Rezania, Production of Functional Glucagon-Secreting-Cells from Human Embryonic Stem Cells, Diabetes, 2011, pp. 239-247, vol. 60, Issue 1.

Richards et al., Comparative Evaluation of Various Human Feeders for Prolonged Undifferentiated Growth of Human Embryonic Stem Cells, Stem Cells, 2003, 546-556, 21, AlphaMed Publlishing.

Richards, et al., Development of Defined Media for the Serum-Free Expansion of Primary Keratinocytes and Human Embryonic Stem Cells, Tissue Engineering, 2008, pp. 221-232, vol. 14, No. 3.

Richardson, et al., Bortezomid (PS-341): A Novel, First-in-Class Proteasome inhibitor for the Treatement of Multiple Myeloma and Other Cancers, Cancer Control, 2003, pp. 361-369, vol. 10, No. 5.

Ricordi et al., Automated Method for Isolation of Human Pancreatic Islets, Diabetes, Apr. 1988, 413-420, 37, American Diabetes Association.

Ross, et al., Cytochrome F450s in the Regulation of Cellular Retinoic Acid Metabolism, Annu. Rev. Nutr., 2011, pp. 65-87, vol. 31.

Rowley, et al., Meeting Lot-Size Challenges of Manufacturing Adherent Cells for Therapy, Cell Therapies Manufacturing, 2012, pp. 16-22, vol. 10, No. 3.

Ryan, et al., Clinical Outcomes and Insulin Secretion After Islet Transplantation with the Edmonton Protocol, Diabetes, Apr. 2001, pp. 710-719, vol. 50.

Sakaguchi, et al., Integration of Adult mesenchymal Stem Cells in the CNS, Society for Neuroscience Abstract Viewer and Itinerary Planner, 2002, XP002519394, Program 237.18.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.

Sato, et al., Manipulation of Self-Renewal in Human Embryonic Stem Cells Through a Novel Pharmacological GSK-3 Inhibitor, Methods in Molecular Biology, 2006, pp. 115-128, vol. 331.

Sato, et al., Molecular Signature of Human Embryonic Stem Cells and its Comparison with the Mouse, Developmental Biology, Apr. 23, 2003, pp. 404-413, vol. 260.

Savno et al., Generation of Interleukin-6 Receptor Antagonists by Molecular-Modeling Guided Mutagenesis of Residues Important for gp130 Activation, EMBO Journal, 1994, 1357-1367, 13-6, IT.

Schisler, et al., The Nkx6.1 Homeodornain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Schraermeyer, et al., Subretinally Transplanted Embryonic Stem Cells Rescue Photoreceptor Cells From Degeneration in the RCS Rats, Cell Transplantation, 2001, pp. 673-680, vol. 10.

Schroeder, et al., Differentiation of Mouse Embryonic Stem Cells to Insulin-Producing Cells, Nature Protocols, 2005, pp. 495-507, vol. 1, No. 2.

Schuldiner, et al., Induced Neuronal Differentiation of Human Embryonic Stem Cells, Brain Research, 2001, pp. 201-205, vol. 913.

Schulz, et al., A Scalable System for Production of Functional Pancreatic Progenitors from Human Embryonic Stem Cells, PLOS One, 2012, pp. 1-17, vol. 7, Issue 5.

Scullica, et al., Diagnosis and Classification of Macular Degenerations: an Approach Based on Retinal Function Testing, Documenta Ophthalmologica, 2001; pp. 237-250, vol. 102.

Seaberg et al., Clonal identification of multipotent precursors from adult ~ mouse pancreas that generate neural and pancreatic lineages, Nature Biotechnology, Sep. 2004, pp. 1115-1124, vol. 22, No. 9, Nature Publishing Group.

Segev, et al., Differentiation of Human Embryonic Stem Cells into Insulin-Producing Clusters, Stem Cells, Jan. 1, 2004, pp. 265-274.

Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.

Shackleton, et al., Generation of a Functional Mammary Gland from a Single Stem Cell, Nature, Jan. 5, 2006, pp. 84-88, XP002567665, vol. 439.

Shamblott et al., Derivation of pluripotent stem cells from cultured human primordial germ cells, Developmental Biology, Nov. 1998, 13726-13731, 95, National Academy of Sciences.

Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.

Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.

(56) References Cited

OTHER PUBLICATIONS

Shim, et al., Directed Differentiation of Human Embryonic Stem Cells Towards a Pancreatic Cell Fate, Diabetologia, 2007, pp. 1228-1238, vol. 50.
Shindler et al., A synthetic nanofibrillar matrix promotes in vivo-like organization and morphogenesis for cells in culture, Biomateriais, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simandi, et al., Retinoid Signaling is a Context-Dependent Regulator of Embryonic Stem Cells, Embryonic Stem Cells Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Sneddon, et al., Self-Renewal of Embryonic-Stem-Cell-Derived Progenitors by Organ-Matched Mesenchyme, Nature, Nov. 29, 2012, pp. 765-770, vol. 491.
Soria et al., Insulin-Secreting Cells Derived From Embryonic Stem Cells Normalize Glycemia in Streptozotocin- Induced Diabetic Mice, Diabetes, Feb. 2000, 1-6, 49, American Diabetes Association.
Soria, et al., From Stem Cells to Beta Cells: New Strategies in Cell Therapy of Diabetes Mellitus, Diabetologia, 2001, pp. 407-415, vol. 44.
Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stacpoole, et al., Efficient Derivation of Neural Precuros Cells, Spinal Motor Neurons and Midbr, Nat Protoc, 2012, pp. 1-26, vol. 6, Issue 8.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stafford, et al., Retinoids Signal Directly to Zebrafish Endoderm to Specify Insuilin-Expressing B-cells, Development, 2005, pp. 949-956, vol. 133 Issue 5.
Stoffel, et al., Navigating the Pathway from Embryonic Stem Cells to Beta Cells, Seminars in Cell & Developmental Biology, 2004, pp. 327-336, vol. 15.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulbacher, et al., Activin A-induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associated Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thermofisher Scientific, B-27 Serum-Free Supplement (50x) Liquid, Technical Resources, 2016, URL:http://www.thermofisher.com/nl/en/home/technical-resources/media-formulation.250.html, retrieved from the Internet.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci. US.
Thomson et al., Primate Embryonic Stem Cells, Current Topics in Developmental Biology, 1998, 133-154, 38, Academic Press, US.
Tomita, et al., Bone Marrow-Derived Stem Cells Can Differentiate into Retinal Cells in injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 877-886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Tulachan et al., TGF-β isoform signaling regulates secondary transition and mesenchymal-induced endocrine development in the embryonic mouse pancreas, Developmental Biology, 2007, 508-521, 305, Elsevier.

(56) References Cited

OTHER PUBLICATIONS

Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Ceiis, Stem Cells, 2006, Internet Citation; XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Valuer, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Choice of Anatomical Site for Islet Transplantation, Cell Transplantation, 2008, pp. 1005-1014. vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., "Vacuum cell seeding: a new method for the fast application of an evenly distributed cell layer on porous vascular grafts" Biomaterials, 1990, pp. 602-606, vol. 11.
Vanderford et al., Multiple kinases regulate rnafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391, page number.
Vieira, et al., Modulation of Neuronal Stem Cell Differentiation by Hypoxia arid Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wachs, et al., High Efficacy of Clonal Growth and Expansion of Adult Neural Stem Cells, Laboratory Investigation, 2003, pp. 949-962, vol. 83, No. 7.
Wang et al., Derivation and Growing Human Embryonic Stem Cells on Feeders Derived from Themselves, Stem Cells, 2005. 1221-1227, 23, AlphaMed Press.
Wang et al., Relationship of Chemical Structures of Anthraquinones with their Effects on the Suppression of Immune Responses, International Journal of Irnmunopharrnacoloay, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942. vol. 33. No 3.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.

Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108; 11-10, Nature Publishing Group.
Wei, et al., Human Amnion-Isolated Cells Normalize Blood Glucose in Strepozotocin Induced Diabetic Mice; Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stern Cells Support Undifferentiated Cell Growth, Stem Cells, 2004, pp. 972-980, vol. 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Xudong, et al., Research Progress in inducing Stem Cels to Differentiate toward the B-like Cells of Pancreatic Islet, Chinese Bulletin of Life Sciences, 2007, pp. 526-530, vol. 19, No. 5.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Evaluation of Humam MSCs Cell Cycle, Viability and Differentiation in Micromass Culture, Biorheology, 2006, p. 489-496, vol. 43.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles; American Journal of Pathology, Jun. 6, 2006, pp. 1879-1888, vol. 168, No. 6.
Zalzman, et al., Differentiation of Human Liver-Derived, Insulin-Producing Cells Toward the B-Cell Phenotype, Diabetes, 2005, pp. 2568-2575, vol. 54.

(56) References Cited

OTHER PUBLICATIONS

Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, a Doctoral Thesis of Chinese PLA Acadamey of Military Medical Sciences, 2003, 1-127, 1-127 (with English Abstract).
Zhang_et_al, Highly Efficient Differentiation of Human ES Cells and iPS Cells into Mature Pancreatic Insulin-Producing Cells, Cell Research, 2009, pp. 429-438, vol. 19, Issue 4.
Zhao et al., The Islet B Cell-enriched MafA Activator is a Key Regulator of insulin Gene Transcription, Journal of Biological Chemistry, Mar. 25, 2005, 11887-11894, 260-12, The Amerian Society for Biochemistry and molecular Biology, Inc.
Zhao, et al., Derivation arid Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Zuscik, et al., Regulation of Chondrogenesis and Chondrocyte Differentiation by Stress, J Clin Invest, 2008, pp. 429-438, vol. 118, Issue 2.
Barnette et al. "Magnetic resonance-guided, real-time targeted delivery and imaging of magnetocapsules immunoprotecting pancreatic islet cells" ePub Nature Medicine, vol. 13(18), pp. 986-991.
Gillespie, KM "Type 1 diabetes: pathogenesis and prevention" CMAJ, vol. 175(2), pp. 165-170 (2006).
Sjoholm et al., "Inflammation and the etiology of type 2 diabetes" Diabetes/Metabolism Res. and Rev., vol. 22, pp. 4-10 (2005).
Levine et al., "No pancreatic endocrine stem cells?" NEJM, vol. 351, pp. 1024-1026 (2004).
Di Marzio et al., "Macroangiopathy in adults and children with diabetes: from molecular mechanisms to vascular damage (part 1)" Horm Metab Res. Nov. 2006;38(11):691-705.
Ichinose et al., "Recent advancement of understanding pathogenesis of type 1 diabetes and potential relevance to diabetic nephropathy" Am J Nephrol. 2007;27(6):554-64. Epub Sep. 6, 2007.
Yang et al., "Lessons on autoimmune diabetes from animal models" Clin Sci (Lond). Jun. 2006;110(6):627-39.
Campbell-Thompson, ML "Collection and Staining protocols for human pancreatic islets" 2012, J. Visualized Experiments, May 23, 2012 (63):1-5.
Furukawa et al., "Role of mitogen-activated protein kinase and phosphoinositide 3-kinase in the differentiation of rat pancreatic AR42J cells induced by hepatocyte growth factor" Diabetologia, vol. 42, pp. 450-456 (1999).
Jensen et al., "Rapid Publication Independent Development of Pancreatic—and Cells From Neurogenin3-Expressing Precursors a Role for the Notch Pathway in Repression of Premature Differentiation" Diabetes, vol. 49, pp. 163-176 (2000).
Apelqvist et al., "Notch signalling controls pancreatic cell differentiation" Nature, vol. 400, pp. 877-881 (1999).
Strooper et al., "A presenilin-1-dependent gamma-secretase-like protease mediates release of Notch intracellular domain." Nature, vol. 398, pp. 518-522 (1999).

\* cited by examiner a)

b)

A.

B.

C.

D.

A.

B.

A.

B.

A.

B.

C.

D.

E.

F.

a.

b.

c.

a.

PDX1

A.

B.

C.

D.

A

Nkx2.2

B.

Pdx1

A.

B.

A. Matrigel 1:60 dilution

B. Matrigel 1:30 dilution

C. Matrigel 1:15 dilution

D. Matrigel 1:10 dilution

E. Growth Factor reduced Matrigel 1:30 dilution

F. Growth Factor reduced Matrigel 1:10 dilution

A.

B.

A.

B.

C.

A.

B.

A.

B.

C.

D.

A.

B.

A.

B.

C.

D.

A.

B.

A.

B.

A.

B.

A.

B.

A.

B.

A.

B.

C.

A. Formation of DE on hu Serum-coated plates

B. Formation of DE on hu serum-coated plates

A.

B.

A.

B.

PANCREATIC ENDOCRINE CELLS AND METHODS THEREOF

CROSS-REFERENCE TO RELATED APPLICATIONS

This application is a continuation of U.S. patent application Ser. No. 14/751,416, filed Jun. 26, 2015, which is a divisional of U.S. patent application Ser. No. 12/183,656, filed Jul. 31, 2008, now U.S. Pat. No. 9,096,832, which claims benefit to U.S. Provisional Patent Application No. 60/983,178, filed Jul. 31, 2007, the disclosures of which are incorporated by reference herein in their entirety.

FIELD OF THE INVENTION

The present invention provides methods to promote the differentiation of pluripotent stem cells. In particular, the present invention provides an improved method for the formation of pancreatic endoderm, pancreatic hormone expressing cells and pancreatic hormone secreting cells. The present invention also provides methods to promote the differentiation of pluripotent stem cells without the use of a feeder cell layer.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3beta, GATA4, Mix11, CXCR4 and Sox-17.

Formation of the pancreas arises from the differentiation of definitive endoderm into pancreatic endoderm. Cells of the pancreatic endoderm express the pancreatic-duodenal homeobox gene, Pdx1. In the absence of Pdx1, the pancreas fails to develop beyond the formation of ventral and dorsal buds. Thus, Pdx1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin A (a member of the TGFβ superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGFβ2 reproducibly yielded a higher proportion of Pdx1 positive cells (Genes Cells. 2005 June; 10(6): 503-16.).

Gordon et al. demonstrated the induction of brachyury$^+$/HNF-3beta$^+$ endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into Pdx1 positive cells after addition of FGF-10 (US 2005/0266554A1).

D'Amour et al. (Nature Biotechnology—24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGFβ antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al, Stem Cells 2006; 24:1923-1930).

Therefore, there still remains a significant need to develop conditions for establishing pluripotent stem cell lines that can be expanded to address the current clinical needs, while retaining the potential to differentiate into pancreatic endocrine cells, pancreatic hormone expressing cells, or pancreatic hormone secreting cells. We have taken an alternative approach to improve the efficiency of differentiating human embryonic stem cells toward pancreatic endocrine cells.

SUMMARY

In one embodiment, the present invention provides a method for differentiating pluripotent stem cells, comprising the steps of:
a. Culturing the pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage.

In one embodiment, cells expressing markers characteristic of the definitive endoderm lineage are differentiated from pluripotent stem cells by treating pluripotent stem cells by any one of the following methods:
a. Culturing the pluripotent stem cells in medium containing activin A in the absence of serum, then culturing the cells with activin A and serum, and then culturing the cells with activin A and serum of a different concentration, or
b. Culturing the pluripotent stem cells in medium containing activin A in the absence of serum, then culturing the cells with activin A with serum of another concentration, or
c. Culturing the pluripotent stem cells in medium containing activin A and a Wnt ligand in the absence of serum, then removing the Wnt ligand and culturing the cells with activin A with serum, or
d. Culturing the pluripotent stem cells on a tissue culture substrate coated with an extracellular matrix, and culturing the pluripotent stem cells with activin A and a Wnt ligand, or
e. Culturing the pluripotent stem cells on a tissue culture substrate coated with an extracellular matrix, then culturing the pluripotent stem cells with activin A and a Wnt ligand in a first culture medium containing serum, then culturing the pluripotent stem cells with activin A in a second culture medium containing serum, or
f. Culturing the pluripotent stem cells on a tissue culture substrate coated with an extracellular matrix, then culturing the pluripotent stem cells with activin A and a Wnt ligand in a first culture medium containing serum, then culturing the pluripotent stem cells with activin A and a Wnt ligand in a second culture medium containing serum of a different concentration.

In one embodiment, cells expressing markers characteristic of the pancreatic endoderm lineage are differentiated from cells expressing markers characteristic of the definitive endoderm lineage by treating cells expressing markers characteristic of the definitive endoderm lineage by any one of the following methods:
a. Treating the cells expressing markers characteristic of the definitive endoderm lineage with a fibroblast growth factor and a hedgehog signaling pathway inhibitor, then removing the medium containing the fibroblast growth factor and the hedgehog signaling pathway inhibitor and subsequently culturing the cells in medium containing retinoic acid, a fibroblast growth factor and the hedgehog signaling pathway inhibitor, or
b. Treating the cells expressing markers characteristic of the definitive endoderm lineage with retinoic acid and at least one fibroblast growth factor, or
c. Treating the cells expressing markers characteristic of the definitive endoderm lineage with retinoic acid, then removing the retinoic acid and subsequently treating the cells with at least one fibroblast growth factor.

In one embodiment, cells expressing markers characteristic of the pancreatic endocrine lineage are differentiated from cells expressing markers characteristic of the pancreatic endoderm lineage by treating cells expressing markers characteristic of the pancreatic endoderm lineage by any one of the following methods:
a. Culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF, or
b. Culturing the cells expressing markers characteristic of the pancreatic endoderm lineage in medium containing exendin 4, then removing the medium containing exendin 4 and subsequently culturing the cells in medium containing exendin 1, IGF-1 and HGF, or
c. Culturing the cells expressing markers characteristic of the pancreatic endoderm lineage in medium containing DAFT and exendin 4, or
d. Culturing the cells expressing markers characteristic of the pancreatic endoderm lineage in medium containing exendin 4, or
e. Treating the cells expressing markers characteristic of the pancreatic endoderm lineage with a factor that inhibits the Notch signaling pathway, or
f. Culturing the cells expressing markers characteristic of the pancreatic endoderm lineage in medium containing from about 10 mM to about 20 mM glucose and exendin 4.

In one embodiment, the present invention provides a method for treating a patient suffering from diabetes, comprising the steps of:
a. Culturing pluripotent stem cells,
b. Differentiating the pluripotent stem cells into cells expressing markers characteristic of the definitive endoderm lineage, c. Differentiating the cells expressing markers characteristic of the definitive endoderm lineage into cells expressing markers characteristic of the pancreatic endoderm lineage,
d. Differentiating the cells expressing markers characteristic of the pancreatic endoderm lineage into cells of a β-cell lineage, and
e. Implanting the cells of a β-cell lineage into the patient.

BRIEF DESCRIPTION OF THE DRAWINGS

FIG. 27 depicts the expression of CXCR4 in cultures of the human embryonic stem cell line H9 at passage 46, by FACS at five days post treatment. Panel (a) depicts CXCR4 expression in the absence of Wnt-3a. Panel (b) depicts CXCR4 expression following treatment with 10 ng/ml Wnt-3a. Panel (c) depicts CXCR4 expression following treatment with 20 ng/ml Wnt-3a, and panel (d) depicts CXCR4 expression following treatment with 50 ng/ml Wnt-3a.

10 ng/ml activin A for all five days plus 100 nM GSK-3B IX inhibitor for the first two days, panel (e): 100 ng/ml activin A for all five days plus 20 ng/ml of Wnt-3a for the first two days, and panel (f):10 ng/ml activin A for all five days plus 20 ng/ml of Wnt-3a for the first two days.

Figure 32:
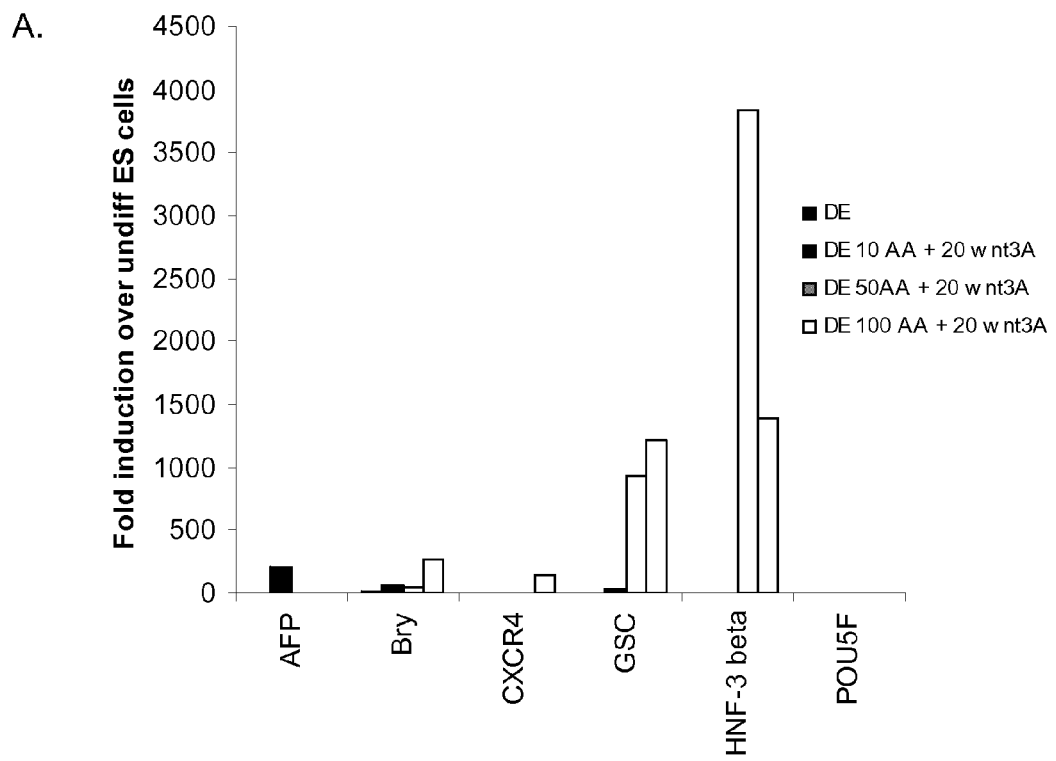
Figure 32:
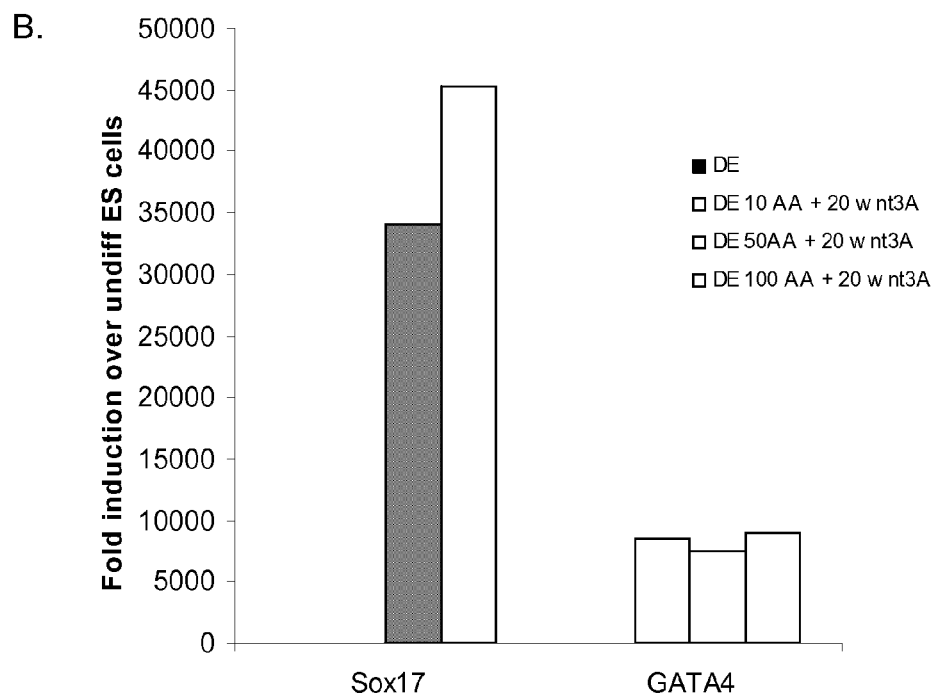

FIG. 32 depicts the gene expression of definitive endoderm markers, as determined by real-time PCR for cultures of the human embryonic stem cell line H9 at passage 49, treated with 10, 50, or 100 ng/ml of activin A plus 20 ng/ml of Wnt-3a: panel (a): expression of AFP, Bry, CXCR4, GSC, HNF-3B, and POU5F (Oct-4) and panel (b): SOX-17 and GATA4. Results are expressed as fold increase over untreated cells.

Figure 33:
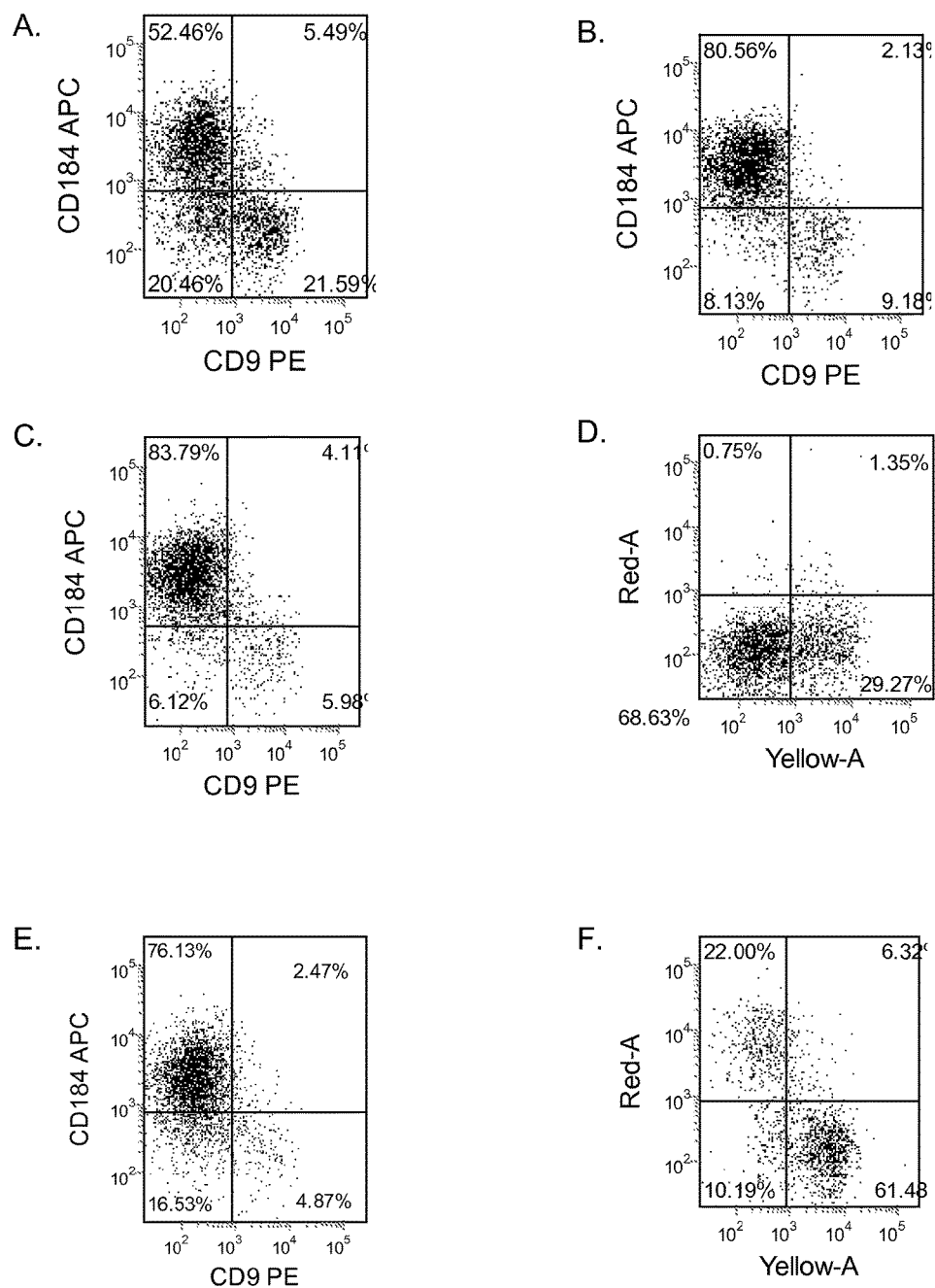

FIG. 33 depicts the expression of CXCR4 by FACS for the embryonic stem cell line H9 at passage 53. Data was obtained 5 days post treatment. Cells were treated with the following conditions: Panel (a): 100 ng/ml activin A for all five days plus 20 ng/ml of Wnt-3a for the first two days and 25 ng/ml BMP-4 for days 3-5; panel (b): 100 ng/ml activin A for all five days plus 20 ng/ml of Wnt-3a for the first two days; panel (c): 100 ng/ml activin A for all five days plus 100 nM of GSK-3B inhibitor IX for the first two days; panel (d): 20 ng/ml Wnt-3a+25 ng/ml BMP-4 for all five days; panel (e): 100 ng/ml activin A for all five days plus 20 ng/ml of Wnt-3a+100 nm GSK-3B inhibitor IX for the first two days, and panel (f): 100 ng/ml activin A+25 ng/ml BMP-4 for all five days. For all the panels, the X-axis represents expression of CD9 and the Y-axis represents expression of CXCR4 (CD184).

Figure 34:
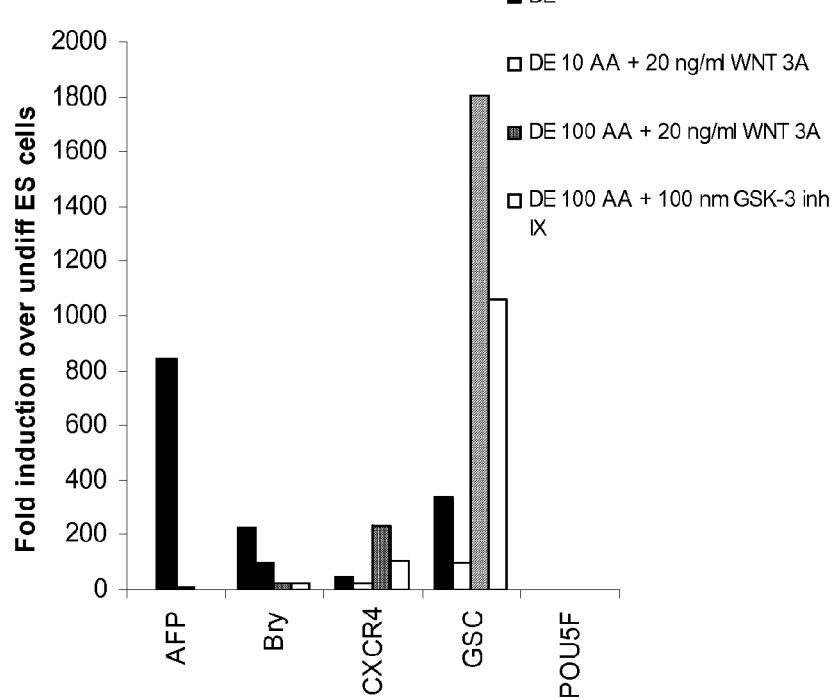
Figure 34:
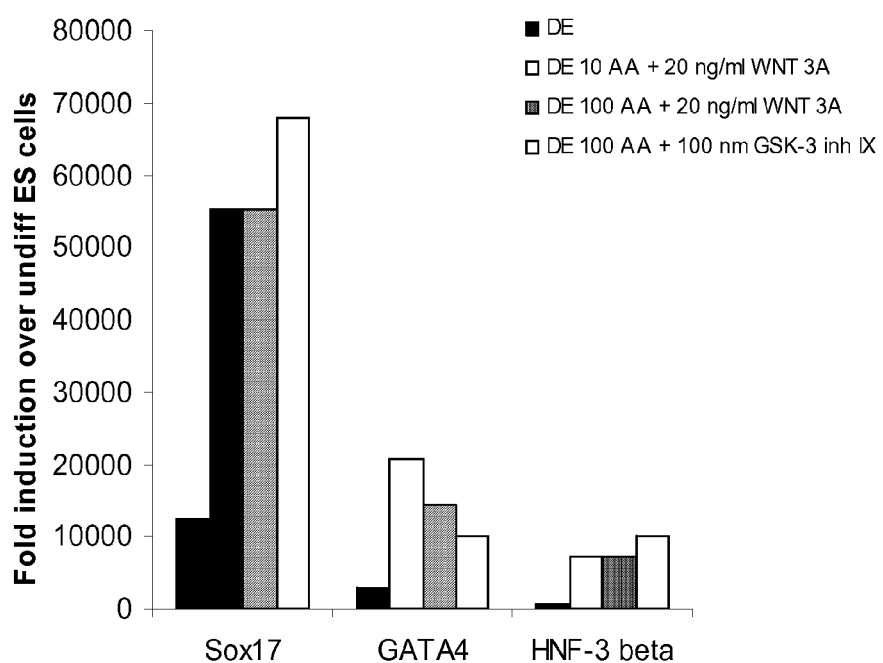

FIG. 34 depicts the gene expression of definitive endoderm markers, as determined by real-time PCR for cultures of the human embryonic stem cell line H1 at passage 46, treated with 10 or 100 ng/ml of activin A plus 20 ng/ml of Wnt-3a or 100 NM GSK-3B inhibitor: panel (a): expression of AFP, Bry, CXCR4, GSC, and POU5F (Oct-4) and panel (b): SOX-17, HNF-3B, and GATA4. Results are expressed as fold increase over untreated cells.

Figure 35:
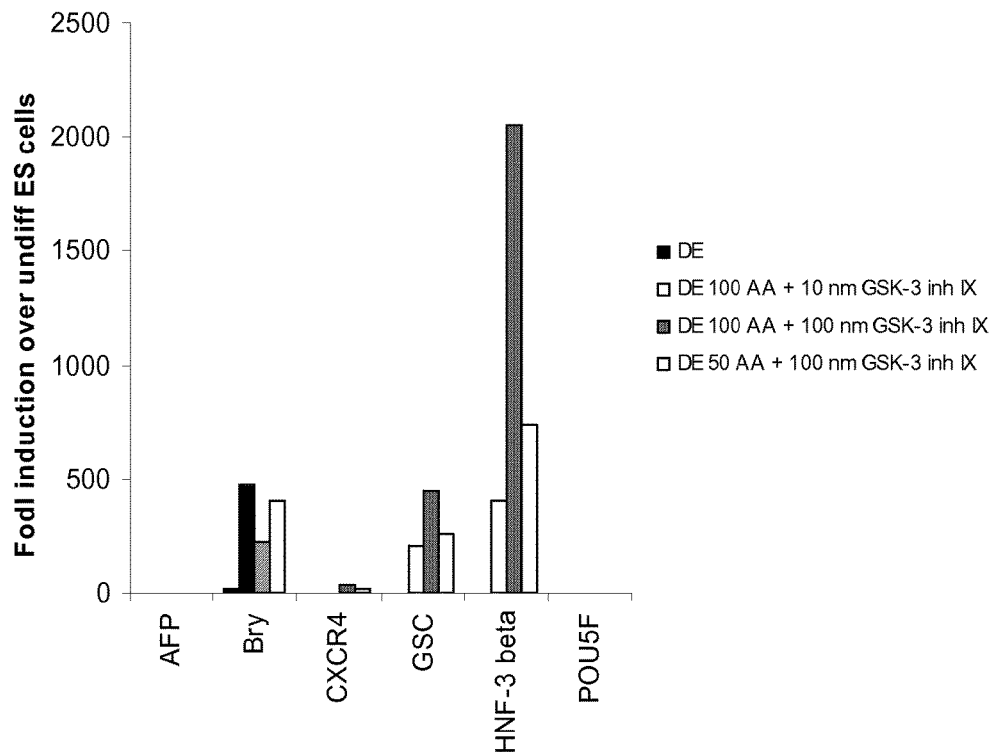
Figure 35:
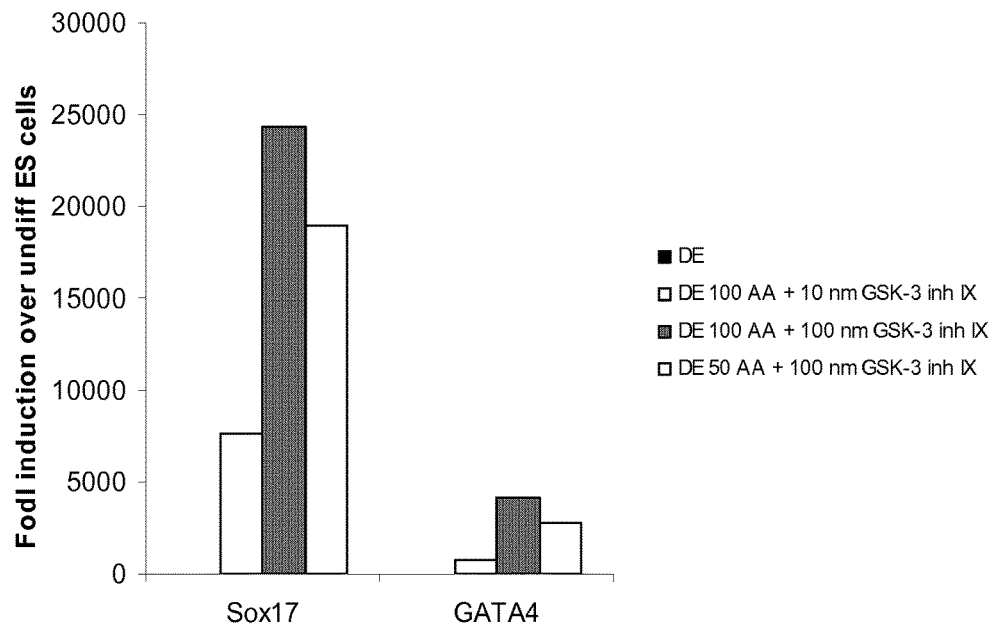

FIG. 35 depicts the gene expression of definitive endoderm markers, as determined by real-time PCR for cultures of the human embryonic stem cell line H9 at passage 49, treated with 50 or 100 ng/ml of activin A plus 10 or 100 nM GSK-3B inhibitor: panel (a): expression of AFP, Bry, CXCR4, GSC, HNF-3B, and POU5F (Oct-4) and panel (b): SOX-17 and GATA4. Results are expressed as fold increase over untreated cells.

Figure 36:
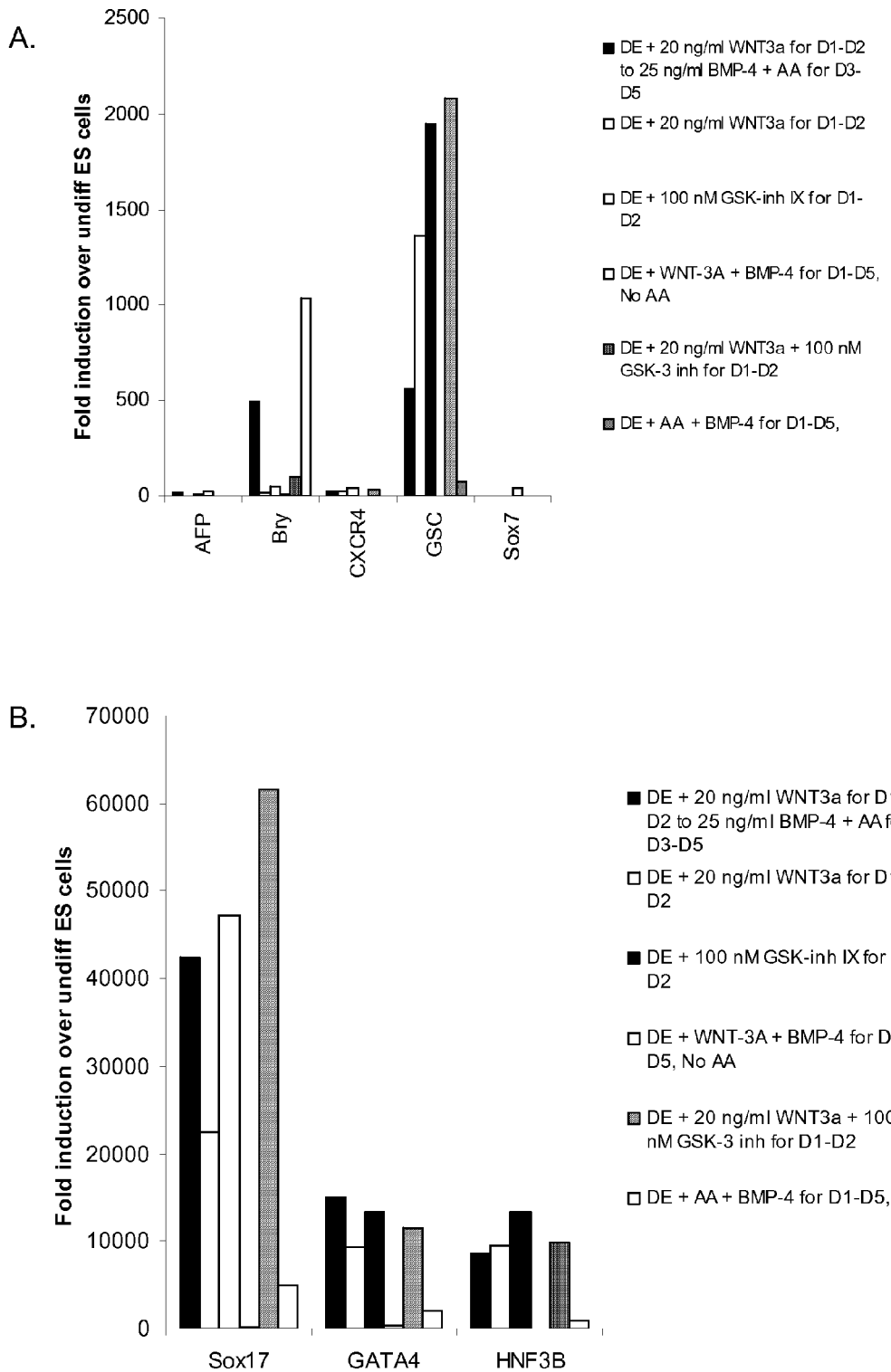

FIG. 36 depicts the gene expression of definitive endoderm markers, as determined by real-time PCR for cultures of the human embryonic stem cell line H9 at passage 53, treated with combinations of activin A, Wnt-3a, GSK-3 inhibitor, and BMP-4, for five days: panel (a): expression of AFP, Bry, CXCR4, GSC, HNF-3B, and SOX7 and panel (b): SOX-17, HNF-3B and GATA4.

Figure 37:
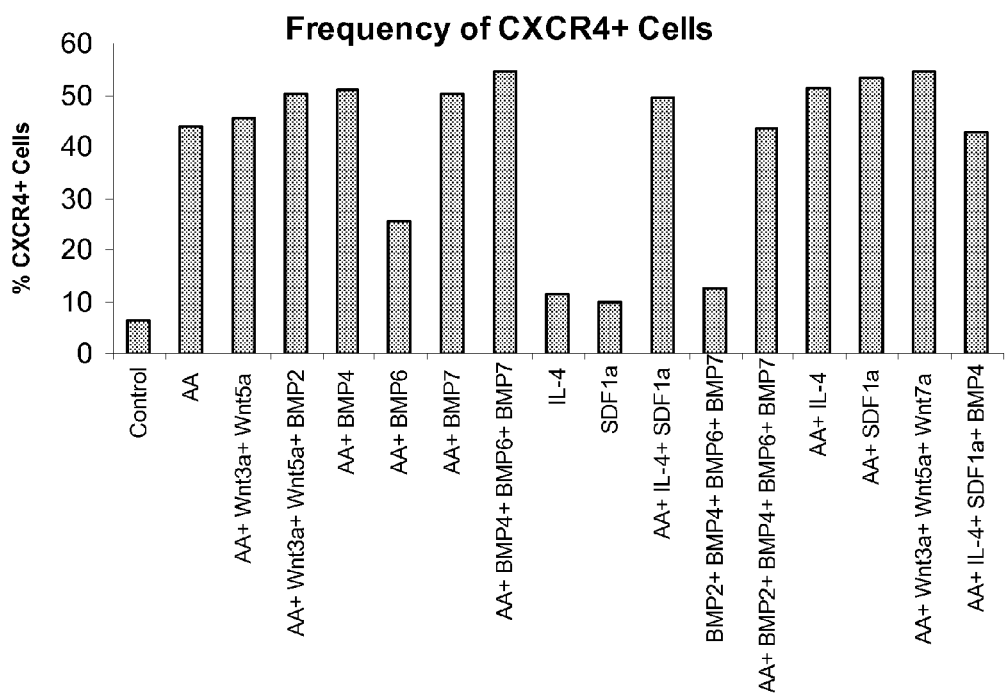

FIG. 37 depicts the percentage of CXCR4 expression, determined by FACS, in cultures of the human embryonic stem cell line H9, treated with the conditions listed in Example 22.

Figure 38:
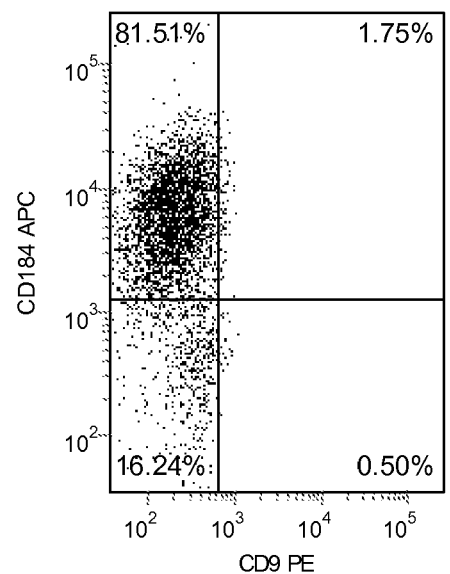
Figure 38:
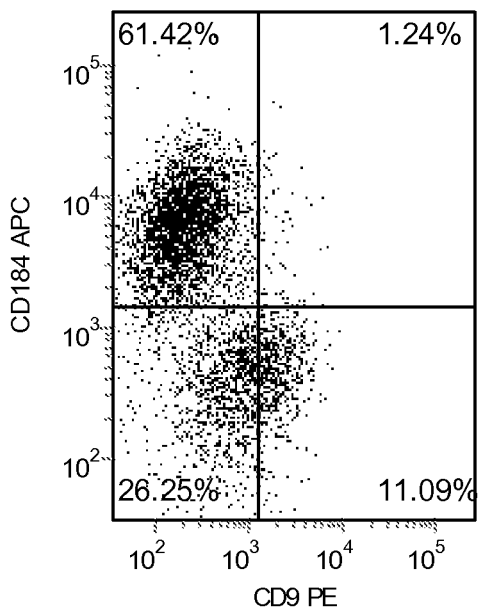

FIG. 38 depicts the expression of definitive endoderm markers as determined by FACS in cultures of the human embryonic stem cell line H9, cultured on fibronectin (panel a) or MATRIGEL™ (panel b).

Figure 39:
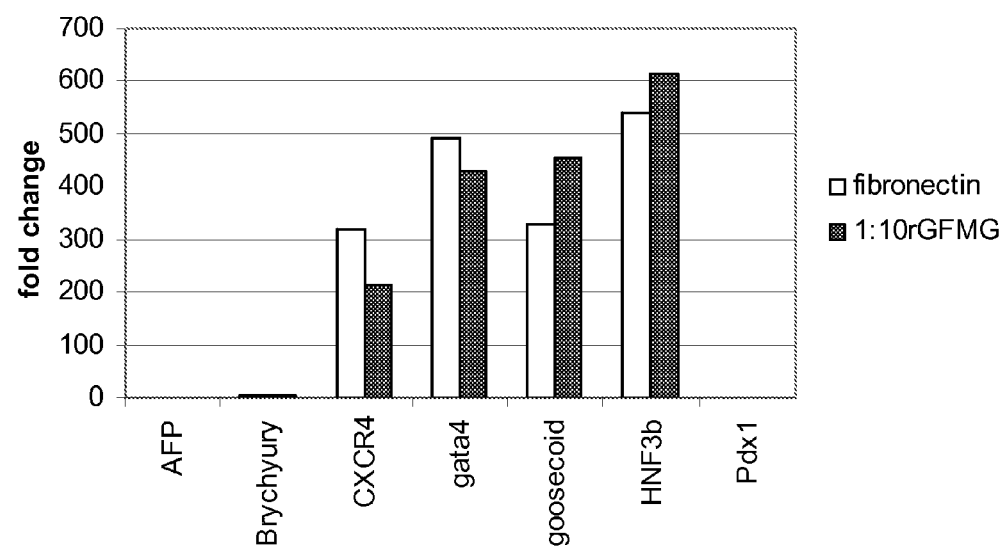

FIG. 39 depicts the expression of definitive endoderm markers as determined by real-time PCR in cultures of the human embryonic stem cell line H9, cultured on fibronectin (□) or a 1:10 dilution of growth factor reduced MATRIGEL (■).

Figure 40:
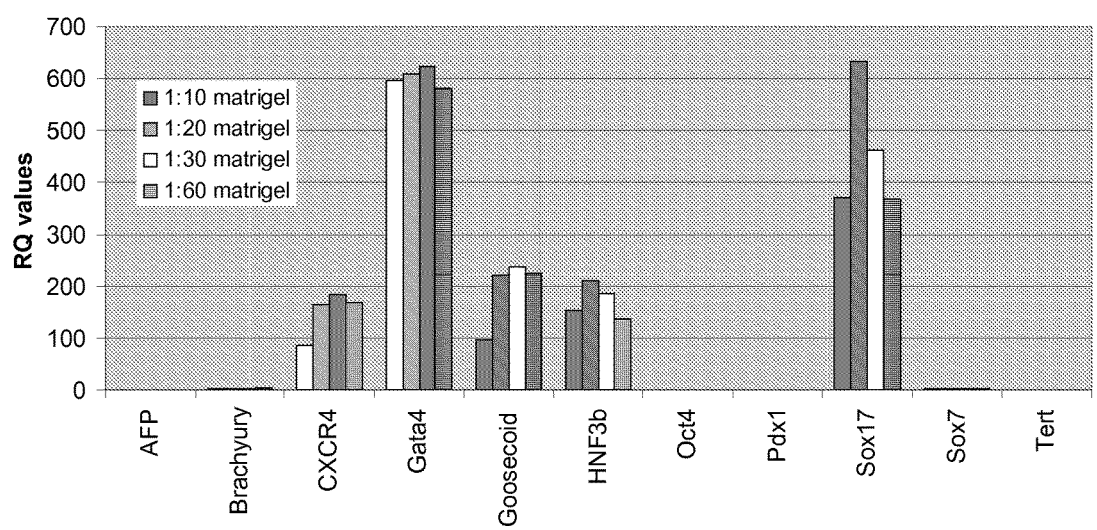

FIG. 40 depicts the effect of various concentrations of MATRIGEL in the presence of low serum, 100 ng/ml of activin A and 20 ng/ml of Wnt-3a on differentiating human embryonic stem cells into definitive endoderm. Cells were treated according to the methods disclosed in Example 4. Results shown are the expression levels of the genes indicated, as determined by real-time PCR.

Figure 41:
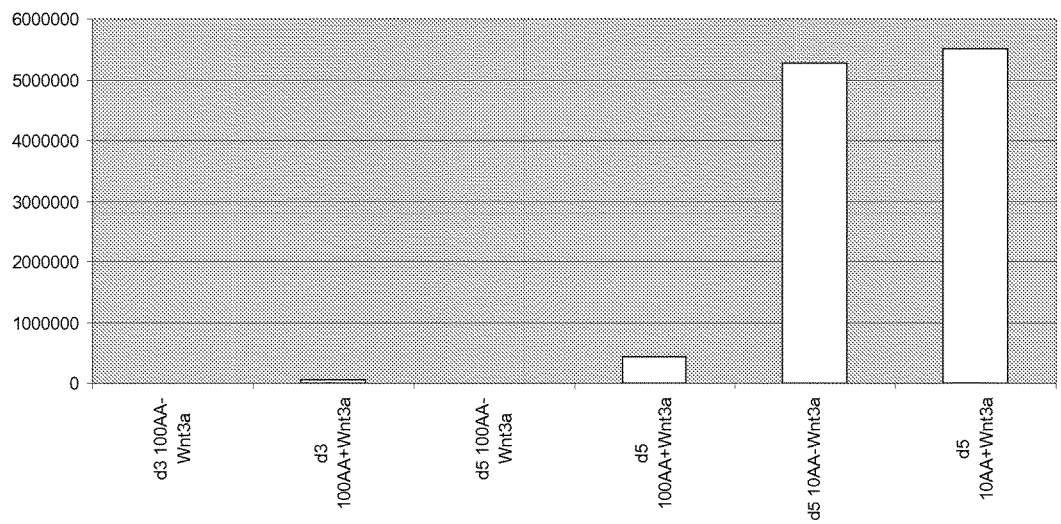
Figure 41:
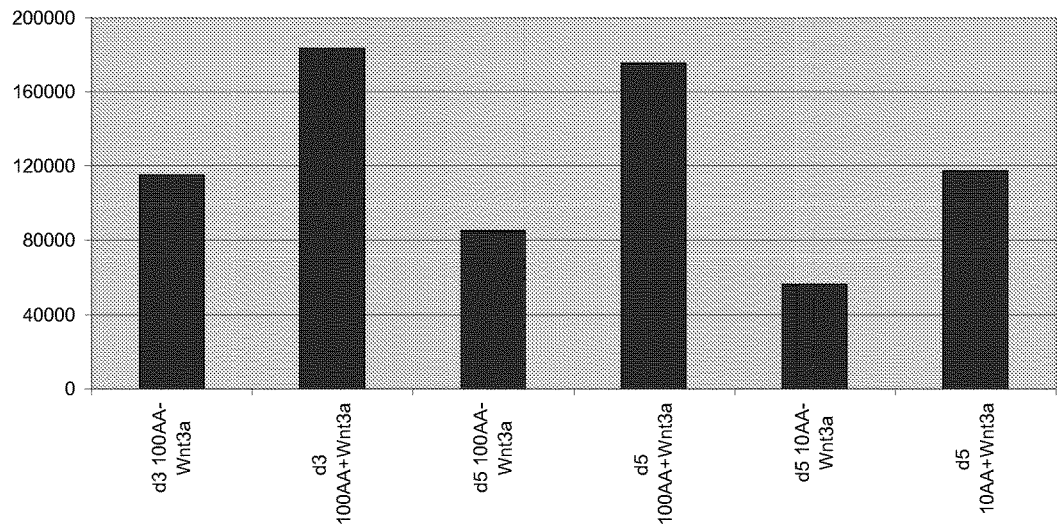
Figure 41:
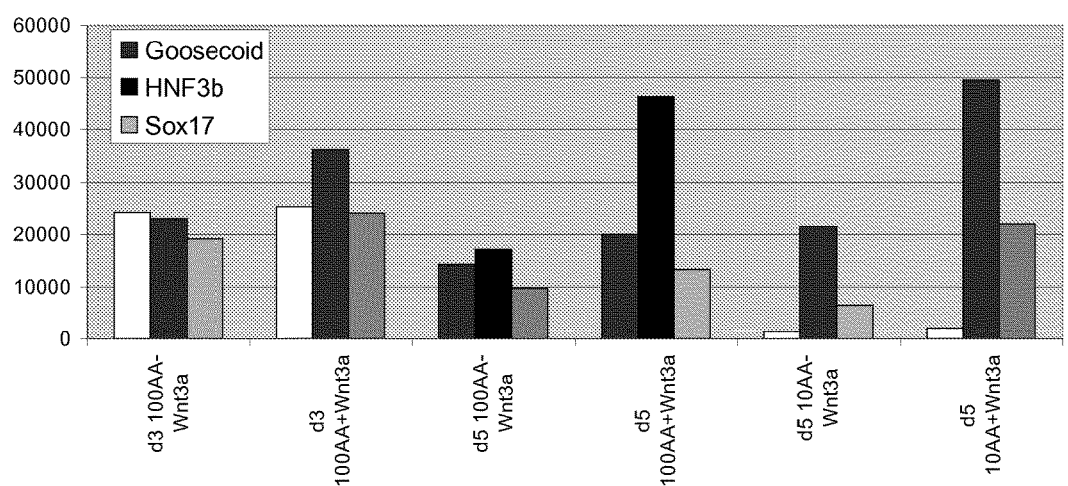
Figure 41:
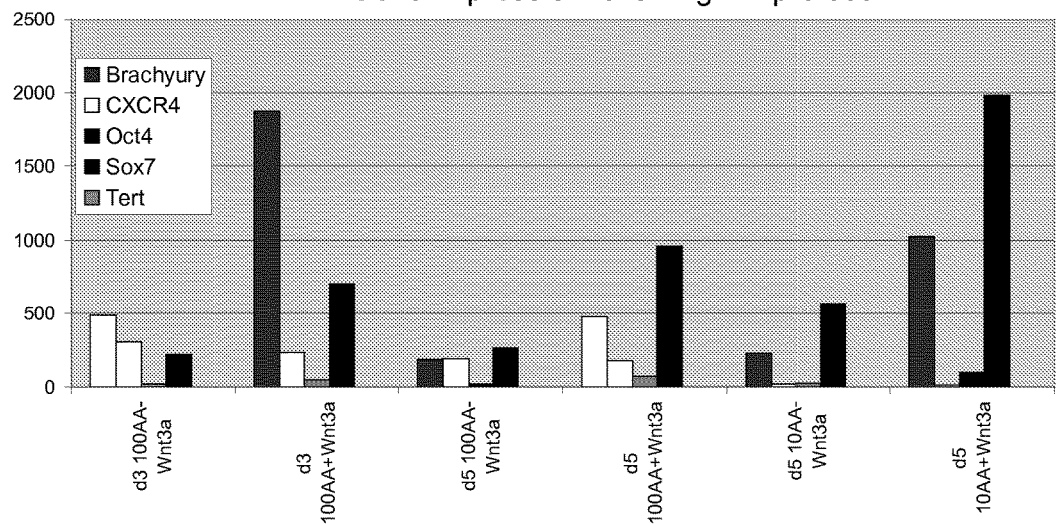
Figure 41:
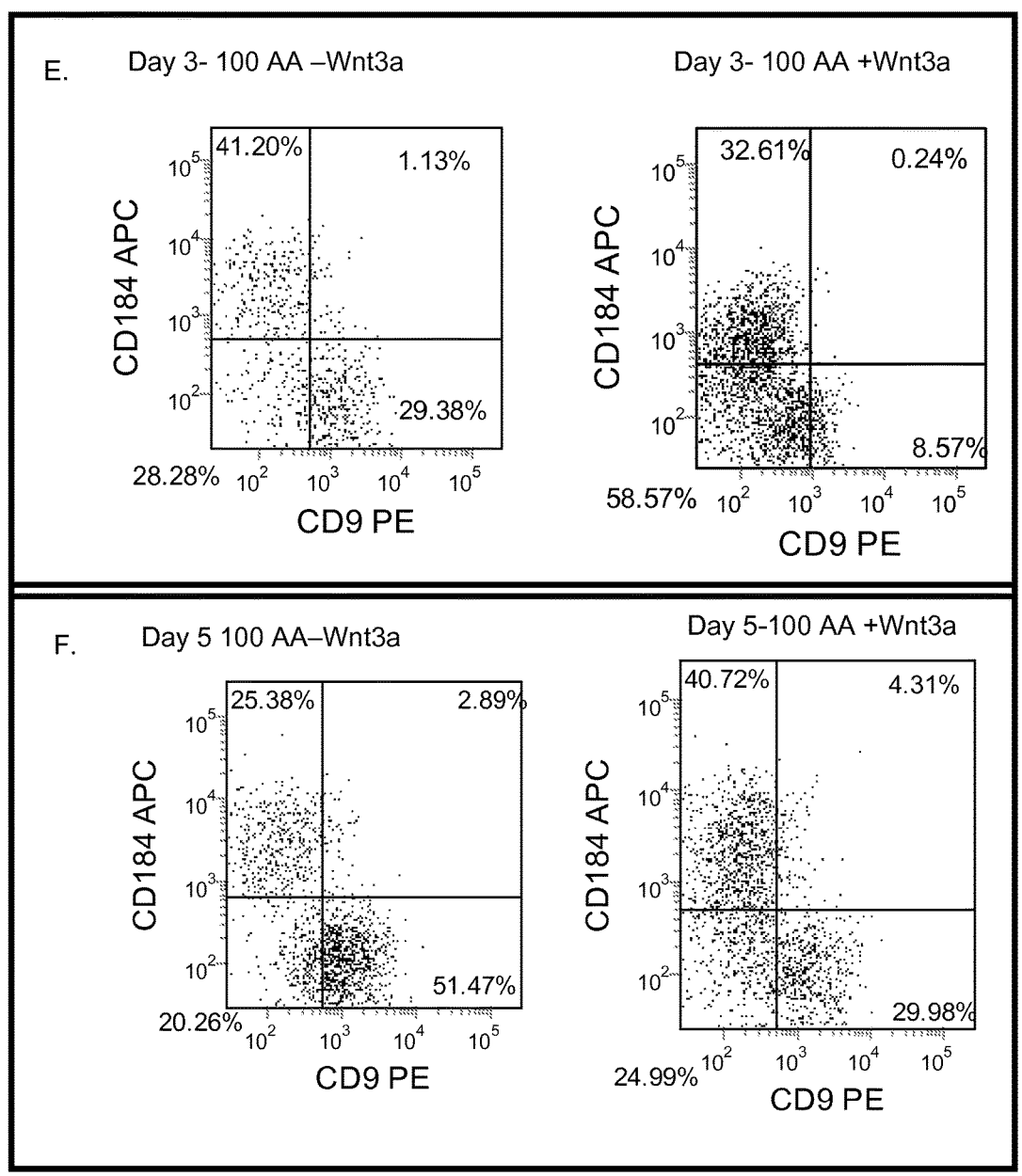
Figure 41:
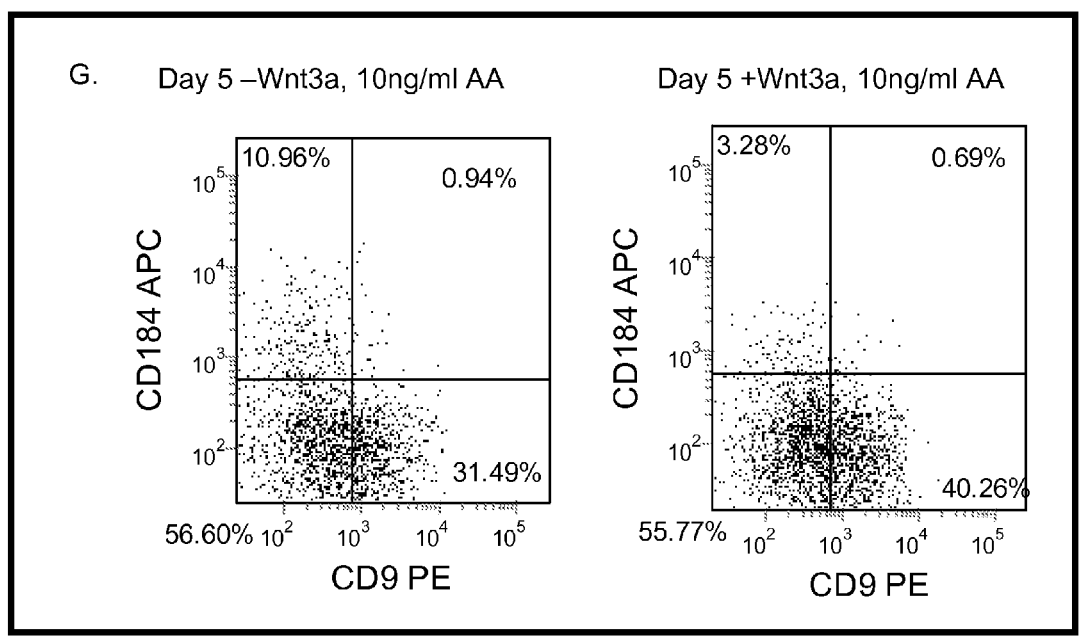

FIG. 41 depicts the role of Wnt-3a in definitive endoderm formation by human embryonic stem cells maintained on MATRIGEL, but differentiated on mouse embryonic fibroblasts. Panels (a-d) show real-time PCR data for the genes indicated. Panels (e-g) show FACS data for the conditions indicated.

Figure 42:
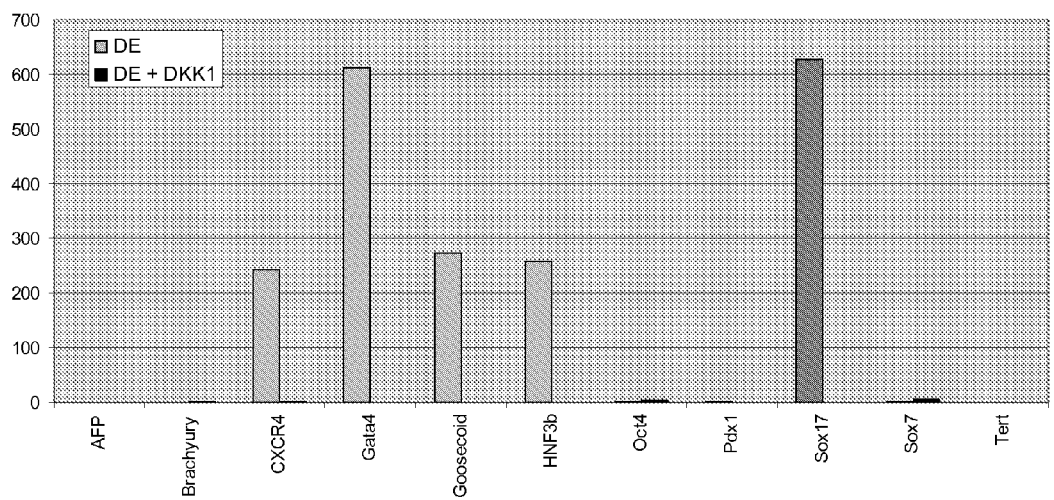

FIG. 42 shows the differentiation of human embryonic stem cells cultured on tissue culture substrate coated with MATRIGEL™ to definitive endoderm following treatment with the Wnt Inhibitor DKK-1. Results shown are the expression of the genes indicated, as determined by real-time PCR in H9 cells treated according to the methods disclosed in Example 4 in the presence of 20 ng/ml of Wnt-3A plus 100 ng/ml of DKK1 (DE+DKK1), or in the absence of DKK1 (DE).

Figure 43:
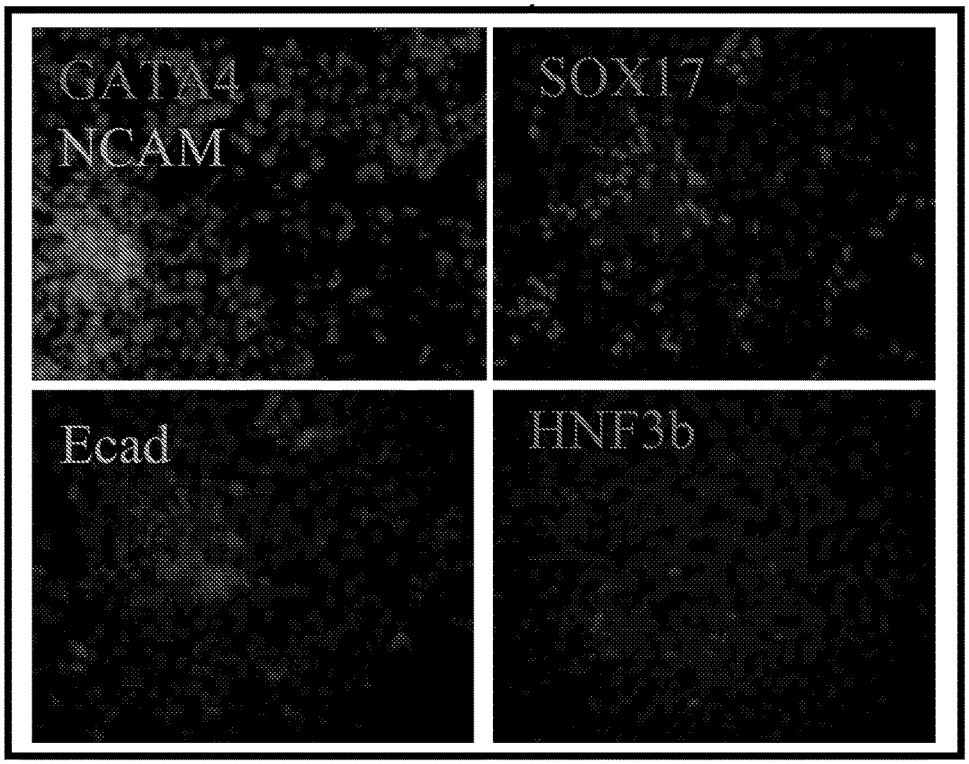
Figure 43:
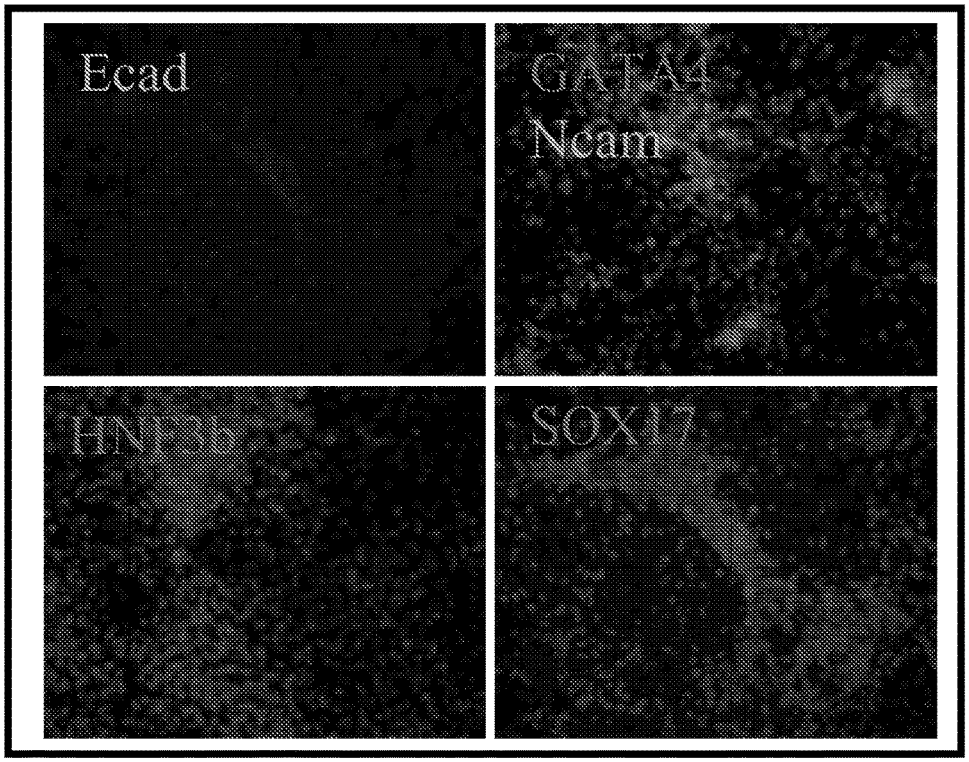
Figure 44:
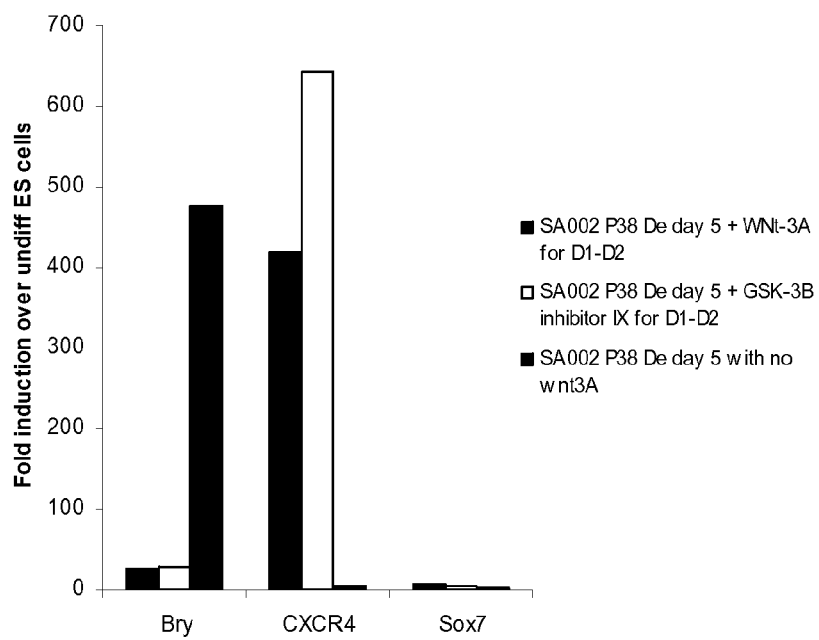
Figure 44:
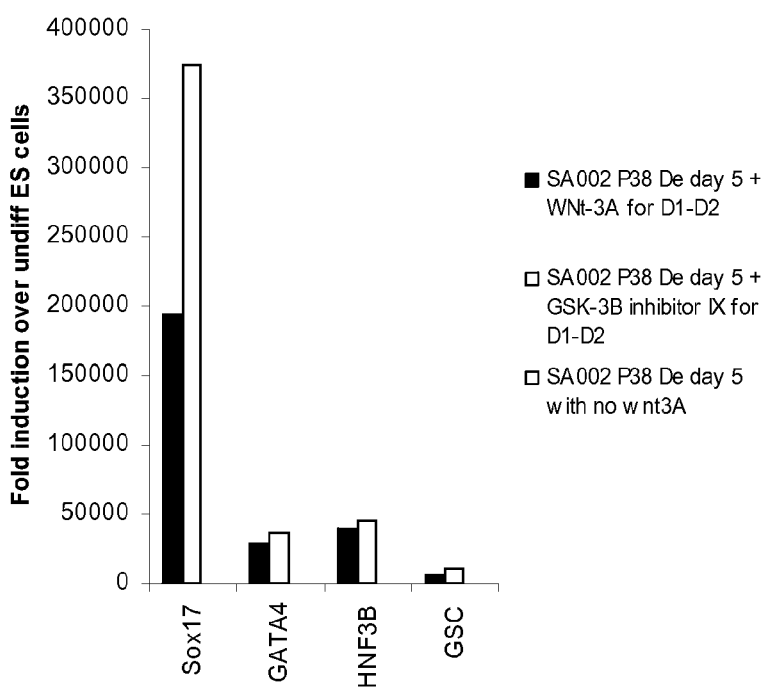

FIG. 43 shows immunofluoresence staining of definitive endoderm markers in cultures of the human embryonic stem cell line H9 cultured on tissue culture substrate coated with MATRIGEL and differentiated in low serum plus 100 ng/ml of activin-A without (panel a), or with (panel b) 20 ng/ml of Wnt-3a. Ecad=E-cadherin, NCAM=N-cadherin, FIG. 44 shows the differentiation of the human embryonic stem cell line SA002 at passage 38 into definitive endoderm. Cells were treated for five days with the conditions indicated and gene expression was determined by real-time PCR, for the genes indicated in the panels.

Figure 45:
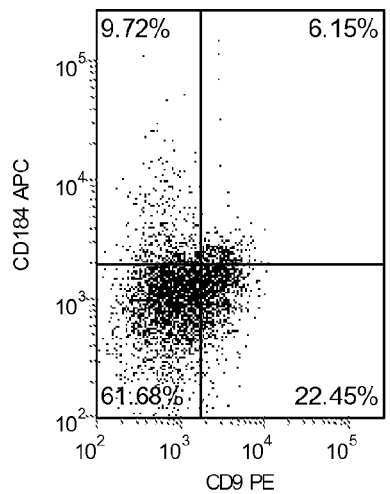
Figure 45:
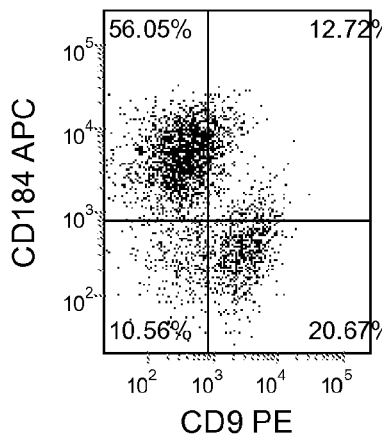
Figure 45:
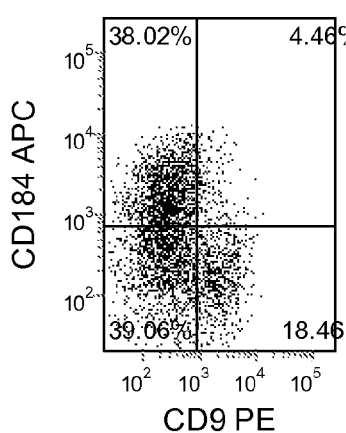

FIG. 45 shows the expression of CXCR4 by FACS in the human embryonic stem cell line SA002 at passage 38, following treatment with 100 ng/ml activin A treatment (panel a), 100 ng/ml activin A+20 ng/ml Wnt-3a (panel b), or 100 ng/ml activin A+100 nM GSK-3B inhibitor IX (panel c). Cells were treated for five days.

Figure 46:
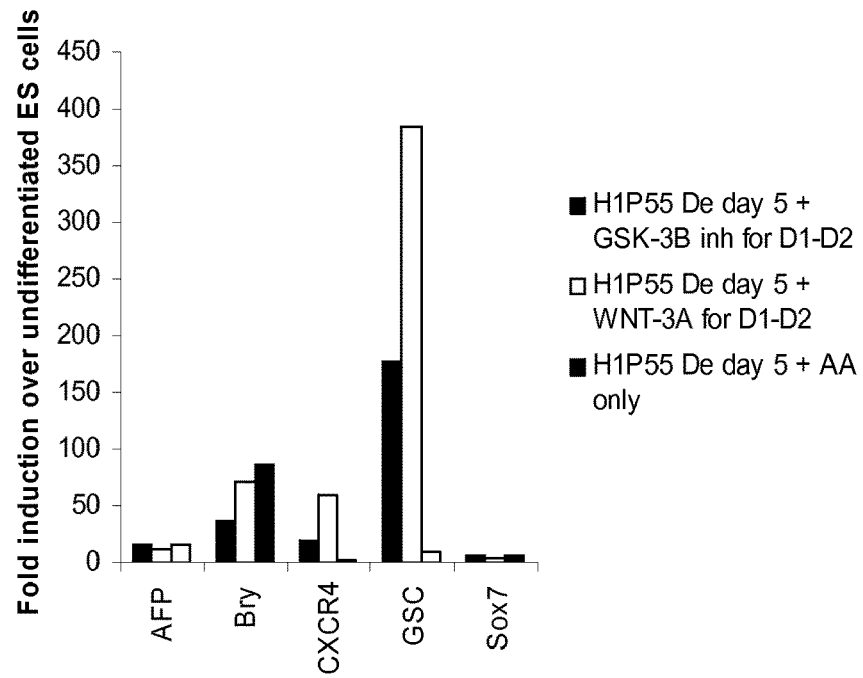
Figure 46:
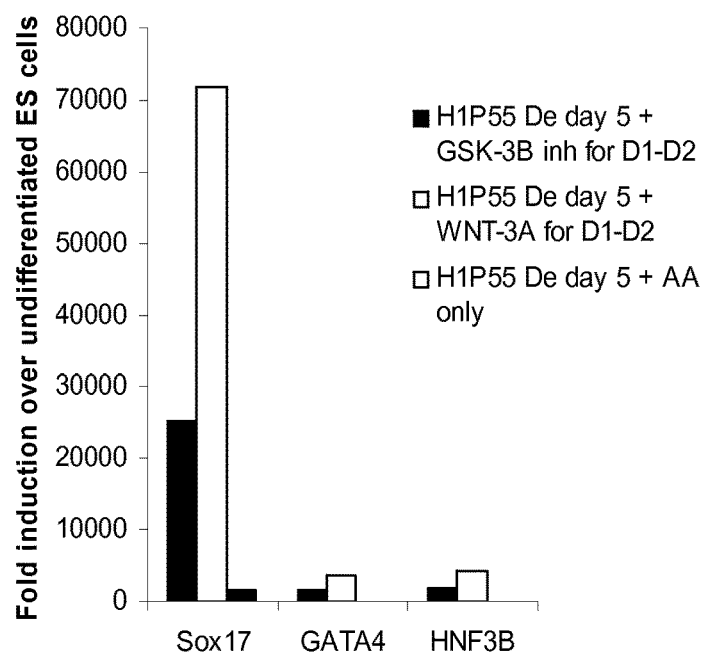

FIG. 46 shows the differentiation of the human embryonic stem cell line H1 at passage 55 into definitive endoderm on tissue culture substrate coated with human serum. Cells were treated with the conditions indicated and gene expression was determined by real-time PCR, for the genes indicated in the panels.

Figure 47:
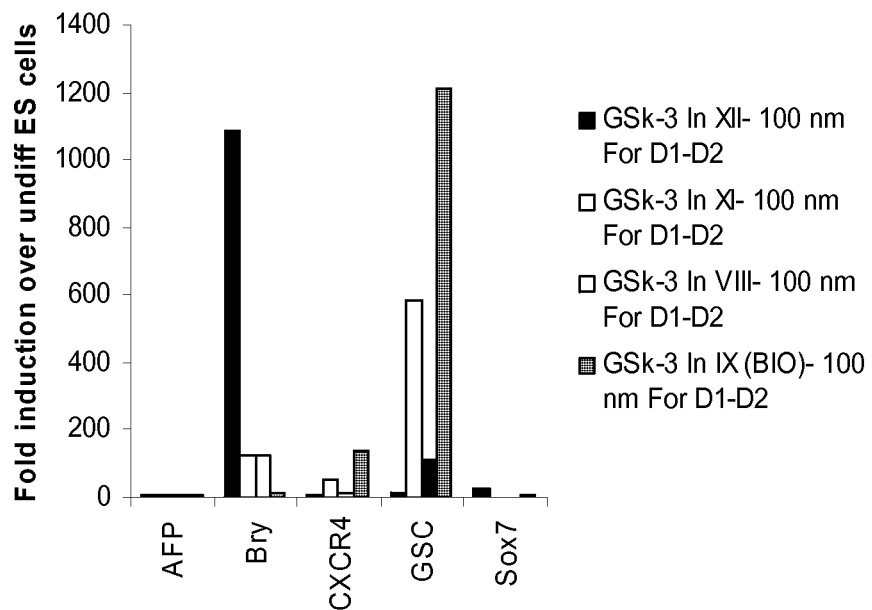
Figure 47:
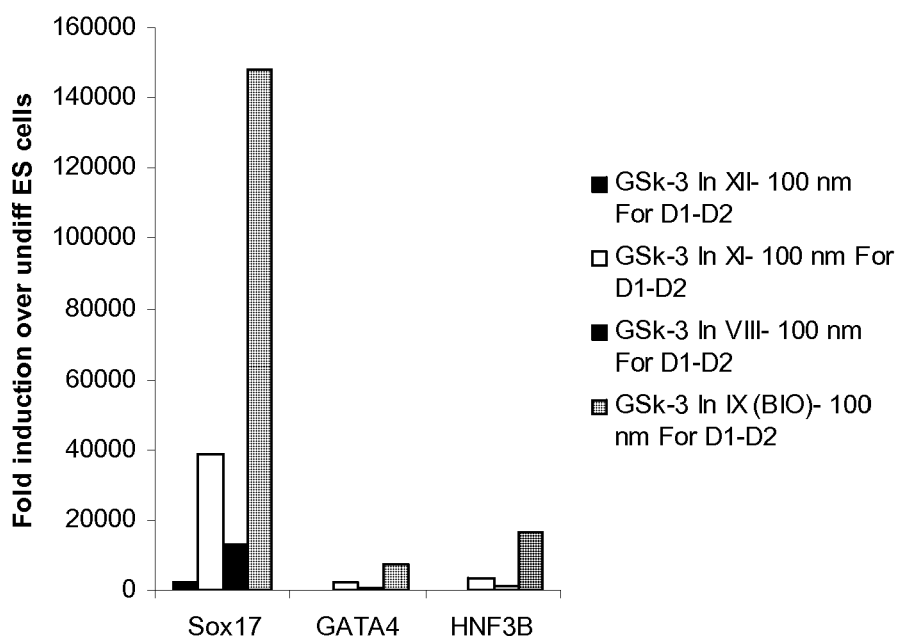

FIG. 47 shows the differentiation of cultures of the human embryonic stem cell line H1 at P54, on tissue culture substrate coated with MATRIGEL™ to definitive endoderm. The effects of various GSK-B inhibitors were tested following a five-day DE protocol. The following GSK-3B inhibitors were evaluated at 100 nM for the first two days of treatment: GSK-3B VIII, IX, XI, and XII.

Figure 48:
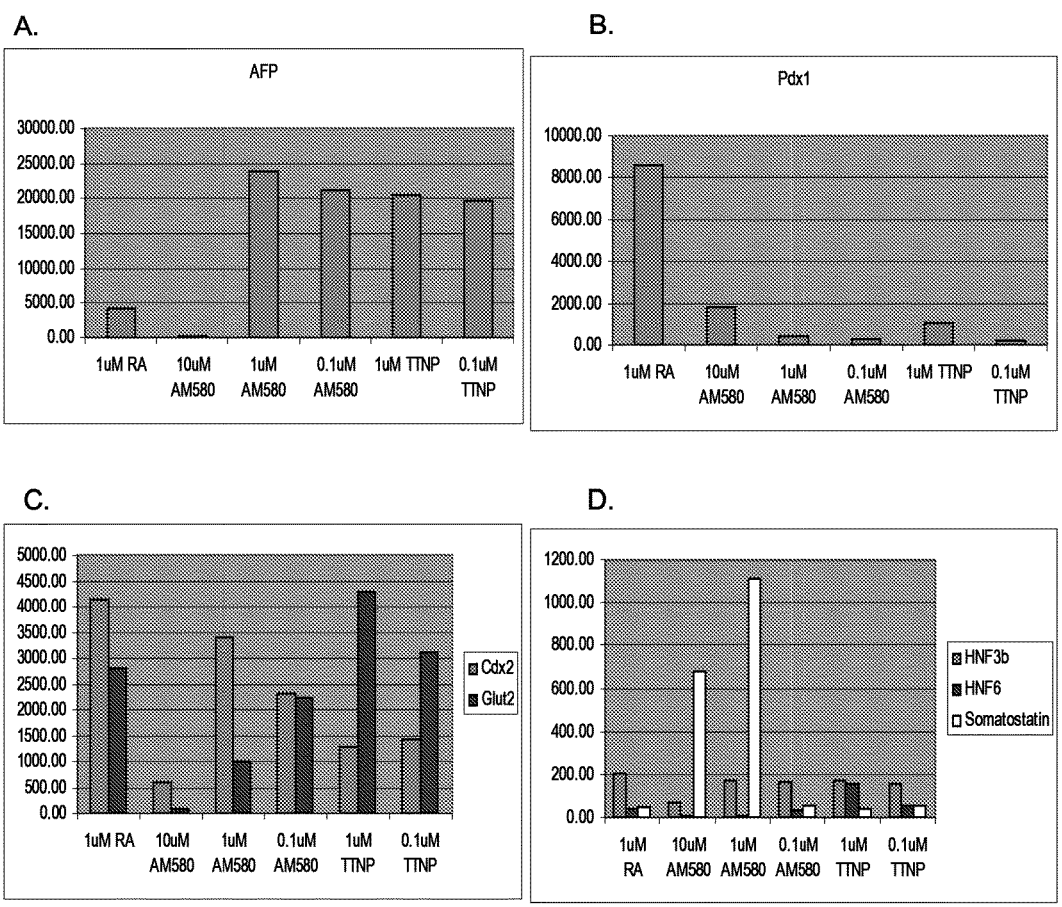

FIG. 48 shows the expression of AFP (panel a), Pdx-1 (panel b), Cdx-2 and Glut-2 (panel c) and HNF-3beta, HNF-6 and somatostatin (panel d) in cultures of the human embryonic stem cell line H9 at passage 49, cultured and treated according to the methods disclosed in Example 4 in the presence of 20 ng/ml of Wnt-3a for the first two days of treatment. Following the treatment, the cells were treated for three additional days with 2% FBS plus 1 µM retinoic acid, 0.1 to 1 µM TTNPB (4-[(E)-2-(5,6,7,8-Tetrahydro-5,5,8,8-tetramethyl-2-naphthalenyl)-1-propenyl]benzoic acid Arotinoid acid), or 0.1-10 µM AM-580 (4-[(5,6,7,8-Tetrahydro-5,5,8,8-tetramethyl-2-naphthalenyl)carboxamido]benzoic acid). The cells were next treated for three additional days in 2% FBS plus 20 ng/ml of bFGF.

Figure 49:
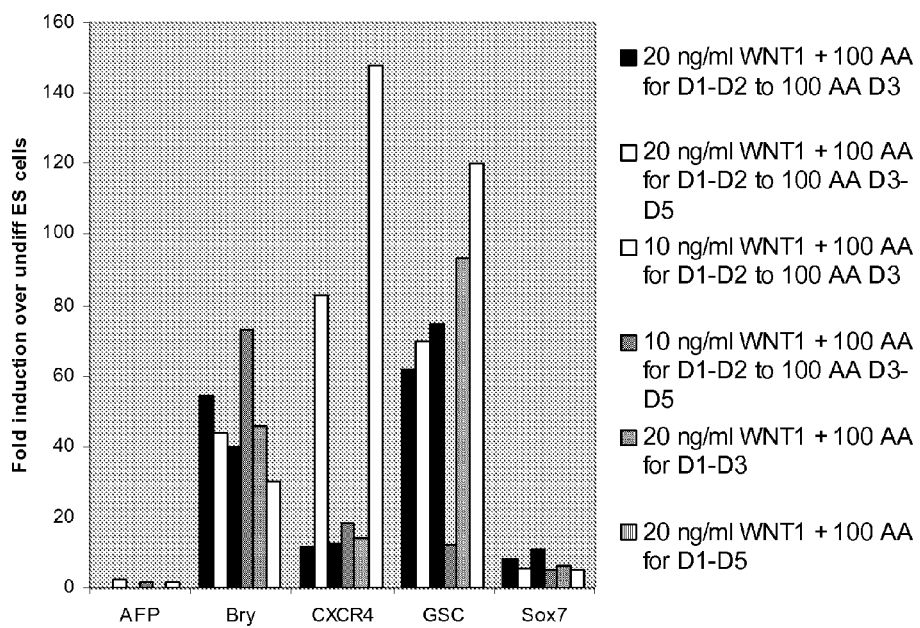
Figure 49:
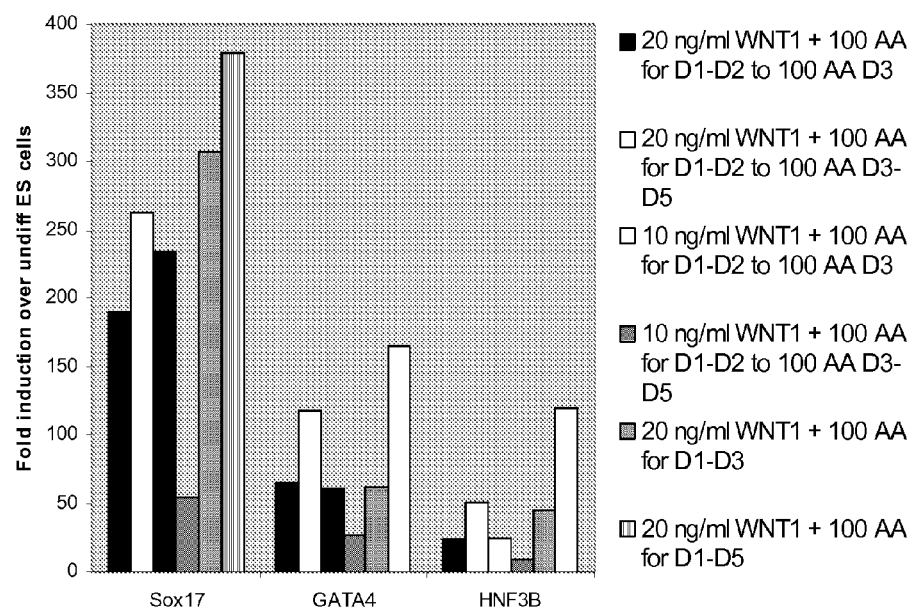

FIG. 49 shows the real-time PCR results of the expression of the definitive endoderm markers indicated in panels a and b. in cultures of the human embryonic stem cell line H1 treated with activin A and Wnt-1 for the times and concentrations indicated.

Figure 50:
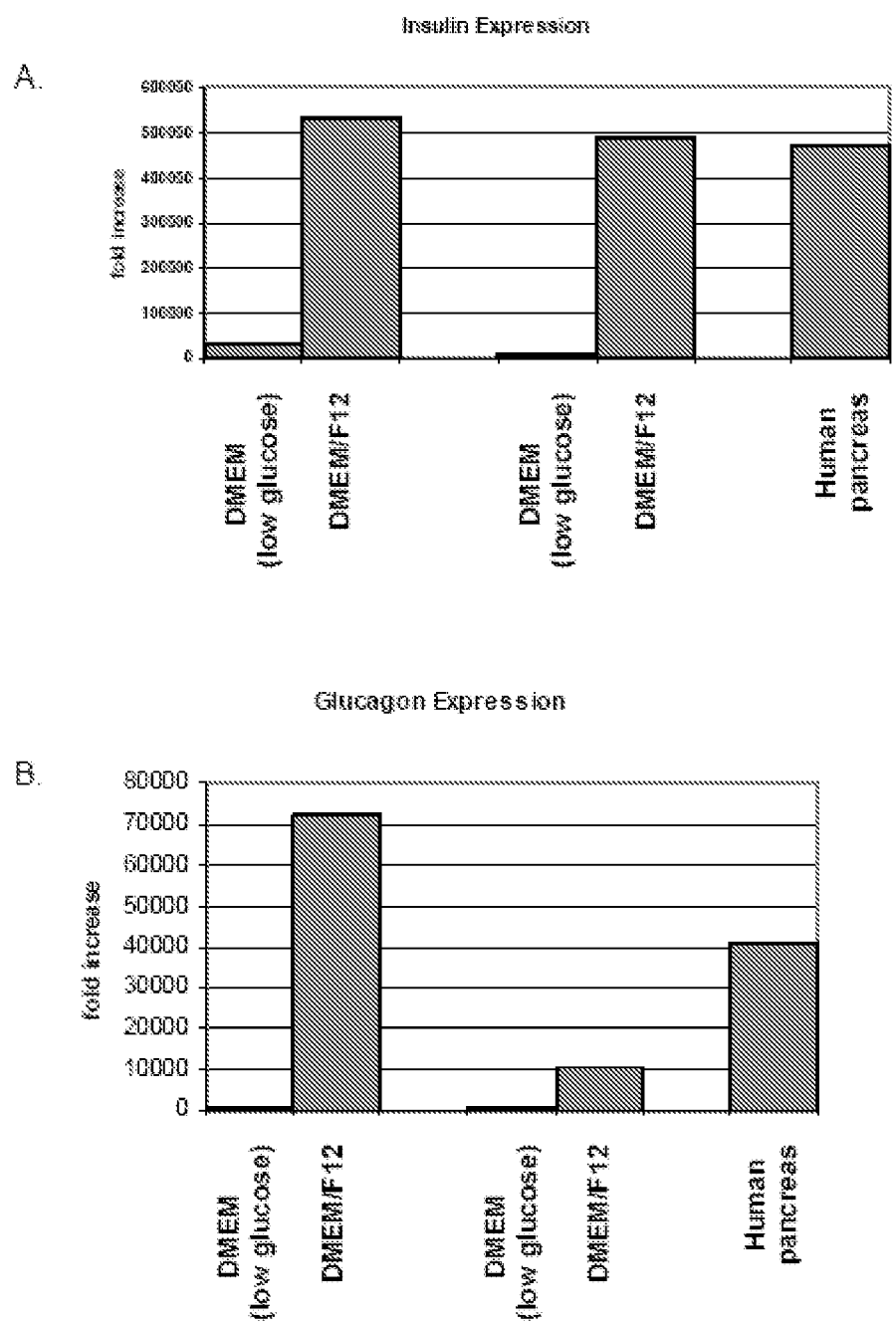

FIG. 50 depicts insulin (panel a) and glucagon (panel b) mRNA expression in cultures of pancreatic endocrine cells, formed from the treatment of pancreatic endoderm cells in DMEM/F12 or DMEM-low glucose. Data shown are results observed from two separate experiments.

Figure 51:
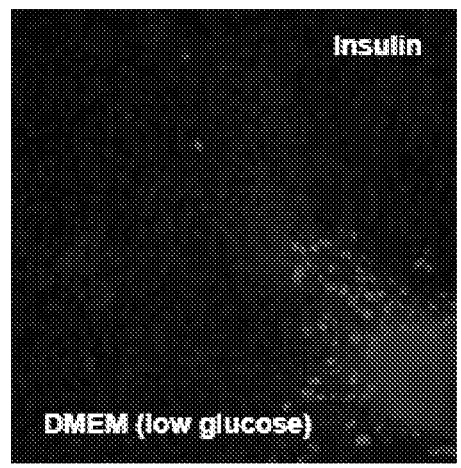
Figure 51:
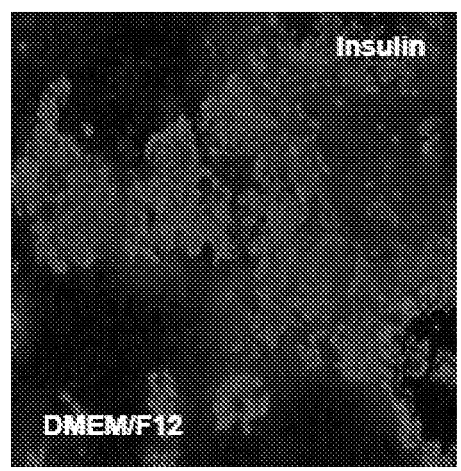
Figure 51:
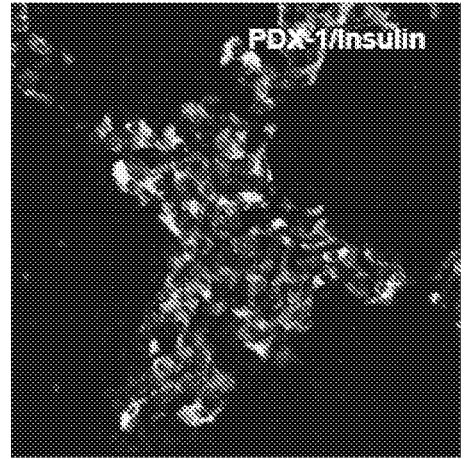

FIG. 51 depicts insulin expression as determined by immunocytochemistry in cells treated in DMDM-low glucose (panel a), DMEM/F12 (panel b). Panel c shows the co-staining of PDX-1 and insulin.

Figure 52:
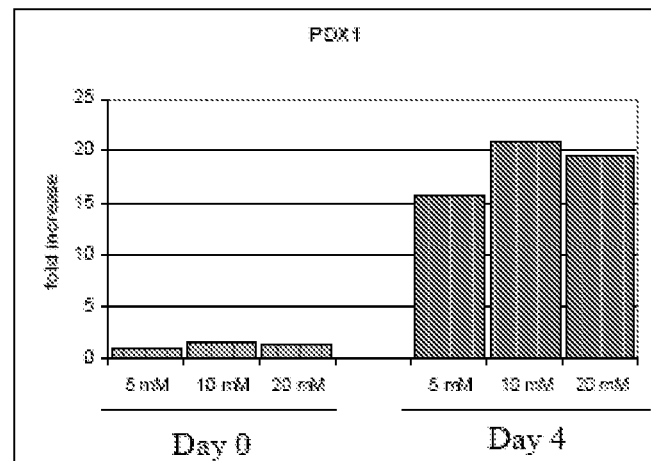
Figure 52:
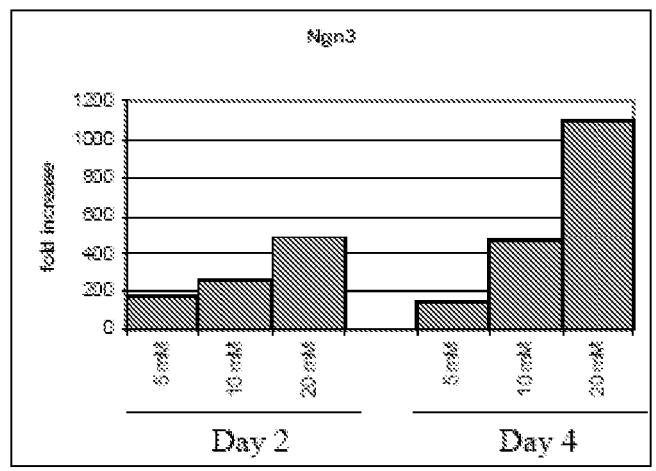
Figure 52:
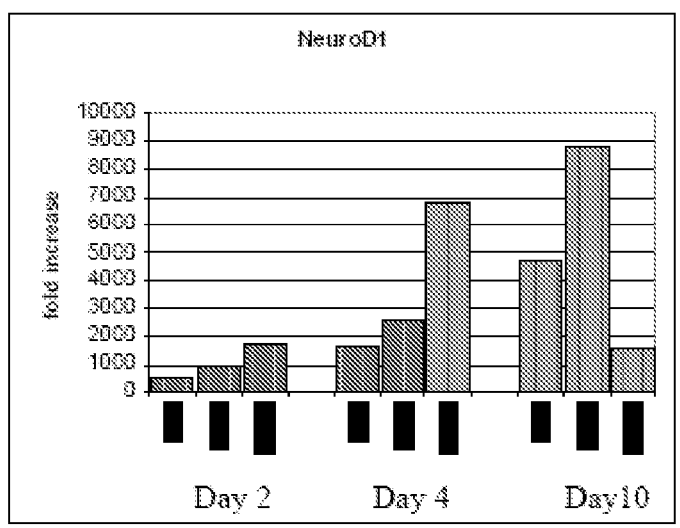
Figure 52:
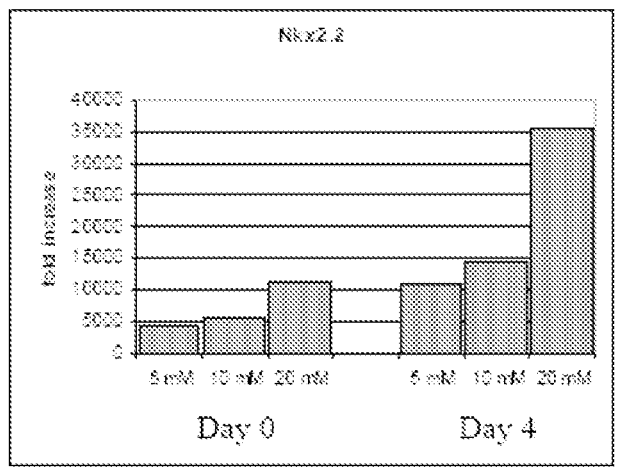
Figure 52:
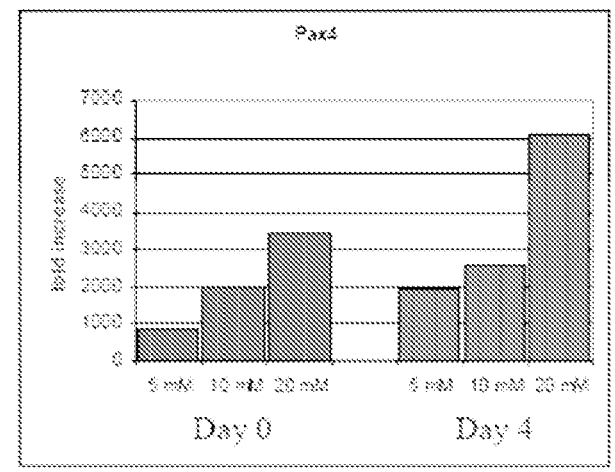
Figure 52:
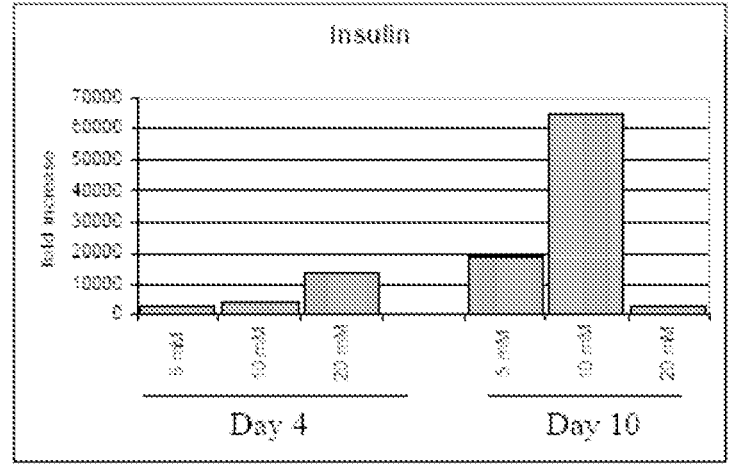
Figure 52:
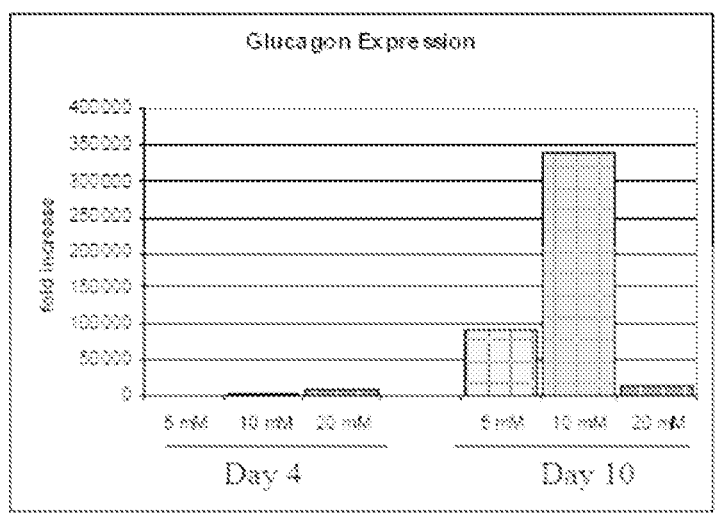

FIG. 52 shows the effect of glucose concentration on gene expression in pancreatic endocrine cells derived from the human embryonic stem cell line H9. Genes are identified in the panels.

Figure 53:
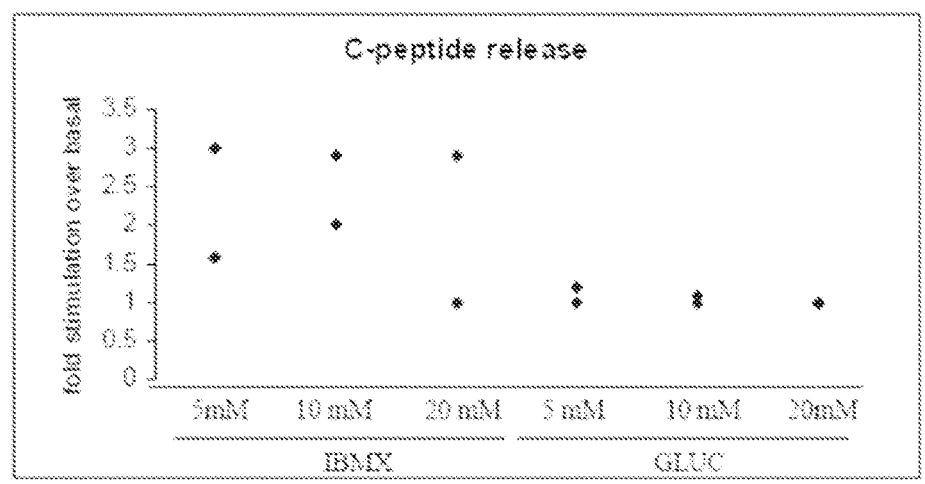

FIG. 53 shows c-peptide release from pancreatic endocrine cells formed in 2, 10 and 20 mM glucose. Cells were stimulated with IBMX or 20 mM glucose.

DETAILED DESCRIPTION

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (selfrenewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Various terms are used to describe cells in culture. "Maintenance" refers generally to cells placed in a growth medium under conditions that facilitate cell growth and/or division, which may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passages depends on many factors, including but not limited to the seeding density, substrate, medium, growth conditions, and time between passaging.

"β-cell lineage" refer to cells with positive gene expression for the transcription factor PDX-1 and at least one of the following transcription factors: NGN-3, Nkx2.2, Nkx6.1, NeuroD, Is1-1, HNF-3 beta, MAFA, Pax4, and Pax6. Cells expressing markers characteristic of the β cell lineage include β cells.

"Cells expressing markers characteristic of the definitive endoderm lineage" as used herein refer to cells expressing at least one of the following markers: SOX-17, GATA-4, HNF-3 beta, GSC, Cer1, Nodal, FGF8, Brachyury, Mixlike homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage" as used herein refer to cells expressing at least one of the following markers: PDX-1, HNF-1beta, HNF-3beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, Ngn-3, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm" as used herein refers to cells which bear the characteristics of cells arising from the epiblast during gastrulation and which form the gastrointestinal tract and its derivatives. Definitive endoderm cells express the following markers: CXCR4, HNF-3 beta, GATA-4, SOX-17, Cerberus, OTX2, goosecoid, c-Kit, CD99, and Mix11.

"Extraembryonic endoderm" as used herein refers to a population of cells expressing at least one of the following markers: SOX-7, AFP, and SPARC.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, GATA-6.

"Pancreatic endocrine cell" or "pancreatic hormone expressing cell" as used herein refers to a cell capable of expressing at least one of the following hormones: insulin, glucagon, somatostatin, pancreatic polypeptide and ghrelin.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Nodal, or FGF8.

"Primitive streak cell" as used herein refers to a cell expressing at least one of the following markers: Brachyury, Mix-like homeobox protein, or FGF4.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Differentiation of Pluripotent Stem Cells in to Cells Expressing Markers Characteristic of the Pancreatic Endocrine Lineage Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FoxD3, Connexin43, Connexin45, Oct4, Sox2, Nanog, hTERT, UTF-1, ZFP42, SSEA-3, SSEA-4, Tra1-60, Tra1-81.

Markers characteristic of the definitive endoderm lineage are selected from the group consisting of SOX-17, GATA4, Hnf-3beta, GSC, Cer1, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesoderm cell. In an alternate aspect, a cell expressing markers characteristic of the definitive endoderm lineage is a definitive endoderm cell.

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN-3, NeuroD, Islet-1, Pdx-1, NKX6.1, Pax-4, Ngn-3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN-3, Nkx2.2, Nkx6.1, NeuroD, Is1-1, HNF-3 beta, MAFA, Pax4, and Pax6. In one aspect of the present invention, a cell expressing markers characteristic of the β cell lineage is a β cell.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D' Amour et al, Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

In one aspect of the present invention, pluripotent stem cells may be differentiated into cells expressing markers characteristic of the definitive endoderm lineage by plating the pluripotent stem cells on a tissue culture substrate coated with an extracellular matrix, then culturing the pluripotent stem cells with activin A and a Wnt ligand in a first culture medium containing serum for a period of time, and then culturing the pluripotent stem cells with activin A in a second culture medium containing a greater concentration of serum for about another period of time.

The concentration of serum in the first culture medium disclosed above may be from about zero to about 0.5 percent, and the culture time may be from about one to about three days. The concentration of serum in the second culture medium disclosed above may be from about 0.5 percent to about two percent, and the culture time may be from about one to about four days.

In an alternate embodiment of the present invention, pluripotent stem cells may be differentiated into cells expressing markers characteristic of the definitive endoderm lineage by plating the pluripotent stem cells on a tissue culture substrate coated with an extracellular matrix, then culturing the pluripotent stem cells with activin A and a Wnt ligand in a first culture medium containing serum for about a period of time, and then culturing the pluripotent stem cells with activin A and a Wnt ligand in a second culture medium containing a greater concentration of serum for another period of time.

The concentration of serum in the first culture medium disclosed above may be from about zero to about 0.5 percent, and the culture time may be from about one to about three days. The concentration of serum in the second culture medium disclosed above may be from about 0.5 percent to about two percent, and the culture time may be from about one to about four days.

In one embodiment, the present invention provides a method for differentiating pluripotent stem cells expressing markers characteristic of the definitive endoderm lineage, comprising the steps of:
a. Plating the pluripotent stem cells on a tissue culture substrate coated with an extracellular matrix, and
b. Culturing the pluripotent stem cells with activin A and a Wnt ligand.

Culturing the pluripotent stem cells with activin A and a Wnt ligand may be performed in a single culture medium. Alternatively, culturing the pluripotent stem cells with activin A and a Wnt ligand may be performed separately or together in more than one culture media. In one embodiment, culturing the pluripotent stem cells with activin A and a Wnt ligand is performed in two culture media.

Extracellular Matrix

In one aspect of the present invention, the pluripotent stem cells are cultured and differentiated on a tissue culture substrate coated with an extracellular matrix. The extracellular matrix may be a solubilized basement membrane preparation extracted from mouse sarcoma cells (which is sold by BD Biosciences under the trade name MATRIGEL). Alternatively, the extracellular matrix may be growth factor-reduced MATRIGEL. Alternatively, the extracellular matrix may fibronectin. In an alternate embodiment, the pluripotent stem cells are cultured and differentiated on tissue culture substrate coated with human serum.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A., et al., J. Cell. Biol. 101:1511 (1985).

In one embodiment, the extracellular matrix is MATRIGEL. In one embodiment, the tissue culture substrate is coated with MATRIGEL at a 1:10 dilution. In an alternate embodiment, the tissue culture substrate is coated with MATRIGEL at a 1:15 dilution. In an alternate embodiment, the tissue culture substrate is coated with MATRIGEL at a 1:30 dilution. In an alternate embodiment, the tissue culture substrate is coated with MATRIGEL at a 1:60 dilution.

In one embodiment, the extracellular matrix is growth factor-reduced MATRIGEL. In one embodiment, the tissue culture substrate is coated with growth factor-reduced MATRIGEL at a 1:10 dilution. In an alternate embodiment, the tissue culture substrate is coated with growth factor-reduced MATRIGEL at a 1:15 dilution. In an alternate embodiment, the tissue culture substrate is coated with growth factor-reduced MATRIGEL at a 1:30 dilution. In an alternate embodiment, the tissue culture substrate is coated with growth factor-reduced MATRIGEL at a 1:60 dilution.

Differentiation of Pluripotent Stem Cells into Cells Expressing Markers Characteristic of the Definitive Endoderm Lineage on an Extracellular Matrix, Using a Single Culture Medium When a single culture medium is used, it should contain sufficiently low concentrations of certain factors to allow the differentiation of pluripotent stem cells to definitive endoderm, such as, for example insulin and IGF (as disclosed in WO2006020919). This may be achieved by lowering the serum concentration, or alternatively, by using chemically defined media that lacks insulin and IGF. Examples of chemically defined media are disclosed in Wiles et al (Exp Cell Res. 1999 Feb. 25; 247(1): 241-8.).

The culture medium may have a serum concentration in the range of about 0% to about 10%. In an alternate embodiment, the concentration may be in the range of about 0% to about 5%. In an alternate embodiment, the concentration may be in the range of about 0% to about 2%. In an alternate embodiment, the concentration may be about 2%.

The time of culturing with activin A and a Wnt ligand may range from about 1 day to about 7 days. In an alternate embodiment, the time of culturing may range from about 1 day to about 3 days. In an alternate embodiment, the time of culturing may be about 3 days.

Activin A may be used at any concentration suitable to cause differentiation of the pluripotent stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3 a, Wnt-5 a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The single culture medium may also contain a GSK-3B inhibitor. The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

The single culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of the TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine 1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), intestinal cell lines such as, for example, FHs 74 (ATCC No: CCL-241), and primary or transformed endothelial cells.

Differentiation of Pluripotent Stem Cells into Cells Expressing Markers Characteristic of the Definitive Endoderm Lineage on an Extracellular Matrix, Using Two Culture Media Differentiation of pluripotent stem cells into cells of a definitive endoderm lineage may be accomplished by culturing the pluripotent stem cells with activin A and a Wnt ligand using two culture media. Thus, the differentiation of the pluripotent stem cells may be accomplished as follows:
a. Plating the pluripotent stem cells on a tissue culture substrate coated with an extracellular matrix,
b. Culturing the pluripotent stem cells with activin A and a Wnt ligand in a first culture medium, and
c. Culturing the pluripotent stem cells with activin A in a second culture medium.

The first culture medium may contain serum at a low concentration, and the second culture medium may contain serum at a higher concentration than the first culture medium.

The second culture medium may contain a Wnt ligand.

First Culture Medium: The first culture medium should contain sufficiently low concentrations of certain factors to allow the differentiation of pluripotent stem cells into cells expressing markers characteristic of the definitive endoderm lineage, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1):241-8.).

In the first culture medium there may be a lower concentration of serum, relative to the second culture medium. Increasing the serum concentration in the second culture medium increases the survival of the cells, or, alternatively, may enhance the proliferation of the cells. The serum concentration of the first medium may be in the range of about 0% to about 10%. Alternatively, the serum concentration of the first medium may be in the range of about 0% to about 2%. Alternatively, the serum concentration of the first medium may be in the range of about 0% to about 1%. Alternatively, the serum concentration of the first medium may be about 0.5%.

When culturing the pluripotent stem cells with activin A and a Wnt ligand using at least two culture media, the time of culturing in the first culture medium may range from about 1 day to about 3 days.

Activin A may be used at any concentration suitable to cause differentiation of the pluripotent stem cells. The concentration maybe from about 1 pg/ml to about 100 µg/ml. In an alternate embodiment, the concentration may be about 1 pg/ml to about 1 µg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3 a, Wnt-5 a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The first culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

The first culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Second Culture Medium: The second culture medium should contain certain factors, such as, for example, insulin and IGF (as disclosed in WO2006020919), at a sufficient concentration to promote the survival of the cultured cells. This may be achieved by increasing the serum concentration, or, alternatively, by using chemically defined media where the concentrations of insulin and IGF are increased relative to the first culture medium. Examples of chemically defined media are disclosed in Wiles et al (Exp Cell Res. 1999 Feb. 25; 247(1):241-8.).

In a second culture medium having higher concentrations of serum, the serum concentration of the second culture medium may be in the range about 0.5% to about 10%. Alternatively, the serum concentration of the second culture medium may be in the range of about 0.5% to about 5%. Alternatively, the serum concentration of the second culture medium may be in the range of about 0.5% to about 2%. Alternatively, the serum concentration of the second culture medium may be about 2%. When culturing pluripotent stem cells with the second culture medium, the time of culturing may range from about 1 day to about 4 days.

Similar to the first culture medium, Activin A may be used at any concentration suitable to cause differentiation of the pluripotent stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be at a concentration of about 1 ng/ml to about 1000 ng/ml. In an alternate embodiment, the concentration may be about 10 ng/ml to about 100 ng/ml.

The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The second culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

Similar to the first culture medium, the second culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Differentiation of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

For example, characteristics of pluripotent stem cells are well known to those skilled in the art, and additional characteristics of pluripotent stem cells continue to be identified. Pluripotent stem cell markers include, for example, the expression of one or more of the following: ABCG2, cripto, FoxD3, Connexin43, Connexin45, Oct4, Sox2, Nanog, hTERT, UTF-1, ZFP42, SSEA-3, SSEA-4, Tra1-60, Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time. That period of time may be from about one to about six days.

In an alternate aspect of the present invention, cells expressing markers characteristic of the definitive endoderm lineage are further differentiated into cells expressing markers characteristic of the pancreatic endoderm lineage, by treating the cells with retinoic acid for a period of time. That period of time maybe from about one to about three days. The retinoic acid is subsequently removed and the cells are treated with at least one fibroblast growth factor for another period of time. That period of time may be from about one to about three days.

In one embodiment, the present invention provides a method for differentiating cells expressing markers characteristic of the definitive endoderm lineage into cells expressing markers characteristic of the pancreatic endoderm lineage, comprising the steps of:
a. Culturing cells expressing markers characteristic of the definitive endoderm lineage, and
b. Treating the cells expressing markers characteristic of the definitive endoderm lineage with retinoic acid and at least one fibroblast growth factor.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm are treated with retinoic acid and at least one fibroblast growth factor for about one to about six days. In one embodiment, the cells expressing markers characteristic of the definitive endoderm are treated with retinoic acid and at least one fibroblast growth factor for about six days.

The at least one fibroblast growth factor is selected from the group consisting of FGF-2, FGF-4 and FGF-10.

Any cell expressing markers characteristic of the definitive endoderm lineage is suitable for differentiating into a cell expressing markers characteristic of the pancreatic endoderm lineage using this method.\

In an alternate embodiment, the present invention provides a method for differentiating cells expressing markers characteristic of the definitive endoderm lineage into cells expressing markers characteristic of the pancreatic endoderm lineage, comprising the steps of:
a. Culturing cells expressing markers characteristic of the definitive endoderm lineage,
b. Treating the cells expressing markers characteristic of the definitive endoderm lineage treating the cells with retinoic acid, and
c. Removing the retinoic acid and subsequently treating the cells with at least one fibroblast growth factor.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm are treated with retinoic acid for about one to about three days. In one embodiment, the cells expressing markers characteristic of the definitive endoderm are treated with retinoic acid for about three days. In one embodiment, the cells expressing markers characteristic of the definitive endoderm are treated with at least one fibroblast growth factor for about one to about three days. In one embodiment, the cells expressing markers characteristic of the definitive endoderm are treated with at least one fibroblast growth factor for about three days.

The at least one fibroblast growth factor is selected from the group consisting of FGF-2, FGF-4 and FGF-10.

Any cell expressing markers characteristic of the definitive endoderm lineage is suitable for differentiating into a cell expressing markers characteristic of the pancreatic endoderm lineage using this method. In one embodiment, the cells expressing markers characteristic of the definitive endoderm lineage are treated with retinoic acid. Alternatively, the cells expressing markers characteristic of the definitive endoderm lineage are treated with FGF-2, or alternatively FGF-4, or alternatively FGF-10. In an alternate embodiment, the cells expressing markers characteristic of the definitive endoderm lineage are treated with at least one of the following factors: retinoic acid, FGF-2, FGF-4 or FGF-10. In an alternate embodiment, the cells expressing markers characteristic of the definitive endoderm lineage are treated with retinoic acid and at least one of the following fibroblast growth factors: FGF-2, FGF-4 or FGF-10. In one embodiment, the cells expressing markers characteristic of the definitive endoderm lineage are treated with retinoic acid and FGF-2. In another embodiment, the cells expressing markers characteristic of the definitive endoderm lineage are treated with retinoic acid and FGF-4. In a further embodiment, the cells expressing markers characteristic of the definitive endoderm lineage are treated with retinoic acid and FGF-10.

Retinoic acid may be used at a concentration from about 1 nM to about 1 mM. In one embodiment, retinoic acid is used at a concentration of 1 µM.

FGF-2 may be used at a concentration from about 50 pg/ml to about 50 µg/ml. In one embodiment, FGF-2 is used at a concentration of 50 ng/ml.

FGF-4 may be used at a concentration from about 50 pg/ml to about 50 µg/ml. In one embodiment, FGF-4 is used at a concentration of 50 ng/ml.

FGF-10 may be used at a concentration from about 50 pg/ml to about 50 µg/ml. In one embodiment, FGF-10 is used at a concentration of 50 ng/ml.

Cells expressing markers characteristic of the definitive endoderm lineage may be treated with at least one other additional factor that may enhance the formation of cells expressing markers characteristic of the pancreatic endoderm lineage. Alternatively, the at least one other additional factor may enhance the proliferation of the cells expressing markers characteristic of the pancreatic endoderm lineage formed by the methods of the present invention. Further, the at least one other additional factor may enhance the ability of the cells expressing markers characteristic of the pancreatic endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, Hlxb9, PTF-1a, PDX-1, HNF-6, HNF-1beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Formation of Cells Expressing Markers Characteristic of the Pancreatic Endocrine Lineage Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D' Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D' Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway. The factor that inhibits the Notch signaling pathway may be an antagonist for the Notch extracellular receptor. Alternatively, the factor may inhibit the biological activity of the Notch receptor. Alternatively, the factor may inhibit or be an antagonist of an element in the Notch signal transduction pathway within a cell.

In one embodiment the factor that inhibits the Notch signaling pathway is a γ-secretase inhibitor. In one embodiment, the y-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

L-685,458 may be used at a concentration from about 0.1 µM to about 100 µM. In one embodiment, L-685,458 is used at a concentration of about 90 µM. In one embodiment, L-685,458 is used at a concentration of about 80 µM. In one embodiment, L-685,458 is used at a concentration of about 70 µM. In one embodiment, L-685,458 is used at a concentration of about 60 µM. In one embodiment, L-685,458 is used at a concentration of about 50 µM. In one embodiment, L-685,458 is used at a concentration of about 40 µM. In one embodiment, L-685,458 is used at a concentration of about 30 µM. In one embodiment, L-685,458 is used at a concentration of about 20 µM. In one embodiment, L-685,458 is used at a concentration of about 10 µM.

In one embodiment, the present invention provides a method for differentiating cells expressing markers characteristic of the pancreatic endoderm lineage into cells expressing markers characteristic of the pancreatic endocrine lineage, comprising the steps of:
a. Culturing cells expressing markers characteristic of the pancreatic endoderm lineage, and
b. Treating the cells with a factor that inhibits the Notch signaling pathway.

Any cell expressing markers characteristic of the pancreatic endoderm lineage is suitable for differentiating into a cell expressing markers characteristic of the pancreatic endocrine lineage using this method.

In one embodiment, factor that inhibits the Notch signaling pathway is a γ-secretase inhibitor. In one embodiment, the y-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

The cells expressing markers characteristic of the pancreatic endoderm lineage are treated with the factor that inhibits the Notch signaling pathway for about one to about five days. Alternatively, the cells expressing markers characteristic of the pancreatic endoderm lineage are treated with the factor that inhibits the Notch signaling pathway for about three to about five days. Alternatively, the cells expressing markers characteristic of the pancreatic endoderm lineage are treated with the factor that inhibits the Notch signaling pathway for about five days.

In one embodiment, factor that inhibits the Notch signaling pathway is a γ-secretase inhibitor. In one embodiment, the y-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

L-685,458 may be used at a concentration from about 0.1 µM to about 100 µM. In one embodiment, L-685,458 is used at a concentration of about 90 µM. In one embodiment, L-685,458 is used at a concentration of about 80 µM. In one embodiment, L-685,458 is used at a concentration of about 70 µM. In one embodiment, L-685,458 is used at a concentration of about 60 µM. In one embodiment, L-685,458 is used at a concentration of about 50 µM. In one embodiment, L-685,458 is used at a concentration of about 40 µM. In one embodiment, L-685,458 is used at a concentration of about 30 µM. In one embodiment, L-685,458 is used at a concentration of about 20 µM. In one embodiment, L-685,458 is used at a concentration of about 10 µM.

Cells expressing markers characteristic of the pancreatic endoderm lineage may be treated with at least one other additional factor that may enhance the formation of cells expressing markers characteristic of the pancreatic endocrine lineage. Alternatively, the at least one other additional factor may enhance the proliferation of the cells expressing markers characteristic of the pancreatic endocrine lineage formed by the methods of the present invention. Further, the at least one other additional factor may enhance the ability of the cells expressing markers characteristic of the pancreatic endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

In one embodiment, the present invention provides an improved method for differentiating cells expressing markers characteristic of the pancreatic endoderm lineage into cells expressing markers characteristic of the pancreatic endocrine lineage, comprising the steps of:
a. Culturing cells expressing markers characteristic of the pancreatic endoderm lineage, and
b. Treating the cells with a factor capable of differentiating cells expressing markers characteristic of the pancreatic endoderm lineage into cells expressing markers characteristic of the pancreatic endocrine lineage, in medium containing glucose at a concentration from about 10 mM to about 20 mM.

Any cell expressing markers characteristic of the pancreatic endoderm lineage is suitable for differentiating into a cell expressing markers characteristic of the pancreatic endocrine lineage using this method.

Any method capable of differentiating cells expressing markers characteristic of the pancreatic endoderm lineage into cells expressing markers characteristic of the pancreatic endocrine lineage is suitable for the improvement of the present invention.

In one embodiment, the cells expressing markers characteristic of the pancreatic endoderm lineage are treated in a medium containing glucose at a concentration of about 10 mM. In an alternate embodiment, the cells are treated in a medium containing glucose at a concentration of about 20 mM.

Cells expressing markers characteristic of the pancreatic endoderm lineage are treated for about 2 to about 30 days. In one embodiment cells expressing markers characteristic of the pancreatic endoderm lineage are treated for about 2 to about 20 days. In one embodiment, cells expressing markers characteristic of the pancreatic endoderm lineage are treated for about 2 to about 10 days. In one embodiment, cells expressing markers characteristic of the pancreatic endoderm lineage are treated for about 10 days. In one embodiment, cells expressing markers characteristic of the pancreatic endoderm lineage are treated for about 4 days. In one embodiment, cells expressing markers characteristic of the pancreatic endoderm lineage are treated for about 2 days.

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN-3, NeuroD, Islet-1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, Pdx1 (pancreatic and duodenal homeobox gene-1), Nkx2.2, Nkx6.1, Is11, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Therapies

In one aspect, the present invention provides a method for treating a patient suffering from, or at risk of developing, Type1 diabetes. This method involves culturing pluripotent stem cells, differentiating the pluripotent stem cells in vitro into a β-cell lineage, and implanting the cells of a β-cell lineage into a patient.

In yet another aspect, this invention provides a method for treating a patient suffering from, or at risk of developing, Type 2 diabetes. This method involves culturing pluripotent stem cells, differentiating the cultured cells in vitro into a β-cell lineage, and implanting the cells of a β-cell lineage into the patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells, prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a β-cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

BACKGROUND

Example 1

Human Embryonic Stem Cell Culture

The human embryonic stem cell lines H1, H7 and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM betamercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 m/ml mitomycin C (Sigma, St. Louis, Mo.) for 3 h to arrest cell division, then trypsinized and plated at $2 \times 10^4/cm^2$ on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5-7 days after plating), human embryonic stem cells were treated with 1 mg/ml collagenase type IV (Invitrogen/GIBCO) for 5-10 min and then gently scraped off the surface using a 5-ml pipette. Cells were spun at 900 rpm for 5 min, and the pellet was resuspended and re-plated at a 1:3 to 1:4 ratio of cells in fresh culture medium.

Example 2

Formation of Definitive Endoderm Cells

The effects of activin A on the expression of markers of definitive endoderm were examined. Activin A (100 ng/ml) was added to populations of human embryonic stem cells cultured on mouse embryonic fibroblasts. Cells were cultured continuously in the presence of activin A and harvested at the times indicated. The level of expression of definitive endoderm markers was examined by PCR (FIG. 1), FACS (results summarized in Table II), and immunohistochemistry (FIG. 2).

Figure 1:
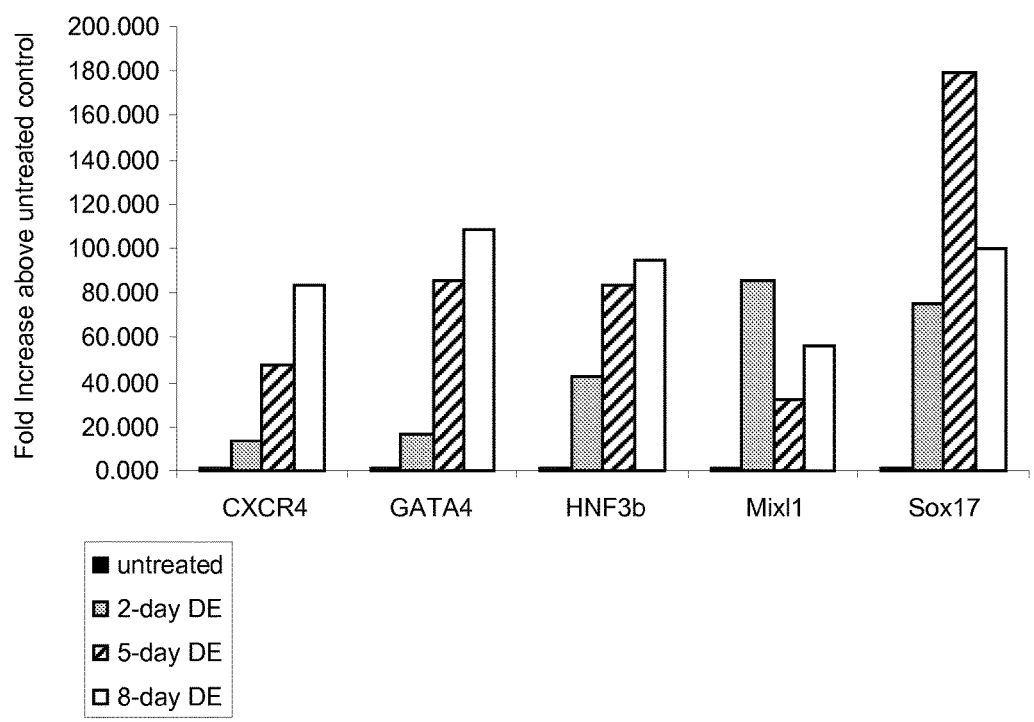
FIG. 1 panel a shows the expression of the definitive endoderm markers CXCR4, GATA4, HNF-3beta, Mix11, Sox-17 in the human embryonic stem cell line H9 following treatment with 100 ng/ml activin A for two, five and eight days. Expression of definitive endoderm markers was assayed at the mRNA level and normalized to expression levels in untreated human embryonic stem cells. Panel b shows the expression of the anterior endoderm markers Cerberus, Otx-1 and Hex genes in the human embryonic stem cell line H9 following treatment with with 100 ng/ml activin A for three and five days.
Figure 1:
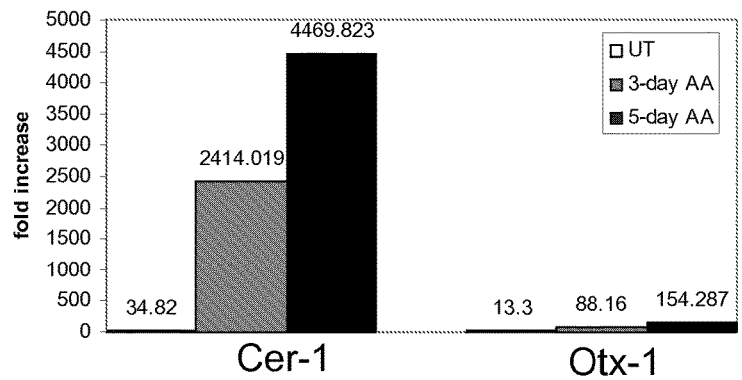
Figure 2:
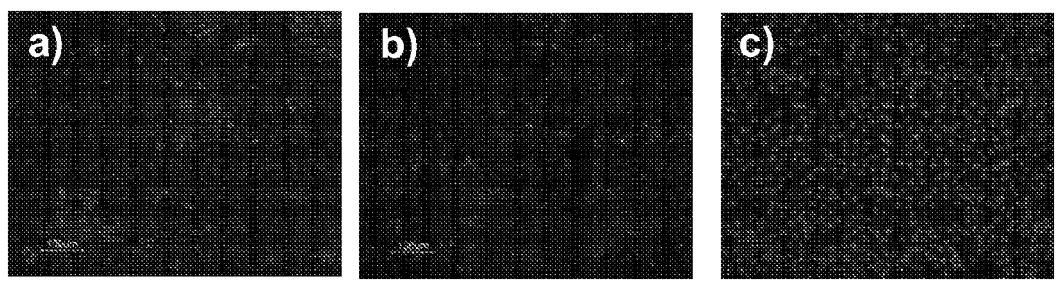
FIG. 2 shows the expression of definitive endoderm markers in the human embryonic stem cell line H9 following treatment with 100 ng/ml activin A for five days. Expression of the definitive endoderm markers was detected by immunohistochemistry. Panel (a) shows Sox-17 expression. Panel (b) shows HNF-3beta expression. Panel (c) shows Oct3/4 expression.

Activin A evoked a time-dependent increase in the expression of CXCR4, GATA4, HNF-3beta, Mix11 and Sox-17 mRNA in the H9 line (FIG. 1, panel a). A significant up regulation of anterior endoderm markers, Cerberus, Otx-1 and Hex genes was also observed (FIG. 1, panel b). An increase in CXCR4 protein was observed by FACS analysis following activin A treatment. The expression of E-cadherin and N-cadherin did not change following activin A treatment (Table IIA). CXCR4 positive cells were also highly positive for C-kit, EPCAM, CD99, and negative for CD9. The expression pattern for these markers was consistent among all three hES cell lines examined (Table IIB for H7 and Table IIC for H1). Immunocytochemistry conducted on cells treated with activin A for five days revealed that 30-40% cells in the treated culture were positive for Sox17 and HNF-3beta. In parallel, almost 100% of the differentiated cells were still Oct4 positive (FIG. 2). With the decrease in expression of surface markers of pluripotency, combined with an increase in the expression of definitive endoderm markers, these data suggest that activin A promotes the differentiation of human embryonic stem cells to definitive endoderm.

Example 3

Formation of Pancreatic Endoderm Cells

Growth factors known to induce the differentiation of human embryonic stem cells to pancreatic endoderm were added to cell cultures. In particular, activin A, bFGF, and retinoic acid, known to induce the formation of pancreatic endoderm, were added to cell cultures.

Figure 3:
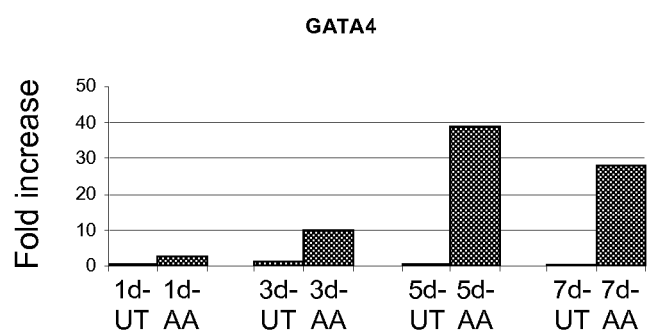
FIG. 3 shows the expression of definitive endoderm markers in the human embryonic stem cell line H9 following a step-wise differentiation protocol. Expression of the definitive endoderm markers was assayed at the mRNA level and normalized to expression levels in untreated human embryonic stem cells. Panel (a) shows GATA4 expression. Panel (b) shows Sox-17 expression. Panel (c) shows HNF-3beta expression. Panel (d) shows Mix11 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).
Figure 3:
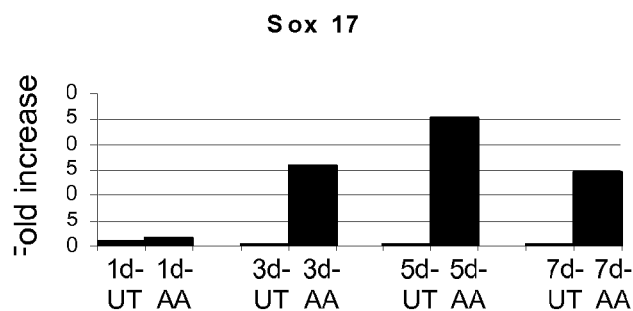
Figure 3:
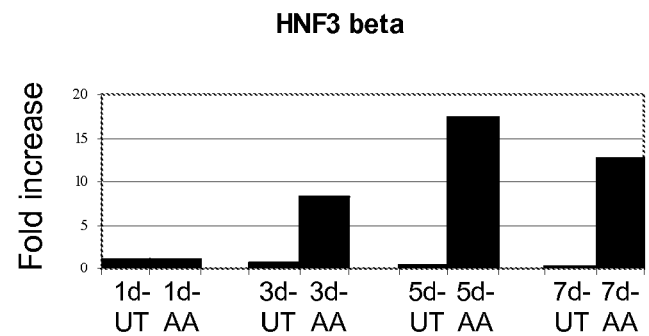
Figure 3:
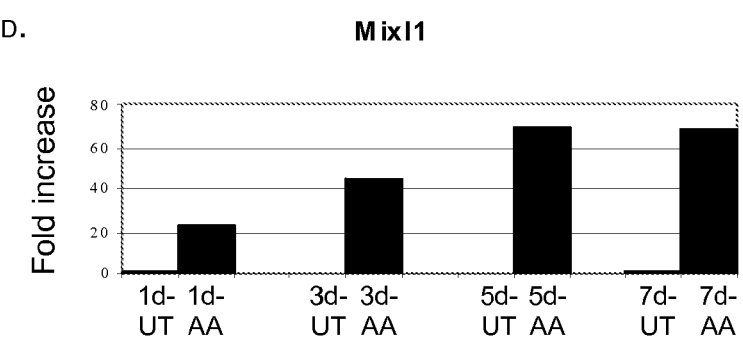
Figure 4:
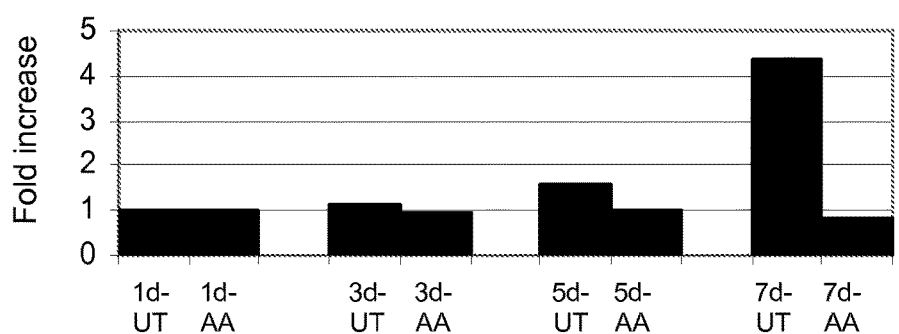
FIG. 4 shows the expression of extra-embryonic endoderm markers in the human embryonic stem cell line H9 following a step-wise differentiation protocol. Expression of the extraembryonic endoderm markers was assayed at the mRNA level and normalized to expression levels in untreated human embryonic stem cells. Panel (a) shows the effect of 100 ng/ml activin A on AFP expression. Panel (b) shows the effect of 100 ng/ml activin A on Sox7 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).
Figure 4:
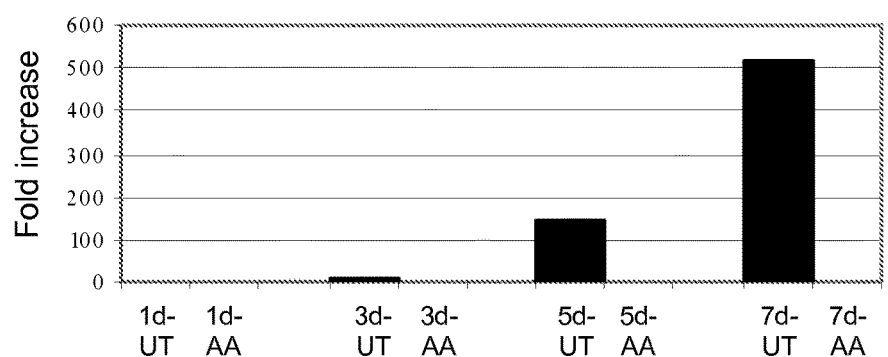
Figure 5:
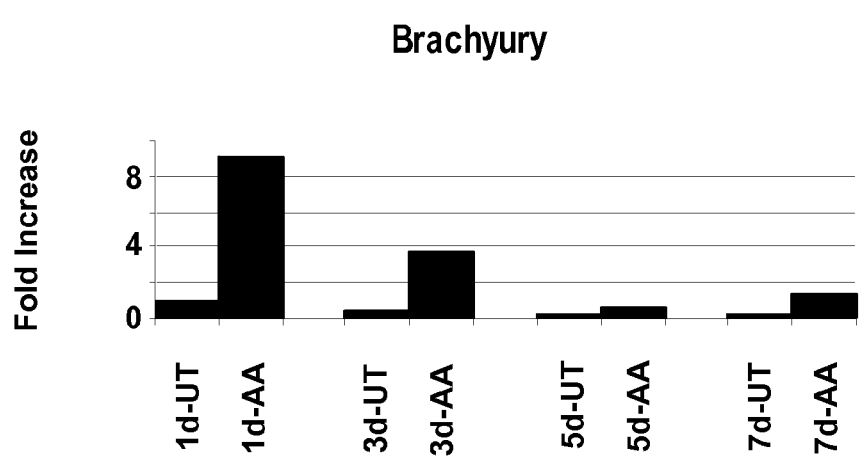
FIG. 5 shows the expression of mesoderm and ectoderm markers in the human embryonic stem cell line H9 following a step-wise differentiation protocol. Expression of the mesoderm and ectoderm markers was assayed at the mRNA level and normalized to expression levels in untreated human embryonic stem cells. Panel (a) shows the effect of 100 ng/ml activin A on Brachyury expression. Panel (b) shows the effect of 100 ng/ml activin A on Zic1 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).
Figure 5:
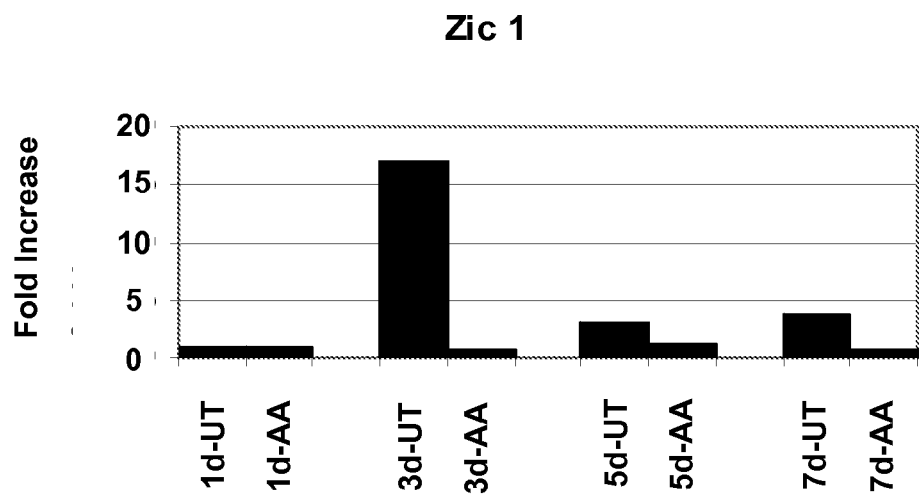
Figure 6:
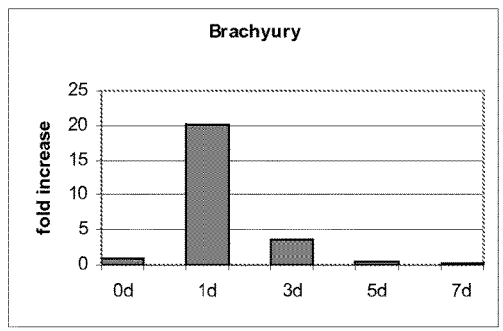
FIG. 6 shows the expression of the definitive endoderm markers Brachyury (panel a) CXCR4 (panel b), Mix11 (panel c), Sox17 (panel d), HNF-3beta (panel e), Oct4 (panel f) in the human embryonic stem cell line H7 following treatment with 100 ng/ml activin A for one, three, five and seven days. Expression of definitive endoderm markers was assayed at the mRNA level and normalized to expression levels in untreated human embryonic stem cells.
Figure 6:
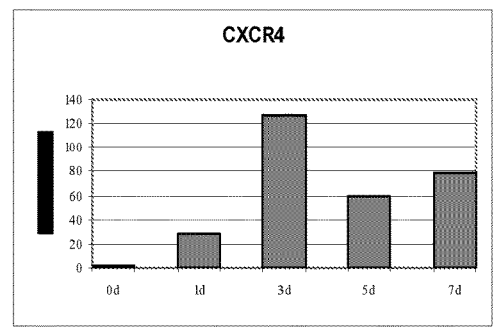
Figure 6:
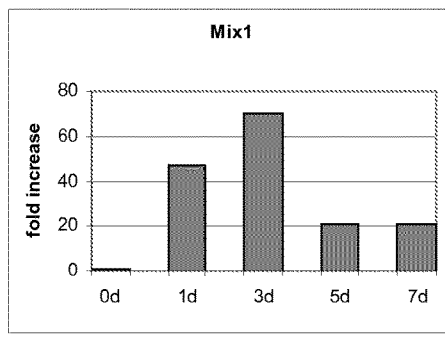
Figure 6:
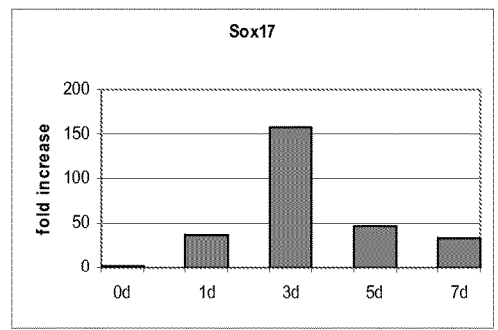
Figure 6:
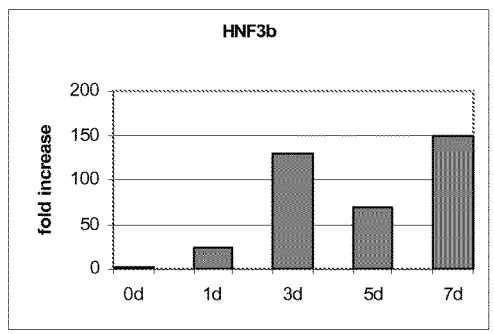
Figure 6:
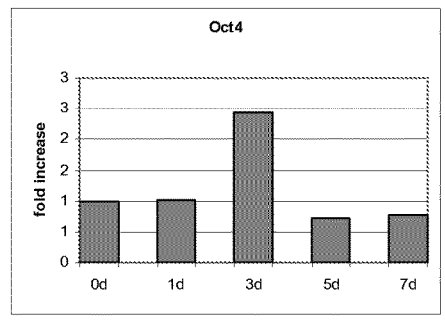

In a first series of experiments, activin A, was added to populations of human embryonic stem cells cultured on mouse embryonic fibroblasts for up to seven days in DMEM/F12 supplemented with 0% to 2% serum and Activin A (100 ng/ml). Cells were harvested at the time points indicated in FIG. 3 and assayed by PCR for the expression of genes shown (FIGS. 3, 4 and 5). In FIG. 3, PCR analysis indicated that activin treated cells expressed a broad spectrum of genes associated with endoderm development, including GATA4 (FIG. 3, panel a), Sox-17 (FIG. 3, panel b), HNF-3beta (FIG. 3, panel c), and Mix1-1 (FIG. 3, panel d). However, no Pdx1 gene expression was observed. The same expression pattern of endoderm lineage markers was observed in Activin A treated H7 cells (FIG. 6, panels a to f). At this stage, there was no significant decrease of Oct4 expression.

Activin A evoked a time-dependent decrease in the expression of the extraembryonic endoderm markers Sox7 (FIG. 4, panel a) and AFP (FIG. 4, panel b). Activin A decreased the expression of Brachyury (FIG. 5, panel a) but had no effect on expression of the neuronal marker Zic1 (FIG. 5, panel b).

Figure 7:
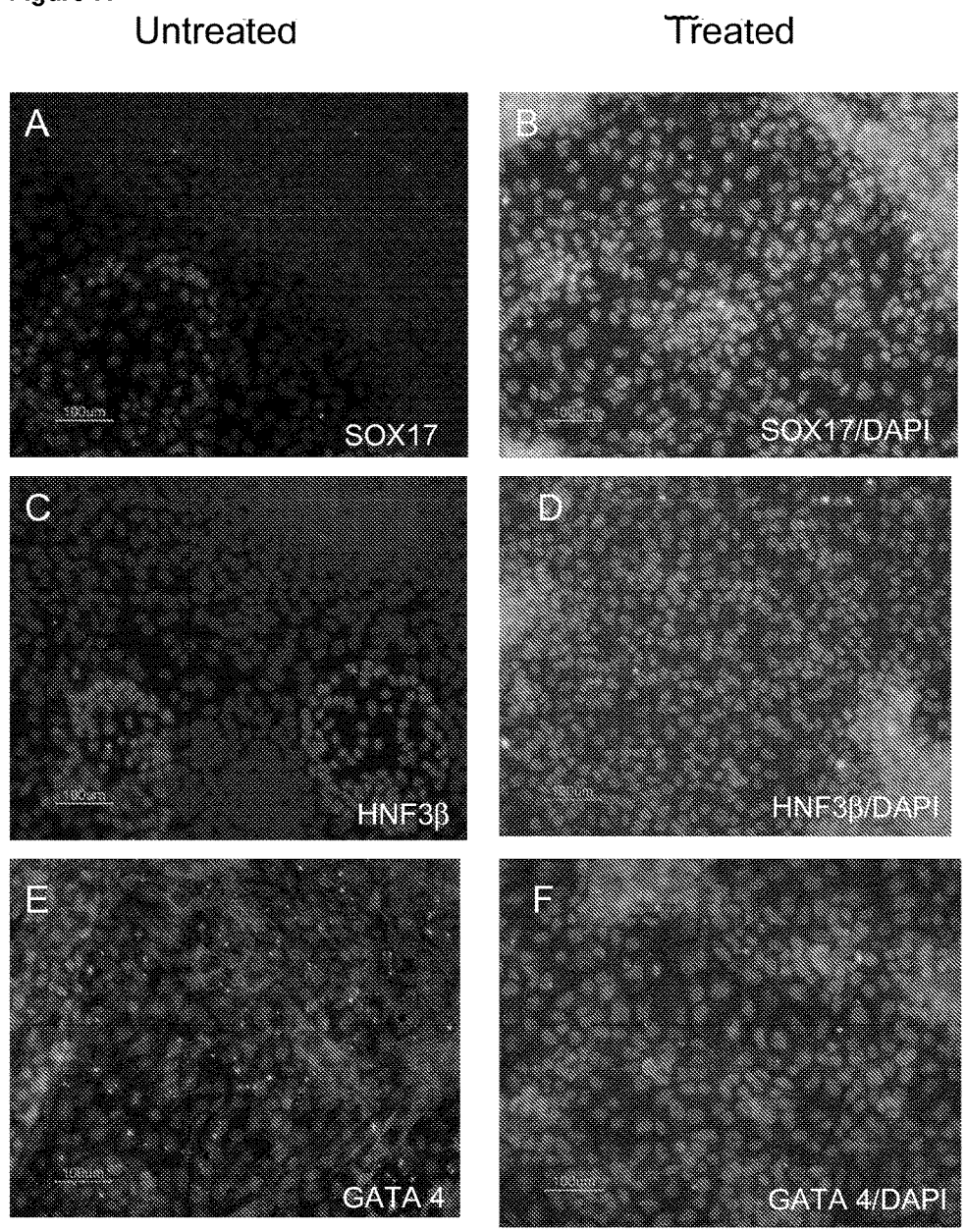
FIG. 7 shows the expression of definitive endoderm markers in the human embryonic stem cell line H9 following application of a differentiation protocol. Expression of the definitive endoderm markers was detected by immunohistochemistry. Panels (a) and (b) show Sox-17 expression. Panels (c) and (d) show HNF-3beta expression. Panels (e) and (f) show GATA4 expression. Panels (b), (d) and (f) show counter staining of the nuclei with DAPI. The columns marked 'treated' denote activin A treatment (100 ng/ml) for five days. The columns marked 'untreated' denote untreated controls.

Taken together, these data suggest that the increased expression of Sox-17, Mix11, Gata4, and HNF-3beta together with the up regulation of anterior endoderm markers Otx1, Cer1 and Hex genes, corresponds to the formation of definitive endoderm in response to activin A treatment. Analysis of definitive endoderm markers by immunocytochemistry revealed that protein expression for these genes also reflected the trends observed in mRNA expression. Levels of expression for HNF-3beta, Sox-17, and GATA4 were low in untreated cells, approximately 10 to 20% of all cells. Activin A (100 ng/ml) treatment for five days increased the expression of HNF-3beta, Sox-17, and GATA4 to approximately 50% to 90% of all cells (FIG. 7).

Figure 8:
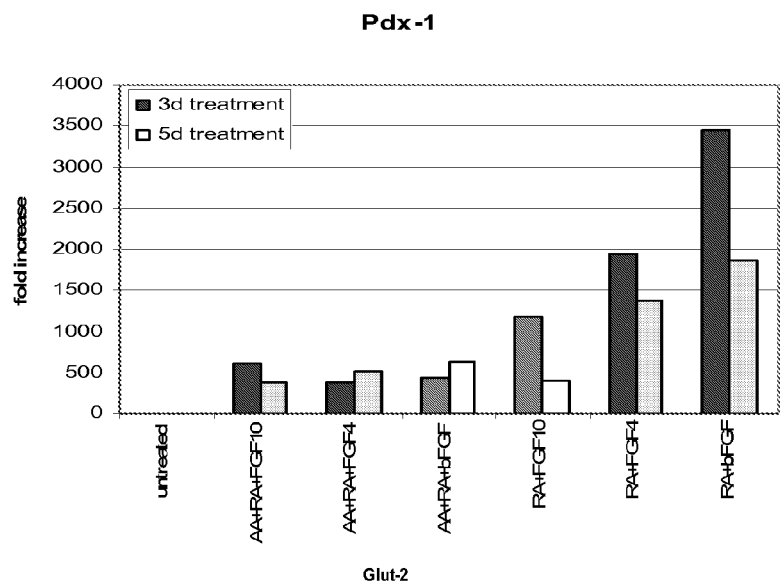
FIG. 8 shows the expression of pancreatic endoderm markers in the human embryonic stem cell line H9 following application of a second differentiation protocol. Expression of the pancreatic endoderm markers was assayed by PCR and normalized to expression levels in activin A treated human embryonic stem cells. Panel (a) shows Pdx1 expression. Panel (b) shows GLUT-2 expression. Panel (c) shows PTF1a expression.
Figure 8:
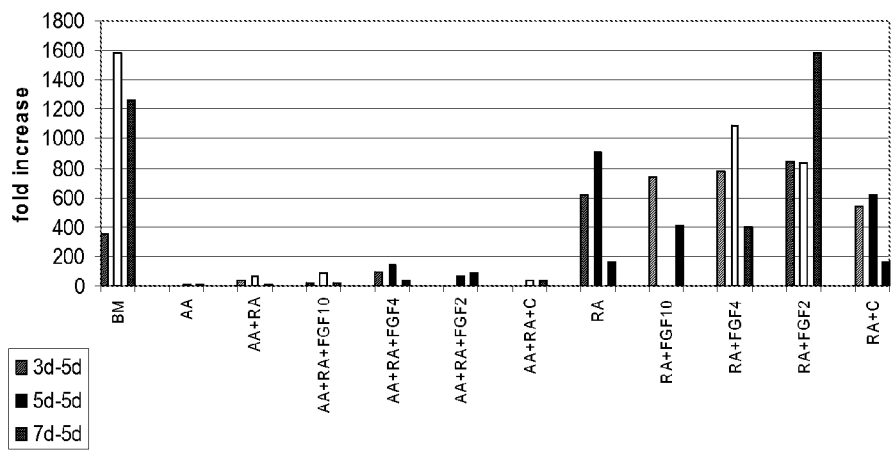
Figure 8:
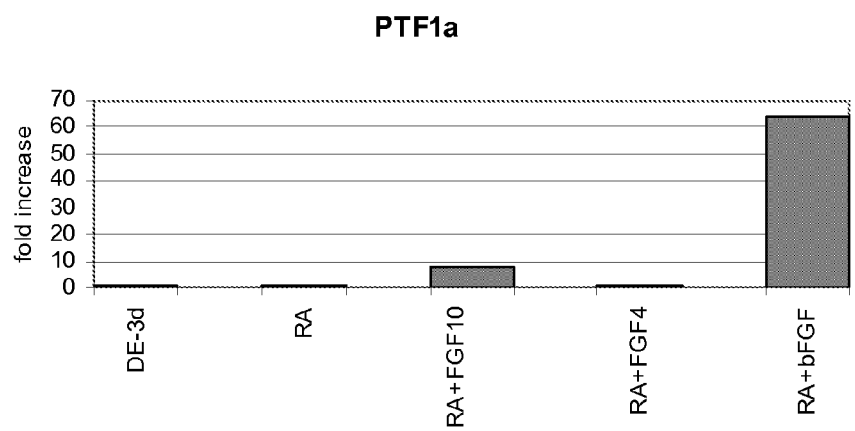

In a second series of experiments, cultures of human embryonic stem cells were maintained in undifferentiated culture conditions for 2-3 days according to the methods described in Example 1. After the cells were 70-80% confluent, the medium was changed to DMEM/F12 with 0 to 2% FBS with addition of activin A at 100 ng/ml and cultured in the presence of activin A for either three, five, or seven days. After this time interval, the cells were then further treated for five to six days with combinations of retinoic acid and bFGF as shown in FIG. 8. Cultures were harvested and samples of mRNA were collected for analysis. Control cultures consisting of cells treated with activin A alone for five days were also included.

Figure 9:
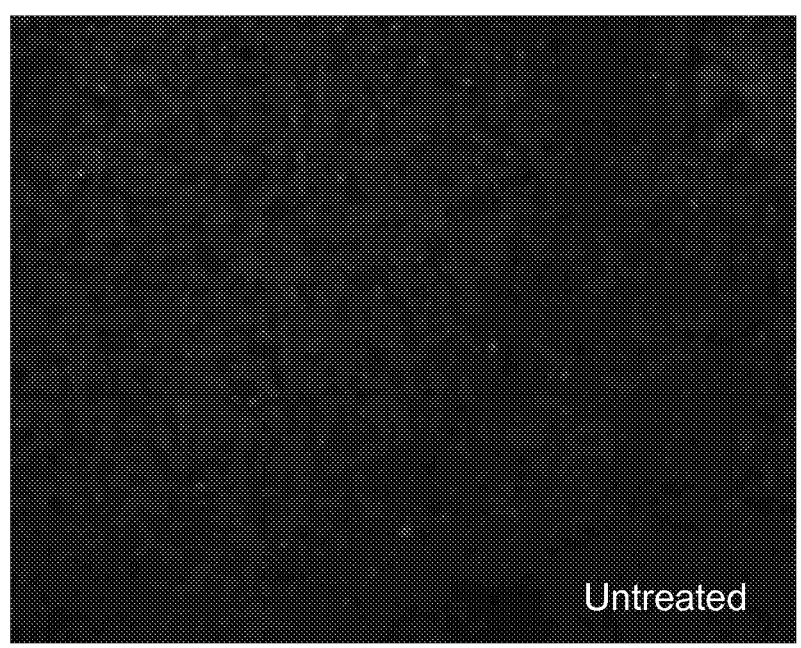
FIG. 9 shows the expression of pancreatic endoderm markers in the human embryonic stem cell line H9 following application of a second differentiation protocol. Expression of the pancreatic endoderm markers was detected by immunohistochemistry. Panel (a) shows Pdx1 expression in the untreated control, and panel (b) shows Pdx1 expression in the culture treated by the stepwise differentiation protocol.

Gene expression analysis revealed that activin A or retinoic acid alone did not induce the expression of Pdx1. Similar results were observed in cultures of cells treated with retinoic acid in combination with FGF and in the presence of activin A (FIG. 8, panel a). However, treatment of cells with retinoic acid and FGF in the absence of activin A increased the expression of Pdx1 still further (FIG. 8, panel a). Cells treated for three days with activin A, then treated for 5 days with 1 µM retinoic acid and 50 ng/ml bFGF (also known as FGF-2) in the absence of activin A showed a level of Pdx1 expression that was approximately 3500-fold higher than that observed in samples with activin A treatment alone for 5 days (FIG. 8, panel a). Immunocytochemistry showed that 5 to 20% of all cells expressed Pdx1 (FIG. 9).

Treatment with 1 µM retinoic acid and bFGF in the absence of activin A also caused an increase in the expression of GLUT-2 and PTF1a (FIG. 8, panel c) that was not observed in cells treated in the presence of activin A alone. The largest increase in expression of GLUT-2 and PTF1a was observed in cells treated with 1 µM retinoic acid and 50 ng/ml bFGF. Taken together, these data suggest that the formation of pancreatic endoderm is further enhanced by removal of activin A from cell cultures after definitive endoderm has been formed.

Example 4

Formation of Pancreatic Endocrine Cells

Cultures of human embryonic stem cells were maintained in undifferentiated culture conditions for 3-4 days according to the methods described in Example 1. After the cells were 50-60% confluent, the medium was changed to DMEM/F12 without FBS, containing activin A at 100 ng/ml, and the cells were cultured in this medium for one day. Following the one day culture, the medium was removed and replaced with medium containing 0.5% FBS with 100 ng/ml activin A, and the cells were cultured for one day. Following the second one-day culture, the medium was removed and replaced with medium containing 2% FBS with 100 ng/ml activin A, and the cells were cultured for one day. After this time interval, the cells were then treated for six days with combinations of retinoic acid and FGF as outlined in Example 2, then the culture medium was removed and replaced with medium comprising DMEM/F12 with 2% FBS, containing the γ-secretase inhibitors L-685,458 at 10 µM for three days. Cultures were harvested and samples of mRNA were collected for analysis. Control cultures consisting of cells treated with activin A alone for five days were also included.

Figure 10:
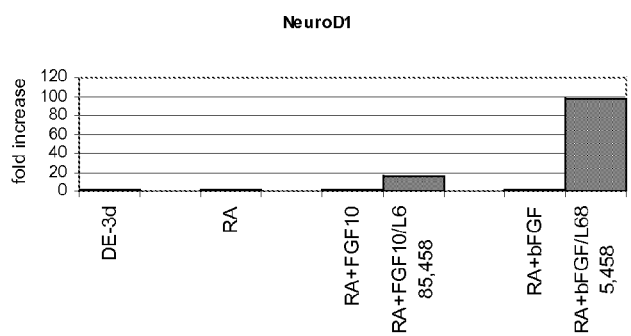
FIG. 10 shows the expression of pancreatic endocrine markers in the human embryonic stem cell line H9 following application of a third differentiation protocol. Expression of the pancreatic endocrine markers was assayed by PCR and normalized to expression levels in activin A treated human embryonic stem cells. Panel (a) shows NeuroD1 expression. Panel (b) shows Ngn3 expression. Panel (c) shows insulin expression. Panel (d) shows Hes-1 expression, the expression level is normalized to pancreatic endoderm cells.
Figure 10:
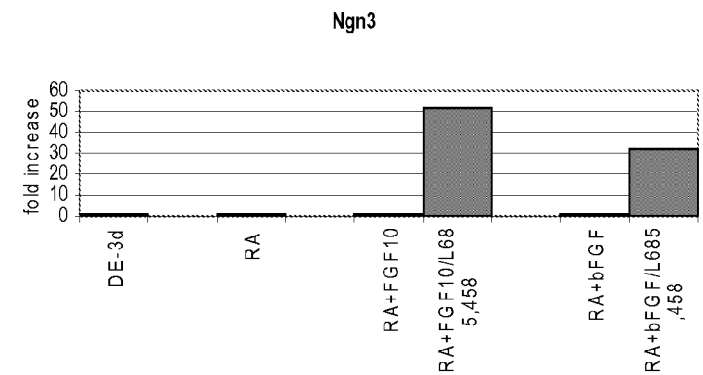
Figure 10:
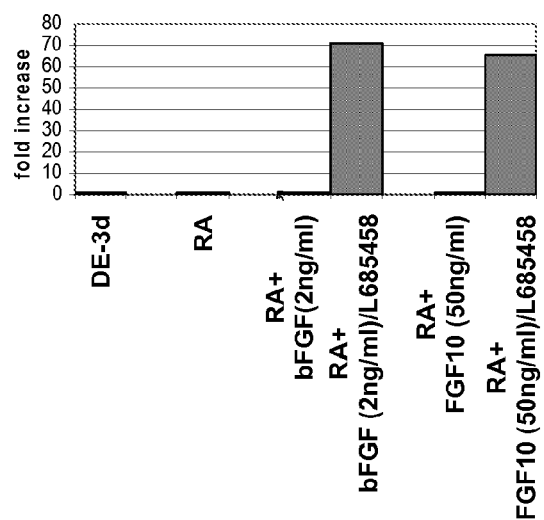
Figure 10:
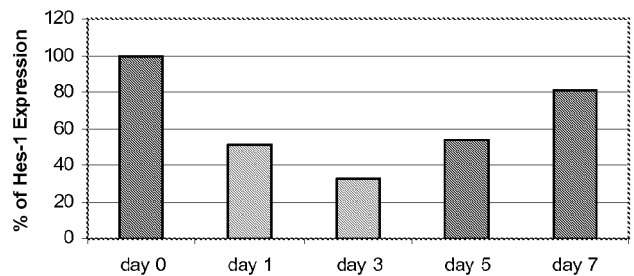

Gene expression analysis revealed that activin A alone or in combination with retinoic acid and FGFs did not induce the expression of Ngn3 or insulin (FIG. 10, panel a, c). A decrease in the expression of Hes-1 was also observed following treatment with L-685,458. The maximal inhibition was observed on day three post treatment (FIG. 10, panel d). However, treatment of cells with L-685,458 induced the expression of Ngn3 to a level approximately 50-fold higher than that observed in samples treated with activin A alone or retinoic acid with FGFs in combination. A 70-fold increase of insulin expression was observed in samples treated with the γ-secretase inhibitor. NeuroD1 expression was also increased further by the L-685,458 treatment (FIG. 10, panel a). Taken together, these data suggest that the formation of endocrine cells is further enhanced by removal of retinoic acid and FGFs from cell culture and the addition of γ-secretase inhibitors after pancreatic endoderm has been formed.

Example 5

Formation of Pancreatic Endocrine Cells Expressing Nkx2.2

Figure 11:
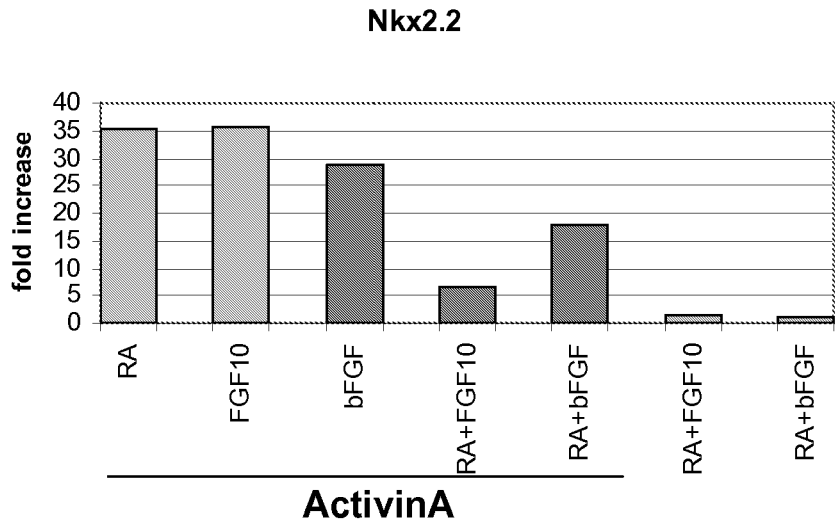
FIG. 11 shows the expression of pancreatic endoderm markers in the human embryonic stem cell line H9 following application of a differentiation protocol. Expression of the pancreatic endoderm markers was assayed by PCR and normalized to expression levels in activin A treated human embryonic stem cells. Panel (a) shows Nkx2.2 expression. Panel (b) shows Pdx1 expression.
Figure 11:
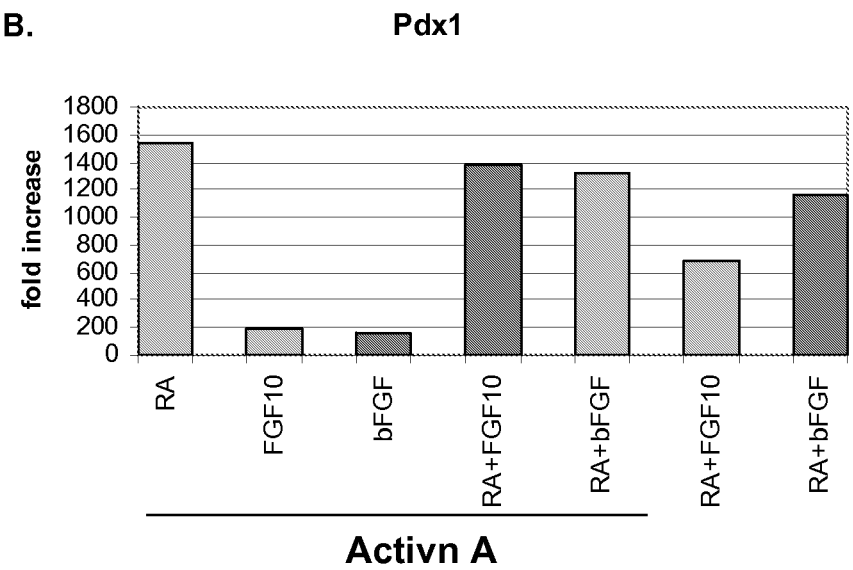

Definitive endoderm cells obtained according to the methods outlined in Example 2 were treated as follows: Cells were cultured in basal medium, comprising DMEM/F12 with 2% FBS plus 50 ng/ml activin A, 50 ng/ml basic FGF and 1 µM of Retinoic Acid for 3 to 5 days. Cells were continuously cultured for another 3 to 5 days in basal medium with retinoic acid at 1 µM, alone or with bFGF. RNA samples were harvested from cells at various time points along this process to help evaluate the directed differentiation of the cells. Furthermore, culture medium and factors were regularly removed and replenished throughout the differentiation protocol. Addition of activin A showed an increase of Nkx2.2 expression about 35-fold compared to samples without activin A. Samples treated with activin A for the first three days of culture maintained Pdx1 expression at a level similar to samples containing no activin A (FIG. 11). Taken together, these data suggest that the expression of the pancreatic endocrine marker Nkx2.2 is further enhanced by adding Activin A to the first three days of retinoic acid and bFGF treatment.

Example 6

Passage and Expansion of Pancreatic Endoderm Cells in Culture

Figure 12:
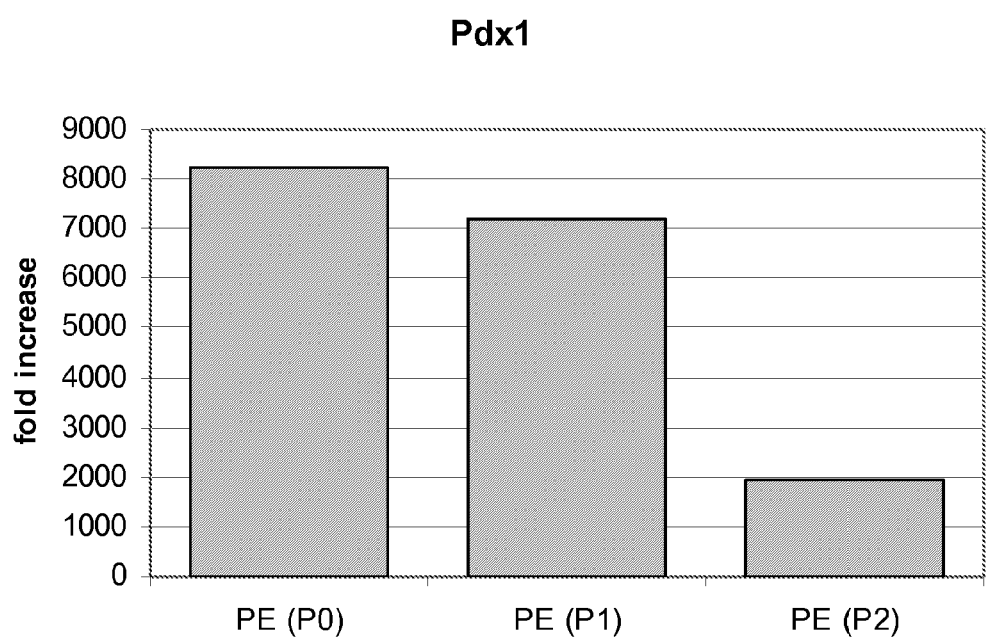
FIG. 12 shows the expression of PDX-1 in cells with each passage (P0, P1 and P2) in culture. Expression of the PDX-1 was assayed by PCR and normalized to expression levels in activin A treated human embryonic stem cells H9.

This example demonstrates that pancreatic endoderm cells derived from human embryonic stem cells herein can be maintained in cell culture and passaged without further differentiation. Pancreatic endoderm cells were differentiated in the presence of 100 ng/ml activin A in low serum DMEM/F12. The low serum DMEM/F12 contained 0% (v/v) fetal bovine serum (FBS) on day 1, 0.5% (v/v) FBS on day two and 2% (v/v) FBS on each day thereafter. After four days of differentiation, the cells were cultured in low serum DMEM/F12 contained 2% (v/v) FBS, 1 µM retinoic acid and 50 ng/ml bFGF for a total of six more days. After the six days of differentiation, the cells were maintained in culture in low serum DMEM/F12 contained 2% (v/v) FBS in the presence of 50 ng/ml FGF10 for a total of 6 days. During the six-day culture period, the pancreatic endoderm cells were passaged twice and cell population-doubling time is about 36 to 48 hours during this 6-day culture. On days 0, 3, and 6 of culture, Q-PCR was used to measure the expression of marker genes indicative of pancreatic endoderm. FIG. 12 shows that cells grown in the presence of 50 ng/ml FGF10 maintained expression of the pancreatic endoderm marker Pdx1 during the 6 day culture period subsequent to their derivation.

Example 7

Derivation of Hepatocytes from Human Embryonic Stem Cells

Cultures of human embryonic stem cells were maintained in undifferentiated culture conditions for 2-3 days according to the methods described in Example 1. After cells were 70-80% confluent, the medium was changed to DMEM/F12 with 2% FBS containing activin A at 100 ng/ml, and cells were cultured in the presence of activin A for seven days. After 7 days treatment with activin A, the cells were then treated for five days with the conditions shown in FIG. 13. After this time, the cells were harvested, and samples of mRNA were collected for analysis.

Figure 13:
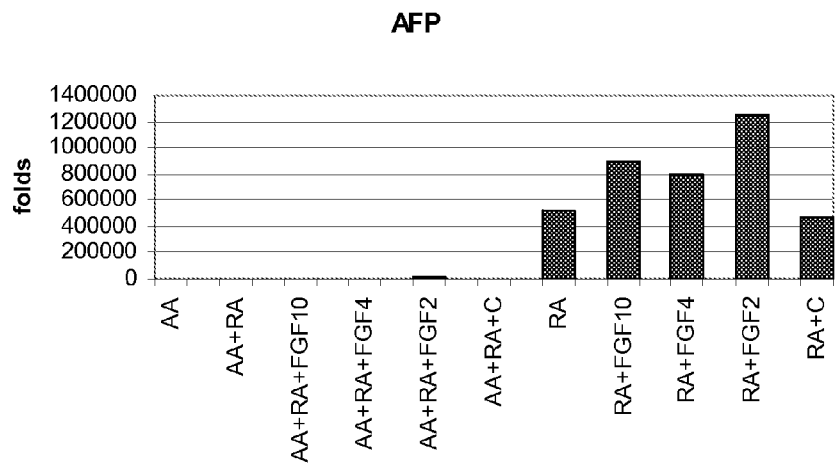
FIG. 13 shows the expression of hepatocyte markers in the human embryonic stem cell line H9 following application of a third differentiation protocol. Expression of the hepatocyte markers was assayed by PCR and normalized to expression levels in activin A treated human embryonic stem cells. Panel (a) shows AFP expression. Panel (b) shows albumin expression.
Figure 13:
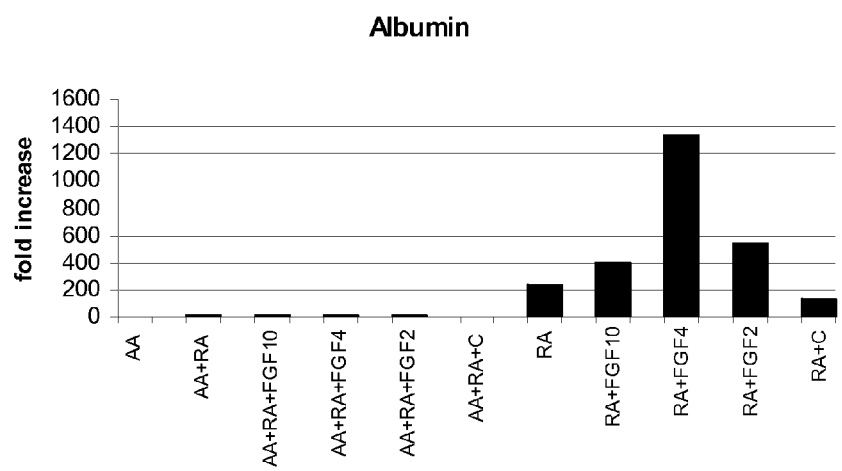

An increase in the expression of α-fetoprotein (AFP) and albumin was observed (FIG. 13, panel a) for cells cultured in the absence of activin A. This was further increased by retinoic acid and FGF-4 (FIG. 13, panel b). Taken together, these data suggest that cultures of human embryonic stem cells are capable of expressing hepatocyte markers following the treatment described above. Furthermore, human embryonic stem cells are capable of being differentiated into cells expressing markers that are characteristic of hepatocytes.

Example 8

Characterization of the H9 Human Embryonic Stem Cell Line

The quality of H9 cells was monitored over time by evaluating expression of several markers expressed by undifferentiated ES cells (Carpenter et al., 2001; Reubinoff et al., 2000; Thomson et al., 1998a). H9 cells exhibited reciprocal expression of stage-specific embryonic antigens (Table III). H9 cells play strong immunoreactivity for SSEA-3, SSEA-4, Tra-1-60, Tra-1-81, AP and CD9 antigens, all of which are characteristic of undifferentiated human embryonic stem cells.

Figure 14:
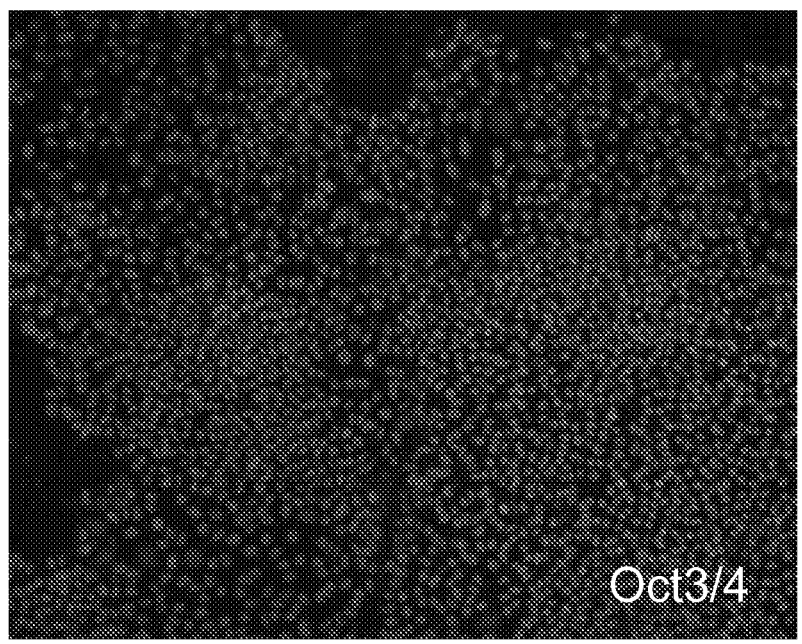
FIG. 14 shows the expression of markers of pluripotency in the human embryonic stem cell line H9. Expression of the markers of pluripotency was assayed by immunohistochemistry. Panel (a) shows Oct-4 expression. Panel (b) shows alkaline phosphatase expression.
Figure 14:
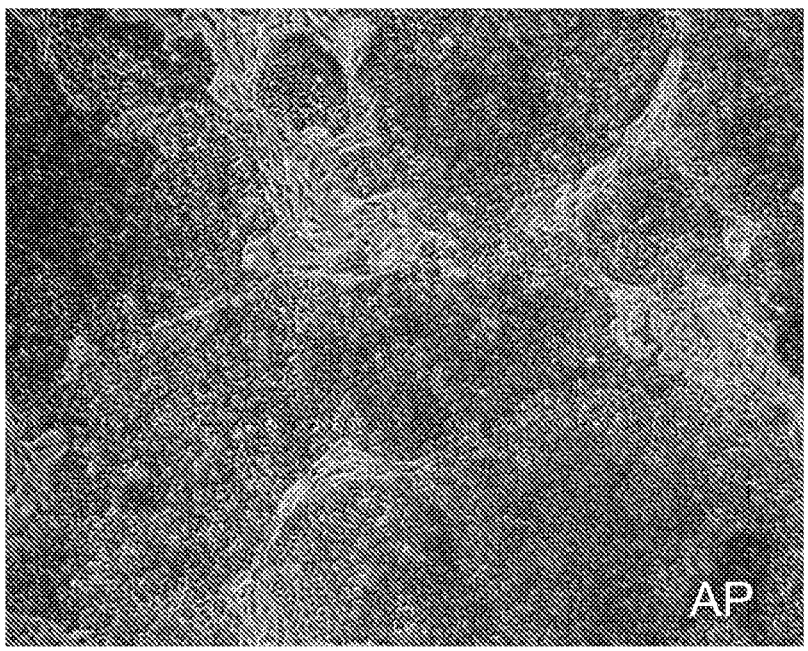

Real-Time PCR was performed to assess the expression of genes characteristic of embryonic stem cells, such as, for example, OCT3/4, SOX-2, UTF-1, REX-1, Cx43, Cx45, ABCG-2 and TERT, confirming that the cells grown in this example appeared similar to previously described undifferentiated embryonic stem cells (Table III). OCT3/4 protein expression and Alkaline Phosphatase activity (Chemicon) were confirmed by immunostaining. A majority of H9 cells were positive for OCT3/4 and AP (FIG. 14). Overall, these results demonstrate that the H9 cells used in this example were not significantly different in morphology, antigen immunostaining, or pluripotency marker expression when compared to reports from other laboratories.

Example 9

Fluorescence-Activated Cell Sorting (FACS) Analysis

Adhered cells were removed from culture plates by five-minute incubation with TrypLE™ Express solution (Invitrogen, CA). Released cells were resuspended in human embryonic stem cell culture medium and recovered by centrifugation, followed by washing and resuspending the cells in a staining buffer consisting of 2% BSA, 0.05% sodium azide in PBS (Sigma, MO). As appropriate, the cells were Fc-receptor blocked for 15 minutes using a 0.1% γ-globulin (Sigma) solution. Aliquots (approximately $10^5$ cells) were incubated with either phycoerythirin (PE) or allophycocyanin (APC) conjugated monoclonal antibodies (5 μl antibody per $10^6$ cells), as indicated in Table I, or with an unconjugated primary antibody. Controls included appropriate isotype matched antibodies, unstained cells, and cells stained only with secondary conjugated antibody. All incubations with antibodies were performed for 30 mins at 4° C. after which the cells were washed with the staining buffer. Samples that were stained with unconjugated primary antibodies were incubated for an additional 30 mins at 4° C. with secondary conjugated PE or -APC labeled antibodies. See Table I for a list of secondary antibodies used. Washed cells were pelleted and resuspended in the staining buffer, and the cell surface molecules were identified using a FACS Array (BD Biosciences) instrument, collecting at least 10,000 events.

Example 10

Immunocytochemistry

Cells seeded on 0.1% Matrigel (BD) coated dishes were fixed with 4% paraformaldheyde for 20 min at room temperature. Fixed cells were blocked for 1 h at room temperature with PBS/0.1% BSA/10% normal chick serum/0.5% Triton X-100 and then incubated overnight with primary antibodies in PBS/0.1% BSA/10% normal chick serum at 4° C. The list of primary antibodies and their working dilutions are shown in Table IB. After three washes in PBS/0.1% BSA, fluorescent secondary antibodies at a 1:100 dilution in PBS were incubated with cells for 1 h at room temperature to allow binding. Control samples included reactions where the primary antibody was omitted or where the primary antibody was replaced with corresponding matched negative control immunoglobulins at the same concentration as the primary antibodies. Stained samples were rinsed; a drop of PROLONG® (Invitrogen, CA) containing diamidino-2-phenylindole, dihydrochloride (DAPI) was added to each sample to counter-stain the nucleus and to function as an anti-fade reagent. Images were acquired using a Nikon Confocal Eclipse C-1 inverted microscope (Nikon, Japan) and a 10-60× objective.

Example 11

PCR Analysis of Undifferentiated Cells

RNA extraction, purification, and cDNA synthesis: RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. cDNA copies were made from purified RNA using an ABI (ABI, CA) high capacity cDNA archive kit.

Real-time PCR amplification and quantitative analysis: Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 μl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Biosystem. Primer and probe sets are listed as follows: Oct3/4 (Hs00742896), SOX-2 (Hs00602736), UTF-1 (Hs00747497), Rex-1 (Hs00399279), Connexin 43 (Hs00748445), Connexin 45 (Hs00271416), ABCG2 (Hs00184979), Tert (Hs00162669), HNF 3β (Hs00232764), GATA-4 (Hs00171403), Mix11 (Hs00430824), Sox7 (Hs00846731), AFP (Hs00173490), Brachyury (Hs00610080), GSC (Hs00418279 ml), Pdx-1 (Hs00426216), PTF1a (Hs00603586), Ngn3 (Hs00360700), NeuroD1 (Hs00159598), Insulin (Hs00355773) and Glu2 (Hs00165775). Sox17 primers were designed using the PRIMERS program (ABI, CA) and were the following sequences: Sox17: TGGCGCAGCAGATACCA (SEQ ID NO:1), AGCGCCTTCCACGACTTG (SEQ ID NO:2) and CCAGCATCTTGCTCAACTCGGCG (SEQ ID NO:3). After an initial incubation at 50° C. for 2 min followed by 95° C. for 10 min, samples were cycled 40 times in two stages—a denaturation step at 95° C. for 15 sec followed by an annealing/extension step at 60° C. for 1 min. Data analysis was carried out using GENEAMP®7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value ($\Delta Ct$). The normalized amount of target was calculated as $2-\Delta Ct$, assuming amplification to be 100% efficiency. Final data were expressed relative to a calibrator sample.

Example 12

Karyotype Analysis

Figure 15:
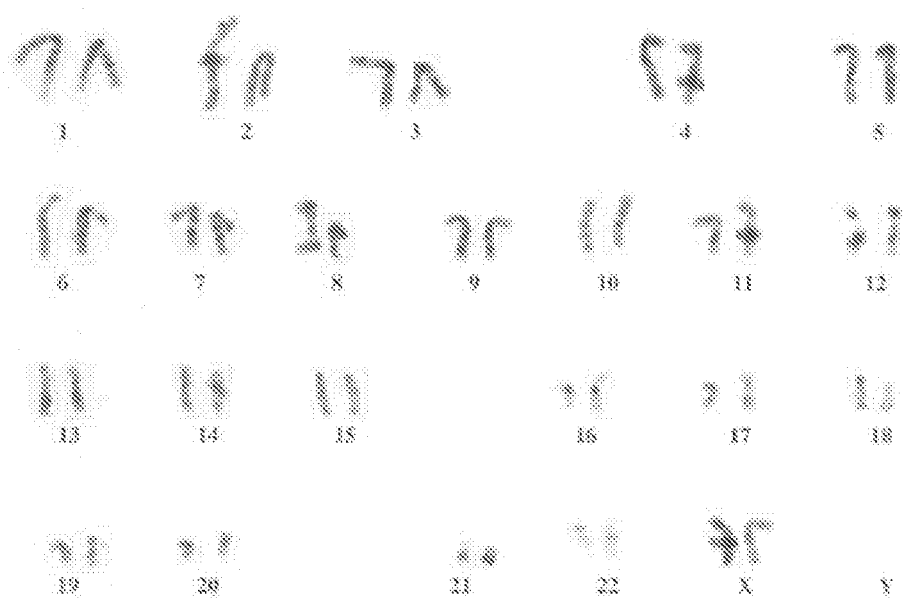
FIG. 15 shows the karyotype of the human embryonic cell line H9. The Karyotype was determined on cells at passage number P36 that were cultured on mouse embryonic fibroblast feeder cells.

The karyotype of H9 cells was determined by standard G-banding karyotype analysis. A total of 100 metaphase spreads were evaluated (Applied Genetics Laboratories, Inc.). No chromosome aberrations were found in 100 cells analyzed. Cytogenetic analysis showed that the cells had a normal number of autosomes and a modal chromosome number of 46. FIG. 15 depicts a typical karyotype obtained from the human embryonic stem cell line H9.

Example 13

Human Embryonic Stem Cell Culture on Tissue Culture Substrate Coated with Extracellular Matrix The human embryonic stem cell lines H1, H7, and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM betamercaptoethanol, 2 mM L-glutamine with 4 ng/ml human basic fibroblast growth factor (bFGF). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 μg/ml mitomycin C (Sigma, St. Louis, Mo.) for 3 h to arrest cell division, then trypsinized and plated at 2×10⁴/cm² on 0.1% bovine gelatin coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5 to 7 days after plating), human embryonic stem cells were treated with 1 mg/ml collagenase type IV (Invitrogen/GIBCO) for 5 to 10 min and then gently scraped off the surface using a 5 ml glass pipette. Cells were centrifuged at 900 rpm for 5 min, and the pellet was resuspended and re-plated at a 1:3 to 1:4 ratio of cells on plates coated with a 1:30 dilution of growth factor reduced MATRIGEL™ (BD Biosciences). Cells were subsequently cultured in MEF-conditioned media supplemented with 8 ng/ml bFGF and collagenase passaged on MATRIGEL coated plates for at least five passages. The cells cultured on MATRIGEL™ were routinely passaged with collagenase IV (Invitrogen/GIBCO), Dispase (BD Biosciences) or Liberase enzyme (Roche, Ind.).

Example 14

Differentiation of Human Embryonic Stem Cells Cultured on Tissue Culture Substrate Coated with Extracellular Matrix to Definitive Endoderm Differentiation of embryonic stem cells to definitive endoderm was carried out as previously described in Nature Biotechnology 23, 1534-1541 (December 2005). Briefly, H9 cultures at approximately 60 to 70% confluency were exposed to DMEM:/F12 medium supplemented with 0.5% FBS and 100 ng/ml activin A for two days, followed by treatment with DMEM/F12 medium supplemented with 2% FBS and 100 ng/ml activin A (AA) for an additional three days. H9 cells were cultured on plates coated with growth factor reduced MATRIGEL at a 1:30 to 1:10 dilution or on regular MATRIGEL at a 1:30 to 1:10 dilution The plates were coated with MATRIGEL for 1 hr at room temperature.

Figure 17:
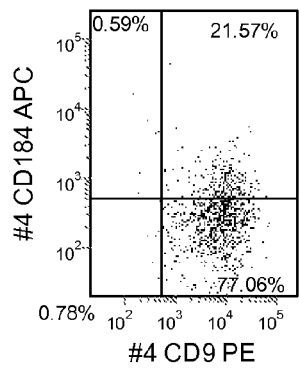
FIG. 17 depicts the FACS profile of human embryonic stem cell line H9 at passage number 44, cultured on varying concentrations of MATRIGEL and exposed to (0.5-2%) low serum and high activin A (100 ng/ml) for 5 days. The expression of definite endoderm marker CXCR4 (CD184) is shown on the Y-axis and the expression of ES marker CD9 is shown on the X-axis.
Figure 17:
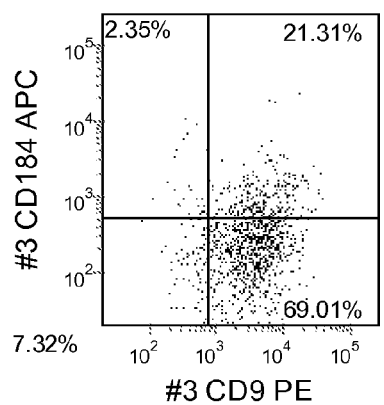
Figure 17:
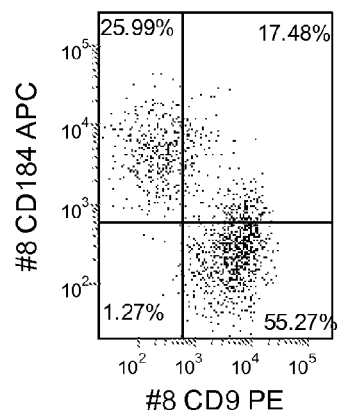
Figure 17:
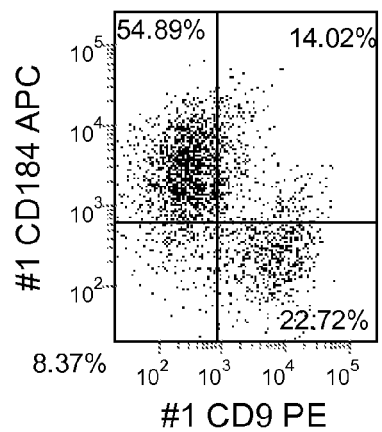
Figure 17:
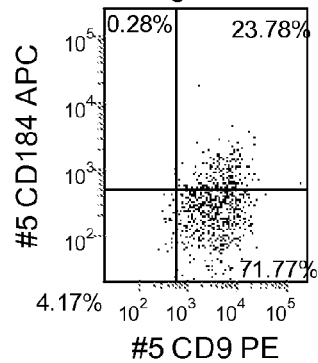
Figure 17:
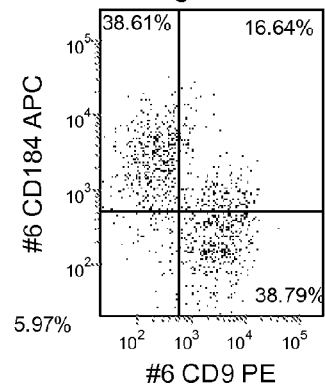

At day 5, the cultures were analyzed by FACS for CXCR4, E-cadherin, CD9, and N-cadherin expression and by real time PCR for SOX-17, SOX-7, Alphafetal protein (AFP), CXCR4, Brychyury (Bry), gooscecoid (GSC), HNF-3 beta, and GATA4. AFP and SOX-7 are regarded as visceral endoderm markers, while GATA4, HNF-3 beta and SOX-17 represent definite endoderm markers, and GSC, Bry, and CXCR4 represent markers of primitive streak. FIG. 17 depicts the expression of CXCR4 by FACS. There was a significant increase in expression of CXCR4 by cells cultured on plates coated with MATRIGEL at a 1:10 dilution as compared to lower concentrations of MATRIGEL. Furthermore, growth factor reduced MATRIGEL was not as effective in formation of definitive endoderm cells as compared to regular MATRIGEL.

Figure 18:
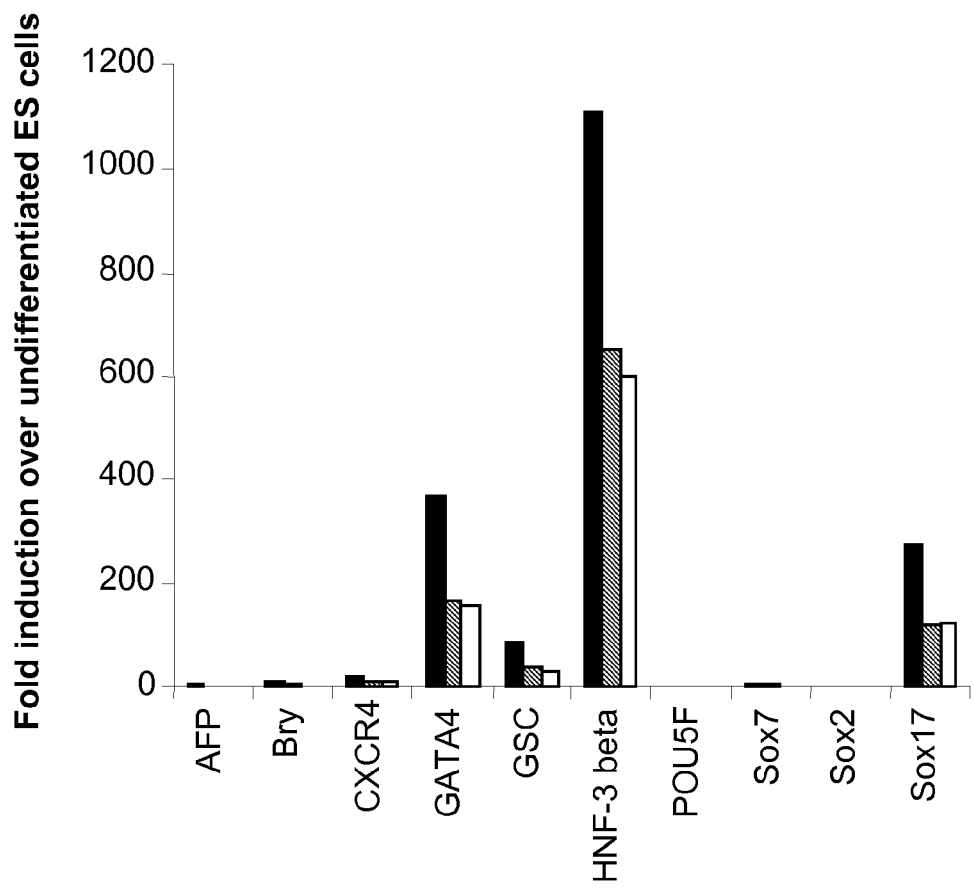
FIG. 18 shows the real-time PCR results for markers of definitive endoderm, from cultures of the human embryonic stem cell line H9 at passage 44 cultured on a 1:10 dilution of MATRIGEL (■), a 1:20 dilution of MATRIGEL (▨), or a 1:30 dilution of MATRIGEL (□) and exposed to the differentiation protocol disclosed in Example 14. The fold induction is relative to undifferentiated cells of the human embryonic stem cell line H9, at passage number 44, cultured in medium conditioned using mouse embryonic fibroblasts.

FIG. 18 shows the real-time PCR results verifying that cells cultured on plates coated with a 1:10 dilution of MATRIGEL showed a significant up regulation of definitive endoderm markers as compared to cells cultured on a 1:30 dilution of MATRIGEL.

Example 15

Microarray Analysis of Changes in Gene Expression in Human Embryonic Stem Cells Following Formation of Definitive Endoderm Total RNA was isolated from the following human embryonic stem cell cultures using an RNeasy mini kit (Qiagen): H9P83 cells cultured on MATRIGEL—coated plates and exposed to DMEM/F12 medium supplemented with 0.5% FBS and 100 ng/ml activin A for two days followed by treatment with DMEM/F12 medium supplemented with 2% FBS and 100 ng/ml Activin A (AA) for an additional three days; H9P44 cells cultured on MEFs and exposed to DMEM/F12 medium supplemented with 0.5% FBS and 100 ng/ml activin A for two days followed by treatment with DMEM/F12 medium supplemented with 2% FBS and 100 ng/ml activin A for an additional three days. Controls for each group included cells plated on MATRIGEL-coated dishes and cultured in MEF-conditioned medium or cells plated on MEFs and cultured in ES medium.

Figure 19:
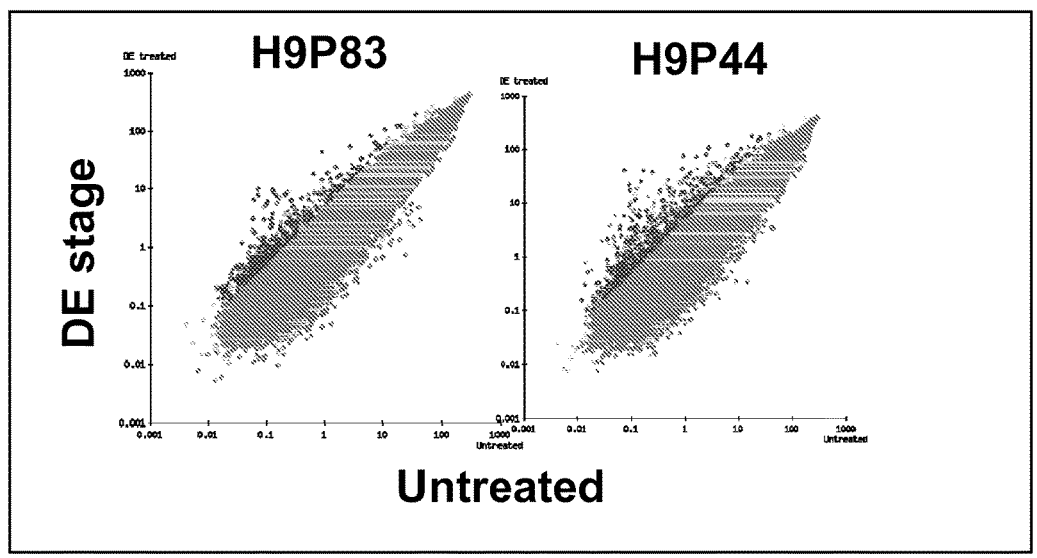
FIG. 19 shows the scatter plots for global gene expression in undifferentiated pluripotent stem cells and definitive endoderm cells obtained from differentiating pluripotent stem cells. Data shown is from cultures of the human embryonic stem cell line H9 cell line at passage 44 cultured on mouse embryonic fibroblasts (right panel) and passage 83 cultured on MATRIGEL (left panel).

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA). The variability within each treatment and among the different treatments was compared using the Pearson correlation coefficient. Variance in gene expression profiles between the different treatments along with the correlation coefficient between the lines are depicted in FIG. 19. Significant differences in gene expression between the samples were evaluated using analysis of variance and an F-test with adjusted P-value (Benjamini and Hochberg correction) of less-than or equal to 0.05. Only genes with a present call were included in the analysis. Table IV lists the genes that are differentially expressed with a difference at least 5-fold between the various samples. The normalized intensity value of the genes that are significantly expressed along with the standard error of the mean (SEM) for each gene are listed.

Example 16

Differentiation of Human Embryonic Stem Cells Cultured on Tissue Culture Substrate Coated with MATRIGEL to Definitive Endoderm Differentiation of embryonic stem cells to definitive endoderm was carried out as previously described in Nature Biotechnology 23, 1534-1541 (December 2005). Briefly, H9, H7, or H1 cells seeded on growth factor reduced MATRIGEL™ (1:30 dilution) cultures at approximately 60 to 70% confluency were exposed to DMEM/F12 medium supplemented with 0.5% FBS and 100 ng/ml activin A (R&D Systems, MN)) for two days followed by treatment with DMEM/F12 media supplemented with 2% FBS and 100 ng/ml activin A (AA) for an additional three days. In all subsequent examples unless otherwise noted, this treatment regimen will be referred to as the definite endoderm (DE) protocol.

In parallel, H9, H7, or H1 cells cultured on MEF feeders were also exposed to the same DE protocol outlined above.

At day 5, the cultures were analyzed by FACS for CXCR4, E-cadherin, CD9, CD99, and N-cadherin (CD56) expression and by real time PCR for SOX-17, SOX-7, Alpha-fetal protein (AFP), CXCR4, Brychyury (Bry), gooscecoid (GSC), HNF-3 beta, and GATA4. AFP and SOX-7 are regarded as visceral endoderm markers while GATA4, HNF-3beta and SOX-17 represent definite endoderm markers and GSC, Bry, and CXCR4 represent markers of primitive streak.

Figure 20:
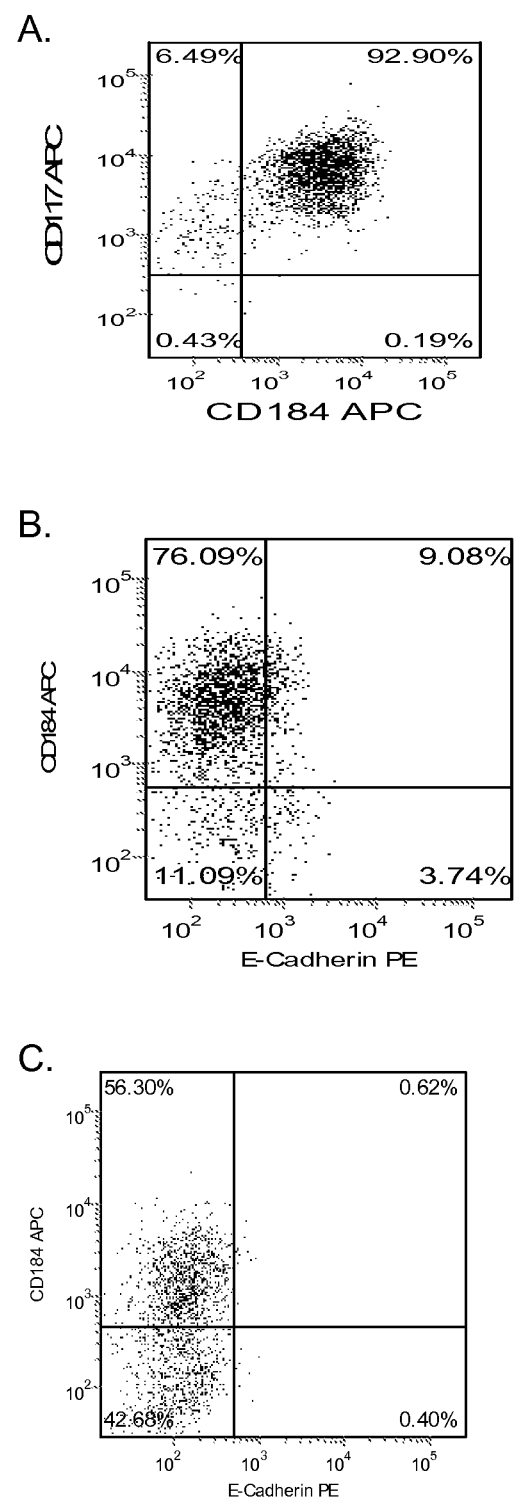
FIG. 20 depicts the expression of CXCR4 by FACS at day 5 for the human embryonic stem cell line H1 (panel a), the human embryonic stem cell line H7 (panel b), and the human embryonic stem cell line H9 (panel c) cultured on mouse embryonic fibroblast feeder cells exposed to the definitive endoderm differentiation protocol disclosed in Example 4.
Figure 21:
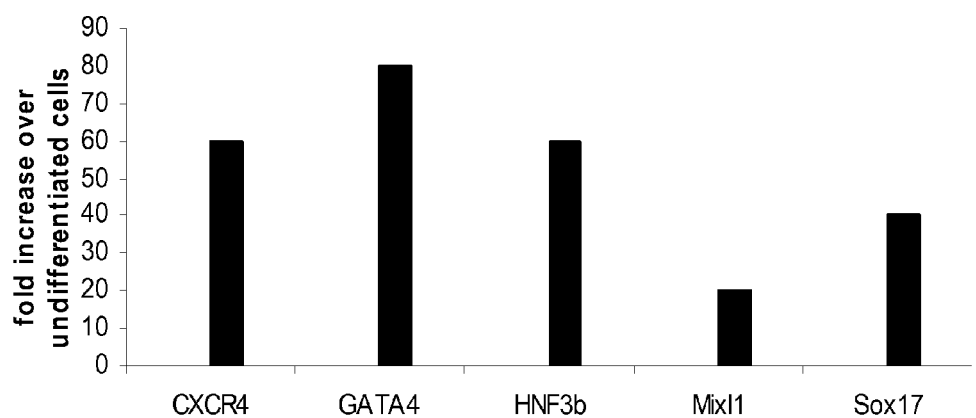
FIG. 21 shows the real-time PCR results of expression of the indicated definitive endoderm markers in cultures of the human embryonic stem cell line H7 (panel a) and the human embryonic stem cell line H9 (panel b) cultured on mouse embryonic fibroblast feeder cells. Results are expressed as fold increase over undifferentiated cells.
Figure 21:
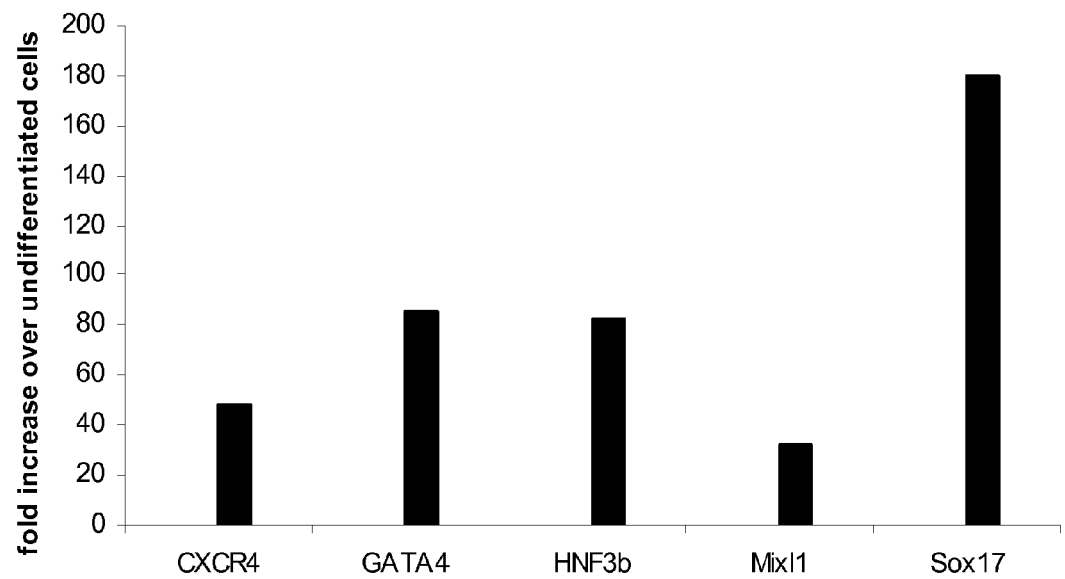

H-lines cultured on mouse feeders and exposed to the DE protocol resulted in a robust expression of DE markers and expression of CXCR4 by FACS (FIG. 20). There was also a significant decrease in expression of E-cadherin following treatment with the DE protocol. Lastly, the CXCR4$^+$ population also stained positive for CD117. FIG. 21 shows a significant up regulation of definitive endoderm markers as compared to untreated H7 (FIG. 21, panel a) and H9 cells (FIG. 21, panel b).

Figure 22:
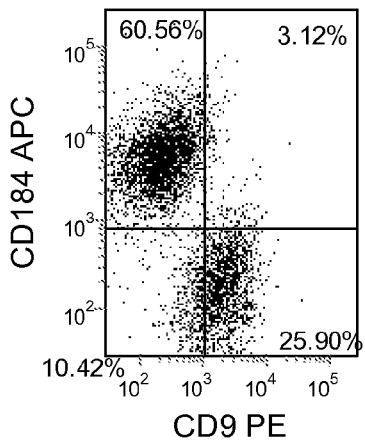
FIG. 22 depicts the expression of CXCR4 by FACS at day 5 for the human embryonic stem cell line H1 (panel a), the human embryonic stem cell line H7 (panel b), and the human embryonic stem cell line H9 (panel c) cultured on MATRIGEL (1:30 dilution) and exposed to the definitive endoderm differentiation protocol disclosed in Example 4.
Figure 22:
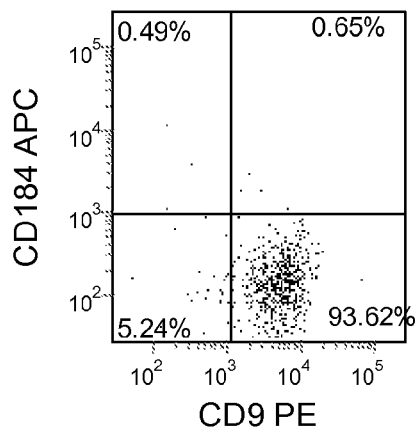
Figure 22:
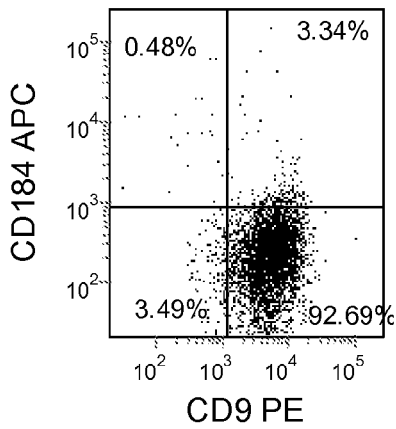
Figure 23:
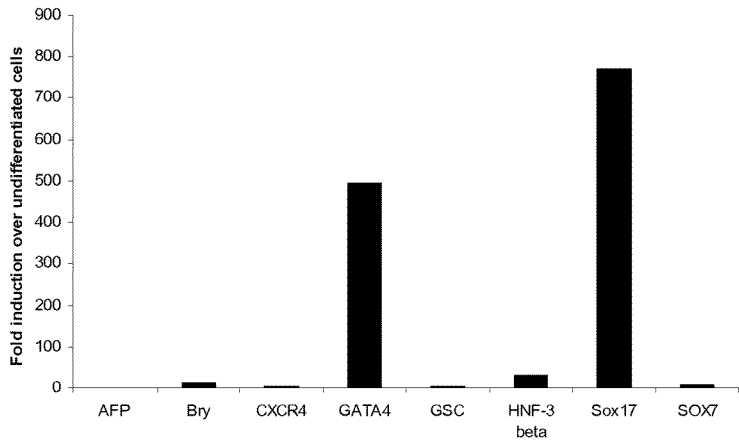
FIG. 23 shows the real-time PCR results of the expression of the indicated definitive endoderm markers in cultures of the human embryonic stem cell line H7 (panel a) and the human embryonic stem cell line H9 (panel b) and the human embryonic stem cell line H1 (panel c). Results are expressed as fold increase over undifferentiated cells. Cells were treated according to the methods disclosed in Example 4.
Figure 23:
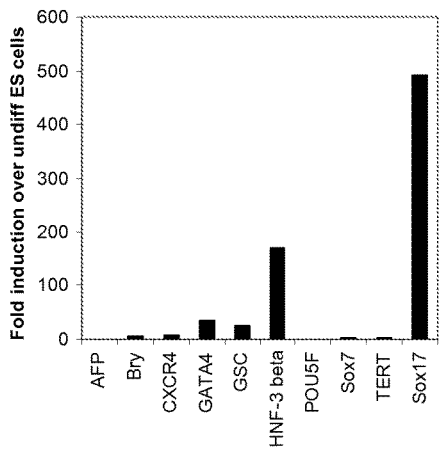
Figure 23:
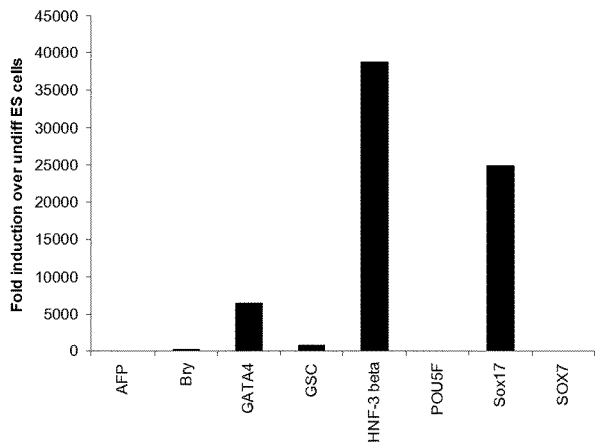

[0328] Unlike H-lines cultured on MEF feeders, H-lines cultured on MATRIGEL™ (1:30 dilution) and treated with the definitive endoderm protocol failed to show robust expression of definitive endoderm markers. In particular, the expression of CXCR4 by FACS and by real-time PCR was significantly lower for cells cultured on MATRIGEL™ as compared to cells cultured on mouse embryonic fibroblasts. Expression of definitive endoderm markers follows a general response pattern with H1 being greater than H9, which is greater than H7 (FIGS. 22 and 23). From FIG. 22, H1 cells showed a significant increase in CXCR4 expression as compared to H7 and H9 lines. Note that in all cases, the expression of CXCR4 was lower for cells cultured on MATRIGEL™ (1:30 dilution) as compared to cells cultured on mouse embryonic fibroblasts. FIG. 23 (panels a-c) shows the real-time PCR results showing that there was modest increase in up regulation of definitive endoderm markers in H7 (FIG. 23, panel a) and H9 (FIG. 23, panel b) lines. However, H1 (FIG. 23, panel c) line showed a more robust up regulation of definitive endoderm markers as compared to H7 and H9 lines.

Example 17

Figure 24:
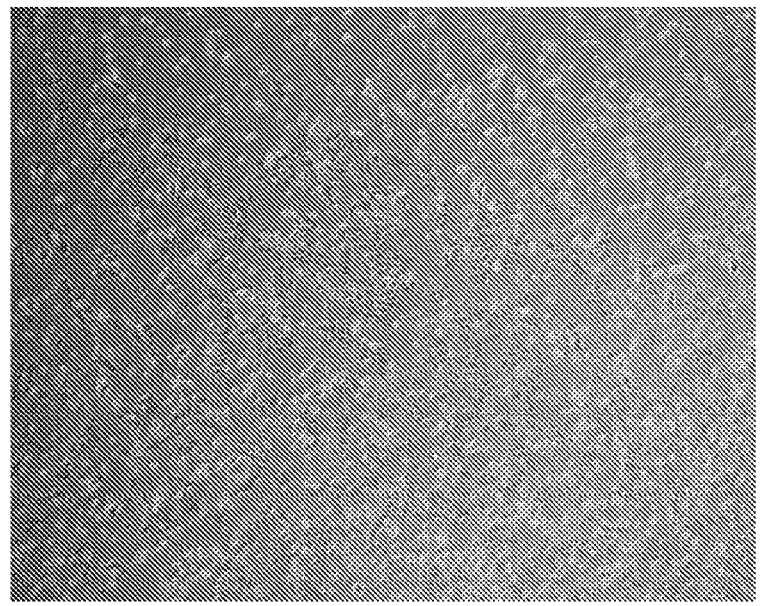
FIG. 24 depicts phase contrast images of cultures of the human embryonic stem cell line H9 at passage 46 in the presence of 100 ng/ml of activin A (panel a) or 100 ng/ml of activin A+20 ng/ml Wnt-3a (panel b). Cells were treated for five days.
Figure 24:
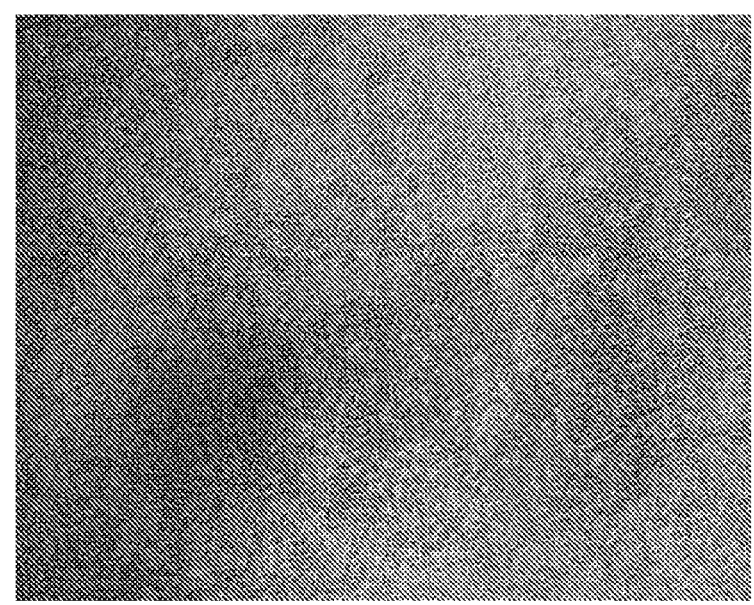
Figure 25:
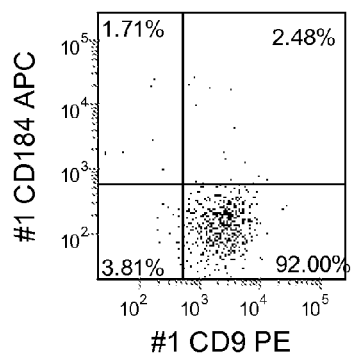
FIG. 25 depicts the expression of CXCR4 by FACS in cultures of the human embryonic stem cell line H7 at passage 44 (panels a & b) and H9 at passage 46 (panels c & d), following treatment according to the methods disclosed in Example 4. Panels b and d show the effect of 20 ng/ml of Wnt-3a on CXCR4 expression. Panels a and c show CXCR4expression in the absence of Wnt-3a. Results were obtained 5 days post treatment.
Figure 25:
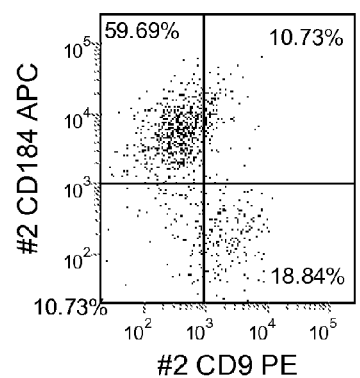
Figure 25:
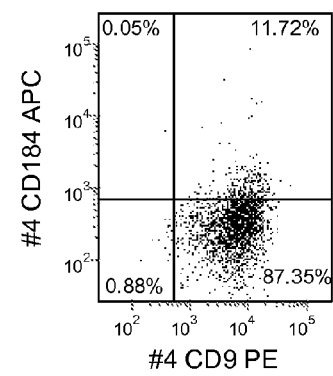
Figure 25:
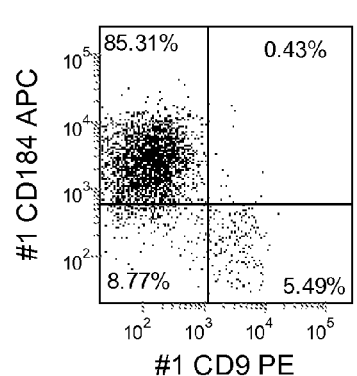
Figure 26:
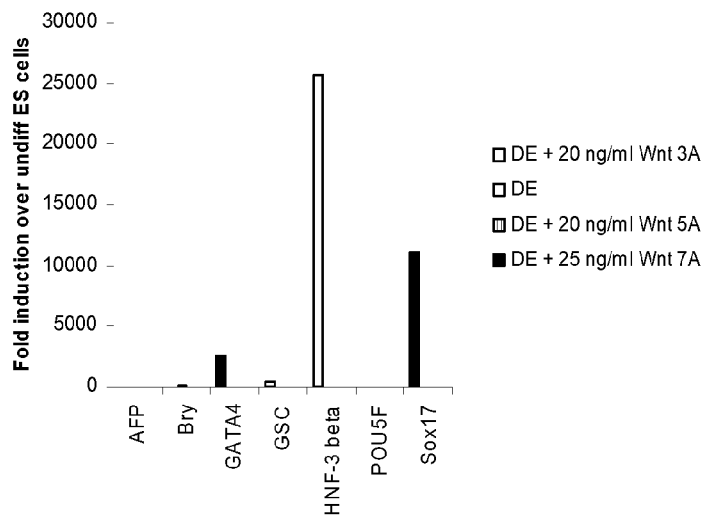
FIG. 26 displays the real-time PCR data for expression of the genes indicated in cultures of the human embryonic stem cell line H7 (panel a) and H9 (panel b). Cultures were treated with the differentiation protocol disclosed in Example 4. The effects of Wnt agonists Wnt-3a (20 ng/ml), Wnt-5a (20 ng/ml) and Wnt-7a (20 ng/ml) were also tested, as indicated in the panels. Cells were treated for 5 days. Results are expressed as fold increase over undifferentiated cells.
Figure 26:
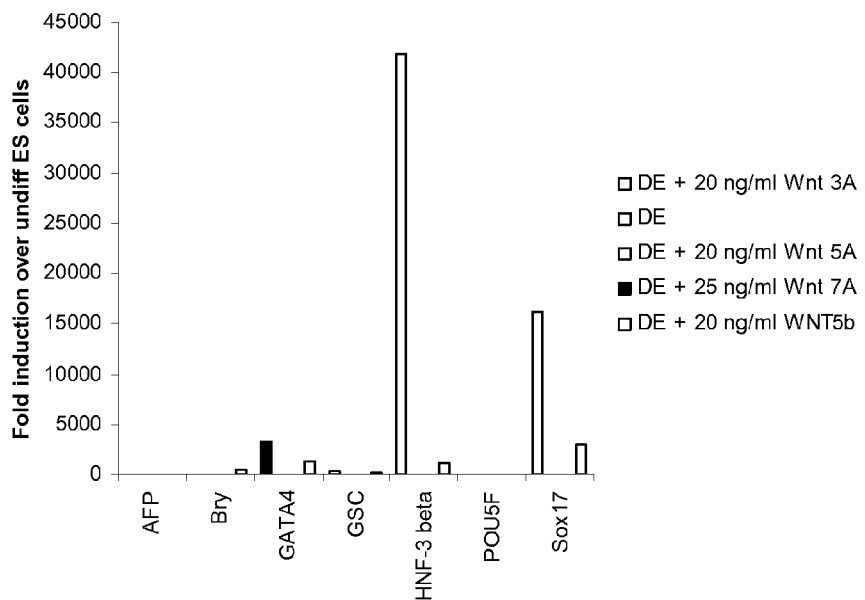

Differentiation of Human Embryonic Stem Cells Cultured on Tissue Culture Substrate Coated with MATRIGEL to Definitive Endoderm—Role of Wnt Ligands H7P44 and H9P46 embryonic stem cells were cultured on MATRIGEL™ (1:10 dilution) coated dishes and exposed to DMEM/F12 medium supplemented with 0.5% FBS, and 100 ng/ml activin A (R&D Systems, MN) for two days followed by treatment with DMEM/F12 media supplemented with 2% FBS and 100 ng/ml activin A (AA) for an additional three days. In some of the cultures 20 ng/ml Wnt-3a (Catalog #1324-WN-002, R&D Systems, MN), 20 ng/ml Wnt-5a (Catalog #654-WN-010, R&D Systems, MN), 25 ng/ml Wnt-7a (Catalog #3008-WN-025, R&D Systems, MN), or 25 ng/ml Wnt-5b (Catalog #3006-WN-025, R&D Systems, MN) was added throughout the five day treatment. FIG. 24 depicts phase contrast images of H9P46 definitive endoderm culture in the presence of high concentration of (a) AA or (b) AA+20 ng/ml Wnt-3a. FIG. 25 depicts the expression of CXCR4 by FACS at day 5 for H7P44, and H9P46 lines cultured on MATRIGEL™ (1:30 dilution) and exposed to the DE protocol+Wnt-3a (FIG. 25, panels b and d) and −Wnt-3a (FIG. 25, panels a and c). Presence of Wnt-3a in DE cultures resulted in robust expression of CXCR4 (CD184) as compared to DE cultures treated with low serum plus high concentration of AA. FIG. 26 displays the real-time PCR data for a) H7 and b) H9 cultures treated with low serum+AA+/−Wnt ligands. For both H lines, addition of WNT-3a resulted in significant up regulation of definitive endoderm markers. In contrast, Wnt 5a, Wnt-5b and Wnt-7a had minimal impact on expression of definitive endoderm markers.

Example 18

Figure 27:
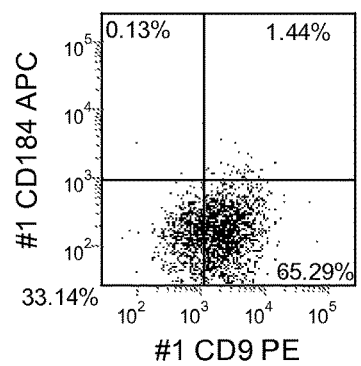
Figure 27:
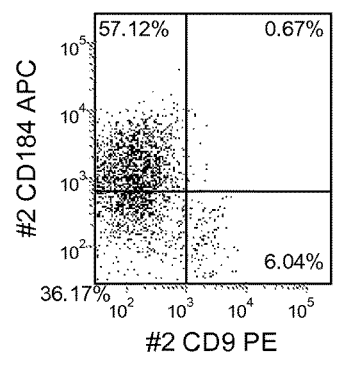
Figure 27:
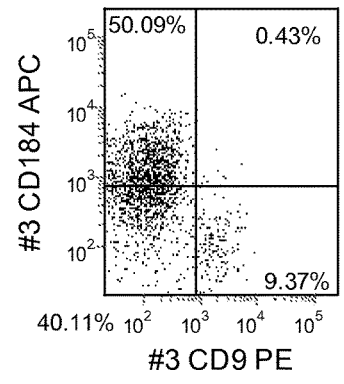
Figure 27:
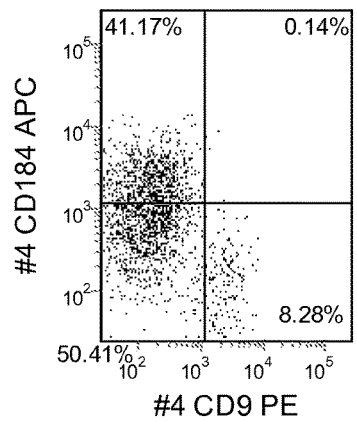

Differentiation of Human Embryonic Stem Cells Cultured on Tissue Culture Substrate Coated with MATRIGEL to Definitive Endoderm—Effective Dose of Wnt-3a H9P46 embryonic stem cells were cultured on MATRIGEL™ coated dishes (1:10 dilution) and exposed to DMEM/F12 medium supplemented with 0.5% FBS, 100 ng/ml Activin A (AA), and 10-50 ng/ml WNt-3a (R&D Systems, MN) for two days followed by treatment with DMEM/F12 media supplemented with 2% FBS, 100 ng/ml activin A (AA), and 10-50 ng/ml Wnt-3a for an additional three days. Control cultures were not treated with Wnt-3a. FIG. 27, panel a depicts the expression of CXCR4 by FACS at day 5 in the absence of Wnt-3a, b) 10 ng/ml Wnt-3a, c) 20 ng/ml Wnt-3a and d) 50 ng/ml Wnt-3a. In the absence of Wnt-3a the expression of CXCR4 was very low. In contrast, addition of 10-50 ng/ml of Wnt-3a significantly increased the number of CXCR4 positive cells. Furthermore, addition of 10 ng/ml of Wnt-3a was as effective as addition of 50 ng/ml of Wnt-3a. Real-time PCR results (FIG. 28, panel a) also confirm this finding.

Figure 28:
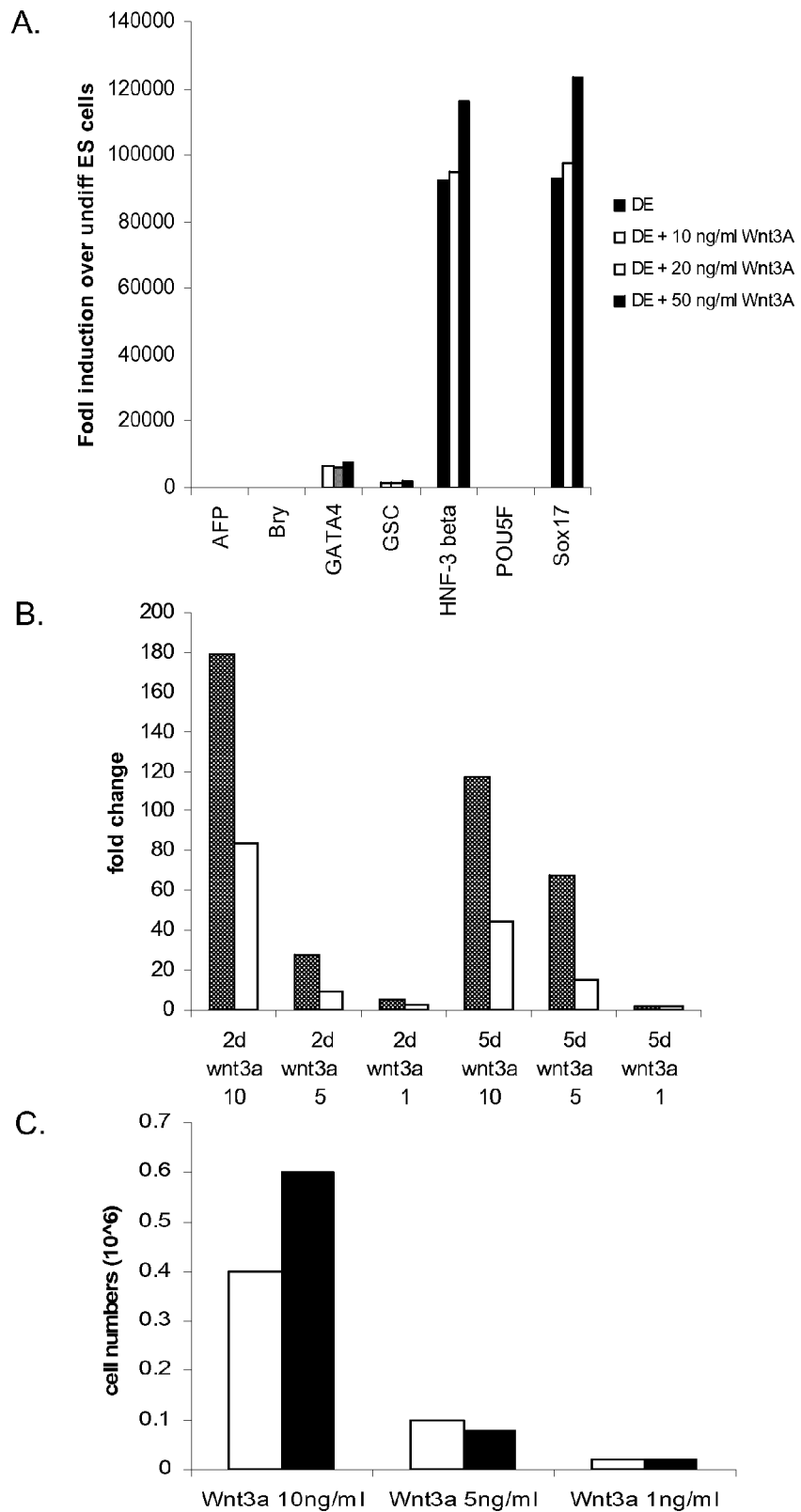
FIG. 28 depicts the expression of definitive markers indicated in cultures of the human embryonic stem cell line H9 after 5 days of treatment. Results are shown as fold increase in expression over untreated cells, as determined by real-time PCR. Panel (a) shows the effect of 10, 20 and 50 ng/ml Wnt-3a on the expression of definitive endoderm marker genes indicated. Panel (b) shows the effect of 1, 5 or 10 ng/ml Wnt-3a (x-axis labels: 10, 5, 1) on the expression on goosecoid (■) and CXCR4 (□) expression, at 2 (2 d) and 5 (5 d) days post treatment. Panel (c) shows the effect of 1, 5 or 10 ng/ml Wnt-3a on cell number, at 2 days (■) or 5 days (□).

In a separate study, H9p52 cells were plated on 1:30 low growth factor MATRIGEL™. For the first 2 days of the DE protocol a range of Wnt-3a doses was used: 10 ng/ml, 5 ng/ml and 1 ng/ml. FIG. 28, panel b shows PCR analysis of the DE markers after 5 days of treatment. The number of cells at the end of the experiment is noted in FIG. 28, panel c. This indicates that cells are proliferating when higher doses of Wnt-3a are used. Extension to 5 days of Wnt-3a treatment (5D) had little effect on DE markers by PCR and did not significantly increase cell numbers (FIG. 28, panel c). These data indicate that 10 ng/ml Wnt3a for 2 days is sufficient to reach optimal cell expansion and definitive endoderm differentiation.

Example 19

Figure 29:
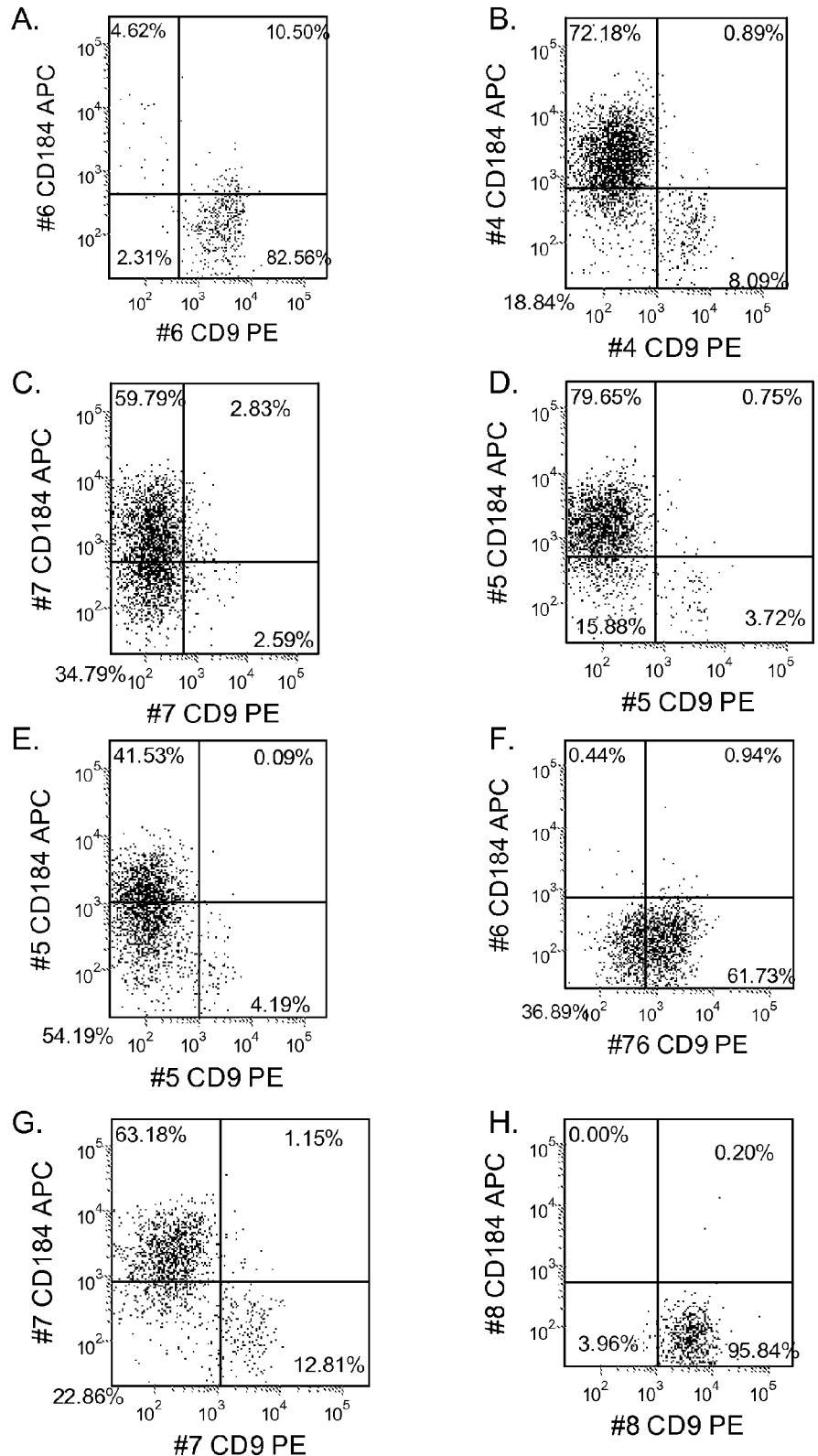
FIG. 29 depicts the expression of CXCR4 in cultures of the human embryonic stem cell line H9 by FACS, following a 5 day treatment with the differentiation protocol disclosed in Example 4. Cells were cultured in the absence of Wnt-3a or GSK-3B inhibitor (panel a), 20 ng/ml Wnt-3a for the entire 5 day period (panel b), 1000 nM GSK-3B inhibitor IX for the entire 5 day period (panel c), 500 nM GSK-3B inhibitor IX for the entire 5 day period (panel d), 100 nM GSK-3B inhibitor IX for the entire 5 day period (panel e), 10 nM GSK-3B inhibitor IX for the entire 5 day period (panel f), 100 nM GSK-3B inhibitor IX for days 1-2 (panel g), 10 nM GSK-3B inhibitor IX for days 1-2 (panel h).

Differentiation of Human Embryonic Stem Cells Cultured on Tissue Culture Substrate Coated with MATRIGEL to Definitive Endoderm—Effect of GSK-3B Inhibitors In order to confirm that the effect of Wnt-3a was through the Wnt pathway, a GSK-3 inhibitor was used to activate the downstream targets of Wnt, such as beta catenin. H9P46-P48 embryonic stem cells were cultured on MATRIGEL™ coated dishes (1:10 dilution) and exposed to DMEM/F12 medium supplemented with 0.5% FBS, 100 ng/ml activin-A (AA), and 10-1000 nM GSK-3B inhibitor IX (Catalog #361550, Calbiochem, CA) for two days followed by treatment with DMEM/F12 media supplemented with 2% FBS, 100 ng/ml activin A (AA), and 0-1000 nM GSK-3B inhibitor IX (Catalog #361550, Calbiochem, CA) for an additional three days. Control cultures were treated with low serum plus high dose of activin A+/−Wnt-3a. FIG. 29, panel a depicts the expression of CXCR4 by FACS at day 5 in the absence of Wnt-3a or GSK-3B inhibitor, b)+20 ng/ml Wnt-3a, c)+1000 nM GSK-3B inhibitor IX, d)+500 nM GSK-3B inhibitor IX, e)+100 nM GSK-3B inhibitor IX, f)+10 nM GSK-3B inhibitor IX, g)+100 nM GSK-3B inhibitor IX for days 1-2, and h)+10 nM GSK-3B inhibitor IX for days 1-2.

Figure 30:
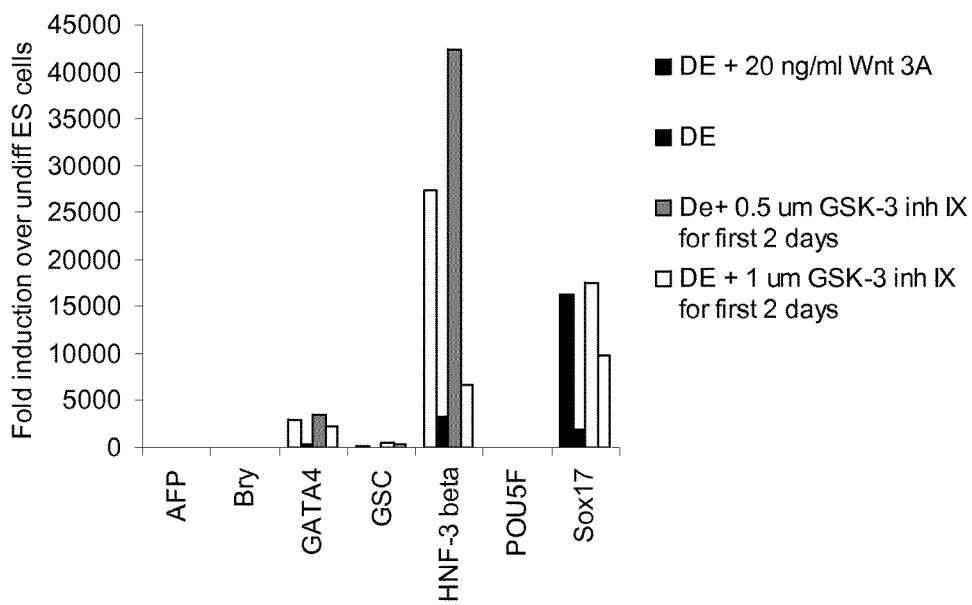
FIG. 30 depicts the gene expression of definitive endoderm markers by real-time PCR. Results are expressed as fold increase over untreated cells. Panel (a) shows data obtained from the human embryonic cell line H9 at passage number 48, treated to the definitive endoderm protocol disclosed in Example 4, containing the Wnt-3a or GSK-3B inhibitor at the concentrations and the times indicated. Panel (b) shows data obtained from the human embryonic cell line H9 at passage number 46, treated to the definitive endoderm protocol disclosed in Example 4, containing the Wnt-3a or GSK-3B inhibitor at the concentrations and the times indicated.
Figure 30:
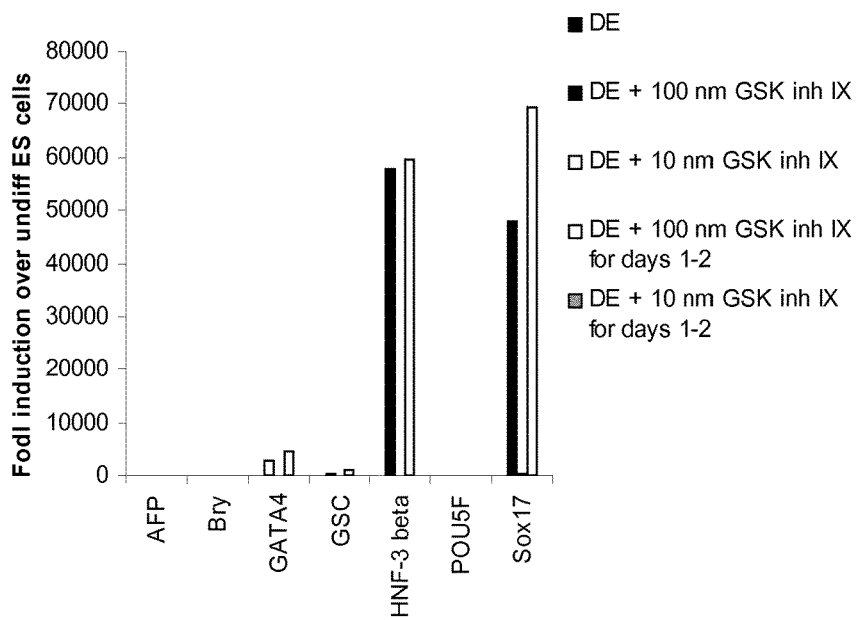

In the absence of Wnt-3a or at 10 nm GSK-3B inhibitor the expression of CXCR4 was very low. In contrast, addition of 20 ng/ml of Wnt-3a or 100-1000 nM GSK-3B inhibitor significantly increased the number of CXCR4 positive cells. Furthermore, addition of 100 nM GSK-3B inhibitor for days 1-2 was as effective as addition of 100 nM GSK-3B inhibitor for the entire five day period. FIG. 30 depicts the gene expression of definitive endoderm markers for (panel a) H9P48 cells and (panel b) H9P46 cells.

Figure 16:
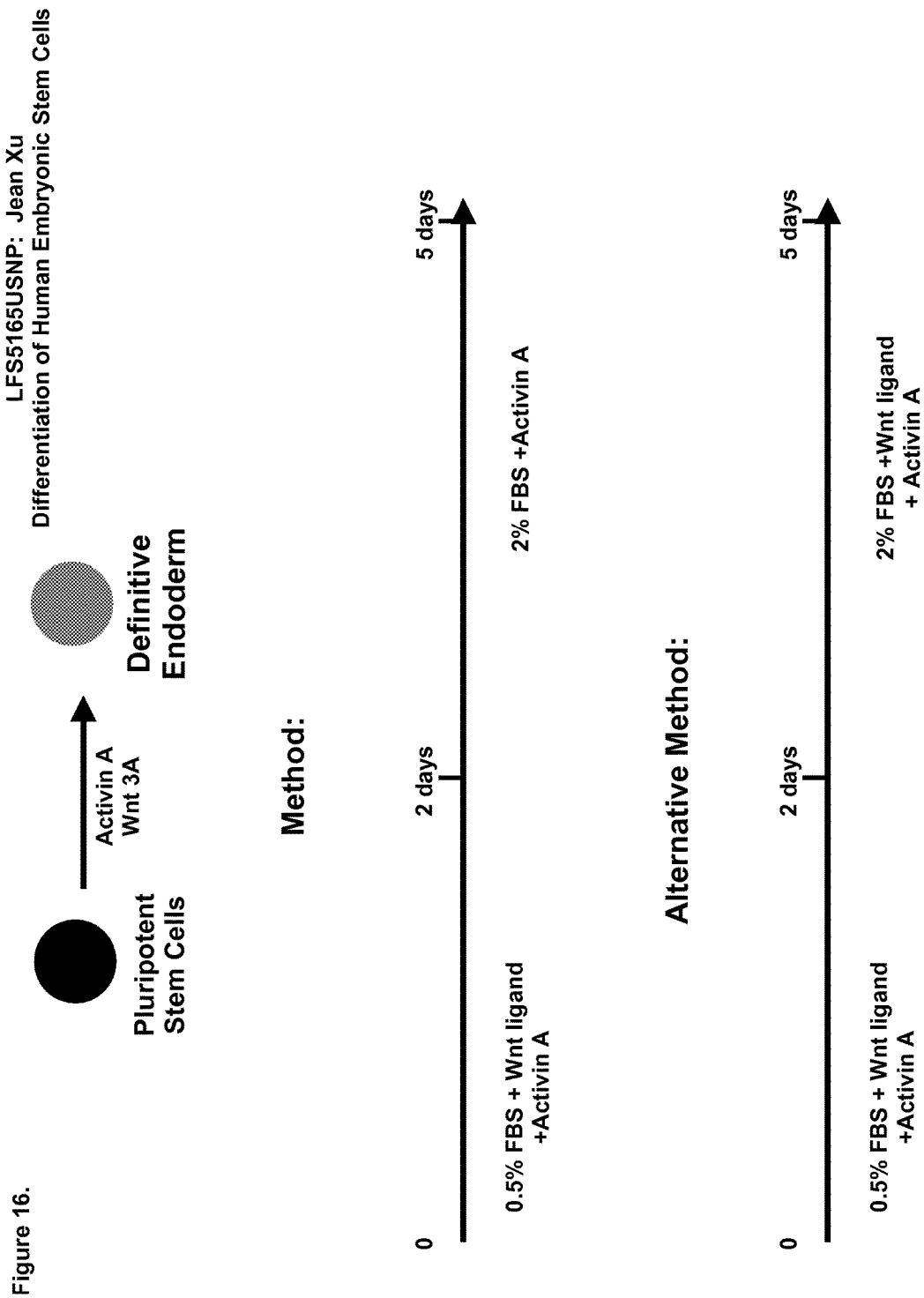
FIG. 16 depicts the outline of a differentiation protocol in this invention, where human embryonic stem cells are differentiated into definitive endoderm in a feeder free system.

FIG. 16 depicts the outline of a differentiation protocol in this invention, where embryonic stem cells are differentiated into definitive endoderm in a feeder free system.

Example 20

Figure 31:
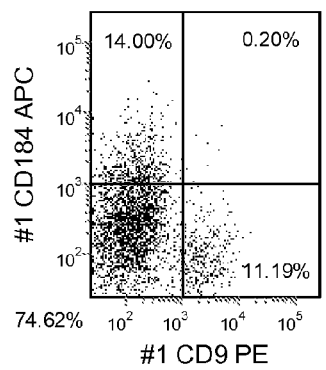
FIG. 31 depicts the expression of CXCR4 by FACS for embryonic stem cell lines used in the present invention. Panels (a-d) show data obtained from the human embryonic stem cell line H9 at passage number 49. Panels (e-f) show data obtained from the human embryonic stem cell line H1 at passage number 46. Data was obtained 5 days post treatment. Cells were treated with the following conditions: Panel (a): 10 ng/ml activin A for all five days plus 20 ng/ml of Wnt-3a for the first two days; panel (b): 100 ng/ml activin A for all five days plus 20 ng/ml of Wnt-3a for the first two days; panel (c): 100 ng/ml activin A for all five days plus 100 nM of GSK-3B inhibitor IX for the first two days; panel (d)
Figure 31:
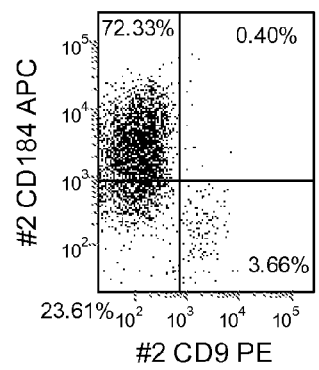
Figure 31:
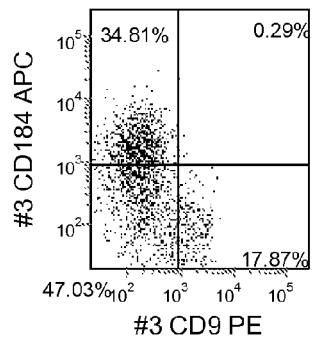
Figure 31:
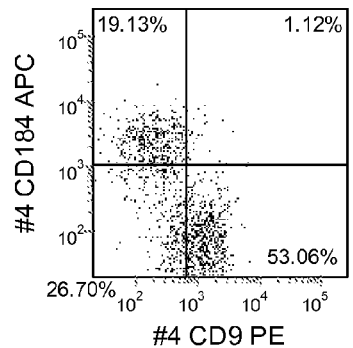
Figure 31:
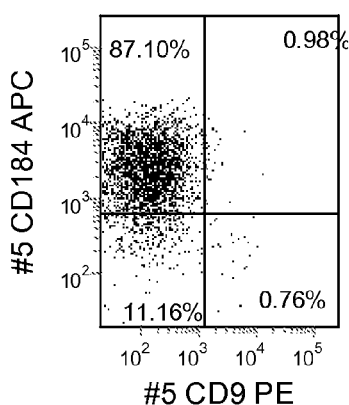
Figure 31:
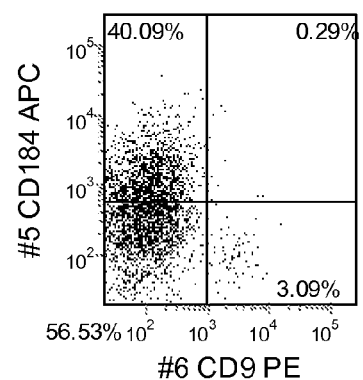

Differentiation of Human Embryonic Stem Cells Cultured on Tissue Culture Substrate Coated with MATRIGEL to Definitive Endoderm—Effective Dose of Activin A in the Presence of a GSK-3B Inhibitor or Wnt-3a H9P49 and H1P46 embryonic stem cells were cultured on MATRIGEL™ coated dishes (1:10 dilution) and exposed to DMEM/F12 medium supplemented with 0.5% FBS, 10-100 ng/ml activin A (AA), and 100 nM GSK-3B inhibitor IX (Catalog #361550, Calbiochem, CA) or 20 ng/ml Wnt-3a for two days followed by treatment with DMEM/F12 media supplemented with 2% FBS, 10-100 ng/ml activin A (AA) for an additional three days. Control cultures were treated with low serum plus 100 ng/ml of activin A. FIG. 31 depicts the expression of CXCR4 by FACS for H9P49 and H1P46 at day 5 with a) 10 ng/ml activin A for all five days plus 20 ng/ml of Wnt-3A for the first two days, b) 100 ng/ml activin A for all five days plus 20 ng/ml of Wnt-3A for the first two days c) 100 ng/ml activin A for all five days plus 100 nM of GSK-3B inhibitor IX for the first two days d) 10 ng/ml activin A for all five days plus 100 nM of GSK-3B inhibitor IX for the first two days, e) 100 ng/ml activin A for all five days plus 20 ng/ml of Wnt-3A for the first two days, and f) 10 ng/ml activin A for all five days plus 20 ng/ml of Wnt-3A for the first two days. FIG. 31 panels a-d is for H9P49 cells and panels e-f is for H1P46 cells. FIG. 32 depicts the gene expression of definitive endoderm markers for H9P49 cultures treated with 10, 50, or 100 ng/ml of activin A plus 20 ng/ml of Wnt-3a: panel a: expression of AFP, Bry, CXCR4, GSC, HNF-3B, and POUSF (Oct-4) and panel b: SOX-17 and GATA4. It appears that robust expression of definitive endoderm markers can be obtained by using 50 ng/ml of AA+20 ng/ml of Wnt-3A or 100 nM GSK-3B inhibitor IX. Lower doses of activin A lead to formation of extraembryonic endoderm.

Example 16

Differentiation of Human Embryonic Stem Cells Cultured on Tissue Culture Substrate Coated with MATRIGEL to Definitive Endoderm—Combination of Wnt-3a and GSK-3B Inhibitors H9P53 embryonic stem cells were cultured on MATRIGEL™ coated dishes (1:30 dilution) and exposed to DMEM/F12 medium supplemented with 0.5% FBS, 100 ng/ml activin A (AA), and 100 nM GSK-3B inhibitor IX (Catalog#361550, Calbiochem, CA)+/−20 ng/ml Wnt-3a for two days followed by treatment with DMEM/F12 media supplemented with 2% FBS, 10-100 ng/ml activin-A (AA) for an additional three days. In parallel, H9P53 cultures were treated with 25 ng/ml BMP-4 (Catalog#314-BP-010, R&D Systems, MN)+/−20 ng/ml Wnt-3A+/−100 ng/ml activin A. Control cultures were treated with low serum plus 100 ng/ml of activin A. FIG. 33 depicts the expression of CXCR4 by FACS at day 5 with a) 100 ng/ml activin A for all five days plus 20 ng/ml of Wnt-3A for the first two days and 25 ng/ml BMP-4 for days 3-5, b) 100 ng/ml activin A for all five days plus 20 ng/ml of Wnt-3A for the first two days c) 100 ng/ml activin A for all five days plus 100 nM of GSK-3B inhibitor IX for the first two days d) 20 ng/ml Wnt-3a+25 ng/ml BMP-4 for all five days, e) 100 ng/ml activin A for all five days plus 20 ng/ml of Wnt-3A+100 nm GSK-3B inhibitor IX for the first two days, and f) 100 ng/ml activin A+25 ng/ml BMP-4 for all five days. FIG. 34 depicts the gene expression of definitive endoderm markers, as determined by real-time PCR for cultures of the human embryonic stem cell line H1 at passage 46, treated with 10 or 100 ng/ml of activin A plus 20 ng/ml of Wnt-3a or 100 NM GSK-3B inhibitor: panel (a): expression of AFP, Bry, CXCR4, GSC, and POUSF (Oct-4) and panel (b): SOX-17, HNF-3B, and GATA4. Results are expressed as fold increase over untreated cells. FIG. 35 depicts the gene expression of definitive endoderm markers, as determined by real-time PCR for cultures of the human embryonic stem cell line H9 at passage 49, treated with 50 or 100 ng/ml of activin A plus 10 or 100 nM GSK-3B inhibitor: panel (a): expression of AFP, Bry, CXCR4, GSC, HNF-3B, and POUSF (Oct-4) and panel (b): SOX-17 and GATA4. Results are expressed as fold increase over untreated cells. FIG. 36 depicts the gene expression of definitive endoderm markers for H9P53 culture treated with combinations of activin A, Wnt-3a, GSK-3 inhibitor, and BMP-4: a) expression of AFP, Bry, CXCR4, GSC, HNF-3B, and SOX7 and b) SOX-17, HNF-3B and GATA4. Addition of BMP-4 to the DE protocol appears to induce formation of mesoderm marker BRY and combination of Wnt-3A and GSK-4B inhibitor did not lead to significant up regulation of definitive endoderm markers as compared to addition of each agent by itself in the presence of activin A.

Example 22

Differentiation of Human Embryonic Stem Cells Cultured on MEFs to Definitive Endoderm—Combination of Wnt-3a, Activin A, Wnt-5a, BMP-2, BMP-4, BMP-6, BMP-7, IL-4, and SDF-1 in Low Serum H9P44 cells were plated onto 6 well plates previously coated with mitomycin treated mouse embryonic fibroblasts (MEF). Cells were grown until 70 to 80% confluency in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine (all from Invitrogen/GIBCO) and 8 ng/ml human basic fibroblast growth factor (bFGF) (R&D Systems).

For DE formation, cells were treated in the presence or absence of Activin A (100 ng/ml) in addition to other growth factors detailed below. Growth factors were added to increasing concentration of FBS in a stepwise manner as indicated in the following regimen:
Day 0: 0% FBS in DMEM/F12
Day 1: 0.5% FBS in DMEM/F12
Day 2: 2% FBS in DMEM/F12.
Day 3: Cells were harvested for FACS analysis and RT-PCR.

All growth factors were purchased from R&D Systems, MN. A detailed description and concentration of growth factors for each treatment group is shown below.

1. Control—No growth factor added
2. Activin A (100 ng/ml)
3. Activin A (100 ng/ml)+Wnt-3a (10 ng/ml)+Wnt5a (10 ng/ml)
4. Activin A (100 ng/ml)+Wnt-3a (10 ng/ml)+Wnt5a (10 ng/ml)+BMP2 (100 ng/ml)
5. Activin A (100 ng/ml)+BMP-4 (100 ng/ml)
6. Activin A (100 ng/ml)+BMP-6 (100 ng/ml)
7. Activin A (100 ng/ml)+BMP-7 (100 ng/ml)
8. Activin A (100 ng/ml)+BMP-4 (100 ng/ml)+BMP-6 (100 ng/ml)+BMP-7 (100 ng/ml)
9. IL-4 (10 ng/ml)
10. SDF1a (20 ng/ml)
11. Activin A (100 ng/ml)+IL-4 (10 ng/ml)+SDF1a (20 ng/ml)
12. BMP2 (100 ng/ml)+BMP-4 (100 ng·ml)+BMP-6 (100 ng/ml)+BMP-7 (100 ng/ml)
13. Activin A (100 ng/ml) BMP-2 (100 ng/ml)+BMP-4 (100 ng·ml)+BMP-6 (100 ng/ml)+BMP-7 (100 ng/ml)
14. Activin A (100 ng/ml)+IL-4 (10 ng/ml)
15. Activin A (100 ng/ml)+(SDF1a (20 ng/ml)
16. Activin A (100 ng/ml)+Wnt-3a (10 ng/ml)+Wnt-5a (10 ng/ml)+Wnt-7a (10 ng/ml)
17. Activin A (100 ng/ml)+IL-4 (10 ng/ml)+SDF1a (20 ng/ml)+BMP-4 (100 ng/ml)

Results:

Cells were harvested on Day 3 of DE protocol treatment. For analysis, an aliquot of treated cells was used for RNA preparation for RT-PCR and the rest of cells used for FACS analysis. The frequency (%) of CXCR4 is shown in FIG. 37. Addition of the above growth factor(s) did not enhance expression of CXCR4 above treatment with 100 ng/ml AA in low serum.

For RT-PCR analysis, cells were analyzed for expression of selected panel of definitive endoderm markers. Results shown were calibrated against cells grown in the base medium but not treated with Activin A or any of the other growth factors. In agreement with the FACS data, Table V shows that there was no significant up regulation of definitive endoderm markers by addition of growth factors, such as Wnt-3a to cultures treated with a high dose of activin A in low serum. This is in contrast to the previous examples showing a significant increase in DE markers for ES cells cultured on feeder-free conditions in the presence of activin A, WNT3A, and low serum.

Example 23

Differentiation of Human Embryonic Stem Cells Cultured on Tissue Culture Substrate Coated with MATRIGEL or Human Fibronectin to Definitive Endoderm H9P55 cells were grown and differentiated on human fibronectin or regular growth factor MATRIGEL™ (BD Biosciences). 1 ml of DMEM/F12 (Invitrogen/GIBCO) containing 1 ug/ml of human fibronectin (R&D systems, MN) was added to each well of 6 well tissue culture treated dish. Alternatively, regular growth factor MATRIGEL™ was diluted 1:10 in DMEM/F12 and 1 ml of diluted MATRIGEL™ was added to each well of 6 well tissue culture treated dish. Cells were passed with collagenase. After cells reached 80% confluency, there were treated as follows: 2 days 0.5% FBS containing 10 ng/ml mouse recombinant Wnt3a (R&D) and 100 ng/ml Activin A (R&D). This was followed by 3 days 2% FBS plus 100 ng/ml Activin A. FIG. 38, panels a-b depict the expression of CXCR4 by embryonic stem cells cultured on fibronectin and MATRIGEL, respectively. Real-time PCR results (FIG. 39) confirm that formation of definitive endoderm was equivalent on fibronectin and MATRIGEL™ coated plates.

Example 24

Differentiation of Human Embryonic Stem Cells Cultured on Tissue Culture Substrate Coated with Varying Concentrations of MATRIGEL to Definitive Endoderm H9 cultures at approximately 60 to 70% confluency were exposed to DMEM/F12 medium supplemented with 0.5% FBS, 20 ng/ml Wnt-3a and 100 ng/ml activin A for two days followed by treatment with DMEM/F12 media supplemented with 2% FBS, 20 ng/ml Wnt-3a and 100 ng/ml activin A (AA) for an additional three days. H9 cells were cultured on plates coated with regular MATRIGEL at a 1:60 to 1:10 dilution. The plates were coated with MATRIGEL for 1 hr at room temperature.

Real time PCR results are shown in FIG. 40. Treatment of human embryonic stem cells with low serum, Activin A and Wnt-3a led to the expression of CXCR4, GATA4, Goosecoid, HNF-3beta, and SOX-17 genes, suggesting that the cells were differentiating to the definitive endoderm stage. However, it does not appear that the in the presence of Wnt-3a concentration of the MATRIGEL™ coating plays an important role in differentiation.

Example 25

Differentiation of Human Embryonic Stem Cells Cultured on Tissue Culture Substrate Coated with Extracellular Matrix and Subsequently Cultured on MEFs to Definitive Endoderm—Role of Wnt-3a Cells from the human embryonic stem cell line H9 cultured on MATRIGEL™ for at least five passages were seeded onto MEF feeders in ES media. When the cells reached 60 to 70% confluency they were exposed to DMEM/F12 medium supplemented with 0.5% FBS and 100 ng/ml activin A for two days followed by treatment with DMEM/F12 media supplemented with 2% FBS and 100 ng/ml activin A (AA) for an additional three days. Additional treatment groups include Wnt-3a at 20 ng/ml for all five days+10-100 ng/ml of activin A.

At day 3 and 5, the cultures were analyzed by real time PCR for SOX-17, SOX-7, Alpha-fetal protein (AFP), CXCR4, Brychyury (Bry), goosecoid (GSC), HNF-3 beta, GATA4, hTERT and Oct4. AFP and SOX-7 are regarded as visceral endoderm markers while GATA4, HNF-3beta and SOX-17 represent definite endoderm markers and GSC, Bry, and CXCR4 represent markers of primitive streak. hTERT and Oct-4 are markers for self renewal and pluripotency respectively. Real time-PCR results are shown in FIG. 41, panels a-d. FACS analysis was also performed at day 3 and 5. Expression levels of CXCR-4, and CD9 were analyzed and reported in FIG. 41, panel e.

In the absence of Wnt-3a, AFP expression levels of cells cultured in 100 ng/ml Activin A are similar to those seen in untreated controls. However, with the addition of Wnt-3a to cells cultured in 100 ng/ml activin A, there is an increase in the expression of AFP that increases over time. When a lower concentration of Activin A is used, AFP expression is very high, regardless of the presence of Wnt3a (FIG. 41, panel a). This suggests that a high concentration of Activin A is necessary to keep the cells from differentiating to extra-embryonic tissues.

By FACS analysis, CXCR4 positive cells ranged from 32-42% of the population in samples treated with a high concentration of Activin A but not treated with Wnt-3a as compared to 23-33% of the population in samples treated with a high concentration of Activin A and Wnt3a at day 3 (FIG. 41, panel e). By day 5 of treatment, 28-32% of cells treated with a high concentration of activin A but not treated with Wnt-3a expressed CXCR4 as compared to 43-51% of cells treated with a high concentration of Activin A and Wnt-3a (FIG. 41, panel f). In cells treated with a low concentration of Activin A, there were more CXCR4 positive cells in the treatment group without Wnt-3a (11 to 20%) as compared to the Wnt-3a treated group (3 to 4%) (FIG. 41, panel g). Overall, Wnt-3a does not appear to play a significant role in differentiation of human embryonic stem cells, cultured on MEFs, to definitive endoderm. This suggests that the feeder layer is probably secreting sufficient Wnt-3a or analogous ligand to enhance activin A induced definitive-endoderm formation.

Example 26

Differentiation of Human Embryonic Stem Cells Cultured on Tissue Culture Substrate Coated with Extracellular Matrix to Definitive Endoderm Following Treatment with the Wnt Inhibitor DKK-1

To determine if the addition of Wnt-3a was causing the increase in differentiation, an inhibitor of Wnt-3 signaling was added to the cultures. H9 cultures at approximately 60 to 70% confluency were exposed to DMEM/F12 medium supplemented with 0.5% FBS, 20 ng/ml Wnt3a, 100 ng/ml Dikkopf-1 (DKK-1) and 100 ng/ml activin A for two days followed by treatment with DMEM/F12 media supplemented with 2% FBS and 100 ng/ml activin A (AA) for an additional three days. H9 cells were cultured on plates coated with Growth Factor Reduced MATRIGEL at a 1:30 dilution. The plates were coated with MATRIGEL for 1 hr at room temperature.

At day 5, the cultures were analyzed by real time PCR for SOX-17, SOX-7, Alpha-fetal protein (AFP), CXCR4, Brychyury (Bry), goosecoid (GSC), HNF-3 beta, GATA4, hTERT and Oct4. AFP and SOX-7 are regarded as visceral endoderm markers while GATA4, HNF-3beta and SOX-17 represent definite endoderm markers and GSC, Bry, and CXCR4 represent markers of primitive streak. hTERT and Oct-4 are markers for self renewal and pluripotency respectively. Results are shown in FIG. 42.

In the presence of Wnt-3a, cells express CXCR4, GATA4, HNF-3beta and SOX17, all markers of definitive endoderm. Markers of primitive streak formation such as goosecoid were also detected at levels higher than that detected in untreated controls. With the addition of DKK1, the expression level of the aforementioned differentiation markers dramatically decrease to levels similar to that of untreated cells.

Example 27

Immunofluoresence Staining of DE Markers for H9 Embryonic Stem Cells Cultured on Tissue Culture Substrate Coated with MATRIGEL and Differentiated in Low Serum Plus Activin A and ±Wnt-3a Day 5 DE cultures of H9 cells were stained according to Example 10 for SOX-17, HNF-3B, GATA-4, N-cadherin, and E-cadherin. All nuclei were counter stained with DAPI. 20 ng/ml Wnt-3a resulted in significantly larger number of nuclei stained positive for SOX-17, HNF-3beta. and GATA-4 as compared to cultures differentiated in the absence of Wnt-3a. Furthermore, addition of Wnt-3a resulted in significant loss of expression of e-cadherin and enhanced expression of N-cadherin (FIG. 43, panel a and FIG. 43, panel b).

Example 28

Microarray Analysis of Changes in Gene Expression in Embryonic Stem Cells Following Formation of Definitive Endoderm on MEFS or MATRIGEL Total RNA was isolated from the following embryonic stem cell cultures using an RNeasy mini kit (Qiagen): A) H9P33 cells cultured on MATRIGEL™-coated plates (1:30 dilution) and exposed to DMEM/F12 medium supplemented with 0.5% FBS and 100 ng/ml activin A for two days followed by treatment with DMEM/F12 medium supplemented with 2% FBS and 100 ng/ml activin A (AA) for an additional three days; B) H9P44 cells cultured on MEFs and exposed to DMEM/F12 medium supplemented with 0.5% FBS and 100 ng/ml Activin A for two days followed by treatment with DMEM/F12 medium supplemented with 2% FBS and 100 ng/ml Activin A for an additional three days, and C) H9P48 cells cultured on MATRIGEL™-coated plates (1:30 dilution) and exposed to DMEM/F12 medium supplemented with 0.5% FBS and 100 ng/ml activin A plus 20 ng/ml Wnt-3a for two days followed by treatment with DMEM/F12 medium supplemented with 2% FBS and 100 ng/ml Activin A (AA) for an additional three days. Controls for each group included cells plated on MATRIGEL-coated dishes and cultured in MEF-conditioned medium or cells plated on MEFs and cultured in ES medium. All groups contained three biological replicates and each biological replicate was repeated on two separate gene chips.

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA). Significant differences in gene expression between the samples were evaluated using analysis of variance and an F-test with adjusted P-value (Benjamini and Hochberg correction) of less-than or equal to 0.05. Only genes with a present call in at least one group were included in the analysis. Table VI lists the mean normalized log transformed signal intensity of genes showing at least 5-fold difference between group A, group B, and group C along with the adjusted P-value for each gene.

Example 29

Differentiation of the SA002 ES Line Cultured on Tissue Culture Substrate Coated with MATRIGEL to Definitive Endoderm SA002 P38 cells (Cellartis, Sweden) previously cultured for at least three passages on MATRIGEL-coated plates (1:30 dilution) in MEF-CM supplemented with 8 ng/ml of bFGF were exposed to DMEM/F12 medium supplemented with 0.5% FBS, and 100 ng/ml activin A (R&D Systems, MN)+/−20 ng/ml of Wnt-3a or 100 nm GSK-3B IX inhibitor for two days followed by treatment with DMEM/F12 media supplemented with 2% FBS and 100 ng/ml activin A (AA) for an additional three days. Real time PCR results are shown in FIG. 44, panels a & b. Similar to H1, H7, and H9 lines, SA002 line also required addition of Wnt-3A for robust expression of DE markers. Expression of CXCR4 is depicted in FIG. 45: a) AA treatment b) AA+Wnt-3a c) AA+GSK-3B inhibitor.

Example 25

Differentiation of Human Embryonic Stem Cells Cultured on Tissue Culture Substrate Coated with Human Serum to Definitive Endoderm Cultures of the human embryonic stem cell line H1 at passage 55 were grown and differentiated on human serum (Sigma, #H1388, MO) coated plates. 0.5 ml of human serum was added to each well of 6 well tissue culture treated dish, incubated for 1 hr at room temperature, and aspirated before adding human embryonic stem cells. After cells reached 80% confluency, they were treated as follows: 2 days 0.5% FBS containing 10 ng/ml mouse recombinant Wnt3a (R&D) or 100 nM GSK-3B inhibitor IX (Catalog #361550, Calbiochem, CA) and 100 ng/ml Activin A (R&D). This was followed by 3 days 2% FBS plus 100 ng/ml Activin A. Cultures were then analyzed by real-time PCR (FIG. 46, panels a & b). Robust expression of definitive endoderm markers were noted for cells treated with activin A+GSK-3B inhibitor or Wnt-3A as compared to cells treated with activin A only. These findings parallel our findings for human embryonic stem cells cultured on MATRIGEL™ or human fibronectin coated plates.

Example 31

Differentiation of Human Embryonic Stem Cells Cultured on Tissue Culture Substrate Coated with MATRIGEL to Definitive Endoderm—Evaluation of Various GSK-3B Inhibitors The effectiveness of a number of commercially available GSK-3B inhibitors was evaluated in formation of DE from human embryonic stem cells. The following GSK-3B inhibitors were evaluated at 100 nM: GSK-3B inhibitor VIII (Catalog #361549, Calbiochem, CA), GSK-3B inhibitor IX (Catalog #361550, Calbiochem, CA), GSK-3B inhibitor XI (Catalog #361553, Calbiochem, CA), GSK-3B inhibitor XII (Catalog #361554, Calbiochem, CA). H1P54 ES cells were cultured on MATRIGEL™ coated dishes (1:30 dilution) and exposed to DMEM/F12 medium supplemented with 0.5% FBS, 100 ng/ml activin A (AA)+/−various GSK-3B inhibitors for two days followed by treatment with DMEM/F12 media supplemented with 2% FBS, 100 ng/ml activin A (AA) for an additional three days. Control cultures were treated with low serum plus high dose of AA. FIG. 47, panels a and b depicts the gene expression of definitive endoderm markers at day 5. GSK-3B inhibitor IX and XI were both effective in inducing DE formation as compared to GSK-3B inhibitor VIII and XII.

Example 32

Formation of Pancreatic Endoderm by Human Embryonic Stem Cells Cultured Under Feeder-Free Conditions—Evaluation of Retinoic Acid Analogues H9P49 embryonic stem cells were cultured on MATRIGEL™ (1:30 dilution) coated dishes and exposed to DMEM/F12 medium supplemented with 0.5% FBS, 20 ng/ml Wnt-3a (Catalog #1324-WN-002, R&D Systems, MN), and 100 ng/ml activin A (R&D Systems, MN) for two days followed by treatment with DMEM/F12 media supplemented with 2% FBS and 100 ng/ml activin A (AA) for an additional three days. At day 5, cells were collected for evaluation by FACS and real-time PCR. As indicated in previous examples, this protocol resulted in robust up regulation of definitive endoderm markers, such as CXCR4 and SOX-17. The resulting definitive endoderm cells at day 5 were exposed to the following media conditions to induce pancreatic endoderm formation: culturing in DMEM/F12 media supplemented with 2% FBS and 1 µM all-trans retinoic acid (RA) (Catalog #R2625, Sigma, MO), or 0.1-10 µM AM-580 (4-[(5,6,7,8-Tetrahydro-5,5,8,8-tetramethyl-2-naphthalenyl)carboxamido]benzoic acid, Catalog #A8843, Sigma, MO), or 0.1-1 µM TTNPB (4-[(E)-2-(5,6,7,8-Tetrahydro-5,5,8,8-tetramethyl-2-naphthalenyl)-1-propenyl]benzoic acid Arotinoid acid, Catalog #T3757, Sigma, MO) for 3 days. AM-580 and TTNPB are retinoic acid analogs with affinity for retinoic acid receptors. RA treatment was followed by additional three day treatment in DMEM/F12 media supplemented with 2% FBS and 20-50 ng/ml bFGF (Catalog #F0291, Sigma, MO). Cultures were harvested and samples of mRNA were collected for analysis.

Gene expression analysis revealed that (FIG. 48, panels a-d) addition of 1 µM RA followed by exposure to bFGF significantly upregulates pancreatic endoderm markers, such as PDX-1. Furthermore, this protocol resulted in robust expression of foregut endoderm markers, such as CDX-2 and AFP. At 104 concentration, addition of RA analogs resulted in equivalent pancreatic endoderm and foregut markers. However, addition of 1 µM RA analogs resulted in more robust expression of AFP as compared to all-trans retinoic acid. However, addition of 10 µM AM-580 suppressed AFP and CDX-2 expression while maintaining a high expression of PDX-1.

Example 34

The Effect of Wnt-3a Treatment on Cytokine Expression in Human Embryonic Stem Cells The effect that Wnt-3a treatment has on cytokine expression was analyzed using a protein array. Cells of the human embryonic stem cell line H9 were cultured according to the methods described in Example 15. At passage 54, cells were differentiated in the presence of 100 ng/ml ActivinA+/-10 ng/ml Wnt3a for 2 days in 0.5% FBS DMEM/F12. Cells were subsequently cultured for an additional three days in 100 ng/ml Activin A and 2% FBS DMEM/F12. At the end of the 5th day, CXCR4 expression was determined by FACS for each treatment group. Cells treated with Activin A only had 1% of cells expressing CXCR4. Cells treated with Activin A and Wnt3a had 73% of cells positive for CXCR4 expression.

Cell lysates were prepared from cells of each treatment group, with a mammalian cell lysis kit (Sigma-Aldrich, MO). Conditioned media from each treatment group was collected and concentrated. Cytokine array analysis was completed using Cytokine Array panels provided by Ray-Biotech, GA (http://www.raybiotech.com/). Table VII lists cytokine, growth factor, and receptor expression following normalization of the data and background subtraction. For each panel, positive and negative controls are also included. The data shown are two independent samples per cell treatment group (1,2).

Noticeable upregulation of Angiogenin, IGFBP-1 and EGF are seen in the Wnt-3a treated cell conditioned media. Numerous proteins are upregulated in the Wnt-3a treated cell lysates including IGFBP-1, TGFbeta-1 and TGFbeta-3. These upregulated proteins can be added back into the differentiation media to replace or enhance Wnt-3a effects on definitive endoderm formation.

Example 35

Differentiation of Human Embryonic Stem Cells Cultured on Tissue Culture Substrate Coated with MATRIGEL to Definitive Endoderm: Role of Wnt1

H1P55 ES cells were cultured on MATRIGEL™ (1:30 dilution) coated dishes and exposed to DMEM/F12 medium supplemented with 0.5% FBS, and 100 ng/ml activin A+/−10-20 ng/ml of WNT-1 (PeproTech, NJ, Catalogue #120-17) for two days followed by treatment with DMEM/F12 media supplemented with 2% FBS, 100 ng/ml activin A (AA) and +/−10 or 20 ng/ml of WNT-1 for an additional three days. The following combinations of WNT1+AA were tested:

a) 20 ng/ml of WNT1+100 ng/ml AA in 0.5% FBS+DM-F12 for days 1-2 followed by 2% FBS+DM-F12+100 ng/ml AA for day three, b) 20 ng/ml of WNT1+100 ng/ml AA in 0.5% FBS+DM-F12 for days 1-2 followed by 2% FBS+DM-F12+100 ng/ml AA for days 3-5, c) 10 ng/ml of WNT1+100 ng/ml AA in 0.5% FBS+DM-F12 for days 1-2 followed by 2% FBS+DMF12+100 ng/ml AA for day three, d) 10 ng/ml of WNT1+100 ng/ml AA in 0.5% FBS+DM-F12 for days 1-2 followed by 2% FBS+DM-F12+100 ng/ml AA for days 3-5, e) 20 ng/ml of WNT1+100 ng/ml AA in 0.5% FBS+DM-F12 for days 1-2 followed by 2% FBS+DM-F12+100 ng/ml AA+20 ng/ml of WNT1 for day three, f) 20 ng/ml of WNT1+100 ng/ml AA in 0.5% FBS+DM-F12 for days 1-2 followed by 2% FBS+DM-F12+100 ng/ml AA+20 ng/ml of WNT1 for days 3-5. FIG. 49, panels a and b displays the real-time PCR data for definitive endoderm markers following treatment of the H1 cells with low serum, AA and Wnt-1. Addition of 20 ng/ml of Wnt1 in the presence of 100 ng/ml of AA resulted in significant up regulation of definitive endoderm markers (Bry, CXCR4, GSC, SOX17, HNF-3B, and GATA-4).

Example 36

The Effect of Glucose on Pancreatic Endocrine Differentiation

The efficiency of differentiating pancreatic endoderm cells into pancreatic endocrine cells depends on many factors, including, for example, the choice of basal media, or the concentration of glucose. The effect of glucose concentration on the differentiation of pancreatic endoderm cells, derived from embryonic stem cells, into pancreatic endocrine cells was examined.

Alteration of Glucose Concentration by Changing the Basal Media:

Cultures of undifferentiated human embryonic stem cells (H1 and H9) were cultured according to the methods described in Example 1, prior to differentiation into pancreatic endoderm cells. Embryonic stem cells were differentiated into pancreatic endoderm cells by culturing the embryonic stem cells in RPMI containing activin A at 100 ng/ml in the absence of serum for one day. After this time, the cells were cultured in RPMI containing activin A at 100 ng/ml and 0.2% FBS for an additional two days. Following this treatment, the medium was replaced with RPMI containing 2% FBS, FGF10 (50 ng/ml) and KAAD-cyclopamine (250 nM). Cells were cultured in this medium for four days. After this time, the medium was replaced with medium supplemented with 1x B27, containing all-trans retinoic acid (2 µM), FGF10 (50 ng/ml) and KAAD-cyclopamine (0.25 µM) for four days to induce the formation of pancreatic endoderm cells. The yield of pancreatic endoderm cells was not significantly different in cultures treated with low-glucose DMEM or DMEM/F12.

Pancreatic endoderm cells were differentiated into pancreatic endocrine cells by treating the cells with Exendin 4 and HGF. Excendin 4 (50 ng/ml) and HGF (50 ng/ml) were added for ten days in either low-glucose DMEM or DMEM/F12 for 10 days. Both media were supplemented with 1x B27. Cultures were harvested and samples of mRNA were collected for analysis. Samples were normalized to pancreatic endoderm obtained according to the methods disclosed in Nature Biotechnology 24, 1392-1401 (2006).

Insulin expression was analyzed by real-time PCR. As shown in FIG. 50, panels a and b, both insulin and glucagon gene expression were strongly increased in cells treated DMEM/F12, compared to cells treated in DMEM-low glucose. Insulin expression was also analyzed by immunohistochemistry (FIG. 51). Treatment in DMEM/F12 resulted in a larger percentage of insulin positive cells, compared to DMEM-low glucose (FIG. 51, panels a and b). Insulin positive cells were also positive for PDX-1 (panel c).

Alteration of Glucose Concentration:

Cultures of undifferentiated human embryonic stem cells (H1 and H9) were cultured according to the methods described in Example 1, prior to differentiation into pancreatic endoderm cells. Embryonic stem cells were differentiated into pancreatic endoderm cells by culturing the embryonic stem cells in RPMI containing activin A at 100 ng/ml in the absence of serum for one day. After this time, the cells were cultured in RPMI containing activin A at 100 ng/ml and 0.2% FBS for an additional two days. Following this treatment, the medium was replaced with RPMI containing 2% FBS, FGF10 (50 ng/ml) and KAAD-cyclopamine (250 nM). Cells were cultured in this medium for four days. After this time, the medium was replaced with CMRL supplemented with 1x B27, containing all trans retinoic acid (2 µM), FGF10 (50 ng/ml) and KAAD-cyclopamine (0.25 µM) for four days to induce the formation of pancreatic endoderm cells. The media was supplemented with 5, 10 or 20 mM glucose. The yield of pancreatic endoderm cells was not significantly different in cultures derived from H9 embryonic stem cells treated with 5, 10 or 20 mM glucose (FIG. 52, panel a).

Pancreatic endoderm cells were differentiated into pancreatic endocrine cells by treating the cells with CMRL supplemented with 1x B27, Exendin 4 (50 ng/ml) and HGF (50 ng/ml) for two, four or 10 days in 5, 10 or 20 mM glucose. Cultures were harvested and samples of mRNA were collected for analysis. Samples were normalized to pancreatic endoderm obtained according to the methods disclosed in Nature Biotechnology 24, 1392-1401 (2006).

FIG. 52, panels b-g show the effect of glucose on the expression of Ngn-3, NeuroD-1, Nkx2.2, Pax-4, insulin and glucagon, in cells derived from the human embryonic stem cell line H9. Ngn3 is the first transcription factor involved in determining the pancreatic endocrine fate and NeuroD1 is a direct target of Ngn3. Glucose stimulates a does-dependent increase in both Ngn3 and NeuroD1 mRNA levels. Another two critical pancreatic markers, Nkx2.2 and Pax4, also showed the similar expression pattern (FIG. 52, panels d and e). Optimal insulin and glucagon expression was observed in cells treated with 10 mM glucose for 10 days (FIG. 52, panels f and g).

Similar results for Ngn-3, NeuroD-1, Nkx2.2, Pax-4 were observed in cultures derived from the human embryonic stem cell line H1 (Table VIII). However, optimal insulin and synaptophysin expression was observed in cells treated with 20 mM glucose for 10 days (Table VIII).

C-Peptide Release from Insulin Expressing Cells Formed by the Methods of the Present Invention:

Glucose-mediated c-peptide release was monitored in insulin positive cells derived from H1 cells, that were treated in 2, 10 or 20 mM glucose. To evoke c-peptide release, cells were first incubated with Krebs-Ringer solution with bicarbonate and HEPES (KRBH; 129 mM NaCl, 4.8 mM KCl, 2.5 mM $CaCl_2$, 1.2 mM $KH_2PO_4$, 1.2 mM $MgSO_4$, 5 mM $NaHCO_3$, 10 mM HEPES, 0.1% BSA), for 1 hr. The medium was discarded and replaced with Krebs-Ringer solution containing 2 mM D-glucose. Cells were stimulated with either 20 mM glucose or 0.5 mM IBMX for 1 hr (all purchased from Sigma). The fold stimulation was calculated for each culture by dividing the C-peptide concentration in the simulation supernatant by the C-peptide concentration in the basal supernatant.

BMX stimulated C-peptide release 1.2 to 3 fold (FIG. 53). 20 mM glucose did not stimulate C-peptide release. There was no significant difference in C-peptide secretion observed between insulin positive cells formed in 2, 10 and 20 mM glucose.

Taken together, our data suggest that glucose induces the dose-dependant up regulation of the endocrine markers, Ngn3 and NeuroD1, suggesting that glucose induces the dose-dependent differentiation of human embryonic cells into pancreatic endocrine cells. The expression of insulin is also regulated by glucose in a dose-dependant manner.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE IA

LIST OF PRIMARY ANTIBODIES USED FOR FACS AND IMMUNOSTAININGANALYSIS.

| Antibody | Supplier | Isotype | Clone |
|---|---|---|---|
| SSEA-1 | Chemicon (CA) | Mouse IgM | MC-480 |
| SSEA-3 | Chemicon (CA) | Mouse IgG3 | MC-631 |
| SSEA-4 | Chemicon (CA) | Rat IgM | MC-813-70 |
| TRA 1-60 | Chemicon (CA) | Mouse IgM | TRA 1-60 |
| TRA 1-81 | Chemicon (CA) | Mouse IgM | TRA 1-81 |
| TRA 1-85 | Chemicon (CA) | Mouse IgG1 | TRA 1-85 |
| AP | R&D Systems | Mouse IgG1 | B4-78 |
| HNF3β | R&D Systems | Goat IgG | |
| PDX1 | Santa Cruz Biotechnology, INC | Goat IgG | A-17 |
| GATA4 | R&D Systems | Goat IgG | |
| Sox 17 | R&D Systems | Goat IgG | |
| CD 9 | BD | Mouse IgG1 | M-L13 |

TABLE IB

LIST OF SECONDARY CONJUGATED ANTIBODIES USED FOR FACS AND IMMUNOSTAININGANALYSIS.

| Secondary Conjugated Antibody | Supplier | Dilution |
|---|---|---|
| Goat Anti-Mouse IgG APC conjugated | Jackson ImmunoResearch (PA) | 1:200 |
| Goat Anti-Mouse IgG PE conjugated | Jackson ImmunoResearch (PA) | 1:200 |
| Donkey anti-rabbit PE or -APC conjugated | Jackson ImmunoResearch (PA) | 1:200 |
| Donkey anti-goat PE or -APC conjugated | Jackson ImmunoResearch (PA) | 1:200 |
| Goat anti-mouse IgM PE | SouthernBiotech (AL) | 1:200 |
| Goat anti-Rat IgM PE | SouthernBiotech (AL) | 1:200 |
| Goat anti-mouse IgG3 PE | SouthernBiotech (AL) | 1:200 |

TABLE IIA

CHANGES IN PROTEIN EXPRESSION IN HUMAN EMBRYONIC STEM CELLS WITH TIME, FOLLOWING ACTIVIN A TREATMENT.

| | 0-DAY | 2-DAY | 5-DAY | 8-DAY |
|---|---|---|---|---|
| SSEA-3 | 98.67% | 92.14% | 42.9% | 22.05% |
| CD9 | 92.64% | 29.42% | 7.27% | 4.1% |
| ECAM | 61.23% | 20.87% | 14.17% | 1.02% |
| NCAM | 7.33% | 5.04% | 21.1% | 8.86% |
| CXCR4 | 8.53% | 20.2% | 55.26% | 56.92% |

TABLE IIB

CHANGES IN PROTEIN EXPRESSION IN HUMAN EMBRYONIC STEM CELLS WITH TIME, FOLLOWING ACTIVIN A TREATMENT.

| | 1-day | | 3-day | | 5-day | |
|---|---|---|---|---|---|---|
| | Untreated | AA 100 ng/ml | Untreated | AA 100 ng/ml | Untreated | AA 100 ng/ml |
| CXCR4+ | 13% | 6% | 7.6% | 38% | 3% | 65.5% |
| CXCR4+ C-Kit+ | 5.32% | 2.97% | 2.9% | 31.56% | 3% | 55.21% |
| CXCR4+ EPCAM+ | 11.5% | 14.58% | 5.26% | 36.67% | 3% | 54.5% |
| CXCR4+ CD9+ | 12.27% | 8.13% | 2.72% | 24.11% | 3% | 2.1% |

TABLE IIC

CHANGES IN PROTEIN EXPRESSION IN HUMAN EMBRYONIC STEM CELLS WITH TIME, FOLLOWING ACTIVIN A TREATMENT.

| | 5-day AA treatment |
|---|---|
| CXCR4+ | 92.78% |
| CXCR4+/C-kit+ | 92.90% |
| CXCR4+/EPCAM | 87.99% |
| CXCR4+/CD99+ | 88.78% |
| CXCR4+/CD9+ | 7.03% |

TABLE III

EXPRESSION PROFILE OF PLURIPOTENCY MARKERS FOR THE EMBRYONIC STEM CELL USED IN THE PRESENT INVENTION.

| | H9 | | |
|---|---|---|---|
| Marker | FACS | RT-PCR | Staining |
| OCT3/4 | | + | + |
| SOX-2 | | + | |
| UTF-1 | | + | |
| REX-1 | | + | |
| hTERT | | + | |
| Cx 43 | | + | |
| Cx 45 | | + | |
| ABCG-2 | | + | |
| SSEA-1 | ± (36.35%) | | |
| SSEA-3 | + (94.38%) | | + |
| SSEA-4 | + (98.77%) | | + |
| TRA-1-81 | + (85.85%) | | + |
| TRA-1-60 | + (78.14%) | | + |
| TRA-1-85 | + (95.96%) | | |
| CD9 | + (92.02%) | | |
| AP | + (99%) | | + |

TABLE IV

DIFFERENTIAL EXPRESSION OF GENES BETWEEN UNDIFFERENTIATED EMBRYONIC STEM CELLS AND DEFINITIVE ENDODERM STAGE CELLS CULTURED ON EITHER MATRIGEL™ OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| D87811 | *Homo sapiens* mRNA for GATA-6, complete cds. /PROD=GATA-6/ FL=gb:U66075.1 gb:NM_005257.1 gb:D87811.1 | GATA6 | −2.12 | 0.19 | 2.82 | 2.20 | −2.56 | 0.46 | 5.34 | 1.79 |
| AW157548 | insulin-like growth factor binding protein 5 /FL=gb:M65062.1 gb:M62782.1 gb:NM_000599.1 gb:AF055033.1 | IGFBP5 | −3.28 | 0.17 | 3.31 | 2.11 | −3.78 | 0.36 | 5.35 | 2.00 |
| NM_001898 | *Homo sapiens* cystatin SN (CST1), mRNA. /PROD=cystatin SN /FL=gb:J03870.1 gb:NM_001898.1 | CST4 | −2.15 | 1.26 | 2.54 | 1.95 | −2.71 | 0.98 | 4.64 | 1.63 |
| AK000680 | *Homo sapiens* cDNA FLJ20673 fis, clone KAIA4464. /FL=gb:AF240634.1 gb:NM_018440.1 | PAG1 | −2.87 | 0.91 | 1.61 | 0.22 | −4.08 | 0.50 | 1.68 | 0.10 |
| NM_022642 | *Homo sapiens* chorionic somatomammotropin hormone 1 (placental lactogen) (CSH1), transcript variant 4, mRNA. /PROD=chorionic somatomammotropin hormone 1, isoform4 /FL=gb:NM_022642.1 | — | −2.24 | 0.12 | 2.97 | 0.42 | −3.78 | 0.07 | 2.51 | 0.44 |
| NM_001317 | *Homo sapiens* chorionic somatomammotropin hormone 1 (placental lactogen) (CSH1), transcript variant 1, mRNA. /PROD=chorionic somatomammotropin hormone 1, isoform 1precursor /FL=gb:NM_001317.2 gb:J00118.1 | CSH1 | −2.95 | 0.57 | 2.69 | 0.36 | −4.04 | 0.51 | 1.86 | 0.68 |
| BC005921 | *Homo sapiens*, chorionic somatomammotropin hormone 1 (placental lactogen), clone MGC:14518, mRNA, complete cds. /PROD=chorionic somatomammotropin hormone 1 (placentallactogen) /FL=gb:BC005921.1 | CSH1 | −2.26 | 0.09 | 3.26 | 0.23 | −2.96 | 0.37 | 2.58 | 0.45 |
| AI796169 | GATA-binding protein 3 /FL=gb:NM_002051.1 gb:M69106.1 gb:BC003070.1 | GATA3 | −4.45 | 0.10 | 0.24 | 1.30 | −4.72 | 0.13 | 0.80 | 2.05 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_020991 | Homo sapiens chorionic somatomammotropin hormone 2 (CSH2), transcript variant 1, mRNA. /PROD=chorionic somatomammotropin hormone 2, isoform 1precursor /FL=gb:NM_020991.2 gb:BC002717.1 | CSH1 | −1.27 | 0.48 | 3.19 | 0.23 | −2.91 | 0.35 | 2.62 | 0.54 |
| NM_021827 | Homo sapiens hypothetical protein FLJ23514 (FLJ23514), mRNA. /PROD=hypothetical protein FLJ23514 /FL=gb:NM_021827.1 | CCDC81 | −0.37 | 0.35 | 3.16 | 2.05 | −2.02 | 1.27 | 5.25 | 1.98 |
| AB028021 | Cluster Incl. AB028021: Homo sapiens HNF-3beta mRNA for hepatocyte nuclear factor-3 beta, complete cds /cds=(196,1569) /gb=AB028021 /gi=4958949 /ug=Hs.155651 /len=1944 | FOXA2 | −2.97 | 0.25 | 0.59 | 3.25 | −3.43 | 0.57 | 4.12 | 2.57 |
| NM_002521 | Homo sapiens natriuretic peptide precursor B (NPPB), mRNA. /PROD=natriuretic peptide precursor B /FL=gb:NM_002521.1 gb:M25296.1 | NPPB | 1.54 | 0.11 | 5.47 | 1.17 | −0.15 | 0.38 | 6.24 | 1.23 |
| AA352113 | ESTs | ST8SIA4 | −4.01 | 1.24 | −0.99 | 2.04 | −4.79 | 1.00 | 1.05 | 1.62 |
| BM128432 | Homo sapiens full length insert cDNA clone YA81B05 | IGFBP5 | −2.73 | 1.11 | 2.31 | 2.30 | −3.48 | 0.56 | 4.45 | 2.02 |
| NM_002770 | Homo sapiens protease, serine, 2 (trypsin 2) (PRSS2), mRNA. /PROD=protease, serine, 2 (trypsin 2) /FL=gb:M27602.1 gb:NM_002770.1 | PRSS1 | −2.77 | 0.33 | 1.59 | 2.68 | −3.13 | 0.48 | 3.88 | 2.95 |
| NM_022579 | Homo sapiens chorionic somatomammotropin hormone-like 1 (CSHL1), transcript variant 3, mRNA. /PROD=chorionic somatomammotropin hormone-like 1, isoform 3 precursor /FL=gb:NM_022579.1 | CSH1 | −1.58 | 0.91 | 2.48 | 0.38 | −3.33 | 0.13 | 1.77 | 0.49 |
| NM_005454 | Homo sapiens cerberus 1 (Xenopus laevis) homolog (cysteine knot superfamily) (CER1), mRNA. /PROD=cerberus 1 /FL=gb:NM_005454.1 | CER1 | 2.82 | 0.09 | 5.78 | 1.04 | 1.48 | 0.05 | 6.74 | 1.18 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_022645 | *Homo sapiens* chorionic somatomammotropin hormone 2 (CSH2), transcript variant 3, mRNA. /PROD=chorionic somatomammotropin hormone 2, isoform 3precursor /FL=gb:NM_022645.1 | CSH1 | −2.30 | 0.33 | 2.95 | 0.31 | −2.78 | 0.24 | 2.45 | 0.34 |
| AI821586 | ESTs, Moderately similar to JE0284 Mm-1 cell derived transplantability-associated protein 1b (*H. sapiens*) | LOC440981 | −3.22 | 0.97 | 0.66 | 3.19 | −2.97 | 0.13 | 4.22 | 2.76 |
| AL121722 | Human DNA sequence from clone RP4-788L20 on chromosome 20 Contains the HNF3B (hepatocyte nuclear factor 3, beta) gene. a novel gene based on ESTs, ESTs, STSs, GSSs and CpG Islands | — | −2.95 | 0.36 | −0.01 | 2.69 | −3.43 | 0.38 | 2.95 | 2.66 |
| NM_001311 | *Homo sapiens* cysteine-rich protein 1 (intestinal) (CRIP1), mRNA. /PROD=cysteine-rich protein 1 (intestinal) /FL=gb:U58630.1 gb:BC002738.1 gb:NM_001311.1 gb:U09770.1 | CRIP1 | 1.66 | 0.17 | 1.90 | 0.07 | −2.96 | 0.66 | 1.80 | 0.24 |
| AY177407 | *Homo sapiens* homeobox protein goosecoid mRNA, complete cds. /PROD=homeobox protein goosecoid /FL=gb:AY177407.1 gb:NM_173849.1 | GSC | −4.59 | 0.18 | −1.08 | 2.89 | −4.64 | 0.06 | 1.89 | 2.79 |
| NM_005442 | *Homo sapiens* eomesodermin (*Xenopus laevis*) homolog (EOMES), mRNA. /PROD=eomesodermin (*Xenopus laevis*) homolog /FL=gb:AB031038.1 gb:NM_005442.1 | EOMES | −0.16 | 0.29 | 2.89 | 1.70 | 0.13 | 0.16 | 4.90 | 1.34 |
| L01639 | Human (clone HSY3RR) neuropeptide Y receptor (NPYR) mRNA, complete cds. /PROD=neuropeptide Y receptor /FL=gb:L06797.1 gb:NM_003467.1 gb:AF025375.1 gb:AF147204.1 gb:M99293.1 gb:L01639.1 | CXCR4 | 0.64 | 0.26 | 3.71 | 1.78 | −0.16 | 0.50 | 5.48 | 1.77 |

TABLE IV-continued

DIFFERENTIAL EXPRESSION OF GENES BETWEEN UNDIFFERENTIATED EMBRYONIC STEM CELLS AND DEFINITIVE ENDODERM STAGE CELLS CULTURED ON EITHER MATRIGELTM OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_022646 | Homo sapiens chorionic somatomammotropin hormone 2 (CSH2), transcript variant 4, mRNA. /PROD=chorionic somatomammotropin hormone 2, isoform4 /FL=gb:NM_022646.1 | — | −1.57 | 0.60 | 2.67 | 0.26 | −1.88 | 0.98 | 2.22 | 0.35 |
| AW007532 | Human insulin-like growth factor binding protein 5 (IGFBP5) mRNA | IGFBP5 | 0.31 | 0.25 | 4.59 | 1.53 | 0.72 | 0.09 | 6.19 | 1.58 |
| NM_002160 | Homo sapiens hexabrachion (tenascin C, cytotactin) (HXB), mRNA. /PROD=hexabrachion (tenascin C, cytotactin) /FL=gb:M55618.1 gb:NM_002160.1 | TNC | −0.24 | 0.29 | 2.23 | 0.80 | −0.81 | 0.81 | 2.85 | 0.82 |
| AA149250 | ESTs, Weakly similar to WDNM RAT WDNM1 PROTEIN PRECURSOR (R. norvegicus) | LOC645638 | 1.27 | 0.61 | 4.23 | 1.26 | −0.64 | 0.40 | 2.47 | 1.23 |
| AW977527 | ESTs | — | −0.91 | 0.99 | 1.18 | 0.68 | −2.52 | 1.01 | 1.59 | 0.64 |
| NM_022454 | Homo sapiens hypothetical protein FLJ22252 similar to SRY-box containing gene 17 (FLJ22252), mRNA. /PROD=hypothetical protein FLJ22252 similar to SRY-boxcontaining gene 17 /FL=gb:NM_022454.1 | SOX17 | −1.01 | 0.33 | 2.29 | 2.08 | −0.14 | 0.15 | 4.60 | 1.73 |
| AI640307 | protocadherin 10 | PCDH10 | −1.89 | 1.37 | 1.53 | 1.32 | −1.33 | 0.38 | 2.99 | 1.19 |
| AJ224869 | Homo sapiens CXCR4 gene encoding receptor CXCR4 | — | 0.98 | 0.18 | 4.22 | 1.88 | 1.34 | 0.17 | 6.36 | 1.49 |
| AI824037 | ESTs, Weakly similar to FCE2 MOUSE LOW AFFINITY IMMUNOGLOBULIN EPSILON FC RECEPTOR (M. musculus) | FREM1 | −1.42 | 0.36 | 1.22 | 1.95 | −1.37 | 0.61 | 3.48 | 1.49 |
| BE222344 | splicing factor, arginineserine-rich 5 | — | 0.50 | 0.05 | 3.01 | 0.93 | −0.94 | 1.18 | 4.27 | 0.94 |
| NM_001643 | Homo sapiens apolipoprotein A-II (APOA2), mRNA. /PROD=apolipoprotein A-II precursor /FL=gb:M29882.1 gb:NM_001643.1 gb:BC005282.1 | APOA2 | −2.25 | 1.05 | 1.72 | 2.60 | −1.20 | 0.44 | 4.47 | 2.42 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI821669 | ESTs | — | −0.94 | 0.79 | 1.71 | 2.19 | −0.89 | 0.21 | 3.91 | 1.94 |
| NM_002608 | Homo sapiens platelet-derived growth factor beta polypeptide (simian sarcoma viral (v-sis) oncogene homolog) (PDGFB), mRNA. /PROD=platelet-derived growth factor beta polypeptide(simian sarcoma viral (v-sis) oncogene homolog) /FL=gb:M12783.1 gb:NM_002 | PDGFB | −0.23 | 0.82 | 1.87 | 0.15 | −2.27 | 0.65 | 1.92 | 0.13 |
| AW444761 | ESTs | CDKN2B | −3.35 | 0.90 | 0.39 | 0.52 | −3.11 | 0.88 | 0.80 | 0.25 |
| BF223214 | ESTs | — | −0.48 | 0.08 | 1.69 | 2.04 | −1.51 | 0.25 | 4.09 | 1.98 |
| AF154054 | Homo sapiens DRM (DRM) mRNA, complete cds. /PROD=DRM /FL=gb:NM_013372.1 gb:AF110137.2 gb:AF045800.1 gb:AF154054.1 | GREM1 | 1.68 | 0.26 | 4.61 | 0.74 | 0.62 | 0.04 | 3.58 | 0.87 |
| NM_021223 | Homo sapiens myosin light chain 2a (LOC58498), mRNA. /PROD=myosin light chain 2a /FL=gb:NM_021223.1 | MYL7 | 1.81 | 0.05 | 4.28 | 0.81 | 0.17 | 0.08 | 4.87 | 0.96 |
| AI817041 | G protein-coupled receptor | CMKOR1 | −0.19 | 0.27 | 2.67 | 1.97 | 0.06 | 0.18 | 5.05 | 1.64 |
| NM_003670 | Homo sapiens basic helix-loop-helix domain containing, class B, 2 (BHLHB2), mRNA. /PROD=differentiated embryo chondrocyte expressed gene1 /FL=gb:AB004066.1 gb:NM_003670.1 | BHLHB2 | 1.09 | 0.08 | 3.85 | 0.10 | −0.11 | 0.17 | 3.46 | 0.03 |
| NM_023915 | Homo sapiens G protein-coupled receptor 87 (GPR87), mRNA. /PROD=G protein-coupled receptor 87 /FL=gb:NM_023915.1 gb:AF237763.1 | GPR87 | −1.70 | 0.61 | 1.64 | 0.18 | −2.99 | 0.06 | 1.40 | 0.23 |
| NM_003867 | Homo sapiens fibroblast growth factor 17 (FGF17), mRNA. /PROD=fibroblast growth factor 17 /FL=gb:NM_003867.1 gb:AB009249.1 | FGF17 | −3.05 | 0.39 | 0.03 | 2.07 | −2.13 | 0.41 | 2.49 | 1.35 |
| NM_024426 | Homo sapiens Wilms tumor 1 (WT1), transcript variant D, mRNA. /PROD=Wilms tumor 1 isoform D /FL=gb:NM_024424.1 gb:NM_024426.1 | WT1 | −3.23 | 0.37 | −1.11 | 0.62 | −4.20 | 0.56 | −2.44 | 1.26 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_033136 | *Homo sapiens* fibroblast growth factor 1 (acidic) (FGF1), transcript variant 2, mRNA. /PROD=fibroblast growth factor 1 (acidic) isoform 2precursor /FL=gb:NM_033137.1 gb:NM_033136.1 | FGF1 | −3.10 | 1.42 | 0.09 | 0.83 | −3.16 | 0.63 | −0.78 | 1.21 |
| X99268 | *H. sapiens* mRNA for B-HLH DNA binding protein. /PROD=B-HLH DNA binding protein /FL=gb:NM_000474.1 | TWIST1 | 0.10 | 0.33 | 3.94 | 0.24 | 0.34 | 0.22 | 3.45 | 0.34 |
| AL524520 | G protein-coupled receptor 49 | LGR5 | −2.27 | 1.43 | 0.76 | 1.40 | −1.58 | 0.40 | 2.51 | 1.35 |
| NM_022557 | *Homo sapiens* growth hormone 2 (GH2), transcript variant 2, mRNA. /PROD=growth hormone 2, isoform 2 precursor /FL=gb:J03756.1 gb:NM_022557.1 | CSH1 | −0.91 | 0.19 | 1.40 | 0.22 | −2.12 | 0.08 | 1.47 | 0.14 |
| AL544576 | ESTs | TMEM88 | −1.96 | 0.68 | 1.75 | 0.58 | −1.45 | 0.86 | 2.08 | 0.70 |
| NM_022580 | *Homo sapiens* chorionic somatomammotropin hormone-like 1 (CSHL1), transcript variant 4, mRNA. /PROD=chorionic somatomammotropin hormone-like 1, isoform 4 /FL=gb:NM_022580.1 | CSH1 | −1.20 | 0.86 | 2.30 | 0.39 | −1.78 | 0.64 | 1.55 | 0.63 |
| J03580 | Human, parathyroid-like protein (associated with humoral hypercalcemia of malignancy) mRNA, complete cds. /FL=gb:J03580.1 | PTHLH | −2.72 | 0.33 | −0.80 | 0.40 | −4.05 | 0.41 | −1.42 | 0.73 |
| BC029835 | *Homo sapiens*, clone IMAGE:5169759, mRNA. | LOC646867 | −2.66 | 1.12 | 1.01 | 1.85 | −1.40 | 0.41 | 3.03 | 1.61 |
| AI452798 | ESTs | MYOCD | 0.98 | 0.13 | 3.31 | 0.66 | −0.07 | 0.28 | 2.80 | 0.98 |
| NM_022559 | *Homo sapiens* growth hormone 1 (GH1), transcript variant 2, mRNA. /PROD=growth hormone 1, isoform 2 precursor /FL=gb:NM_022559.1 | CSH1 | −1.56 | 0.38 | 2.00 | 0.32 | −2.07 | 0.42 | 1.47 | 0.28 |
| NM_001318 | *Homo sapiens* chorionic somatomammotropin hormone-like 1 (CSHL1), transcript variant 1, mRNA. /PROD=chorionic somatomammotropin hormone-like 1, isoform 1 /FL=gb:NM_001318.2 | CSH1 | 0.15 | 0.41 | 2.83 | 0.40 | −1.30 | 0.34 | 2.37 | 0.50 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| M65062 | Human insulin-like growth factor binding protein 5 (IGFBP-5) mRNA, complete cds. /PROD=insulin-like growth factor binding protein 5 /FL=gb:M65062.1 gb:M62782.1 gb:NM_000599.1 gb:AF055033.1 | IGFBP5 | −2.80 | 1.17 | 2.19 | 2.00 | −0.99 | 0.23 | 4.11 | 1.81 |
| AF207990 | Homo sapiens fer-1 like protein 3 (FER1L3) mRNA, complete cds. /PROD=fer-1 like protein 3 /FL=gb:AF207990.1 | FER1L3 | 0.49 | 0.40 | 3.00 | 0.81 | −0.16 | 0.09 | 4.02 | 0.92 |
| AI079944 | ESTs | — | −0.78 | 0.22 | 0.08 | 0.59 | −3.56 | 0.24 | −0.13 | 0.73 |
| BC003070 | Homo sapiens, GATA-binding protein 3, clone MGC:2346, mRNA, complete cds. /PROD=GATA-binding protein 3 /FL=gb:NM_002051.1 gb:M69106.1 gb:BC003070.1 | GATA3 | 1.07 | 0.04 | 3.23 | 0.96 | 0.31 | 0.26 | 4.45 | 0.80 |
| BE877796 | collagen, type VIII, alpha 1 /FL=gb:NM_001850.1 | COL8A1 | −3.76 | 1.17 | −1.28 | 0.73 | −4.89 | 0.54 | −1.33 | 1.64 |
| NM_022560 | Homo sapiens growth hormone 1 (GH1), transcript variant 3, mRNA. /PROD=growth hormone 1, isoform 3 precursor /FL=gb:NM_022560.1 | CSH1 | −2.23 | 0.74 | 1.95 | 0.08 | −2.01 | 0.51 | 1.47 | 0.31 |
| BE328496 | hypothetical protein PRO2032 /FL=gb:AF116683.1 gb:NM_018615.1 | — | −0.59 | 0.25 | 1.76 | 0.13 | −2.01 | 0.97 | 1.73 | 0.26 |
| NM_022469 | Homo sapiens hypothetical protein FLJ21195 similar to protein related to DAC and cerberus (FLJ21195), mRNA. /PROD=hypothetical protein FLJ21195 similar to proteinrelated to DAC and cerberus /FL=gb:NM_022469.1 | GREM2 | −1.15 | 0.25 | 0.09 | 0.88 | −3.43 | 0.90 | 0.76 | 0.47 |
| NM_001362 | Homo sapiens deiodinase, iodothyronine, type III (DIO3), mRNA. /PROD=thyroxine deiodinase type III /FL=gb:NM_001362.1 gb:S79854.1 | DIO3 | −1.73 | 0.70 | 1.99 | 1.92 | −1.05 | 0.79 | 4.23 | 1.51 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_022581 | *Homo sapiens* chorionic somatomammotropin hormone-like 1 (CSHL1), transcript variant 5, mRNA. /PROD=chorionic somatomammotropin hormone-like 1, isoform 5 precursor /FL=gb:NM_022581.1 | CSH1 | −1.56 | 0.67 | 2.08 | 0.42 | −1.63 | 0.80 | 1.47 | 0.53 |
| NM_013372 | *Homo sapiens* cysteine knot superfamily 1, BMP antagonist 1 (CKTSF1B1), mRNA. /PROD=cysteine knot superfamily 1, BMP antagonist 1 /FL=gb:NM_013372.1 gb:AF110137.2 gb:AF045800.1 gb:AF154054.1 | GREM1 | 1.61 | 0.07 | 4.15 | 0.64 | 0.91 | 0.15 | 3.20 | 0.81 |
| NM_022561 | *Homo sapiens* growth hormone 1 (GH1), transcript variant 4, mRNA. /PROD=growth hormone 1, isoform 4 precursor /FL=gb:NM_022561.1 | CSH1 | −1.32 | 0.60 | 1.91 | 0.25 | −1.66 | 0.46 | 1.57 | 0.22 |
| NM_022659 | *Homo sapiens* hypothetical protein FLJ11500 similar to EBF2 (FLJ11500), mRNA. /PROD=hypothetical protein FLJ11500 similar to EBF2 /FL=gb:NM_022659.1 | — | −1.58 | 0.75 | −1.24 | 1.79 | −3.62 | 0.20 | −1.81 | 1.25 |
| AF006060 | *Homo sapiens* placental growth hormone 20 kDa isoform (hGH-V) mRNA, complete cds. /PROD=placental growth hormone 20 kDa isoform /FL=gb:AF006060.1 gb:NM_022556.1 | CSH1 | −1.21 | 0.06 | 1.13 | 0.05 | −3.08 | 0.63 | 0.50 | 0.17 |
| AI688418 | plexin A2 | PLXNA2 | −0.18 | 0.14 | 0.84 | 1.58 | −1.28 | 0.53 | 2.74 | 0.96 |
| M86849 | *Homo sapiens* connexin 26 (GJB2) mRNA, complete cds. /PROD=connexin 26 /FL=gb:NM_004004.1 gb:M86849.2 | — | −5.08 | 0.26 | 0.54 | 0.47 | −1.64 | 0.19 | −0.09 | 0.44 |
| N71923 | fibronectin leucine rich transmembrane protein 3 /FL=gb:AF169677.1 gb:NM_013281.1 | — | 0.30 | 0.24 | 2.83 | 1.46 | 0.53 | 0.12 | 4.38 | 1.46 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_013281 | *Homo sapiens* fibronectin leucine rich transmembrane protein 3 (FLRT3), mRNA. /PROD=fibronectin leucine rich transmembrane protein3 /FL=gb:AF169677.1 gb:NM_013281.1 | FLRT3 | −0.20 | 0.33 | 2.14 | 1.61 | 0.00 | 0.15 | 3.96 | 1.39 |
| AI601101 | *Homo sapiens* cDNA: FLJ21410 fis, clone COL03938 | FAM84A | 0.46 | 0.38 | 3.07 | 0.46 | −0.32 | 0.46 | 3.82 | 0.48 |
| NM_000325 | *Homo sapiens* paired-like homeodomain transcription factor 2 (PITX2), mRNA. /PROD=paired-like homeodomain transcription factor 2 /FL=gb:NM_000325.1 gb:U69961.1 gb:AF048720.1 | PITX2 | 1.37 | 0.17 | 3.51 | 0.47 | 0.89 | 0.16 | 4.02 | 0.47 |
| AI692659 | heat shock 90 kD protein 1, alpha | PRDM1 | 0.21 | 0.25 | 1.67 | 0.77 | −0.67 | 0.17 | 2.61 | 0.80 |
| NM_000602 | *Homo sapiens* serine (or cysteine) proteinase inhibitor, clade E (nexin, plasminogen activator inhibitor type 1), member 1 (SERPINE1), mRNA. /PROD=serine (or cysteine) proteinase inhibitor, cladeE (nexin, plasminogen activator inhibitor type 1), membe | SERPINE1 | 2.97 | 0.16 | 4.75 | 1.89 | 1.55 | 0.22 | 2.75 | 1.87 |
| NM_001480 | *Homo sapiens* galanin receptor 1 (GALR1), mRNA. /PROD=galanin receptor 1 /FL=gb:NM_001480.2 gb:U23854.1 gb:L34339.1 gb:U53511.1 | GALR1 | −1.90 | 0.68 | 0.04 | 0.73 | −2.42 | 0.72 | −0.34 | 0.73 |
| NM_000393 | *Homo sapiens* collagen, type V, alpha 2 (COL5A2), mRNA. /PROD=collagen, type V, alpha 2 /FL=gb:NM_000393.1 | COL5A2 | 4.29 | 0.14 | 5.25 | 0.21 | 2.62 | 0.02 | 5.48 | 0.13 |
| N63706 | ESTs | — | 0.06 | 0.18 | 1.73 | 1.89 | −0.74 | 0.13 | 3.75 | 1.75 |
| AF132818 | *Homo sapiens* colon Kruppel-like factor (CKLF) mRNA, complete cds. /PROD=colon Kruppel-like factor /FL=gb:AF132818.1 gb:AF287272.1 gb:AB030824.1 gb:NM_001730.1 gb:D14520.1 | KLF5 | 0.63 | 0.11 | 3.16 | 0.50 | 0.07 | 0.42 | 3.40 | 0.44 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| X59065 | H. sapiens FGF gene, exon 3 /FL=gb:NM_000800.1 gb:M13361.1 | — | −1.17 | 1.11 | −0.39 | 1.06 | −2.61 | 0.26 | −0.96 | 1.01 |
| R73554 | Human insulin-like growth factor binding protein 5 (IGFBP5) mRNA | IGFBP5 | −0.12 | 0.15 | 2.63 | 1.41 | −0.69 | 0.16 | 4.00 | 1.65 |
| NM_002149 | Homo sapiens hippocalcin-like 1 (HPCAL1), mRNA. /PROD=hippocalcin-like 1 /FL=gb:NM_002149.1 gb:D16227.1 | HPCAL1 | −0.18 | 0.28 | 1.81 | 0.44 | −1.98 | 0.86 | 1.18 | 0.22 |
| AI093327 | ESTs | — | 0.69 | 0.11 | 3.09 | 0.58 | 0.45 | 0.07 | 2.29 | 0.85 |
| NM_003240 | Homo sapiens endometrial bleeding associated factor (left-right determination, factor A; transforming growth factor beta superfamily) (EBAF), mRNA. /PROD=transforming growth factor, beta 4 /FL=gb:U81523.1 gb:NM_003240.1 gb:AF081513.1 | PYCR2 | 6.22 | 0.16 | 6.97 | 0.60 | 4.16 | 0.07 | 7.51 | 0.68 |
| AI263909 | ras homolog gene family, member B /FL=gb:NM_004040.1 | RHOB | 3.89 | 0.16 | 5.88 | 0.13 | 3.01 | 0.15 | 5.64 | 0.10 |
| NM_001792 | Homo sapiens cadherin 2, type 1, N-cadherin (neuronal) (CDH2), mRNA. /PROD=cadherin 2, type 1, N-cadherin (neuronal) /FL=gb:NM_001792.1 gb:M34064.1 | CDH2 | 3.83 | 0.17 | 6.01 | 0.11 | 2.85 | 0.13 | 5.74 | 0.17 |
| NM_003897 | Homo sapiens immediate early response 3 (IER3), mRNA. /PROD=immediate early response 3 /FL=gb:BC005080.1 gb:BC000844.1 gb:AF083421.1 gb:NM_003897.1 | IER3 | 5.45 | 0.15 | 6.97 | 0.17 | 4.33 | 0.11 | 6.75 | 0.27 |
| AF278532 | Homo sapiens beta-netrin mRNA, complete cds. /PROD=beta-netrin /FL=gb:AF119916.1 gb:AF297711.1 gb:NM_021229.1 gb:AF278532.1 | NTN4 | −0.16 | 0.30 | 1.70 | 0.91 | −0.67 | 0.48 | 2.66 | 0.74 |
| AF348491 | Homo sapiens chemokine receptor CXCR4 mRNA, complete cds. /PROD=chemokine receptor CXCR4 /FL=gb:AF348491.1 | CXCR4 | 1.39 | 0.21 | 4.05 | 1.58 | 1.45 | 0.07 | 5.67 | 1.65 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_030781 | Homo sapiens scavenger receptor with C-type lectin (SRCL), mRNA. /PROD=scavenger receptor with C-type lectin /FL=gb:NM_030781.1 | COLEC12 | 1.93 | 0.13 | 3.64 | 1.66 | 1.96 | 0.18 | 5.68 | 1.51 |
| NM_000599 | Homo sapiens insulin-like growth factor binding protein 5 (IGFBP5), mRNA. /PROD=insulin-like growth factor binding protein 5 /FL=gb:M65062.1 gb:M62782.1 gb:NM_000599.1 gb:AF055033.1 | IGFBP5 | −0.31 | 0.34 | 3.03 | 1.85 | 0.12 | 0.24 | 4.51 | 1.75 |
| AI348094 | KIAA0882 protein | TBC1D9 | 0.13 | 0.26 | 3.21 | 1.13 | 0.96 | 0.13 | 4.67 | 1.08 |
| BG287862 | AHNAK nucleoprotein (desmoyokin) | AHNAK | 1.47 | 0.20 | 3.72 | 0.51 | 1.37 | 0.17 | 4.34 | 0.58 |
| AI676059 | ESTs | FOXQ1 | −0.32 | 0.55 | 3.08 | 1.63 | 0.50 | 0.17 | 4.81 | 1.47 |
| AI127440 | ESTs | — | −0.85 | 0.36 | 0.60 | 1.22 | −0.65 | 0.27 | 2.13 | 1.13 |
| AL574210 | serine (or cysteine) proteinase inhibitor, clade E (nexin, plasminogen activator inhibitor type 1), member 1 /FL=gb:NM_000602.1 gb:M16006.1 | SERPINE1 | 2.81 | 0.24 | 5.07 | 0.88 | 2.13 | 0.15 | 3.96 | 0.86 |
| AB037810 | Homo sapiens mRNA for KIAA1389 protein, partial cds. /PROD=KIAA1389 protein | SIPA1L2 | 3.88 | 0.04 | 5.66 | 0.08 | 3.18 | 0.11 | 5.85 | 0.11 |
| NM_001394 | Homo sapiens dual specificity phosphatase 4 (DUSP4), mRNA. /PROD=dual specificity phosphatase 4 /FL=gb:NM_001394.2 gb:BC002671.1 gb:U48807.1 gb:U21108.1 | DUSP4 | 0.22 | 0.37 | 2.88 | 1.09 | 0.50 | 0.14 | 4.12 | 0.99 |
| BC029442 | Homo sapiens, Similar to immunity associated protein 1, clone MGC:32707 IMAGE:4618467, mRNA, complete cds. /PROD=Similar to immunity associated protein 1 /FL=gb:BC029442.1 | — | 2.04 | 0.20 | 3.80 | 0.74 | 1.18 | 0.05 | 4.50 | 0.65 |
| NM_000700 | Homo sapiens annexin A1 (ANXA1), mRNA. /PROD=annexin I /FL=gb:BC001275.1 gb:NM_000700.1 | ANXA1 | 5.00 | 0.18 | 6.27 | 1.28 | 3.67 | 0.05 | 4.96 | 1.25 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC000740 | Homo sapiens, cholecystokinin B receptor, clone MGC:2199, mRNA, complete cds. /PROD=cholecystokinin B receptor /FL=gb:L07746.1 gb:L08112.1 gb:S70057.1 gb:BC000740.1 gb:L04473.1 gb:NM_000731.1 | CCKBR | 1.08 | 0.36 | 3.93 | 1.84 | 1.93 | 0.03 | 5.86 | 1.82 |
| N36408 | hypothetical protein FLJ23306 /FL=gb:NM_024530.1 | FOSL2 | −0.09 | 0.40 | 2.07 | 0.04 | −0.85 | 0.24 | 1.71 | 0.28 |
| AF072242 | Homo sapiens methyl-CpG binding protein MBD2 (MBD2) mRNA, complete cds. /PROD=methyl-CpG binding protein MBD2 /FL=gb:NM_003927.2 gb:AF072242.1 | MBD2 | −3.98 | 0.38 | −0.59 | 0.27 | −3.07 | 0.22 | −1.70 | 0.68 |
| AF211891 | Homo sapiens Mix-like homeobox protein 1 (MILD1) mRNA, complete cds. /PROD=Mix-like homeobox protein 1 /FL=gb:AF211891.1 | MIXL1 | −0.63 | 0.38 | 0.77 | 0.95 | −2.29 | 0.44 | 0.92 | 1.71 |
| BF063186 | ESTs | CALD1 | 1.16 | 0.19 | 2.03 | 0.42 | −1.20 | 1.02 | 1.65 | 0.27 |
| NM_000362 | Homo sapiens tissue inhibitor of metalloproteinase 3 (Sorsby fundus dystrophy, pseudoinflammatory) (TIMP3), mRNA. /PROD=tissue inhibitor of metalloproteinase 3precursor /FL=gb:NM_000362.2 gb:U14394.1 gb:U67195.1 gb:U02571.1 | TIMP3 | 0.08 | 0.32 | 1.98 | 0.09 | −0.34 | 0.33 | 1.80 | 0.26 |
| AK022852 | Homo sapiens cDNA FLJ12790 fis, clone NT2RP2001985, weakly similar to Homo sapiens high-risk human papilloma viruses E6 oncoproteins targeted protein E6TP1 alpha mRNA. | SIPA1L2 | 2.87 | 0.12 | 4.50 | 0.09 | 1.87 | 0.01 | 4.55 | 0.09 |
| BE500942 | Homo sapiens mRNA; cDNA DKFZp761M0111 (from clone DKFZp761M0111) | C6orf155 | 3.23 | 0.10 | 4.68 | 0.86 | 1.95 | 0.03 | 3.77 | 0.96 |
| AW665892 | paternally expressed 3 | MFAP5 | −1.82 | 0.54 | 0.37 | 0.60 | −1.54 | 0.39 | −0.01 | 0.28 |
| AK025063 | Homo sapiens cDNA: FLJ21410 fis, clone COL03938. | FAM84A | −1.34 | 0.84 | 0.75 | 0.45 | −2.35 | 0.85 | 1.01 | 0.53 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_001828 | Homo sapiens Charot-Leyden crystal protein (CLC), mRNA. /PROD=Charot-Leyden crystal protein /FL=gb:NM_001828.3 gb:L01664.1 | CLC | 2.17 | 0.21 | 3.53 | 1.07 | 0.45 | 0.08 | 2.11 | 1.27 |
| M15329 | Human interleukin 1-alpha (IL1A) mRNA, complete cds. /PROD=interleukin 1-alpha /FL=gb:M15329.1 | IL1A | 0.85 | 0.32 | 2.72 | 0.30 | −0.88 | 0.60 | 2.20 | 0.22 |
| BC002671 | Homo sapiens, dual specificity phosphatase 4, clone MGC:3713, mRNA, complete cds. /PROD=dual specificity phosphatase 4 /FL=gb:NM_001394.2 gb:BC002671.1 gb:U48807.1 gb:U21108.1 | DUSP4 | 1.79 | 0.03 | 4.30 | 1.39 | 2.10 | 0.10 | 5.60 | 1.22 |
| AA524250 | deleted in liver cancer 1 | DLC1 | 1.02 | 0.05 | 2.35 | 0.98 | 0.10 | 0.38 | 3.26 | 0.96 |
| BC001211 | Homo sapiens, kinesin family member C3, clone MGC:3226, mRNA, complete cds. /PROD=kinesin family member C3 /FL=gb:BC001211.1 gb:NM_005550.1 gb:AF004426.1 | KIFC3 | −1.53 | 0.72 | 0.81 | 0.38 | −2.08 | 0.42 | 0.75 | 0.16 |
| NM_004560 | Homo sapiens receptor tyrosine kinase-like orphan receptor 2 (ROR2), mRNA. /PROD=receptor tyrosine kinase-like orphan receptor 2 /FL=gb:M97639.1 gb:NM_004560.1 | ROR2 | 0.76 | 0.08 | 2.20 | 0.81 | 0.08 | 0.14 | 3.06 | 0.95 |
| BC000125 | Homo sapiens, Similar to transforming growth factor, beta 1, clone MGC:3119, mRNA, complete cds. /PROD=Similar to transforming growth factor, beta 1 /FL=gb:M38449.1 gb:BC001180.1 gb:BC000125.1 gb:NM_000660.1 | TGFB1 | 1.16 | 0.18 | 3.43 | 0.08 | 0.72 | 0.14 | 3.30 | 0.16 |
| NM_016931 | Homo sapiens NADPH oxidase 4 (NOX4), mRNA. /PROD=NADPH oxidase 4 /FL=gb:AF261943.1 gb:NM_016931.1 gb:AF254621.1 gb:AB041035.1 | NOX4 | 1.83 | 0.06 | 3.31 | 1.29 | 1.20 | 0.14 | 2.28 | 1.27 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC001830 | *Homo sapiens*, Similar to transforming growth factor beta 1 induced transcript 1, clone MGC:4078, mRNA, complete cds. /PROD=Similar to transforming growth factor beta 1induced transcript 1 /FL=gb:NM_015927.1 gb:BC001830.1 gb:AF116343.1 | TGFB1I1 | 0.95 | 0.17 | 3.59 | 0.73 | 1.52 | 0.09 | 2.74 | 0.69 |
| NM_024576 | *Homo sapiens* hypothetical protein FLJ21079 (FLJ21079), mRNA. /PROD=hypothetical protein FLJ21079 /FL=gb:NM_024576.1 | OGFRL1 | 3.15 | 0.13 | 4.49 | 0.82 | 1.63 | 0.06 | 3.30 | 0.98 |
| NM_001963 | *Homo sapiens* epidermal growth factor (beta-urogastrone) (EGF), mRNA. /PROD=epidermal growth factor (beta-urogastrone) /FL=gb:NM_001963.2 | EGF | 0.12 | 0.22 | 1.82 | 1.15 | −0.62 | 0.36 | 2.68 | 1.23 |
| BE620374 | ESTs | C6orf155 | 1.97 | 0.05 | 3.35 | 1.01 | 0.59 | 0.17 | 2.10 | 1.05 |
| AL359062 | *Homo sapiens* mRNA full length insert cDNA clone EUROIMAGE 1913076. | COL8A1 | −1.31 | 0.25 | 2.32 | 0.94 | 0.03 | 0.12 | 3.51 | 1.02 |
| AL117653 | *Homo sapiens* mRNA; cDNA DKFZp586C0224 (from clone DKFZp586C0224). | MITF | −0.12 | 0.61 | 2.32 | 0.10 | 0.21 | 0.13 | 2.56 | 0.06 |
| AL021977 | Cluster Incl. AL021977:b K447C4.1 (novel MAFF (v-maf musculoaponeurotic fibrosarcoma (avian) oncogene family, protein F) LIKE protein) /cds=(0.494) /gb=AL021977 /gi=4914526 /ug=Hs.51305 /len=2128 | — | 1.92 | 0.14 | 4.53 | 0.43 | 2.15 | 0.12 | 4.66 | 0.22 |
| NM_003564 | *Homo sapiens* transgelin 2 (TAGLN2), mRNA. /PROD=transgelin 2 /FL=gb:D21261.1 gb:NM_003564.1 | TAGLN2 | 5.43 | 0.12 | 6.76 | 0.06 | 3.48 | 0.27 | 6.69 | 0.04 |
| BC005107 | *Homo sapiens*, clone IMAGE:3840937, mRNA, partial cds. /PROD=Unknown (protein for IMAGE:3840937) | — | 7.08 | 0.07 | 6.42 | 0.26 | 2.60 | 0.07 | 6.93 | 0.22 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_001124 | Homo sapiens adrenomedullin (ADM), mRNA. /PROD=adrenomedullin /FL=gb:NM_001124.1 gb:D14874.1 | ADM | 4.70 | 0.22 | 7.61 | 0.19 | 5.21 | 0.06 | 7.58 | 0.21 |
| AF280545 | Homo sapiens neuropilin-2b(5) (NRP2) mRNA, complete cds, alternatively spliced. /PROD=neuropilin-2b(5) /FL=gb:AF280544.1 gb:AF280545.1 | NRP2 | −0.29 | 0.33 | 1.40 | 0.30 | −1.67 | 0.61 | 1.22 | 0.33 |
| NM_014624 | Homo sapiens S100 calcium-binding protein A6 (calcyclin) (S100A6), mRNA. /PROD=S100 calcium-binding protein A6 /FL=gb:NM_014624.2 gb:BC001431.1 | S100A6 | 3.08 | 0.38 | 3.10 | 0.18 | −0.57 | 0.37 | 3.24 | 0.19 |
| AB030824 | Homo sapiens mRNA for transcription factor BTEB2, complete cds. /PROD=transcription factor BTEB2 /FL=gb:AF132818.1 gb:AF287272.1 gb:AB030824.1 gb:NM_001730.1 gb:D14520.1 | KLF5 | 0.57 | 0.24 | 2.16 | 0.49 | −0.41 | 0.05 | 2.53 | 0.17 |
| NM_015675 | Homo sapiens growth arrest and DNA-damage-inducible, beta (GADD45B), mRNA. /PROD=DKFZP566B133 protein /FL=gb:NM_015675.1 gb:AF090950.1 | GADD45B | 2.47 | 0.22 | 4.44 | 0.46 | 2.02 | 0.09 | 4.64 | 0.33 |
| BF347089 | tissue inhibitor of metalloproteinase 3 (Sorsby fundus dystrophy, pseudoinflammatory) /FL=gb:NM_000362.2 gb:U14394.1 gb:U67195.1 gb:U02571.1 | TIMP3 | 0.57 | 0.13 | 2.01 | 0.29 | −0.19 | 0.20 | 2.09 | 0.44 |
| BF056473 | ESTs | — | −0.64 | 0.87 | 1.79 | 0.10 | −0.73 | 0.34 | 1.57 | 0.23 |
| AA809487 | Homo sapiens cDNA: FLJ21715 fis, clone COL10287, highly similar to AF071569 Homo sapiens multifunctional calciumcalmodulin-dependent protein kinase II delta2 isoform mRNA | — | 0.52 | 0.22 | 3.68 | 0.43 | 1.39 | 0.22 | 3.89 | 0.48 |
| AL575735 | collagen, type V, alpha 2 /FL=gb:NM_000393.1 | — | 5.54 | 0.11 | 6.65 | 0.14 | 4.57 | 0.08 | 6.68 | 0.07 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF003934 | Homo sapiens prostate differentiation factor mRNA, complete cds. /PROD=prostate differentiation factor /FL=gb:U88323.1 gb:BC000529.1 gb:AF003934.1 gb:NM_004864.1 gb:AF019770.1 gb:AB000584.1 | GDF15 | 2.74 | 0.20 | 4.01 | 0.41 | 0.72 | 0.17 | 4.34 | 0.50 |
| NM_000313 | Homo sapiens protein S (alpha) (PROS1), mRNA. /PROD=protein S (alpha) /FL=gb:M15036.1 gb:NM_000313.1 | PROS1 | −1.54 | 0.10 | 0.98 | 0.83 | −0.62 | 0.09 | 1.79 | 0.86 |
| NM_016651 | Homo sapiens heptacellular carcinoma novel gene-3 protein (LOC51339), mRNA. /PROD=heptacellular carcinoma novel gene-3 protein /FL=gb:NM_016651.2 gb:AF251079.2 | DACT1 | 2.37 | 0.26 | 4.79 | 0.67 | 2.46 | 0.14 | 3.92 | 0.78 |
| NM_020129 | Homo sapiens placental protein 13-like protein (LOC56891), mRNA. /PROD=placental protein 13-like protein /FL=gb:NM_020129.1 gb:AF267852.1 | LGALS14 | 1.38 | 0.30 | 3.15 | 0.70 | 0.79 | 0.04 | 2.47 | 0.66 |
| NM_013451 | Homo sapiens fer-1 (C. elegans)-like 3 (myoferlin) (FER1L3), mRNA. /PROD=fer-1 (C. elegans)-like 3 (myoferlin) /FL=gb:NM_013451.1 gb:AF182316.1 | FER1L3 | 1.75 | 0.15 | 4.02 | 0.97 | 1.59 | 0.13 | 5.14 | 0.82 |
| R72286 | microfibrillar-associated protein 4 | MFAP4 | −1.15 | 0.60 | −1.76 | 0.61 | −2.37 | 0.22 | −0.60 | 0.72 |
| AI417362 | ESTs, Moderately similar to ALU1_HUMAN ALU SUBFAMILY J SEQUENCE CONTAMINATION WARNING ENTRY (H. sapiens) | FUT1 | 2.42 | 0.14 | 2.32 | 0.72 | −0.46 | 0.53 | 1.70 | 0.59 |
| NM_001553 | Homo sapiens insulin-like growth factor binding protein 7 (IGFBP7), mRNA. /PROD=insulin-like growth factor binding protein 7 /FL=gb:NM_001553.1 gb:L19182.1 | IGFBP7 | 3.41 | 0.19 | 4.63 | 1.07 | 1.65 | 0.10 | 3.34 | 1.16 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel- DE stage | SEM | H9P44 on MEFs | SEM | H9P44 on MEFs- DE stage | SEM |
|---|---|---|---|---|---|---|---|---|---|---|
| BG285011 | *Homo sapiens* mRNA; cDNA DKFZp586N012 (from clone DKFZp586N012) | ARID5B | 0.05 | 0.22 | 1.79 | 0.21 | −0.95 | 0.42 | 1.16 | 0.55 |
| BE967311 | *Homo sapiens* mRNA; cDNA DKFZp762O1615 (from clone DKFZp762O1615) | — | 1.99 | 0.06 | 4.08 | 0.92 | 2.28 | 0.17 | 5.01 | 0.87 |
| BC005047 | *Homo sapiens*, clone MGC:12852, mRNA, complete cds. /PROD=Unknown (protein for MGC:12852) /FL=gb:NM_001946.1 gb:AB013382.1 gb:BC003562.1 gb:BC003143.1 gb:BC005047.1 | DUSP6 | 2.50 | 0.32 | 4.04 | 0.67 | 1.56 | 0.16 | 2.94 | 0.84 |
| AW005572 | putative 47 kDa protein | ANKS1B | −0.59 | 0.12 | 0.19 | 0.70 | −1.59 | 0.07 | 0.86 | 0.92 |
| AW294092 | ESTs | RERG | 0.54 | 0.16 | −0.68 | 1.55 | −2.78 | 0.92 | −0.58 | 0.97 |
| NM_001899 | *Homo sapiens* cystatin S (CST4), mRNA. /PROD=cystatin S /FL=gb:NM_001899.1 | CST4 | 0.14 | 0.52 | 2.46 | 1.59 | 0.53 | 0.14 | 3.87 | 1.40 |
| AI917371 | ESTs | — | −1.47 | 0.95 | 0.18 | 1.43 | −1.24 | 0.33 | 2.21 | 1.17 |
| NM_000515 | *Homo sapiens* growth hormone 1 (GH1), transcript variant 1, mRNA. /PROD=growth hormone 1, isoform 1 precursor /FL=gb:NM_000515.2 | CSH1 | −2.36 | 0.29 | 1.92 | 0.10 | −0.73 | 0.57 | 1.37 | 0.21 |
| NM_004414 | *Homo sapiens* Down syndrome critical region gene 1 (DSCR1), mRNA. /PROD=Down syndrome critical region protein 1 /FL=gb:U28833.2 gb:NM_004414.2 | DSCR1 | 2.14 | 0.03 | 3.85 | 0.26 | 1.74 | 0.16 | 3.34 | 0.36 |
| AI355441 | sprouty (*Drosophila*) homolog 4 | — | 0.24 | 0.48 | 1.72 | 0.50 | −1.12 | 0.40 | 2.03 | 0.61 |
| AB032953 | *Homo sapiens* mRNA for KIAA1127 protein, partial cds. /PROD=KIAA1127 protein | ODZ2 | 0.00 | 0.14 | 0.65 | 0.35 | −1.74 | 0.74 | 0.88 | 0.03 |
| BE048571 | ESTs | MGC16121 | −1.66 | 0.78 | 1.44 | 1.00 | −1.31 | 0.21 | 0.10 | 1.22 |
| AW471145 | ESTs | PRSS23 | 0.87 | 0.10 | 3.46 | 0.35 | 1.13 | 0.11 | 3.37 | 0.53 |
| BF196943 | ESTs | USP53 | 1.43 | 0.03 | 3.24 | 0.92 | 0.85 | 0.26 | 2.32 | 0.88 |
| AF498927 | *Homo sapiens* Rho GDP dissociation inhibitor beta (ARHGDIB) mRNA, complete cds. /PROD=Rho GDP dissociation inhibitor beta /FL=gb:AF498927.1 | ARHGDIB | −0.03 | 0.19 | 0.04 | 0.96 | −3.00 | 0.54 | −0.85 | 0.93 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF329092 | Homo sapiens GPBP-interacting protein 90 mRNA, complete cds. /PROD=GPBP-interacting protein 90 /FL=gb:AF329092.1 | DOC1 | −2.38 | 0.45 | 1.00 | 0.19 | −1.62 | 0.74 | 0.75 | 0.11 |
| BG250721 | Homo sapiens mRNA; cDNA DKFZp564C2063 (from clone DKFZp564C2063) | — | 2.48 | 0.04 | 4.54 | 0.95 | 2.63 | 0.14 | 5.31 | 0.83 |
| N69091 | ESTs | PCDH17 | 0.59 | 0.10 | 1.49 | 0.88 | −1.11 | 0.69 | 2.49 | 0.78 |
| BF589359 | ESTs | PAG1 | −1.11 | 0.52 | −0.09 | 0.43 | −1.54 | 0.12 | 0.50 | 0.13 |
| BF968270 | ESTs | SLC35F3 | 0.37 | 0.02 | 1.84 | 0.30 | 0.10 | 0.17 | 2.46 | 0.36 |
| NM_006183 | Homo sapiens neurotensin (NTS), mRNA. /PROD=neurotensin precursor /FL=gb:NM_006183.2 gb:U91618.1 | NTS | 4.77 | 0.15 | 4.73 | 1.45 | 3.01 | 0.19 | 3.21 | 1.47 |
| D28124 | Cluster Incl. D28124:Human mRNA for unknown product, complete cds /cds=(61,603) /gb=D28124 /gi=641821 /ug=Hs.76307 /len=1929 | NBL1 | 2.90 | 0.03 | 4.24 | 0.37 | 2.09 | 0.08 | 4.44 | 0.38 |
| AW129593 | tudor repeat associator with PCTAIRE 2 | TDRD7 | 1.19 | 0.19 | 2.40 | 0.87 | 0.92 | 0.04 | 3.27 | 0.89 |
| BE675435 | core promoter element binding protein /FL=gb:AF001461.1 gb:BC000311.1 gb:NM_001300.2 gb:AB017493.1 gb:BC004301.1 | KLF6 | 0.29 | 0.30 | 2.91 | 1.02 | 0.54 | 0.24 | 3.68 | 0.94 |
| AI202327 | ESTs | CPEB2 | 1.88 | 0.09 | 3.42 | 0.07 | 0.99 | 0.10 | 3.36 | 0.03 |
| NM_002228 | Homo sapiens v-jun avian sarcoma virus 17 oncogene homolog (JUN), mRNA. /PROD=v-jun avian sarcoma virus 17 oncogene homolog /FL=gb:NM_002228.2 gb:BC002646.1 | JUN | 2.12 | 0.16 | 4.09 | 0.56 | 1.62 | 0.13 | 4.53 | 0.41 |
| AF005775 | Homo sapiens caspase-like apoptosis regulatory protein 2 (clarp) mRNA, alternatively spliced, complete cds. /PROD=caspase-like apoptosis regulatory protein 2 /FL=gb:AF005775.1 | CFLAR | 2.88 | 0.18 | 3.70 | 1.56 | 0.35 | 0.17 | 5.22 | 1.69 |
| NM_007173 | Homo sapiens protease, serine, 23 (SPUVE), mRNA. /PROD=protease, serine, 23 /FL=gb:BC001278.1 gb:AF193611.1 gb:AF015287.1 gb:AL136914.1 gb:NM_007173.1 | PRSS23 | 3.02 | 0.10 | 5.11 | 0.21 | 2.90 | 0.05 | 5.22 | 0.23 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_012413 | Homo sapiens glutaminyl-peptide cyclotransferase (glutaminyl cyclase) (QPCT), mRNA. /PROD=glutaminyl-peptide cyclotransferase precursor /FL=gb:NM_012413.2 | QPCT | 1.44 | 0.09 | 0.97 | 0.85 | -2.46 | 0.65 | 0.19 | 1.10 |
| BU683415 | Homo sapiens, clone IMAGE:4096273, mRNA | KLF6 | 3.40 | 0.06 | 5.28 | 0.85 | 3.46 | 0.09 | 6.01 | 0.85 |
| AV729634 | DnaJ (Hsp40) homolog, subfamily B, member 6 /FL=gb:AB007942.1 gb:NM_014787.1 | DNAJC6 | 0.62 | 0.20 | 2.59 | 0.79 | 0.99 | 0.19 | 3.35 | 0.65 |
| BC038556 | Homo sapiens, clone IMAGE:3446976, mRNA. | — | -0.79 | 0.40 | 0.12 | 0.99 | -2.17 | 0.62 | -0.08 | 0.38 |
| NM_014942 | Homo sapiens KIAA0957 protein (KIAA0957), mRNA. /PROD=KIAA0957 protein /FL=gb:AB023174.1 gb:NM_014942.1 | ANKRD6 | 0.62 | 0.04 | 2.17 | 1.11 | 0.59 | 0.23 | 3.30 | 1.07 |
| AF260333 | Homo sapiens AD036 mRNA, complete cds. /PROD=AD036 /FL=gb:AF260333.1 | C4orf18 | -1.58 | 0.10 | 0.21 | 1.21 | -3.19 | 1.07 | 1.60 | 1.12 |
| AA448956 | Homo sapiens cDNA: FLJ21715 fis, clone COL10287, highly similar to AF071569 Homo sapiens multifunctional calciumcalmodulin-dependent protein kinase II delta2 isoform mRNA /FL=gb:AF071569.1 | CAMK2D | 1.47 | 0.18 | 2.75 | 0.42 | 0.21 | 0.21 | 2.97 | 0.39 |
| BE349115 | ESTs | COL22A1 | -0.02 | 0.52 | 2.04 | 0.25 | 0.24 | 0.06 | 2.38 | 0.22 |
| BF209337 | Homo sapiens cDNA FLJ10934 fis, clone OVARC1000640 | LOC541471 | 4.83 | 0.17 | 5.80 | 0.73 | 3.13 | 0.02 | 4.84 | 0.81 |
| AB019695 | Homo sapiens mRNA for thioredoxin reductase II beta, complete cds. /PROD=thioredoxin reductase II beta /FL=gb:AB019695.1 | — | 2.43 | 0.01 | 4.15 | 0.40 | 1.42 | 0.05 | 3.50 | 0.29 |
| AK090497 | Homo sapiens cDNA FLJ33178 fis, clone ADRGL2002753. | LOC284576 | -3.78 | 0.56 | -2.87 | 1.42 | -4.94 | 0.07 | -4.74 | 0.53 |
| NM_006763 | Homo sapiens BTG family, member 2 (BTG2), mRNA. /PROD=BTG family, member 2 /FL=gb:U72649.1 gb:NM_006763.1 | BTG2 | 2.30 | 0.10 | 3.28 | 0.62 | 0.85 | 0.25 | 3.84 | 0.74 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC002616 | *Homo sapiens*, transgelin 2, clone MGC:2989, mRNA, complete cds. /PROD=transgelin 2 /FL=gb:BC002616.1 | TAGLN2 | 5.61 | 0.20 | 5.56 | 0.17 | 2.91 | 0.18 | 5.40 | 0.12 |
| AF078077 | *Homo sapiens* growth arrest and DNA-damage-inducible protein GADD45beta mRNA, complete cds. /PROD=growth arrest and DNA-damage-inducible proteinGADD45beta /FL=gb:AF087853.1 gb:AF078077.1 | GADD45B | 1.30 | 0.17 | 3.41 | 0.31 | 0.61 | 0.12 | 3.05 | 0.29 |
| NM_001854 | *Homo sapiens* collagen, type XI, alpha 1 (COL11A1), mRNA. /PROD=collagen, type XI, alpha 1 /FL=gb:J04177.1 gb:NM_001854.1 | COL11A1 | 2.90 | 0.02 | 4.06 | 1.44 | 1.87 | 0.06 | 2.68 | 1.43 |
| AI830201 | ESTs | KIAA0773 | −0.75 | 0.82 | 1.24 | 0.22 | −1.87 | 0.51 | 0.40 | 0.22 |
| N95437 | ESTs | LMCD1 | 0.74 | 0.12 | 2.72 | 0.57 | 0.39 | 0.14 | 3.05 | 0.42 |
| BC002511 | *Homo sapiens*, carbonyl reductase 1, clone MGC:1920, mRNA, complete cds. /PROD=carbonyl reductase 1 /FL=gb:BC002511.1 gb:NM_001757.1 gb:J04056.1 | CBR1 | 3.72 | 0.02 | 1.03 | 2.43 | −4.10 | 0.16 | −1.64 | 2.36 |
| AV682252 | HIV-1 rev binding protein 2 | — | −0.33 | 0.15 | 1.78 | 1.36 | −0.24 | 0.17 | 0.41 | 1.29 |
| AW263497 | ESTs | SYTL5 | −1.05 | 0.25 | 1.44 | 0.38 | −0.55 | 0.41 | 2.11 | 0.47 |
| AF130095 | *Homo sapiens* clone FLC0562 PRO2841 mRNA, complete cds. /PROD=PRO2841 /FL=gb:AF130095.1 | — | 5.80 | 0.14 | 6.80 | 0.49 | 4.54 | 0.10 | 7.35 | 0.36 |
| H92988 | tyrosine 3-monooxygenase-tryptophan 5-monooxygenase activation protein, eta polypeptide | C9orf19 | 2.00 | 0.06 | 3.54 | 0.91 | 1.93 | 0.14 | 4.61 | 0.81 |
| X02761 | Human mRNA for fibronectin (FN precursor). /PROD=fibronectin precursor | FN1 | 5.67 | 0.17 | 6.65 | 0.54 | 4.52 | 0.21 | 7.21 | 0.42 |
| AI016316 | ESTs | — | 0.24 | 0.18 | 1.19 | 1.17 | −0.33 | 0.18 | 0.25 | 1.18 |
| NM_006622 | *Homo sapiens* serum-inducible kinase (SNK), mRNA. /PROD=serum-inducible kinase /FL=gb:AF059617.1 gb:NM_006622.1 gb:AF223574.1 | PLK2 | 4.64 | 0.14 | 5.88 | 0.45 | 3.50 | 0.06 | 5.19 | 0.47 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_013238 | Homo sapiens DNAJ domain-containing (MCJ), mRNA. /PROD=DNAJ domain-containing /FL=gb:NM_013238.1 gb:AF126743.1 | DNAJC15 | −2.27 | 0.60 | 3.79 | 2.03 | 4.07 | 0.09 | 5.58 | 2.31 |
| AK026737 | Homo sapiens cDNA: FLJ23084 fis, clone LNG06602, highly similar to HSFIB1 Human mRNA for fibronectin (FN precursor). | FN1 | 5.86 | 0.14 | 6.85 | 0.49 | 4.66 | 0.08 | 7.39 | 0.37 |
| NM_001458 | Homo sapiens filamin C, gamma (actin-binding protein-280) (FLNC), mRNA. /PROD=gamma filamin /FL=gb:AF089841.1 gb:NM_001458.1 | FLNC | 3.28 | 0.17 | 4.17 | 0.70 | 2.11 | 0.17 | 3.39 | 0.64 |
| AK025843 | Homo sapiens cDNA: FLJ22190 fis, clone HRC01053. /FL=gb:AF151909.1 gb:AF077041.1 gb:NM_016081.1 | PALLD | 1.58 | 0.31 | 3.38 | 0.15 | 1.03 | 0.20 | 3.29 | 0.19 |
| BC005858 | Homo sapiens, clone MGC:3255, mRNA, complete cds. /PROD=Unknown (protein for MGC:3255) /FL=gb:BC005858.1 | FN1 | 5.86 | 0.10 | 6.86 | 0.49 | 4.70 | 0.19 | 7.37 | 0.36 |
| BG491844 | v-jun avian sarcoma virus 17 oncogene homolog /FL=gb:NM_002228.2 gb:BC002646.1 | JUN | 3.53 | 0.08 | 5.45 | 0.47 | 3.42 | 0.11 | 5.91 | 0.34 |
| AA284532 | tyrosine 3-monooxygenase-tryptophan 5-monooxygenase activation protein, eta polypeptide | C9orf19 | 2.19 | 0.11 | 4.12 | 0.84 | 2.43 | 0.08 | 4.93 | 0.90 |
| AA192306 | triadin /FL=gb:U18985.1 gb:NM_006073.1 | TRDN | −2.54 | 0.69 | 0.02 | 0.61 | −1.99 | 0.31 | 0.57 | 0.63 |
| AF116676 | Homo sapiens PRO1957 mRNA, complete cds. /PROD=PRO1957 /FL=gb:AF116676.1 | — | 1.50 | 0.18 | 3.31 | 1.11 | 1.37 | 0.15 | 4.23 | 1.05 |
| NM_003033 | Homo sapiens sialyltransferase 4A (beta-galactosidase alpha-2,3-sialyltransferase) (SIAT4A), mRNA. /PROD=sialyl-transferase 4A (beta-galactosidase-alpha-2,3-sialyltransferase) /FL=gb:L13972.1 gb:L29555.1 gb:NM_003033.1 | ST3GAL1 | −0.08 | 0.18 | 1.68 | 1.04 | 0.20 | 0.16 | 2.74 | 0.74 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI222435 | ESTs | — | −4.14 | 1.52 | −0.73 | 0.32 | −2.33 | 0.62 | −0.33 | 0.12 |
| NM_001924 | Homo sapiens growth arrest and DNA-damage-inducible, alpha (GADD45A), mRNA. /PROD=growth arrest and DNA-damage-inducible, alpha /FL=gb:M60974.1 gb:NM_001924.2 | GADD45A | 3.59 | 0.09 | 5.04 | 0.44 | 3.06 | 0.17 | 5.38 | 0.48 |
| NM_001425 | Homo sapiens epithelial membrane protein 3 (EMP3), mRNA. /PROD=epithelial membrane protein 3 /FL=gb:U52101.1 gb:NM_001425.1 gb:U87947.1 | EMP3 | 2.76 | 0.18 | 3.90 | 0.64 | 1.51 | 0.06 | 3.13 | 0.57 |
| AB017493 | Homo sapiens mRNA for DNA-binding zinc finger(GBF), complete cds. /PROD=DNA-binding zinc finger(GBF) /FL=gb:AF001461.1 gb:BC000311.1 gb:NM_001300.2 gb:AB017493.1 gb:BC004301.1 | KLF6 | 1.69 | 0.20 | 4.02 | 1.01 | 1.80 | 0.08 | 4.87 | 0.87 |
| X58851 | Human MLC1emb gene for embryonic myosin alkaline light chain, promoter and exon 1 | — | 0.99 | 0.16 | 2.75 | 1.28 | 1.12 | 0.15 | 4.04 | 1.14 |
| BE327172 | v-jun avian sarcoma virus 17 oncogene homolog | — | 0.86 | 0.15 | 2.94 | 0.51 | 1.14 | 0.08 | 3.57 | 0.45 |
| U37283 | Human microfibril-associated glycoprotein-2 MAGP-2 mRNA, complete cds. /PROD=microfibril-associated glycoprotein-2 MAGP-2 /FL=gb:NM_003480.1 gb:U37283.1 | MFAP5 | 0.48 | 0.19 | 1.87 | 0.26 | 0.15 | 0.35 | 1.36 | 0.47 |
| AI819043 | ESTs | CREB5 | 0.92 | 0.26 | 2.63 | 0.73 | 0.65 | 0.15 | 1.80 | 0.79 |
| NM_001511 | Homo sapiens GRO1 oncogene (melanoma growth stimulating activity, alpha) (GRO1), mRNA. /PROD=GRO1 oncogene (melanoma growth stimulatingactivity, alpha) /FL=gb:NM_001511.1 | CXCL1 | 1.01 | 0.13 | 2.95 | 0.35 | 0.31 | 0.08 | 2.39 | 0.27 |
| NM_006736 | Homo sapiens heat shock protein, neuronal DNAJ-like 1 (HSJ1), mRNA. /PROD=heat shock protein, neuronal DNAJ-like 1 /FL=gb:NM_006736.1 | DNAJB2 | 2.23 | 0.04 | 3.46 | 0.44 | 1.10 | 0.02 | 3.75 | 0.41 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AA534817 | ESTs, Weakly similar to ALU8_HUMAN ALU SUBFAMILY SX SEQUENCE CONTAMINATION WARNING ENTRY (*H. sapiens*) | EDG3 | 2.32 | 0.06 | 3.28 | 1.04 | 2.08 | 0.04 | 4.58 | 1.04 |
| U82164 | Human transmembrane protein CD99 type II mRNA, complete cds. /PROD=CD99 typeII /FL=gb:BC002584.1 gb:NM_002414.1 gb:M16279.1 gb:BC003147.1 gb:U82164.1 | CD99 | 4.73 | 0.15 | 5.69 | 0.73 | 3.19 | 0.07 | 6.36 | 0.93 |
| NM_000389 | *Homo sapiens* cyclin-dependent kinase inhibitor 1A (p21, Cip1) (CDKN1A), mRNA. /PROD=cyclin-dependent kinase inhibitor 1A (p21, Cip1) /FL=gb:U03106.1 gb:BC000275.1 gb:BC001935.1 gb:L25610.1 gb:U09579.1 gb:NM_000389.1 gb:L26165.1 | CDKN1A | 4.03 | 0.02 | 4.20 | 0.12 | 1.81 | 0.07 | 4.16 | 0.05 |
| NM_001299 | *Homo sapiens* calponin 1, basic, smooth muscle (CNN1), mRNA. /PROD=calponin 1, basic, smooth muscle /FL=gb:U37019.1 gb:NM_001299.1 gb:D17408.1 | CNN1 | 3.75 | 0.15 | 5.75 | 0.50 | 3.47 | 0.11 | 5.14 | 0.43 |
| M36172 | Human embryonic myosin alkali light chain (MLC1) mRNA, complete cds. /FL=gb:M36172.1 gb:M24121.1 gb:NM_002476.1 | MYL4 | 1.55 | 0.21 | 3.30 | 1.05 | 1.21 | 0.13 | 4.11 | 1.06 |
| AB033831 | *Homo sapiens* hSCDGF mRNA for spinal cord-derived growth factor, complete cds. /PROD=spinal cord-derived growth factor /FL=gb:NM_016205.1 gb:AB033831.1 gb:AF091434.1 gb:AF244813.1 | PDGFC | 0.48 | 0.21 | 0.63 | 0.15 | −1.87 | 0.96 | 0.21 | 0.16 |
| NM_014333 | *Homo sapiens* immunoglobulin superfamily, member 4 (IGSF4), mRNA. /PROD=immunoglobulin superfamily, member 4 /FL=gb:NM_014333.1 gb:AF132811.1 | IGSF4 | 3.11 | 0.09 | 4.12 | 0.27 | 1.85 | 0.06 | 3.79 | 0.24 |
| AF345910 | *Homo sapiens* NYD-SP14 mRNA, complete cds. /PROD=NYD-SP14 /FL=gb:AF345910.1 | TTC29 | 0.35 | 0.26 | 1.53 | 0.93 | −0.51 | 0.52 | 0.91 | 0.72 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_004297 | Homo sapiens guanine nucleotide binding protein (G protein), alpha 14 (GNA14), mRNA. /PROD=guanine nucleotide binding protein (G protein), alpha 14 /FL=gb:AF105201.1 gb:NM_004297.1 | GNA14 | 4.59 | 0.06 | 4.52 | 1.59 | 1.95 | 0.11 | 2.95 | 1.50 |
| AK057525 | Homo sapiens cDNA FLJ32963 fis, clone TESTI2008405. | — | 3.60 | 0.08 | 4.45 | 0.44 | 2.00 | 0.16 | 4.80 | 0.46 |
| BC000893 | Homo sapiens, H2B histone family, member A, clone MGC:5132, mRNA, complete cds. /PROD=H2B histone family, member A /FL=gb:BC000893.1 | HIST1H2BK | 2.80 | 0.06 | 3.99 | 0.90 | 2.48 | 0.09 | 4.81 | 0.82 |
| NM_007038 | Homo sapiens a disintegrin-like and metalloprotease (reprolysin type) with thrombospondin type 1 motif, 5 (aggrecanase-2) (ADAMTS5), mRNA. /PROD=a disintegrin and metalloprotease withthrombospondin motifs-5 preproprotein /FL=gb:NM_007038.1 gb:AF14209 | ADAMTS5 | 0.23 | 0.17 | 1.80 | 0.48 | 0.45 | 0.28 | 1.11 | 0.73 |
| AW241910 | ESTs, Weakly similar to JX0369 collagen alpha 1(XIX) chain precursor (H. sapiens) | COL22A1 | −0.21 | 0.12 | 1.15 | 0.47 | −0.57 | 0.18 | 1.90 | 0.51 |
| AI860150 | ESTs, Weakly similar to A49134 Ig kappa chain V-I region (H. sapiens) | FOSL2 | −0.43 | 0.55 | 1.59 | 0.37 | −0.34 | 0.10 | 1.08 | 0.20 |
| NM_005902 | Homo sapiens MAD (mothers against decapentaplegic, Drosophila) homolog 3 (MADH3), mRNA. /PROD=MAD (mothers against decapentaplegic, Drosophila) homolog 3 /FL=gb:U68019.1 gb:U76622.1 gb:NM_005902.1 | SMAD3 | 1.09 | 0.41 | 1.49 | 0.25 | −1.10 | 0.89 | 1.73 | 0.10 |
| AA777512 | Homo sapiens cDNA: FLJ21715 fis, clone COL10287, highly similar to AF071569 Homo sapiens multifunctional calciumcalmodulin-dependent protein kinase II delta2 isoform mRNA | CAMK2D | 2.27 | 0.15 | 3.67 | 0.47 | 1.67 | 0.08 | 3.99 | 0.51 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI130705 | ESTs, Weakly similar to A46302 PTB-associated splicing factor, long form (*H. sapiens*) | FAM89A | 0.80 | 0.00 | 1.96 | 0.99 | 0.43 | 0.18 | 2.70 | 0.97 |
| NM_007061 | *Homo sapiens* serum constituent protein (MSE55), mRNA. /PROD=serum constituent protein /FL=gb:M88338.1 gb:NM_007061.1 | CDC42EP1 | 1.86 | 0.11 | 2.51 | 0.29 | 0.16 | 0.27 | 2.00 | 0.17 |
| NM_003407 | *Homo sapiens* zinc finger protein homologous to Zfp-36 in mouse (ZFP36), mRNA. /PROD=zinc finger protein homologous to Zfp-36 inmouse /FL=gb:NM_003407.1 gb:M92843.1 gb:M63625.1 | ZFP36 | 2.55 | 0.14 | 3.53 | 0.55 | 1.49 | 0.28 | 3.98 | 0.47 |
| BC033088 | *Homo sapiens*, Similar to lamin AC, clone MGC:45654 IMAGE:3623265, mRNA, complete cds. /PROD=Similar to lamin AC /FL=gb:BC033088.1 | LMNA | 2.03 | 0.22 | 2.89 | 0.45 | 0.69 | 0.24 | 1.79 | 0.50 |
| U97075 | *Homo sapiens* FLICE-like inhibitory protein short form mRNA, complete cds. /PROD=FLICE-like inhibitory protein short form /FL=gb:U97075.1 | CFLAR | 2.50 | 0.09 | 3.39 | 1.45 | 0.73 | 0.08 | 4.93 | 1.54 |
| AF133207 | *Homo sapiens* protein kinase (H11) mRNA, complete cds. /PROD=protein kinase /FL=gb:AF133207.1 | HSPB8 | 2.54 | 0.07 | 4.47 | 0.62 | 2.22 | 0.04 | 4.88 | 0.58 |
| NM_005979 | *Homo sapiens* S100 calcium-binding protein A13 (S100A13), mRNA. /PROD=S100 calcium-binding protein A13 /FL=gb:BC000632.1 gb:NM_005979.1 | S100A13 | 4.10 | 0.11 | 5.67 | 1.17 | 3.92 | 0.02 | 6.81 | 1.20 |
| AL040178 | ESTs | PEAR1 | −0.87 | 0.08 | 0.51 | 0.36 | −1.16 | 0.30 | 0.48 | 0.26 |
| AL117523 | *Homo sapiens* mRNA; cDNA DKFZp434H0350 (from clone DKFZp434H0350); partial cds. /PROD=hypothetical protein | SAMD4A | 0.47 | 0.06 | 1.59 | 0.61 | −0.24 | 0.30 | 1.28 | 0.53 |
| AB051826 | *Homo sapiens* hG28K mRNA for GTP-binding protein like 1, complete cds. /PROD=GTP-binding protein like 1 /FL=gb:AF282258.1 gb:NM_021205.1 gb:AB051826.1 | RHOU | 0.55 | 0.23 | 2.18 | 0.61 | 0.17 | 0.29 | 2.73 | 0.65 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC005961 | Homo sapiens, parathyroid hormone-like hormone, clone MGC:14611, mRNA, complete cds. /PROD=parathyroid hormone-like hormone /FL=gb:BC005961.1 | PTHLH | −3.33 | 0.69 | −0.88 | 0.81 | −2.86 | 0.77 | −1.97 | 1.36 |
| AI670948 | ESTs | NODAL | 2.13 | 0.04 | 2.37 | 0.22 | 0.42 | 0.13 | 2.78 | 0.38 |
| AI685060 | caldesmon 1 /FL=gb:M64110.1 gb:NM_004342.2 | CALD1 | 4.34 | 0.33 | 6.42 | 0.73 | 4.45 | 0.09 | 5.63 | 0.82 |
| BF797381 | Homo sapiens cDNA: FLJ21715 fis, clone COL10287, highly similar to AF071569 Homo sapiens multifunctional calciumcalmodulin-dependent protein kinase II delta2 isoform mRNA | CAMK2D | 3.16 | 0.13 | 4.91 | 0.65 | 3.10 | 0.10 | 5.49 | 0.61 |
| AF026219 | Homo sapiens HP protein (HP) mRNA, complete cds. /PROD=HP protein /FL=gb:AF026219.1 gb:AF035119.1 gb:NM_006094.2 | DLC1 | 1.16 | 0.07 | 2.28 | 1.13 | 0.61 | 0.09 | 3.52 | 0.84 |
| AK024480 | Homo sapiens mRNA for FLJ00074 protein, partial cds. /PROD=FLJ00074 protein | LOC126917 | 1.64 | 0.11 | 2.86 | 0.24 | 1.19 | 0.06 | 2.58 | 0.25 |
| N29837 | ESTs | LIX1 | −1.43 | 0.15 | −0.11 | 0.33 | −1.50 | 0.45 | −0.22 | 0.22 |
| AK001022 | Homo sapiens cDNA FLJ10160 fis, clone HEMBA1003545, highly similar to INSULIN GENE ENHANCER PROTEIN ISL-2. | ISL2 | 0.41 | 0.34 | 2.14 | 0.39 | 0.32 | 0.08 | 1.57 | 0.49 |
| NM_000047 | Homo sapiens arylsulfatase E (chondrodysplasia punctata 1) (ARSE), mRNA. /PROD=arylsulfatase E precursor /FL=gb:X83573.1 gb:NM_000047.1 | ARSE | 1.37 | 0.11 | 2.45 | 1.03 | 0.59 | 0.05 | 3.18 | 1.23 |
| NM_006379 | Homo sapiens sema domain, immunoglobulin domain (Ig), short basic domain, secreted, (semaphorin) 3C (SEMA3C), mRNA. /PROD=sema domain, immunoglobulin domain (Ig), shortbasic domain, secreted, (semaphorin) 3C /FL=gb:NM_006379.1 gb:AB000220.1 | SEMA3C | 0.24 | 0.25 | 1.08 | 0.00 | −0.34 | 0.05 | 0.86 | 0.18 |
| NM_007127 | Homo sapiens villin 1 (VIL1), mRNA. /PROD=villin 1 /FL=gb:NM_007127.1 | VIL1 | 0.31 | 0.30 | 1.92 | 0.49 | 0.02 | 0.22 | 2.54 | 0.68 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| U76549 | Human cytokeratin 8 mRNA, complete cds. /PROD=cytokeratin 8 /FL=gb:BC000654.1 gb:U76549.1 gb:NM_002273.1 gb:M26324.1 gb:M34225.1 | KRT8 | 5.41 | 0.16 | 5.87 | 0.56 | 3.79 | 0.05 | 6.34 | 0.57 |
| NM_004904 | Homo sapiens cAMP response element-binding protein CRE-BPa (H_GS165L15.1), mRNA. /PROD=cAMP response element-binding protein CRE-BPa /FL=gb:NM_004904.1 gb:L05911.1 | CREB5 | 0.92 | 0.23 | 1.84 | 0.37 | 0.00 | 0.06 | 1.21 | 0.80 |
| AW082836 | ESTs, Weakly similar to B34087 hypothetical protein (H. sapiens) | WNK4 | −1.17 | 0.26 | 0.98 | 0.38 | −0.97 | 0.20 | 0.05 | 0.86 |
| BE568134 | death receptor 6 /FL=gb:NM_014452.1 gb:AF068868.1 | TNFRSF21 | 4.76 | 0.06 | 5.90 | 0.54 | 3.94 | 0.08 | 6.28 | 0.58 |
| NM_002845 | Homo sapiens protein tyrosine phosphatase, receptor type, M (PTPRM), mRNA. /PROD=protein tyrosine phosphatase, receptor type, mupolypeptide /FL=gb:NM_002845.1 | PTPRM | 2.50 | 0.10 | 3.43 | 0.46 | 1.34 | 0.19 | 3.76 | 0.50 |
| AI949419 | ESTs | — | −0.11 | 0.21 | 1.72 | 0.64 | −0.47 | 0.01 | 2.39 | 0.77 |
| AK024680 | Homo sapiens cDNA: FLJ21027 fis, clone CAE07110. /FL=gb:NM_018534.1 | NRP2 | 0.42 | 0.02 | 2.65 | 0.17 | 0.98 | 0.09 | 2.86 | 0.17 |
| BE542563 | ESTs | LOC643277 | 2.20 | 0.10 | 0.54 | 1.49 | −3.73 | 0.40 | −1.74 | 1.96 |
| AW005572 | putative 47 kDa protein | ANKS1B | −1.21 | 0.52 | −0.24 | 0.82 | −1.19 | 0.55 | 1.05 | 0.64 |
| AW665892 | paternally expressed 3 | MFAP5 | −3.87 | 0.82 | −1.56 | 1.24 | −2.40 | 0.24 | −3.49 | 2.10 |
| NM_006206 | Homo sapiens platelet-derived growth factor receptor, alpha polypeptide (PDGFRA), mRNA. /PROD=platelet-derived growth factor receptor, alphapolypeptide /FL=gb:NM_006206.1 gb:M21574.1 | PDGFRA | 0.92 | 0.18 | 2.34 | 0.74 | 0.72 | 0.09 | 3.18 | 0.62 |
| NM_002425 | Homo sapiens matrix metalloproteinase 10 (stromelysin 2) (MMP10), mRNA. /PROD=matrix metalloproteinase 10 preproprotein /FL=gb:BC002591.1 gb:NM_002425.1 | MMP10 | −1.21 | 0.70 | 1.21 | 0.88 | −0.37 | 0.28 | 0.52 | 0.45 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_004338 | Homo sapiens chromosome 18 open reading frame 1 (C18ORF1), mRNA. /PROD=chromosome 18 open reading frame 1 /FL=gb:NM_004338.1 gb:AF009426.1 | C18orf1 | −0.79 | 0.22 | −0.09 | 0.39 | −1.57 | 0.43 | 0.50 | 0.02 |
| AF052094 | Homo sapiens clone 23698 mRNA sequence. /FL=gb:U51626.1 gb:U81984.1 gb:NM_001430.1 | EPAS1 | 0.75 | 0.12 | 2.28 | 0.19 | 0.42 | 0.21 | 1.74 | 0.33 |
| BF126155 | ESTs | S100A10 | −0.32 | 0.25 | 1.24 | 0.28 | −0.65 | 0.33 | 1.02 | 0.44 |
| AI860212 | phosphoprotein associated with GEMs /FL=gb:AF240634.1 gb:NM_018440.1 | PAG1 | −0.17 | 0.22 | 1.37 | 0.28 | −0.40 | 0.23 | 1.25 | 0.13 |
| AL110298 | Homo sapiens mRNA; cDNA DKFZp564K1672 (from clone DKFZp564K1672); partial cds. /PROD=hypothetical protein | SLC2A14 | 5.13 | 0.06 | 6.03 | 0.58 | 3.97 | 0.24 | 6.33 | 0.73 |
| AY048775 | Homo sapiens mandaselin long form mRNA, complete cds. /PROD=mandaselin long form /FL=gb:AY048775.1 | MANEA | −0.47 | 0.40 | 0.71 | 0.90 | −0.69 | 0.35 | 1.23 | 0.81 |
| M99436 | Cluster Incl. M99436:Human transducin-like enhancer protein (TLE2) mRNA, complete cds /cds=(25,2256) /gb=M99436 /gi=307511 /ug=Hs.173063 /len=2271 | TLE2 | 2.65 | 0.07 | 4.05 | 0.66 | 1.95 | 0.13 | 4.76 | 0.61 |
| NM_014061 | Homo sapiens APR-1 protein (APR-1), mRNA. /PROD=APR-1 protein /FL=gb:AF320912.1 gb:AF143235.3 gb:NM_014061.1 | MAGEH1 | 2.04 | 0.23 | 3.84 | 1.17 | 1.08 | 0.24 | 4.86 | 1.12 |
| AL577531 | caldesmon 1 /FL=gb:M64110.1 gb:NM_004342.2 | CALD1 | 5.79 | 0.06 | 6.06 | 0.75 | 4.07 | 0.06 | 5.13 | 0.77 |
| AI082237 | proprotein convertase subtilisinkexin type 7 | TAGLN | 1.38 | 0.21 | 3.20 | 0.33 | 1.55 | 0.15 | 2.74 | 0.44 |
| BF055171 | acyl-Coenzyme A oxidase 3, pristanoyl /FL=gb:NM_003501.1 | ACOX3 | 0.88 | 0.22 | 2.52 | 0.83 | 1.27 | 0.06 | 3.73 | 0.81 |
| AF231124 | Homo sapiens testican-1 mRNA, complete cds. /PROD=testican-1 /FL=gb:NM_004598.1 gb:AF231124.1 | SPOCK1 | 2.84 | 0.09 | 4.17 | 0.95 | 2.71 | 0.07 | 5.38 | 1.00 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AA588092 | ESTs | SLC40A1 | −1.53 | 0.23 | −0.94 | 0.51 | −2.42 | 0.33 | 0.27 | 0.27 |
| AK094809 | Homo sapiens cDNA FLJ37490 fis, clone BRAWH2014934, highly similar to GUANINE NUCLEOTIDE RELEASING PROTEIN. | RASGRF2 | 3.20 | 0.05 | 3.64 | 0.77 | 1.95 | 0.24 | 2.95 | 0.74 |
| NM_013959 | Homo sapiens neuregulin 1 (NRG1), transcript variant SMDF, mRNA. /PROD=neuregulin 1 isoform SMDF /FL=gb:L41827.1 gb:NM_013959.1 | NRG1 | 1.50 | 0.20 | 3.22 | 0.68 | 1.34 | 0.13 | 3.78 | 0.75 |
| NM_004887 | Homo sapiens small inducible cytokine subfamily B (Cys-X-Cys), member 14 (BRAK) (SCYB14), mRNA. /PROD=small inducible cytokine subfamily B(Cys-X-Cys), member 14 (BRAK) /FL=gb:AF144103.1 gb:AF106911.1 gb:AF073957.1 gb:BC003513.1 gb:NM_004887.1 | CXCL14 | 0.70 | 0.07 | 1.70 | 0.37 | −0.15 | 0.11 | 2.36 | 0.63 |
| T77995 | Homo sapiens cDNA FLJ13392 fis, clone PLACE1001280 | — | −0.20 | 0.16 | 0.82 | 0.50 | −1.70 | 0.24 | 1.17 | 0.06 |
| NM_030971 | Homo sapiens similar to rat tricarboxylate carrier-like protein (BA108L7.2), mRNA. /PROD=similar to rat tricarboxylate carrier-likeprotein /FL=gb:NM_030971.1 | SFXN3 | −0.43 | 0.59 | −0.01 | 0.78 | −1.92 | 0.17 | −1.25 | 0.43 |
| H25097 | KIAA1350 protein | USP53 | 3.25 | 0.05 | 4.57 | 0.20 | 2.96 | 0.04 | 4.47 | 0.13 |
| NM_004932 | Homo sapiens cadherin 6, type 2, K-cadherin (fetal kidney) (CDH6), mRNA. /PROD=cadherin 6, type 2, K-cadherin (fetal kidney) /FL=gb:D31784.1 gb:NM_004932.1 | CDH6 | −3.58 | 1.16 | −1.12 | 0.51 | −2.14 | 0.63 | −0.88 | 0.39 |
| N21426 | hypothetical protein FLJ20163 | SYTL2 | 2.41 | 0.09 | 3.44 | 1.22 | 1.70 | 0.06 | 2.02 | 1.21 |
| AA234096 | KIAA0963 protein | MGC16121 | 0.38 | 0.16 | 1.74 | 0.63 | −0.13 | 0.04 | 1.10 | 0.65 |
| AV734843 | hypothetical protein FLJ22833 | OBFC2A | 0.62 | 0.06 | 1.62 | 0.79 | 0.09 | 0.02 | 1.25 | 0.73 |
| AL519710 | immunoglobulin superfamily, member 4 /FL=gb:NM_014333.1 gb:AF132811.1 | IGSF4 | 3.86 | 0.02 | 4.95 | 0.26 | 3.22 | 0.12 | 4.66 | 0.27 |
| N32834 | HIV-1 rev binding protein 2 | — | −0.28 | 0.36 | 1.58 | 0.97 | −0.23 | 0.18 | 0.33 | 1.17 |
| AF132811 | Homo sapiens nectin-like protein 2 (NECL2) mRNA, complete cds. /PROD=nectin-like protein 2 /FL=gb:NM_014333.1 gb:AF132811.1 | IGSF4 | 2.23 | 0.07 | 3.85 | 0.28 | 2.17 | 0.10 | 3.58 | 0.34 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| J04177 | Cluster Incl. J04177:Human alpha-1 type XI collagen (COL11A1) mRNA, complete cds /cds=(161,5581) /gb=J04177 /gi=179729 /ug=Hs.82772 /len=6158 | COL11A1 | 3.28 | 0.22 | 4.44 | 1.22 | 2.32 | 0.03 | 3.03 | 1.31 |
| AI982754 | clusterin (complement lysis inhibitor, SP-40,40, sulfated glycoprotein 2, testosterone-repressed prostate message 2, apolipoprotein J) | CLU | 0.17 | 0.14 | 1.86 | 0.94 | 0.39 | 0.13 | 0.97 | 0.83 |
| NM_003501 | *Homo sapiens* acyl-Coenzyme A oxidase 3, pristanoyl (ACOX3), mRNA. /PROD=acyl-Coenzyme A oxidase 3, pristanoyl /FL=gb:NM_003501.1 | ACOX3 | 0.43 | 0.32 | 2.10 | 0.91 | 0.79 | 0.08 | 3.19 | 0.95 |
| AF144103 | *Homo sapiens* NJAC protein (NJAC) mRNA, complete cds. /PROD=NJAC protein /FL=gb:AF144103.1 gb:AF106911.1 gb:AF073957.1 gb:BC003513.1 gb:NM_004887.1 | CXCL14 | 1.69 | 0.13 | 2.16 | 0.55 | 0.40 | 0.21 | 2.73 | 0.69 |
| NM_005451 | *Homo sapiens* enigma (LIM domain protein) (ENIGMA), mRNA. /PROD=enigma protein /FL=gb:BC001093.1 gb:NM_005451.2 gb:AF265209.1 | PDLIM7 | 2.58 | 0.12 | 3.12 | 0.50 | 1.30 | 0.16 | 2.65 | 0.37 |
| NM_004472 | *Homo sapiens* forkhead box D1 (FOXD1), mRNA. /PROD=forkhead box D1 /FL=gb:U59832.1 gb:NM_004472.1 | FOXD1 | −0.85 | 0.80 | 2.04 | 0.55 | 0.71 | 0.23 | 1.70 | 0.74 |
| AF332197 | *Homo sapiens* adult SIX2 (SIX2) mRNA, complete cds. /PROD=SIX2 /FL=gb:AF332197.1 gb:NM_016932.1 gb:AF136940.1 | SIX2 | 0.36 | 0.24 | 0.72 | 0.12 | −0.44 | 0.35 | 1.05 | 0.15 |
| AB046817 | *Homo sapiens* mRNA for KIAA1597 protein, partial cds. /PROD=KIAA1597 protein | SYTL2 | 2.88 | 0.17 | 4.09 | 1.09 | 2.50 | 0.05 | 3.12 | 1.03 |
| AK093435 | *Homo sapiens* cDNA FLJ36116 fis, clone TESTI2022338. | FLJ36116 | 4.75 | 0.02 | 4.59 | 1.53 | 2.46 | 0.18 | 6.15 | 1.46 |
| NM_004815 | *Homo sapiens* PTPL1-associated RhoGAP 1 (PARG1), mRNA. /PROD=PTPL1-associated RhoGAP 1 /FL=gb:U90920.1 gb:NM_004815.1 | ARHGAP29 | 2.18 | 0.02 | 3.18 | 0.82 | 1.69 | 0.03 | 4.15 | 0.69 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BG028597 | ESTs | COL11A1 | 0.19 | 0.02 | 1.61 | 1.02 | −0.11 | 0.38 | 0.48 | 1.09 |
| AB019562 | Homo sapiens mRNA expressed only in placental villi, clone SMAP41. | SPP1 | 0.58 | 0.14 | 2.79 | 1.07 | 1.10 | 0.02 | 1.21 | 1.06 |
| NM_002346 | Homo sapiens lymphocyte antigen 6 complex, locus E (LY6E), mRNA. /PROD=lymphocyte antigen 6 complex, locus E /FL=gb:U42376.1 gb:NM_002346.1 gb:U56145.1 | LY6E | 3.54 | 0.06 | 3.92 | 1.16 | 1.81 | 0.23 | 4.93 | 1.39 |
| BF589515 | ESTs | TMEM16D | 0.63 | 0.24 | 1.94 | 0.85 | 0.90 | 0.20 | 1.47 | 0.75 |
| AL037401 | nuclear receptor subfamily 2, group F, member 2 /FL=gb:M64497.1 | NR2F2 | −2.00 | 0.30 | 0.58 | 0.67 | −2.19 | 0.13 | 0.82 | 0.66 |
| NM_000783 | Homo sapiens cytochrome P450, subfamily XXVIA, polypeptide 1 (CYP26A1), mRNA. /PROD=cytochrome P450, subfamily XXVIA, polypeptide 1 /FL=gb:NM_000783.1 gb:AF005418.1 | CYP26A1 | 3.92 | 0.27 | 6.28 | 1.06 | 6.29 | 0.09 | 7.31 | 0.98 |
| U16307 | Human glioma pathogenesis-related protein (GliPR) mRNA, complete cds. /PROD=glioma pathogenesis-related protein /FL=gb:NM_006851.1 gb:U16307.1 | GLIPR1 | −0.11 | 0.03 | 1.16 | 0.95 | −0.46 | 0.77 | 0.35 | 0.77 |
| NM_001233 | Homo sapiens caveolin 2 (CAV2), mRNA. /PROD=caveolin 2 /FL=gb:AF035752.1 gb:BC005256.1 gb:NM_001233.1 | CAV2 | 4.07 | 0.07 | 4.42 | 0.90 | 2.82 | 0.08 | 3.44 | 0.85 |
| AA211909 | ESTs | C20orf100 | 0.62 | 0.17 | 1.93 | 1.00 | −0.21 | 0.11 | 0.72 | 0.99 |
| AK057525 | Homo sapiens cDNA FLJ32963 fis, clone TESTI2008405. | — | 2.17 | 0.13 | 2.97 | 0.77 | 0.97 | 0.08 | 3.68 | 0.60 |
| BF344237 | Homo sapiens mRNA; cDNA DKFZp564N1116 (from clone DKFZp564N1116) | — | −2.82 | 0.20 | −0.92 | 0.64 | −0.73 | 0.67 | −1.25 | 1.03 |
| NM_014481 | Homo sapiens apurinicapyrimidinic endonuclease(APEX nuclease)-like 2 protein (APEXL2), mRNA. /PROD=apurini-capyrimidinic endo-nuclease(APEXnuclease)-like 2 protein /FL=gb:AB049211.1 gb:NM_014481.1 gb:BC002959.1 gb:AB021260.1 gb:AF119046.1 | APEX2 | 2.76 | 0.15 | 3.18 | 0.80 | 1.57 | 0.11 | 3.91 | 0.93 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI912583 | HIV-1 rev binding protein 2 | KRR1 | 1.10 | 0.23 | 2.68 | 1.04 | 1.31 | 0.06 | 1.53 | 1.01 |
| BI254089 | Homo sapiens full length insert cDNA clone ZD50E03 | ADAMTS5 | −1.40 | 0.26 | −0.01 | 0.31 | −1.71 | 0.64 | −0.79 | 0.52 |
| BF197655 | caveolin 2 /FL=gb:AF035752.1 gb:BC005256.1 gb:NM_001233.1 | CAV2 | 3.51 | 0.10 | 3.54 | 0.94 | 2.32 | 0.09 | 2.70 | 0.85 |
| NM_001955 | Homo sapiens endothelin 1 (EDN1), mRNA. /PROD=endothelin 1 /FL=gb:NM_001955.1 | EDN1 | 2.84 | 0.15 | 2.97 | 0.95 | 1.01 | 0.14 | 1.75 | 1.03 |
| NM_003319 | Homo sapiens titin (TTN), mRNA. /PROD=titin /FL=gb:NM_003319.1 | TTN | 1.28 | 0.19 | 0.62 | 0.86 | −0.92 | 0.42 | 2.00 | 0.55 |
| BE965029 | Homo sapiens cDNA: FLJ22463 fis, clone HRC10126 | MICAL2 | 0.60 | 0.21 | 1.95 | 0.64 | 0.21 | 0.19 | 0.83 | 0.78 |
| AI452457 | ESTs | C1orf168 | −1.48 | 0.53 | 0.02 | 0.93 | −1.87 | 0.07 | 1.05 | 0.94 |
| AI733465 | collagen, type IX, alpha 2 /FL=gb:NM_001852.1 | COL9A2 | 0.96 | 0.13 | 1.99 | 1.00 | 1.17 | 0.14 | 2.94 | 0.86 |
| NM_006103 | Homo sapiens epididymis-specific, whey-acidic protein type, four-disulfide core; putative ovarian carcinoma marker (HE4), mRNA. /PROD=epididymis-specific, whey-acidic protein type, four-disulfide core; putative ovarian carcinoma marker /FL=gb:NM_00610 | WFDC2 | 4.02 | 0.11 | 5.11 | 1.05 | 3.39 | 0.04 | 6.19 | 1.10 |
| NM_017540 | Homo sapiens hypothetical protein DKFZp586H0623 (DKFZp586H0623), mRNA. /PROD=hypothetical protein DKFZp586H0623 /FL=gb:NM_017540.1 | GALNT10 | 1.46 | 0.18 | 2.68 | 0.78 | 0.97 | 0.23 | 3.47 | 0.82 |
| W72527 | phosphoserine aminotransferase | SLC1A4 | −0.65 | 0.09 | 0.38 | 0.80 | −0.63 | 0.62 | −0.72 | 0.09 |
| NM_003468 | Homo sapiens frizzled (Drosophila) homolog 5 (FZD5), mRNA. /PROD=frizzled 5 /FL=gb:NM_003468.1 gb:U43318.1 | FZD5 | 1.35 | 0.26 | 3.43 | 1.21 | 1.45 | 0.10 | 4.43 | 1.16 |
| H15920 | ESTs, Weakly similar to RTA RAT PROBABLE G PROTEIN-COUPLED RECEPTOR RTA (R. norvegicus) | MRGPRF | 2.34 | 0.18 | 3.62 | 1.02 | 2.11 | 0.11 | 2.87 | 0.84 |
| U83508 | Human angiopoietin-1 mRNA, complete cds. /PROD=angiopoietin-1 /FL=gb:NM_001146.1 gb:D13628.1 gb:U83508.1 | ANGPT1 | 1.06 | 0.11 | 1.49 | 0.44 | −0.32 | 0.27 | 0.32 | 0.79 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF043179 | Homo sapiens T cell receptor beta chain (TCRBV13S1-TCRBJ2S1) mRNA, complete cds. /PROD=T cell receptor beta chain /FL=gb:AF043179.1 | PRSS1 | 2.42 | 0.12 | 3.07 | 0.81 | 1.71 | 0.10 | 2.30 | 0.60 |
| AU157541 | hypothetical protein FLJ22833 /FL=gb:NM_022837.1 | — | 1.39 | 0.08 | 2.12 | 0.42 | 0.55 | 0.18 | 1.41 | 0.77 |
| AF114264 | Homo sapiens clone HH409 unknown mRNA. /PROD=unknown | NEXN | 1.37 | 0.21 | 2.86 | 0.51 | 1.72 | 0.16 | 1.96 | 0.76 |
| BE965029 | Homo sapiens cDNA: FLJ22463 fis, clone HRC10126 | MICAL2 | 1.58 | 0.19 | 2.58 | 0.51 | 1.32 | 0.13 | 1.40 | 0.74 |
| AB028976 | Homo sapiens mRNA for KIAA1053 protein, partial cds. /PROD=KIAA1053 protein | SAMD4A | 2.89 | 0.08 | 3.65 | 0.66 | 2.04 | 0.17 | 2.78 | 0.81 |
| AI670862 | ESTs, Weakly similar to A49134 Ig kappa chain V-I region (H. sapiens) | FOSL2 | 0.17 | 0.21 | 2.05 | 0.57 | 0.45 | 0.16 | 1.18 | 0.65 |
| L03203 | Human peripheral myelin protein 22 (GAS3) mRNA, complete cds. /PROD=peripheral myelin protein 22 /FL=gb:L03203.1 | PMP22 | 0.37 | 0.24 | 1.95 | 0.84 | 0.31 | 0.26 | 2.77 | 0.91 |
| AI571798 | Rho GDP dissociation inhibitor (GDI) alpha | ARHGDIA | 0.89 | 0.06 | −0.54 | 0.26 | −3.00 | 0.89 | −2.58 | 0.87 |
| X57348 | Cluster Incl. X57348: H. sapiens mRNA (clone 9112) /cds=(165,911) /gb=X57348 /gi=23939 /ug=Hs.184510 /len=1407 | — | 2.94 | 0.04 | 4.07 | 0.41 | 2.70 | 0.08 | 3.69 | 0.41 |
| AF051851 | Homo sapiens supervillin mRNA, complete cds. /PROD=supervillin /FL=gb:AF051851.1 gb:NM_003174.2 gb:AF051850.1 | SVIL | 2.03 | 0.18 | 2.28 | 0.62 | 1.13 | 0.20 | 1.71 | 0.69 |
| M95929 | Human homeobox protein (PHOX1) mRNA, 3 end. /PROD=homeobox protein | — | 0.07 | 0.43 | 1.27 | 0.58 | −0.02 | 0.19 | 0.64 | 0.61 |
| BG251266 | FOS-like antigen-1 /FL=gb:NM_005438.1 | FOSL1 | 1.94 | 0.06 | 2.41 | 0.46 | 1.25 | 0.05 | 1.93 | 0.36 |
| AW298375 | ESTs | — | −0.40 | 0.30 | 0.46 | 0.63 | −0.09 | 0.20 | −0.58 | 1.07 |
| NM_004362 | Homo sapiens calmegin (CLGN), mRNA. /PROD=calmegin /FL=gb:NM_004362.1 gb:D86322.1 | CLGN | 0.90 | 0.30 | 1.95 | 0.96 | 0.69 | 0.11 | 3.11 | 1.01 |
| AF001540 | calcineurin-binding protein calsarcin-1 | — | 0.10 | 0.15 | 2.84 | 0.70 | 0.42 | 0.44 | 1.64 | 0.39 |
| NM_001191 | Homo sapiens BCL2-like 1 (BCL2L1), mRNA. /PROD=BCL 2-like 1 /FL=gb:NM_001191.1 | BCL2L1 | 1.21 | 0.22 | 0.58 | 0.35 | −1.89 | 0.35 | −1.09 | 1.03 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
| --- | --- | --- | --- | --- | --- | --- | --- | --- | --- | --- |
| NM_003316 | *Homo sapiens* tetratricopeptide repeat domain 3 (TTC3), mRNA. /PROD=tetra-tricopeptide repeat domain 3 /FL=gb:D84295.1 gb:NM_003316.1 | TTC3 | 3.90 | 0.15 | 5.15 | 0.98 | 3.68 | 0.12 | 6.19 | 0.97 |
| L16895 | Human lysyl oxidase (LOX) gene, exon 7 | — | −0.66 | 0.24 | 0.53 | 0.14 | −0.63 | 0.15 | 0.14 | 0.19 |
| AI912976 | ESTs | RASGRF2 | 3.13 | 0.08 | 4.05 | 0.56 | 2.66 | 0.16 | 3.54 | 0.64 |
| NM_012242 | *Homo sapiens* dickkopf (*Xenopus laevis*) homolog 1 (DKK1), mRNA. /PROD=dickkopf (*Xenopus laevis*) homolog 1 /FL=gb:AF177394.1 gb:NM_012242.1 gb:AF127563.1 | DKK1 | 0.47 | 0.29 | 0.73 | 0.04 | 0.49 | 0.51 | 1.09 | 0.23 |
| AL096776 | Human DNA sequence from clone RP4-646B12 on chromosome 1q42.11-42.3. Contains an FTH1 (ferritin, heavy polypeptide 1) (FTHL6) pseudogene, the gene for a novel Ras family protein, ESTs, STSs, GSSs and a putative CpG island /FL=gb:AF282258.1 gb:NM_0212 | — | 1.94 | 0.07 | 3.41 | 0.16 | 2.40 | 0.07 | 3.40 | 0.14 |
| BC005997 | *Homo sapiens*, clone MGC:14801, mRNA, complete cds. /PROD=Unknown (protein for MGC:14801) /FL=gb:BC005997.1 | — | 1.12 | 0.25 | 0.95 | 0.44 | 2.04 | 0.07 | 1.51 | 0.22 |
| AF074979 | *Homo sapiens* regulator of G protein signaling-Z (RGSZ1) mRNA, complete cds. /PROD=regulator of G protein signaling /FL=gb:AF060877.2 gb:AF074979.1 gb:NM_003702.2 | RGS20 | −0.52 | 0.18 | −0.04 | 0.38 | −1.30 | 0.09 | −0.34 | 0.13 |
| BF060767 | ESTs | ADAMTS5 | −0.36 | 0.15 | 0.80 | 0.33 | 0.22 | 0.14 | 0.40 | 0.56 |
| AU151151 | *Homo sapiens* cDNA FLJ13536 fis, clone PLACE1006521 | LEPR | 1.72 | 0.18 | 2.38 | 0.80 | 1.85 | 0.10 | 1.71 | 0.69 |
| L27624 | *Homo sapiens* tissue factor pathway inhibitor-2 mRNA, complete cds. /PROD=tissue factor pathway inhibitor-2 /FL=gb:D29992.1 gb:L27624.1 gb:NM_006528.1 gb:BC005330.1 | TFPI2 | 3.77 | 0.06 | 3.57 | 0.77 | 2.59 | 0.11 | 2.44 | 0.89 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_003174 | *Homo sapiens* supervillin (SVIL), transcript variant 1, mRNA. /PROD=supervillin, isoform 1 /FL=gb:AF051851.1 gb:NM_003174.2 gb:AF051850.1 | SVIL | 3.15 | 0.09 | 3.68 | 0.44 | 2.91 | 0.01 | 3.27 | 0.46 |
| AF052127 | *Homo sapiens* clone 23850 mRNA sequence. | RELN | −3.13 | 1.04 | −1.36 | 0.26 | −0.88 | 0.17 | −0.40 | 0.11 |
| AL031290 | Human DNA sequence from clone 774I24 on chromosome 1q24.1-24.3 Contains protein similar to pregnancy-associated plasma protein A precursor neuronal migration protein astrotactin, ESTs, STS and GSS | — | 0.38 | 0.06 | 1.39 | 0.46 | 0.40 | 0.05 | 0.95 | 0.44 |
| AI129628 | ESTs | SAMD3 | −0.30 | 0.18 | −0.01 | 0.25 | 0.72 | 0.06 | 0.17 | 0.21 |
| NM_016206 | *Homo sapiens* colon carcinoma related protein (LOC51159), mRNA. /PROD=colon carcinoma related protein /FL=gb:NM_016206.1 gb:AF099505.1 | VGLL3 | −0.39 | 0.36 | 0.05 | 1.03 | −0.31 | 0.29 | −1.05 | 1.01 |
| BE348291 | ESTs | — | 1.62 | 0.06 | −0.19 | 0.98 | −3.65 | 0.10 | −2.75 | 1.84 |
| AW242720 | *Homo sapiens* cDNA FLJ10561 fis, clone NT2RP2002672 | LOC143381 | −1.62 | 0.34 | −1.20 | 0.94 | −0.08 | 0.24 | −0.08 | 0.77 |
| NM_001146 | *Homo sapiens* angiopoietin 1 (ANGPT1), mRNA. /PROD=angiopoietin 1 /FL=gb:NM_001146.1 gb:D13628.1 gb:U83508.1 | ANGPT1 | 1.86 | 0.06 | 2.09 | 0.81 | 1.10 | 0.16 | 0.87 | 1.05 |
| AU152579 | *Homo sapiens* cDNA FLJ13034 fis, clone NT2RP3001232 | PCSK5 | 2.41 | 0.14 | 2.47 | 0.86 | 2.04 | 0.15 | 1.11 | 1.20 |
| NM_006200 | *Homo sapiens* proprotein convertase subtilisinkexin type 5 (PCSK5), mRNA. /PROD=proprotein convertase subtilisinkexin type 5 /FL=gb:U56387.2 gb:NM_006200.1 | PCSK5 | 3.01 | 0.21 | 2.88 | 0.92 | 2.28 | 0.11 | 1.52 | 1.25 |
| BF342661 | KIAA0036 gene product | MAP2 | −0.77 | 0.30 | −0.19 | 0.44 | 0.12 | 0.17 | −2.21 | 1.64 |
| AF063824 | *Homo sapiens* trp-related protein 4 truncated variant delta mRNA, complete cds. /PROD=trp-related protein 4 truncated variant delta /FL=gb:AF063824.1 | TRPC4 | −3.03 | 0.39 | 0.05 | 0.49 | 1.28 | 0.17 | 0.21 | 0.92 |
| AA723810 | cDNA for differentially expressed CO16 gene /FL=gb:BC001291.1 | LY6K | 0.07 | 0.20 | −0.13 | 1.23 | 0.15 | 0.14 | −0.38 | 1.27 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| N29877 | interleukin 14 | — | 1.94 | 0.13 | 0.51 | 0.48 | 0.78 | 0.64 | −1.57 | 0.65 |
| NM_007287 | *Homo sapiens* membrane metallo-endopeptidase (neutral endopeptidase, enkephalinase, CALLA, CD10) (MME), transcript variant 1bis, mRNA. /PROD=membrane metallo-endopeptidase /FL=gb:NM_007288.1 gb:NM_007287.1 gb:J03779.1 | MME | 2.59 | 0.03 | 1.81 | 0.40 | 1.89 | 0.21 | 2.14 | 0.30 |
| AB050856 | *Homo sapiens* beta3GalNAcT-1 mRNA for globoside synthase, complete cds, clone:type 2. /PROD=globoside synthase /FL=gb:AB050856.1 | B3GALNT1 | 1.39 | 0.05 | 0.20 | 0.22 | −0.13 | 0.21 | −0.10 | 0.17 |
| AI827455 | *Homo sapiens* cDNA: FLJ21042 fis, clone CAE11204 | BCL6B | 0.65 | 0.31 | 0.62 | 0.21 | 1.07 | 0.24 | 0.90 | 0.29 |
| AF017987 | *Homo sapiens* secreted apoptosis related protein 2 (SARP2) mRNA, complete cds. /PROD=secreted apoptosis related protein 2 /FL=gb:AF056087.1 gb:NM_003012.2 gb:AF017987.1 gb:AF001900.1 | SFRP1 | 4.15 | 0.22 | 4.37 | 1.24 | 6.02 | 0.06 | 5.74 | 1.01 |
| AL117451 | *Homo sapiens* mRNA; cDNA DKFZp586E2317 (from clone DKFZp586E2317). | C1orf108 | −0.73 | 0.20 | 0.68 | 0.24 | 1.06 | 0.05 | 0.82 | 0.21 |
| AW268357 | ESTs, Highly similar to AF155116 1 NY-REN-60 antigen (*H. sapiens*) | USP32 | 0.73 | 0.20 | 0.36 | 0.19 | 0.70 | 0.03 | 0.09 | 0.18 |
| BE465243 | ESTs | ARFGEF1 | 0.50 | 0.23 | 0.16 | 0.32 | 1.03 | 0.08 | 0.47 | 0.06 |
| AA993400 | ESTs | ADAL | 0.89 | 0.22 | 0.48 | 0.28 | 0.83 | 0.10 | 0.29 | 0.43 |
| AI970898 | Cluster Incl. AI970898:wr 21c03.x1 *Homo sapiens* cDNA, 3 end /clone=IMAGE-2488324 /clone_end=3 /gb=AI970898 /gi=5767724 /ug=Hs.234898 /len=382 | ACACB | 0.69 | 0.15 | 0.51 | 0.53 | 1.46 | 0.11 | −0.87 | 0.83 |
| BG026457 | ESTs, Weakly similar to ALU5_HUMAN ALU SUBFAMILY SC SEQUENCE CONTAMINATION WARNING ENTRY (*H. sapiens*) | KIAA1909 | 0.60 | 0.07 | 0.23 | 0.59 | 0.98 | 0.03 | −2.11 | 1.28 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BC041933 | *Homo sapiens*, clone IMAGE:5300703, mRNA. | UBE3C | 0.83 | 0.23 | 0.11 | 0.51 | 0.55 | 0.05 | 0.41 | 0.92 |
| AI638611 | KIAA1373 protein | STAMBPL1 | 2.20 | 0.17 | 1.37 | 0.58 | 2.32 | 0.08 | −0.39 | 1.24 |
| AI341686 | ESTs, Highly similar to RF1M_HUMAN MITOCHONDRIAL PEPTIDE CHAIN RELEASE FACTOR 1 PRECURSOR (*H. sapiens*) | MTRF1 | 1.36 | 0.14 | 0.45 | 0.48 | 1.43 | 0.09 | −1.09 | 0.99 |
| NM_003182 | *Homo sapiens* tachykinin, precursor 1 (substance K, substance P, neurokinin 1, neurokinin 2, neuromedin L, neurokinin alpha, neuropeptide K, neuropeptide gamma) (TAC1), transcript variant beta, mRNA. /PROD=tachykinin 2 precursor, isoform beta /FL=gb:U3 | TAC1 | 1.89 | 0.20 | 1.65 | 0.13 | 2.46 | 0.09 | 1.48 | 0.26 |
| M80634 | Human keratinocyte growth factor receptor mRNA, complete cds. /PROD=keratinocyte growth factor receptor /FL=gb:M80634.1 gb:NM_022969.1 gb:M97193.1 | FGFR2 | 3.63 | 0.06 | 2.25 | 0.39 | 2.79 | 0.19 | 2.07 | 0.84 |
| AK021452 | *Homo sapiens* cDNA FLJ11390 fis, clone HEMBA1000561, weakly similar to ZINC FINGER PROTEIN 91. | ZNF521 | −0.20 | 0.16 | −1.15 | 1.12 | 1.31 | 0.05 | 0.36 | 0.18 |
| AA541622 | ESTs | SYNPO2 | −0.49 | 0.30 | −0.90 | 0.06 | 0.35 | 0.09 | −2.58 | 0.93 |
| N50714 | ESTs | — | −1.13 | 0.13 | −1.34 | 0.52 | 0.10 | 0.12 | −0.21 | 0.28 |
| NM_002674 | *Homo sapiens* pro-melanin-concentrating hormone (PMCH), mRNA. /PROD=pro-melanin-concentrating hormone /FL=gb:NM_002674.1 gb:M57703.1 | PMCH | 0.62 | 0.24 | 1.10 | 0.48 | 1.64 | 0.03 | 0.09 | 0.80 |
| BM666010 | *Homo sapiens* cDNA FLJ23803 fis, clone HEP22811. | LOC200169 | 1.36 | 0.16 | 0.45 | 0.74 | 1.49 | 0.12 | −1.65 | 1.41 |
| AI343467 | *Homo sapiens* cDNA FLJ11041 fis, clone PLACE1004405 | — | −0.44 | 0.08 | −1.50 | 0.82 | 1.11 | 0.19 | −0.64 | 0.20 |
| AA046424 | ESTs, Weakly similar to YZ28_HUMAN HYPOTHETICAL PROTEIN ZAP128 (*H. sapiens*) | ACOT4 | 0.58 | 0.27 | −0.94 | 0.66 | −1.08 | 0.38 | −1.09 | 0.25 |
| R38389 | olfactomedin related ER localized protein | OLFM1 | 4.27 | 0.11 | 3.02 | 0.76 | 4.53 | 0.07 | 2.17 | 0.96 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BF724270 | ESTs | — | 2.03 | 0.22 | 0.72 | 0.42 | 2.36 | 0.06 | 0.01 | 0.97 |
| NM_001819 | *Homo sapiens* chromogranin B (secretogranin 1) (CHGB), mRNA. /PROD=chromogranin B precursor /FL=gb:BC000375.1 gb:NM_001819.1 | CHGB | 1.40 | 0.18 | 0.50 | 0.75 | 1.66 | 0.05 | −0.74 | 1.03 |
| AK026387 | *Homo sapiens* cDNA: FLJ22734 fis, clone HUV00109. | — | 0.03 | 0.28 | −0.05 | 0.52 | 1.23 | 0.26 | 0.52 | 0.67 |
| BF062139 | polymerase (RNA) III (DNA directed) (32 kD) /FL=gb:NM_006467.1 gb:U93868.1 | — | 5.23 | 0.06 | 4.31 | 0.74 | 5.80 | 0.07 | 3.37 | 0.86 |
| BG540454 | ESTs | SCGB3A2 | 4.64 | 0.02 | 2.91 | 0.84 | 4.13 | 0.07 | 1.72 | 0.83 |
| AI659533 | ArgAbl-interacting protein ArgBP2 | SORBS2 | 0.02 | 0.12 | 1.12 | 0.71 | 2.17 | 0.05 | −1.08 | 1.48 |
| AA531287 | ESTs | — | 2.94 | 0.27 | 1.32 | 0.72 | 2.57 | 0.04 | 0.22 | 0.90 |
| NM_013243 | *Homo sapiens* secretogranin III (SCG3), mRNA. /PROD=secretogranin III /FL=gb:AF078851.1 gb:NM_013243.1 | SCG3 | 3.30 | 0.20 | 2.13 | 0.95 | 3.67 | 0.19 | 0.87 | 1.06 |
| AI307586 | *Homo sapiens* mRNA; cDNA DKFZp566H0124 (from clone DKFZp566H0124) | C10orf95 | 0.34 | 0.22 | −1.15 | 0.24 | −0.49 | 0.16 | −3.61 | 0.99 |
| BC032004 | *Homo sapiens*, Similar to glutamate receptor, ionotrophic, AMPA 3, clone IMAGE:4753474, mRNA. | GRIA3 | −0.02 | 0.23 | −0.15 | 0.33 | 0.47 | 0.04 | 0.17 | 0.07 |
| AW205739 | ESTs, Weakly similar to ORF YGL050w (*S. cerevisiae*) | TYW3 | 0.47 | 0.01 | 0.81 | 1.35 | 3.72 | 0.18 | 2.46 | 1.15 |
| NM_153262 | *Homo sapiens* hypothetical protein FLJ34198 (FLJ34198), mRNA. /FL=gb:NM_153262.1 | SYT14 | −0.01 | 0.17 | −0.84 | 0.51 | 0.00 | 0.18 | −3.88 | 1.64 |
| AA156873 | albumin | PELO | 0.77 | 0.12 | −0.23 | 0.93 | 0.65 | 0.14 | −2.33 | 1.01 |
| BC012375 | *Homo sapiens*, Similar to KIAA1001 protein, clone MGC:8996 IMAGE:3882163, mRNA, complete cds. /PROD=Similar to KIAA1001 protein /FL=gb:AB023218.1 gb:NM_014960.1 gb:BC012375.1 | ARSG | −0.46 | 0.48 | −0.78 | 0.42 | 0.57 | 0.22 | −0.41 | 0.55 |
| AA843242 | ESTs | BNC2 | 2.12 | 0.37 | 1.03 | 0.47 | 2.89 | 0.06 | 0.43 | 0.80 |
| BF792954 | ESTs | HDLBP | −1.53 | 1.04 | −2.75 | 0.91 | 0.30 | 0.16 | −0.72 | 0.26 |
| AA780067 | heparan sulfate (glucosamine) 3-O-sulfotransferase 3B1 | HS3ST3B1 | 0.41 | 0.19 | 0.30 | 0.61 | 2.61 | 0.18 | 0.78 | 0.60 |
| AA909330 | ESTs | RP1-32F7.2 | 0.98 | 0.17 | −1.67 | 0.51 | 0.79 | 0.02 | −0.38 | 0.12 |
| AF141339 | *Homo sapiens* LYST-interacting protein LIP3 mRNA, partial cds. /PROD=LYST-interacting protein LIP3 | ZNF521 | −0.41 | 0.12 | −0.97 | 0.93 | 1.67 | 0.11 | −0.31 | 0.80 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BF435123 | bromodomain and PHD finger containing, 3 | — | 2.28 | 0.17 | 1.31 | 0.51 | 2.70 | 0.12 | 1.30 | 1.00 |
| AK056212 | *Homo sapiens* cDNA FLJ31650 fis, clone NT2RI2004079. | — | 1.03 | 0.14 | 0.14 | 0.27 | 1.10 | 0.07 | −1.41 | 0.51 |
| NM_001446 | *Homo sapiens* fatty acid binding protein 7, brain (FABP7), mRNA. /PROD=fatty acid binding protein 7, brain /FL=gb:U81235.1 gb:D88648.1 gb:U51338.1 gb:NM_001446.1 gb:D50373.1 | FABP7 | 2.07 | 0.15 | 0.74 | 0.29 | 2.20 | 0.04 | 1.08 | 0.16 |
| AW051591 | ESTs, Moderately similar to unnamed protein product (*H. sapiens*) | RNF175 | 1.41 | 0.32 | 0.22 | 0.10 | 2.60 | 0.06 | 0.96 | 0.20 |
| BC041970 | *Homo sapiens*, clone IMAGE:5302687, mRNA. | C9orf122 | 0.74 | 0.03 | −0.35 | 0.49 | 0.76 | 0.06 | −2.31 | 1.25 |
| BC013077 | *Homo sapiens*, clone IMAGE:3459334, mRNA. | — | 2.51 | 0.11 | 0.80 | 1.15 | 2.85 | 0.06 | 0.08 | 0.89 |
| AW572379 | ESTs | — | 1.80 | 0.03 | 0.60 | 0.84 | 1.45 | 0.07 | 1.88 | 0.53 |
| BE644917 | nuclear receptor subfamily 1, group I, member 3 | XIST | −3.88 | 1.26 | −0.54 | 1.28 | 1.94 | 0.13 | −0.20 | 1.94 |
| NM_171999 | *Homo sapiens* sal-like 3 (*Drosophila*) (SALL3), mRNA. /PROD=sal-like 3 /FL=gb:NM_171999.1 | SALL3 | 2.97 | 0.18 | 2.04 | 0.71 | 3.79 | 0.08 | 1.02 | 0.74 |
| AI654224 | ESTs | — | 0.46 | 0.36 | 0.14 | 0.44 | 1.03 | 0.07 | −0.81 | 0.85 |
| AA167449 | nuclear receptor subfamily 1, group I, member 3 | XIST | −3.08 | 0.10 | −0.47 | 2.59 | 4.59 | 0.07 | 2.80 | 1.86 |
| BF977837 | KIAA0527 protein | SUSD5 | 1.64 | 0.02 | 0.50 | 0.68 | 1.96 | 0.16 | −1.52 | 1.66 |
| BC029425 | *Homo sapiens*, Similar to KIAA1275 protein, clone IMAGE:4616553, mRNA. | FILIP1 | −0.83 | 0.45 | −0.03 | 0.62 | 0.76 | 0.20 | −0.29 | 0.44 |
| AI978754 | ESTs | — | 2.76 | 0.14 | 1.54 | 0.57 | 3.57 | 0.06 | 2.31 | 0.69 |
| AA628440 | nuclear receptor subfamily 1, group I, member 3 | XIST | 0.18 | 0.13 | 1.42 | 1.52 | 4.80 | 0.02 | 3.01 | 1.50 |
| L36861 | L36861 /FEATURE= expanded_cds /DEFINITION=HUMGCAPB *Homo sapiens* guanylate cyclase activating protein (GCAP) gene exons 1-4, complete cds | — | 2.75 | 0.17 | 2.01 | 0.82 | 3.63 | 0.09 | 3.00 | 0.97 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AW023227 | ESTs | MKX | −0.91 | 0.60 | −1.31 | 0.06 | 0.27 | 0.13 | −2.90 | 0.52 |
| NM_021614 | Homo sapiens potassium intermediate small conductance calcium-activated channel, subfamily N, member 2 (KCNN2), mRNA. /PROD=potassium intermediate small conductance calcium-activated channel, subfamily N, member 2 /FL=gb:NM_021614.1 gb:AF239613.1 | KCNN2 | 3.45 | 0.13 | 2.52 | 0.83 | 4.40 | 0.14 | 1.54 | 0.80 |
| NM_000956 | Homo sapiens prostaglandin E receptor 2 (subtype EP2), 53 kD (PTGER2), mRNA. /PROD=prostaglandin E receptor 2 (subtype EP2), 53 kD /FL=gb:U19487.1 gb:NM_000956.1 | PTGER2 | −0.71 | 0.71 | −0.73 | 0.57 | 0.63 | 0.33 | −2.38 | 0.61 |
| NM_013381 | Homo sapiens thyrotropin-releasing hormone degrading ectoenzyme (TRHDE), mRNA. /PROD=thyrotropin-releasing hormone degradingectoenzyme /FL=gb:AF126372.1 gb:NM_013381.1 | TRHDE | 1.96 | 0.16 | 0.25 | 0.36 | 1.81 | 0.03 | 0.82 | 0.23 |
| NM_016354 | Homo sapiens solute carrier family 21 (organic anion transporter), member 12 (SLC21A12), mRNA. /PROD=organic anion transporter OATP-E /FL=gb:AB031051.1 gb:NM_016354.1 gb:AF205072.1 gb:AF187817.1 | SLCO4A1 | 2.18 | 0.06 | 1.01 | 0.37 | 2.35 | 0.05 | −0.91 | 1.23 |
| BC028359 | Homo sapiens, clone IMAGE:4828836, mRNA. | ZNF141 | −1.05 | 0.39 | −0.59 | 0.65 | 1.25 | 0.17 | −1.48 | 0.72 |
| AI193252 | ESTs, Weakly similar to AF133270 1 SLIT2 (H. sapiens) | LRRN6A | 4.38 | 0.11 | 2.47 | 0.43 | 4.23 | 0.11 | 1.90 | 0.37 |
| H09780 | Human (clone CTG-A4) mRNA sequence | — | 2.04 | 0.19 | 0.56 | 0.07 | 2.50 | 0.11 | 0.12 | 0.40 |
| BC040605 | Homo sapiens, clone IMAGE:5271039, mRNA. | — | 2.64 | 0.16 | 1.61 | 1.08 | 3.59 | 0.09 | 0.45 | 1.14 |
| AW057589 | ESTs | — | −0.96 | 0.26 | −2.77 | 0.81 | 0.25 | 0.24 | −1.21 | 0.35 |
| M31213 | Human papillary thyroid carcinoma-encoded protein mRNA, complete cds. /FL=gb:M31213.1 | RET | 0.42 | 0.10 | −1.86 | 0.83 | 1.77 | 0.12 | −0.64 | 0.15 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel- DE stage | SEM | H9P44 on MEFs | SEM | H9P44 on MEFs- DE stage | SEM |
|---|---|---|---|---|---|---|---|---|---|---|
| Z92546 | Human DNA sequence from clone CTA-65A6 on chromosome 22q11-12 Contains the 3 part of the gene for the ortholog of rat CAIN (KIAA0330), the gene for a novel Sushi domain (SCR repeat) containing protein similar to Mucins, ESTs, an STS, GSSs and two . . . | — | 0.58 | 0.13 | −1.16 | 0.54 | 1.07 | 0.12 | −1.27 | 0.14 |
| AA974416 | protein phosphatase 2 (formerly 2A), regulatory subunit B (PR 52), beta isoform | PPP2R2B | 4.02 | 0.16 | 3.52 | 0.23 | 5.22 | 0.07 | 3.12 | 0.15 |
| AW138143 | ESTs | SORBS2 | 3.44 | 0.16 | 2.89 | 0.88 | 4.47 | 0.10 | 1.88 | 1.15 |
| NM_014862 | Homo sapiens KIAA0307 gene product (KIAA0307), mRNA. /PROD=KIAA0307 gene product /FL=gb:AB002305.1 gb:NM_014862.1 | ARNT2 | 1.29 | 0.08 | −0.68 | 0.97 | 2.00 | 0.08 | 0.02 | 0.24 |
| AI765540 | ESTs | — | 1.28 | 0.22 | 0.07 | 0.39 | 1.50 | 0.07 | −0.11 | 0.26 |
| NM_018013 | Homo sapiens hypothetical protein FLJ10159 (FLJ10159), mRNA. /PROD=hypothetical protein FLJ10159 /FL=gb:NM_018013.1 | FLJ10159 | 1.30 | 0.21 | 0.38 | 0.39 | 2.89 | 0.02 | 0.62 | 0.21 |
| BF382322 | ESTs, Weakly similar to unnamed protein product (H. sapiens) | — | −0.40 | 0.09 | −2.09 | 0.67 | −0.12 | 0.08 | −1.73 | 0.50 |
| AV699347 | nuclear receptor subfamily 1, group I, member 3 | XIST | −1.37 | 0.38 | 0.45 | 1.69 | 4.28 | 0.02 | 2.25 | 1.53 |
| BC011549 | Homo sapiens, clone MGC:19945 IMAGE:4554461, mRNA, complete cds. /PROD=Unknown (protein for MGC:19945 /FL=gb:BC011549.1 | ATP5S | 0.69 | 0.19 | 0.96 | 0.68 | 2.57 | 0.29 | −0.02 | 0.52 |
| NM_001889 | Homo sapiens crystallin, zeta (quinone reductase) (CRYZ), mRNA. /PROD=crystallin, zeta (quinone reductase) /FL=gb:NM_001889.1 gb:L13278.1 gb:S58039.1 | CRYZ | −1.68 | 0.26 | 0.23 | 1.38 | 3.75 | 0.07 | 1.78 | 1.11 |

TABLE IV-continued

DIFFERENTIAL EXPRESSION OF GENES BETWEEN UNDIFFERENTIATED EMBRYONIC STEM CELLS AND DEFINITIVE ENDODERM STAGE CELLS CULTURED ON EITHER MATRIGEL™ OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel- DE stage | SEM | H9P44 on MEFs | SEM | H9P44 on MEFs- DE stage | SEM |
|---|---|---|---|---|---|---|---|---|---|---|
| BC002665 | *Homo sapiens*, proteolipid protein (Pelizaeus-Merzbacher disease, spastic paraplegia 2, uncomplicated), clone MGC:3940, mRNA, complete cds. /PROD=proteolipid protein (Pelizaeus-Merzbacherdisease, spastic paraplegia 2, uncomplicated) /FL=gb:BC002665.1 | PLP1 | 4.57 | 0.15 | 2.95 | 0.64 | 4.70 | 0.06 | 2.32 | 0.52 |
| NM_001243 | *Homo sapiens* tumor necrosis factor receptor superfamily, member 8 (TNFRSF8), mRNA. /PROD=CD30 antigen (Ki-1 antigen) /FL=gb:NM_001243.1 gb:D86042.1 gb:M83554.1 | TNFRSF8 | 3.75 | 0.03 | 1.45 | 0.35 | 3.24 | 0.11 | 0.89 | 0.46 |
| NM_001195 | *Homo sapiens* beaded filament structural protein 1, filensin (BFSP1), mRNA. /PROD=filensin /FL=gb:AF039655.1 gb:NM_001195.2 gb:Y16717.2 | BFSP1 | 0.57 | 0.33 | −1.65 | 1.30 | 0.60 | 0.14 | −0.86 | 0.73 |
| NM_024582 | *Homo sapiens* hypothetical protein FLJ23056 (FLJ23056), mRNA. /PROD=hypothetical protein FLJ23056 /FL=gb:NM_024582.1 | FAT4 | 2.16 | 0.27 | −0.49 | 0.30 | 1.54 | 0.28 | −1.35 | 1.01 |
| NM_000767 | *Homo sapiens* cytochrome P450, subfamily IIB (phenobarbital-inducible), polypeptide 6 (CYP2B6), mRNA. /PROD=cytochrome P450, subfamily IIB (phenobarbital-inducible), polypeptide 6 /FL=gb:NM_000767.2 gb:AF182277.1 gb:M29874.1 | CYP2B6 | 2.60 | 0.18 | 0.87 | 0.96 | 1.47 | 0.12 | −0.69 | 1.03 |
| AW665509 | ESTs | MGC42174 | −0.10 | 0.33 | −0.87 | 0.72 | 1.20 | 0.08 | −2.60 | 1.40 |
| NM_001104 | *Homo sapiens* actinin, alpha 3 (ACTN3), mRNA. /PROD=skeletal muscle specific actinin, alpha 3 /FL=gb:M86407.1 gb:NM_001104.1 | ACTN3 | 2.12 | 0.13 | 1.64 | 0.28 | 3.35 | 0.03 | 1.67 | 0.36 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_021069 | *Homo sapiens* ArgAbl-interacting protein ArgBP2 (ARGBP2), transcript variant 2, mRNA. /PROD=ArgAbl-interacting protein 2, isoform 2 /FL=gb:AB018320.1 gb:NM_021069.1 | SORBS2 | −0.49 | 0.43 | 0.30 | 1.36 | 2.03 | 0.07 | −1.13 | 1.15 |
| T65020 | ESTs | — | 0.51 | 0.16 | −0.84 | 0.26 | 1.10 | 0.15 | −1.50 | 0.38 |
| NM_152647 | *Homo sapiens* hypothetical protein FLJ32800 (FLJ32800), mRNA. /FL=gb:NM_152647.1 | GALK2 | 0.08 | 0.56 | −1.42 | 0.52 | 0.03 | 0.17 | −2.34 | 0.91 |
| BC036917 | *Homo sapiens*, clone MGC:46457 IMAGE:5201433, mRNA, complete cds. /PROD=Unknown (protein for MGC:46457) /FL=gb:BC036917.1 | C6orf141 | −0.82 | 0.30 | −1.18 | 0.40 | 0.88 | 0.11 | −2.18 | 0.62 |
| AI969112 | *Homo sapiens*, clone IMAGE:5260603, mRNA, partial cds | PHIP | −1.07 | 0.13 | −2.88 | 0.91 | −0.37 | 0.02 | −2.23 | 0.33 |
| AW449813 | KIAA0918 protein | SLITRK5 | 0.32 | 0.26 | −1.89 | 0.50 | 0.46 | 0.10 | −0.57 | 0.13 |
| AW044658 | ESTs | — | 0.16 | 0.16 | −1.47 | 0.25 | 0.90 | 0.14 | −0.89 | 0.16 |
| AI694300 | ESTs | — | −0.52 | 0.02 | −1.34 | 0.52 | 0.27 | 0.08 | −1.00 | 0.08 |
| NM_017631 | *Homo sapiens* hypothetical protein FLJ20035 (FLJ20035), mRNA. /PROD=hypothetical protein FLJ20035 /FL=gb:NM_017631.1 | FLJ20035 | 1.35 | 0.13 | 0.05 | 0.19 | 1.51 | 0.17 | 0.32 | 0.15 |
| AF298547 | *Homo sapiens* nucleotide-binding site protein 1 mRNA, complete cds. /PROD=nucleotide-binding site protein 1 /FL=gb:AF298547.1 | NALP2 | 1.54 | 0.08 | 1.22 | 1.61 | 5.04 | 0.05 | 3.23 | 1.36 |
| NM_030631 | *Homo sapiens* oxodicarboxylate carrier (ODC1), mRNA. /PROD=oxodi-carboxylate carrier /FL=gb:NM_030631.1 | SLC25A21 | 1.96 | 0.25 | 0.33 | 0.81 | 2.47 | 0.11 | −0.28 | 0.63 |
| BF196255 | ESTs | — | 2.94 | 0.05 | 1.18 | 0.43 | 3.15 | 0.08 | 0.54 | 0.57 |
| NM_003247 | *Homo sapiens* thrombospondin 2 (THBS2), mRNA. /PROD=thrombospondin 2 /FL=gb:NM_003247.1 gb:L12350.1 | THBS2 | 2.62 | 0.20 | 1.04 | 0.28 | 2.70 | 0.04 | 0.27 | 0.45 |
| NM_001446 | *Homo sapiens* fatty acid binding protein 7, brain (FABP7), mRNA. /PROD=fatty acid binding protein 7, brain /FL=gb:U81235.1 gb:D88648.1 gb:U51338.1 gb:NM_001446.1 gb:D50373.1 | FABP7 | 0.95 | 0.09 | −0.75 | 0.37 | 0.20 | 0.22 | −1.73 | 0.99 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AW004016 | ESTs | ST6GAL2 | 1.57 | 0.14 | 0.89 | 0.32 | 3.30 | 0.07 | 1.48 | 0.43 |
| AW072790 | contactin 1 | CNTN1 | 0.50 | 0.20 | 0.18 | 0.98 | 1.84 | 0.10 | 1.01 | 1.39 |
| AL512686 | Homo sapiens mRNA; cDNA DKFZp761I177 (from clone DKFZp761I177). | GNAO1 | 2.16 | 0.50 | −0.28 | 1.03 | 1.67 | 0.18 | −1.12 | 0.37 |
| AI638063 | ESTs | CBX5 | 0.49 | 0.16 | −0.34 | 0.34 | 0.98 | 0.11 | −2.71 | 1.22 |
| AU157049 | Homo sapiens cDNA FLJ14284 fis, clone PLACE1005898 | LOC153346 | 2.24 | 0.20 | 0.34 | 0.47 | 2.24 | 0.09 | −0.44 | 0.96 |
| NM_002738 | Homo sapiens protein kinase C, beta 1 (PRKCB1), mRNA. /PROD=protein kinase C, beta 1 /FL=gb:NM_002738.1 | PRKCB1 | 0.99 | 0.28 | −0.15 | 0.45 | 1.42 | 0.08 | −1.02 | 1.04 |
| AI185136 | ESTs | DYDC2 | 0.12 | 0.31 | −0.80 | 0.08 | 0.72 | 0.08 | −0.60 | 0.09 |
| AI928037 | ESTs | RPIB9 | −0.55 | 0.55 | −2.71 | 0.74 | 0.49 | 0.12 | −0.89 | 0.27 |
| NM_016179 | Homo sapiens transient receptor potential channel 4 (TRPC4), mRNA. /PROD=transient receptor potential 4 /FL=gb:NM_016179.1 gb:AF175406.1 | TRPC4 | −1.51 | 0.85 | −1.87 | 1.42 | 1.71 | 0.11 | −0.13 | 1.23 |
| AW138143 | ESTs | SORBS2 | 3.29 | 0.13 | 2.35 | 1.05 | 4.28 | 0.10 | 1.32 | 1.07 |
| NM_001876 | Homo sapiens carnitine palmitoyltransferase I, liver (CPT1A), nuclear gene encoding mitochondrial protein, mRNA. /PROD=liver carnitine palmitoyltransferase I /FL=gb:L39211.1 gb:NM_001876.1 | CPT1A | 1.63 | 0.18 | −0.15 | 0.21 | 1.32 | 0.07 | −0.20 | 0.33 |
| AA903862 | ESTs | C20orf54 | 1.61 | 0.15 | −1.17 | 0.30 | 0.68 | 0.21 | −1.49 | 0.23 |
| AI670947 | phosphatidyl-inositol-4-phosphate 5-kinase, type I, beta | — | 3.91 | 0.05 | 0.55 | 1.54 | 3.33 | 0.10 | 1.17 | 0.68 |
| AV648405 | polymerase (RNA) III (DNA directed) (32 kD) | — | −0.01 | 0.11 | 0.23 | 0.52 | 1.73 | 0.14 | −1.23 | 1.15 |
| BF435123 | bromodomain and PHD finger containing, 3 | — | 1.80 | 0.13 | −1.35 | 1.01 | 1.14 | 0.03 | 0.37 | 0.24 |
| NM_016582 | Homo sapiens peptide transporter 3 (LOC51296), mRNA. /PROD=peptide transporter 3 /FL=gb:NM_016582.1 gb:AB020598.1 | SLC15A3 | 1.77 | 0.16 | −0.88 | 1.35 | 1.30 | 0.23 | −2.04 | 1.23 |
| AI830490 | glycerol kinase | GK | 0.61 | 0.01 | −0.65 | 0.79 | 1.25 | 0.20 | −0.38 | 0.33 |
| AW134979 | HSPC156 protein | STXBP6 | 2.28 | 0.03 | 0.55 | 0.28 | 2.05 | 0.03 | 0.30 | 0.44 |
| AI354636 | ESTs | — | 2.81 | 0.11 | 0.68 | 1.17 | 3.02 | 0.20 | 0.19 | 0.76 |
| BE672659 | ESTs | — | 0.20 | 0.64 | −0.43 | 0.61 | 1.98 | 0.12 | −0.69 | 0.45 |
| AF284095 | Homo sapiens alpha-2A adrenergic receptor mRNA, complete cds. /PROD=alpha-2A adrenergic receptor /FL=gb:AF284095.1 gb:NM_000681.1 | ADRA2A | 0.63 | 0.21 | −0.74 | 0.98 | 1.85 | 0.03 | 0.55 | 0.31 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_021136 | Homo sapiens reticulon 1 (RTN1), mRNA. /PROD=reticulon 1 /FL=gb:L10333.1 gb:L10334.1 gb:NM_021136.1 | RTN1 | −0.30 | 0.03 | −1.39 | 0.35 | 0.80 | 0.07 | −1.23 | 0.39 |
| NM_014729 | Homo sapiens KIAA0808 gene product (KIAA0808), mRNA. /PROD=KIAA0808 gene product /FL=gb:AB018351.1 gb:NM_014729.1 | TOX | 0.34 | 0.03 | −0.46 | 0.12 | 0.90 | 0.18 | −1.86 | 0.40 |
| BE674118 | ESTs | — | 0.78 | 0.07 | −1.32 | 0.73 | 0.28 | 0.19 | −0.96 | 0.74 |
| BC026969 | Homo sapiens, clone IMAGE:5116073, mRNA, partial cds. | WDR67 | 2.95 | 0.11 | 0.75 | 0.92 | 3.08 | 0.08 | 0.45 | 0.61 |
| AF131783 | Homo sapiens clone 25181 mRNA sequence. | PAP2D | −0.42 | 0.26 | −2.00 | 1.05 | 0.31 | 0.22 | −1.56 | 0.70 |
| U11058 | Homo sapiens large conductance calcium- and voltage-dependent potassium channel alpha subunit (MaxiK) mRNA, complete cds. /PROD=large conductance calcium- and voltage-dependentpotassium channel alpha subunit /FL=gb:U23767.1 gb:NM_002247.1 gb:AF025999 | KCNMA1 | 1.56 | 0.09 | −0.16 | 1.08 | 2.29 | 0.18 | −0.79 | 0.86 |
| BF510715 | fibroblast growth factor 4 (heparin secretory transforming protein 1, Kaposi sarcoma oncogene) /FL=gb:M17446.1 gb:NM_002007.1 | — | 2.67 | 0.27 | 0.84 | 0.17 | 3.29 | 0.01 | 0.64 | 0.51 |
| BE897866 | ESTs | ACADSB | 1.41 | 0.23 | 0.08 | 0.34 | 3.10 | 0.10 | −0.27 | 0.88 |
| AI735586 | ESTs | LOC152573 | 0.60 | 0.13 | 0.00 | 1.14 | 2.84 | 0.07 | 1.12 | 1.30 |
| AL573058 | complement component 1, r subcomponent | C1R | 0.92 | 0.14 | −1.67 | 0.38 | 0.73 | 0.02 | −0.96 | 0.77 |
| AF429305 | Homo sapiens C23up NCRMS mRNA, partial sequence; alternatively spliced. | RMST | −0.48 | 0.03 | −2.49 | 0.51 | −0.25 | 0.20 | −1.89 | 0.27 |
| BF195118 | ESTs, Weakly similar to ALU7_HUMAN ALU SUBFAMILY SQ SEQUENCE CONTAMINATION WARNING ENTRY (H. sapiens) | ATP5J | 0.09 | 0.13 | −0.92 | 0.42 | 1.57 | 0.16 | −0.53 | 0.08 |
| NM_005460 | Homo sapiens synuclein, alpha interacting protein (synphilin) (SNCAIP), mRNA. /PROD=synuclein alpha interacting protein /FL=gb:AF076929.1 gb:NM_005460.1 | SNCAIP | 1.76 | 0.16 | −0.84 | 0.52 | 1.61 | 0.19 | −0.92 | 0.88 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_024893 | Homo sapiens hypothetical protein FLJ14220 (FLJ14220), mRNA. /PROD=hypothetical protein FLJ14220 /FL=gb:NM_024893.1 | C20orf39 | 1.16 | 0.29 | −0.56 | 0.42 | 2.36 | 0.15 | −0.06 | 0.17 |
| NM_022034 | Homo sapiens estrogen regulated gene 1 (ERG-1), mRNA. /PROD=estrogen regulated gene 1 /FL=gb:AF305835.1 gb:NM_022034.1 | CUZD1 | 1.31 | 0.08 | 0.80 | 0.28 | 2.78 | 0.07 | 0.24 | 0.58 |
| NM_014788 | Homo sapiens KIAA0129 gene product (KIAA0129), mRNA. /PROD=KIAA0129 gene product /FL=gb:D50919.1 gb:NM_014788.1 | TRIM14 | 3.12 | 0.09 | 1.22 | 0.59 | 3.54 | 0.08 | 1.02 | 0.45 |
| AV646597 | ESTs, Weakly similar to ALU7_HUMAN ALU SUBFAMILY SQ SEQUENCE CONTAMINATION WARNING ENTRY (H. sapiens) | XIST | −0.77 | 0.18 | 0.06 | 1.55 | 3.78 | 0.25 | 2.28 | 0.98 |
| BF062629 | DKFZP586E1621 protein | TMEM158 | 4.00 | 0.19 | 2.41 | 0.27 | 4.87 | 0.00 | 1.93 | 0.19 |
| AW440492 | ATPase, Na+K+ transporting, alpha 2 (+) polypeptide /FL=gb:NM_000702.1 | ATP1A2 | 1.33 | 0.07 | −2.12 | 1.07 | 1.27 | 0.06 | −0.53 | 0.11 |
| AF283777 | Homo sapiens clone TCBAP0702 mRNA sequence. | CD72 | −0.08 | 0.45 | −1.88 | 1.19 | 0.41 | 0.24 | −1.42 | 1.13 |
| NM_005375 | Homo sapiens v-myb avian myeloblastosis viral oncogene homolog (MYB), mRNA. /PROD=v-myb avian myeloblastosis viral oncogenehomolog /FL=gb:NM_005375.1 gb:AF104863.1 gb:M15024.1 | MYB | 2.11 | 0.17 | −0.52 | 0.18 | 2.24 | 0.03 | 0.10 | 0.08 |
| NM_017671 | Homo sapiens hypothetical protein FLJ20116 (FLJ20116), mRNA. /PROD=hypothetical protein FLJ20116 /FL=gb:NM_017671.1 | C20orf42 | 3.19 | 0.12 | 0.97 | 0.70 | 3.26 | 0.07 | 0.16 | 0.94 |
| BG283790 | ESTs | MATR3 | 2.27 | 0.11 | 0.95 | 0.57 | 3.53 | 0.04 | 0.89 | 0.51 |
| NM_000702 | Homo sapiens ATPase, Na+K+ transporting, alpha 2 (+) polypeptide (ATP1A2), mRNA. /PROD=ATPase, Na+K+ transporting, alpha 2 (+)polypeptide /FL=gb:NM_000702.1 | ATP1A2 | 2.12 | 0.17 | 0.76 | 0.38 | 2.93 | 0.16 | 0.51 | 0.12 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_025135 | Homo sapiens hypothetical protein FLJ22297 (KIAA1695), mRNA. /PROD=hypothetical protein KIAA1695 /FL=gb:NM_025135.1 | FHOD3 | 1.02 | 0.18 | 0.80 | 0.40 | 2.34 | 0.10 | −0.77 | 0.72 |
| NM_012281 | Homo sapiens potassium voltage-gated channel, ShaI-related subfamily, member 2 (KCND2), mRNA. /PROD=potassium voltage-gated channel, ShaI-relatedsubfamily, member 2 /FL=gb:NM_012281.1 gb:AB028967.1 gb:AF121104.1 | KCND2 | 1.67 | 0.30 | 0.05 | 0.15 | 2.70 | 0.09 | −0.26 | 0.38 |
| BF449063 | collagen, type XIV, alpha 1 (undulin) | COL14A1 | 1.61 | 0.15 | 0.30 | 0.38 | 2.68 | 0.17 | −0.33 | 0.68 |
| AA280904 | ESTs | C9orf39 | 0.23 | 0.21 | −1.58 | 1.26 | 1.13 | 0.14 | −0.78 | 0.42 |
| NM_022467 | Homo sapiens N-acetylgalactos-amine-4-O-sulfo-transferase (GALNAC-4-ST1), mRNA. /PROD=N-acetyl-galactosamine-4-O-sulfotransferase /FL=gb:NM_022467.1 gb:AF300612.1 | CHST8 | 2.11 | 0.20 | −0.51 | 0.30 | 2.17 | 0.10 | 0.48 | 0.02 |
| BE468066 | ESTs | RMST | 3.26 | 0.09 | 1.49 | 0.10 | 3.80 | 0.09 | 1.63 | 0.08 |
| AL120674 | ESTs | — | 1.00 | 0.11 | −1.35 | 1.73 | 1.55 | 0.15 | −2.20 | 0.86 |
| NM_133329 | Homo sapiens potassium voltage-gated channel, subfamily G, member 3 (KCNG3), transcript variant 1, mRNA. /PROD=potassium voltage-gated channel, subfamily G, member 3 isoform 1 /FL=gb:AF454548.1 gb:AF348982.1 gb:AB070604.1 gb:NM_133329.4 | KCNG3 | 2.18 | 0.27 | 0.74 | 0.29 | 3.67 | 0.01 | 0.26 | 0.28 |
| AI742043 | ESTs | — | 0.94 | 0.34 | −0.76 | 0.37 | 1.77 | 0.10 | −1.45 | 0.52 |
| NM_005103 | Homo sapiens fasciculation and elongation protein zeta 1 (zygin I) (FEZ1), transcript variant 1, mRNA. /PROD=zygin 1, isoform 1 /FL=gb:U60060.1 gb:U69139.1 gb:NM_005103.2 | FEZ1 | 2.80 | 0.11 | 2.08 | 0.25 | 4.98 | 0.06 | 2.20 | 0.26 |
| NM_000277 | Homo sapiens phenylalanine hydroxylase (PAH), mRNA. /PROD=phenylalanine hydroxylase /FL=gb:U49897.1 gb:NM_000277.1 | PAH | 0.65 | 0.11 | −1.08 | 0.08 | 1.46 | 0.18 | −0.42 | 0.12 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| BF698797 | ESTs | — | 0.93 | 0.10 | −0.74 | 0.11 | 2.07 | 0.10 | −0.40 | 0.44 |
| BF437747 | ESTs, Weakly similar to ALU7_HUMAN ALU SUBFAMILY SQ SEQUENCE CONTAMINATION WARNING ENTRY (H. sapiens) | C20orf118 | 4.26 | 0.07 | 1.99 | 0.45 | 4.57 | 0.09 | 1.75 | 0.39 |
| NM_003020 | Homo sapiens secretory granule, neuroendocrine protein 1 (7B2 protein) (SGNE1), mRNA. /PROD=secretory granule, neuroendocrine protein 1 (7B2protein) /FL=gb:BC005349.1 gb:NM_003020.1 | SCG5 | 4.03 | 0.14 | 2.53 | 0.32 | 5.01 | 0.12 | 3.11 | 0.24 |
| NM_002800 | Homo sapiens proteasome (prosome, macropain) subunit, beta type, 9 (large multifunctional protease 2) (PSMB9), mRNA. /PROD=proteasome (prosome, macropain) subunit, betatype, 9 (large multifunctional protease 2) /FL=gb:U01025.1 gb:NM_002800.1 | PSMB9 | 1.38 | 0.10 | 0.27 | 0.34 | 2.05 | 0.07 | −1.43 | 1.14 |
| BE972639 | ESTs | LOC646326 | 0.00 | 0.15 | −2.71 | 0.55 | 0.33 | 0.22 | −2.24 | 0.61 |
| BC044830 | Homo sapiens, Similar to RIKEN cDNA 1700011F14 gene, clone MGC:35062 IMAGE:5166167, mRNA, complete cds. /PROD=Similar to RIKEN cDNA 1700011F14 gene /FL=gb:BC044830.1 | C10orf96 | 1.38 | 0.12 | −0.32 | 0.82 | 2.28 | 0.06 | −1.39 | 0.90 |
| AI961231 | KIAA0808 gene product /FL=gb:AB018351.1 gb:NM_014729.1 | TOX | 3.28 | 0.13 | 1.23 | 0.06 | 4.00 | 0.01 | 1.13 | 0.37 |
| U17496 | Human proteasome subunit LMP7 (allele LMP7B) mRNA, complete cds. /PROD=proteasome subunit LMP7 /FL=gb:U17497.1 gb:U17496.1 | PSMB8 | 3.43 | 0.21 | 0.46 | 1.17 | 3.30 | 0.06 | 0.09 | 0.64 |
| N23651 | ESTs | SDK2 | −1.16 | 0.31 | −2.65 | 0.42 | 1.27 | 0.09 | −2.07 | 0.75 |
| NM_007015 | Homo sapiens chondromodulin I precursor (CHM-I), mRNA. /PROD=chondromodulin I precursor /FL=gb:NM_007015.1 gb:AB006000.1 | LECT1 | 4.83 | 0.12 | 2.27 | 0.84 | 5.36 | 0.09 | 1.83 | 0.69 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGEL™
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| NM_015474 | Homo sapiens DKFZP564A032 protein (DKFZP564A032), mRNA. /PROD=DKFZP564A032 protein /FL=gb:AF228421.1 gb:AL050267.1 gb:AB013847.1 gb:NM_015474.1 | SAMHD1 | 2.63 | 0.17 | 0.57 | 0.33 | 2.89 | 0.09 | 0.29 | 0.22 |
| AF147427 | Homo sapiens full length insert cDNA clone YP80A10. | SAMHD1 | 1.33 | 0.03 | −0.99 | 0.88 | 1.35 | 0.08 | −2.30 | 0.97 |
| NM_004688 | Homo sapiens N-myc (and STAT) interactor (NMI), mRNA. /PROD=N-myc and STAT interactor /FL=gb:BC001268.1 gb:NM_004688.1 gb:U32849.1 | NMI | 3.54 | 0.04 | 0.96 | 0.07 | 3.80 | 0.07 | 1.13 | 0.34 |
| AB040812 | Homo sapiens mRNA for protein kinase PAK5, complete cds. /PROD=protein kinase PAK5 /FL=gb:AB040812.1 | PAK7 | −1.37 | 0.60 | −3.89 | 1.62 | −0.49 | 0.07 | −4.18 | 0.12 |
| AI985987 | ESTs, Moderately similar to ALU1_HUMAN ALU SUBFAMILY J SEQUENCE CONTAMINATION WARNING ENTRY (H. sapiens) | SCNN1G | −0.28 | 0.31 | −0.99 | 0.35 | 0.12 | 0.19 | −2.70 | 0.59 |
| NM_001877 | Homo sapiens complement component (3dEpstein Barr virus) receptor 2 (CR2), mRNA. /PROD=complement component (3dEpstein Barr virus)receptor 2 /FL=gb:NM_001877.1 gb:M26004.1 | CR2 | 1.50 | 0.13 | −0.43 | 1.05 | 2.35 | 0.14 | −1.44 | 1.51 |
| NM_001351 | Homo sapiens deleted in azoospermia-like (DAZL), mRNA. /PROD=deleted in azoospermia-like /FL=gb:U66726.2 gb:NM_001351.1 gb:U65918.1 gb:U66078.1 | DAZL | 1.69 | 0.24 | −0.81 | 0.76 | 1.93 | 0.12 | −0.73 | 0.06 |
| NM_022168 | Homo sapiens melanoma differentiation associated protein-5 (MDA5), mRNA. /PROD=melanoma differentiation associated protein-5 /FL=gb:AY017378.1 gb:NM_022168.1 gb:AF095844.1 | IFIH1 | −2.03 | 1.08 | −2.76 | 0.83 | −0.10 | 0.15 | −2.15 | 0.40 |
| AF052108 | Homo sapiens clone 23687 mRNA sequence. | LOC157627 | 1.49 | 0.33 | 0.22 | 1.02 | 2.26 | 0.40 | −1.33 | 1.19 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AI056877 | Human DNA sequence from clone RP4-530I15 on chromosome 20. Contains the 3 end of the PTPN1 gene for protein tyrosine phosphatase, non-receptor type 1 (EC 3.1.3.48), the gene for a novel protein similar to placental protein DIFF40, an RPL36 (60S Ribos | LOC200230 | 0.11 | 0.30 | −2.37 | 0.94 | 1.15 | 0.18 | −1.35 | 0.75 |
| NM_002522 | *Homo sapiens* neuronal pentraxin I (NPTX1), mRNA. /PROD=neuronal pentraxin I precursor /FL=gb:NM_002522.1 gb:U61849.1 | NPTX1 | 2.35 | 0.25 | −0.48 | 0.19 | 2.17 | 0.09 | −1.19 | 0.83 |
| N21096 | ESTs | STXBP6 | 2.42 | 0.16 | 0.99 | 0.08 | 3.69 | 0.09 | 1.14 | 0.04 |
| AI693516 | ESTs | COL14A1 | 0.39 | 0.23 | −1.63 | 0.96 | 0.96 | 0.17 | −1.81 | 0.67 |
| NM_018043 | *Homo sapiens* hypothetical protein FLJ10261 (FLJ10261), mRNA. /PROD=hypothetical protein FLJ10261 /FL=gb:NM_018043.1 | TMEM16A | −0.90 | 0.37 | −1.93 | 0.70 | 0.25 | 0.43 | −3.93 | 0.49 |
| AF110400 | *Homo sapiens* fibroblast growth factor 19 (FGF19) mRNA, complete cds. /PROD=fibroblast growth factor 19 /FL=gb:AF110400.1 gb:NM_005117.1 gb:AB018122.1 | FGF19 | 2.12 | 0.14 | −0.08 | 0.34 | 2.18 | 0.04 | −0.91 | 0.18 |
| AK098525 | *Homo sapiens* cDNA FLJ25659 fis, clone TST00427, highly similar to *Mus musculus* hedgehog-interacting protein (Hip) mRNA. | HHIP | 1.76 | 0.14 | −0.57 | 0.63 | 3.32 | 0.06 | −0.11 | 0.15 |
| AV715309 | ESTs, Weakly similar to ALU7_HUMAN ALU SUBFAMILY SQ SEQUENCE CONTAMINATION WARNING ENTRY (*H. sapiens*) | C20orf118 | 4.28 | 0.13 | 1.89 | 0.39 | 4.76 | 0.10 | 1.48 | 0.42 |
| U96136 | *Homo sapiens* delta-catenin mRNA, complete cds. /PROD=delta-catenin /FL=gb:NM_001332.1 gb:U72665.1 gb:AB013805.1 gb:U96136.1 gb:AF035302.1 | CTNND2 | 0.78 | 0.11 | −1.33 | 0.87 | 1.18 | 0.12 | −1.17 | 0.67 |
| NM_002590 | *Homo sapiens* protocadherin 8 (PCDH8), mRNA. /PROD=protocadherin 8 /FL=gb:NM_002590.2 gb:AF061573.2 | PCDH8 | −0.80 | 0.34 | −0.83 | 0.82 | 2.18 | 0.02 | 0.12 | 0.33 |

TABLE IV-continued

DIFFERENTIAL EXPRESSION OF GENES BETWEEN UNDIFFERENTIATED EMBRYONIC
STEM CELLS AND DEFINITIVE ENDODERM STAGE CELLS CULTURED ON EITHER MATRIGELTM
OR MOUSE EMBRYONIC FIBROBLASTS AFTER 5 DAYS OF TREATMENT.

| Gene Identifier | Gene Title | Gene ID | H9P83 on Matrigel | SEM | H9P83 on Matrigel-DE stage | SEM | H9P44 on MEFs | SEM | H9P44 on MEFs-DE stage | SEM |
|---|---|---|---|---|---|---|---|---|---|---|
| AF107846 | *Homo sapiens* neuroendocrine-specific Golgi protein p55 (XLalphas) gene, exon XL2 and complete cds | — | 0.44 | 0.20 | −0.25 | 0.12 | 2.12 | 0.14 | −2.56 | 0.81 |
| BG169832 | adenylate kinase 5 /FL=gb:NM_012093.1 gb:AF062595.1 | AK5 | 0.62 | 0.36 | −2.79 | 0.50 | 1.03 | 0.36 | −1.94 | 0.32 |
| BE968806 | ESTs, Weakly similar to ALU4_HUMAN ALU SUBFAMILY SB2 SEQUENCE CONTAMINATION WARNING ENTRY (*H. sapiens*) | ATP5S | −1.15 | 0.14 | −3.03 | 0.71 | −0.34 | 0.15 | −4.73 | 0.74 |
| BU729850 | hypothetical protein LOC153469 | JAKMIP2 | 2.30 | 0.07 | 0.43 | 1.78 | 3.86 | 0.04 | −1.56 | 1.92 |
| AL832535 | *Homo sapiens* mRNA; cDNA DKFZp547J1816 (from clone DKFZp547J1816). | LOC157627 | 2.25 | 0.18 | −0.04 | 1.00 | 3.14 | 0.25 | −1.50 | 1.19 |
| NM_000439 | *Homo sapiens* proprotein convertase subtilisinkexin type 1 (PCSK1), mRNA. /PROD=proprotein convertase subtilisinkexin type 1 /FL=gb:NM_000439.2 gb:M90753.1 | PCSK1 | −0.63 | 0.18 | −2.68 | 0.53 | 0.69 | 0.30 | −3.19 | 1.03 |
| M34455 | Human interferon-gamma-inducible indoleamine 2,3-dioxygenase (IDO) mRNA, complete cds. /FL=gb:NM_002164.1 gb:M34455.1 | INDO | 4.39 | 0.23 | 1.58 | 0.09 | 5.44 | 0.08 | 1.69 | 0.13 |
| AB014737 | *Homo sapiens* mRNA for SMAP-2b, complete cds. /PROD=SMAP-2b /FL=gb:AB014737.1 | SMOC2 | 1.25 | 0.12 | −2.04 | 0.48 | 1.94 | 0.06 | −2.27 | 1.12 |
| BM682352 | *Homo sapiens* cDNA FLJ37204 fis, clone BRALZ2006976. | HCN1 | −0.41 | 0.14 | −4.38 | 1.19 | 0.35 | 0.31 | −3.88 | 0.32 |

TABLE V

RELATIVE EXPRESSION OF DEFINITE ENDODERM MARKERS FOR CONDITIONS OUTLINED IN EXAMPLE 10. ALL VALUES WERE NORMALIZED TO GROUP 1 (CONTROL).

|  | Sox17 | CXCR4 | Goosecoid | HNF-3B | SOX-2 | Oct-4 |
|---|---|---|---|---|---|---|
| Group 1-control | 1 | 1 | 1 | 1 | 1 | 1 |
| Group 2 | 45 | 19.5 | 2.8 | 0.64 | 0.91 | 1.1 |
| Group 3 | 45 | 30 | 2.9 | 0.74 | 0.70 | 0.76 |
| Group 4 | 8 | 14 | 2.7 | 1.11 | 0.18 | 0.36 |
| Group 5 | 23 | 16 | 3.1 | 1.76 | 0.16 | 0.41 |
| Group 6 | 41 | 5.8 | 3.0 | 1.87 | 0.61 | 0.57 |
| Group 7 | 25 | 19.5 | 2.7 | 0.62 | 0.34 | 0.48 |
| Group 8 | 6 | 15.9 | 2.9 | 2.0 | 0.13 | 0.43 |
| Group 9 | 1 | 1.4 | 0.9 | 0.89 | 1.2 | 0.85 |
| Group 10 | 22 | 1.5 | 1.4 | 1.20 | 1.36 | 0.68 |
| Group 11 | 54 | 23 | 2.5 | 0.71 | 0.66 | 0.65 |
| Group 12 | 68 | 0.7 | 0.9 | 1.51 | 0.02 | 0.30 |
| Group 13 | 13.9 | 12.7 | 3.0 | 2.1 | 0.11 | 0.30 |
| Group 14 | 52.6 | 20.6 | 2.9 | 0.82 | 0.69 | 0.70 |
| Group 15 | 68 | 27.7 | 2.9 | 0.68 | 0.68 | 0.85 |
| Group 16 | 13.9 | 21 | 2.4 | 0.79 | 0.46 | 0.72 |
| Group 17 | 52 | 14.9 | 3.5 | 2.12 | 0.22 | 0.44 |

TABLE VI

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | −4.82708 | 2.63968 | −4.26995 | 8.62E−05 |
| microfibrillar-associated protein 4 | 0.063791 | 5.16358 | −0.60091 | 3.48E−03 |
| *Homo sapiens*, alpha-1 (VI) collagen | −3.66187 | 2.36459 | −2.26934 | 1.45E−04 |
| ESTs | −3.43712 | 2.14508 | −2.6475 | 0.00E+00 |
| *Homo sapiens* cystatin SN (CST1), mRNA./PROD = cystatin SN/ FL = gb: J03870.1 gb: NM_001898.1 | 0.072931 | 7.53908 | 4.63955 | 4.46E−03 |
| solute carrier family 16 (monocarboxylic acid transporters), member 3/ FL = gb: U81800.1 gb: NM_004207.1 | −0.066405 | 5.23572 | 0.279005 | 4.27E−04 |
| *Homo sapiens* fibroblast growth factor 17 (FGF17), mRNA./PROD = fibroblast growth factor 17/FL = gb: NM_003867.1 gb: AB009249.1 | −0.894644 | 5.75417 | 2.4872 | 4.93E−03 |
| Human link protein mRNA, complete cds./PROD = link protein/ FL = gb: NM_001884.1 gb: U43328.1 | −1.93991 | 3.31348 | −1.26346 | 1.14E−02 |
| *Homo sapiens* solute carrier family 16 (monocarboxylic acid transporters), member 3 (SLC16A3), mRNA./ PROD = solute carrier family 16 (monocarboxylic acidtransporters), member 3/FL = gb: U81800.1 gb: NM_004207.1 | 0.710321 | 6.12971 | 1.72403 | 0.00E+00 |
| *Homo sapiens* apolipoprotein A-I (APOA1), mRNA./PROD = apolipoprotein A-I precursor/FL = gb: M27875.1 gb: M11791.1 gb: NM_000039.1 gb: BC005380.1 | −1.47073 | 5.37558 | 2.46891 | 5.07E−03 |
| *Homo sapiens* cytidine deaminase (CDA), mRNA./PROD = cytidine deaminase/FL = gb: L27943.1 gb: NM_001785.1 | −3.89129 | 2.05822 | −1.67035 | 2.23E−03 |
| ESTs, Moderately similar to JE0284 Mm-1 cell derived transplantability-associated protein 1b (*H. sapiens*) | −2.37712 | 5.75671 | 4.22227 | 2.56E−02 |
| ESTs | −0.04716 | 5.28231 | 0.966974 | 0.00E+00 |
| glycophorin B (includes Ss blood group) | −2.85201 | 3.32812 | −0.12969 | 1.45E−04 |
| *Homo sapiens* homeobox protein goosecoid mRNA, complete cds./ PROD = homeobox protein goosecoid/ FL = gb: AY177407.1 gb: NM_173849.1 | −4.42042 | 3.55326 | 1.89424 | 2.50E−02 |
| MCP-1 = monocyte chemotactic protein (human, aortic endothelial cells, mRNA, 661 nt)./PROD = MCP-1 | −2.27571 | 5.13499 | 2.95543 | 2.92E−02 |
| *Homo sapiens* Mix-like homeobox protein 1 (MILD1) mRNA, complete cds./ PROD = Mix-like homeobox protein 1/ FL = gb: AF211891.1 | −1.54648 | 4.47601 | 0.921971 | 2.01E−02 |
| ESTs | −4.93603 | 2.17917 | −0.23735 | 1.12E−04 |
| *Homo sapiens* lumican (LUM), mRNA./ PROD = lumican/FL = gb: NM_002345.1 gb: U18728.1 gb: U21128.1 | −4.05726 | 3.21064 | 0.948822 | 3.39E−02 |
| *Homo sapiens* HNF-3beta mRNA for hepatocyte nuclear factor-3 beta, complete cds./PROD = hepatocyte nuclear factor-3 beta/ FL = gb: AB028021.1 gb: NM_021784.1 | −2.71785 | 4.68666 | 2.82506 | 3.71E−02 |
| *Homo sapiens* reserved (KCNK12), mRNA./PROD = tandem pore domain potassium channel THIK-2/ FL = gb: NM_022055.1 gb: AF287302.1 | −0.468745 | 6.28184 | 3.77969 | 1.97E−02 |
| *Homo sapiens* atrophin-1 interacting protein 1; activin receptor interacting protein 1 (KIAA0705), mRNA./ PROD = atrophin-1 interacting protein 1; activinreceptor interacting protein 1/ FL = gb: NM_012301.1 gb: AF038563.1 | −4.30828 | 1.80825 | −1.32021 | 9.63E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | −2.33636 | 2.25176 | −2.32124 | 5.26E-04 |
| Homo sapiens glutamate decarboxylase 1 (brain, 67 kD) (GAD1), transcript variant GAD25, mRNA./PROD = glutamate decarboxylase 1, isoform GAD25/FL = gb: NM_013445.1 gb: AF178853.1 gb: BC002815.1 | −2.424 | 2.31908 | −1.87965 | 4.07E-04 |
| Homo sapiens cardiac ventricular troponin C mRNA, complete cds./PROD = cardiac ventricular troponin C/FL = gb: NM_003280.1 gb: AF020769.1 | −0.549728 | 4.89072 | 1.4377 | 2.99E-03 |
| ESTs | −2.89554 | 3.42817 | 0.926036 | 2.62E-02 |
| Homo sapiens fibroblast growth factor 8 (androgen-induced) (FGF8), mRNA./PROD = fibroblast growth factor 8 (androgen-induced)/FL = gb: U36223.1 gb: U46212.1 gb: NM_006119.1 | −4.32791 | 2.19561 | 0.015827 | 5.91E-03 |
| ESTs | −3.09818 | 1.66254 | −2.20564 | 8.62E-05 |
| Homo sapiens haptoglobin-related protein (HPR), mRNA./PROD = haptoglobin-related protein/FL = gb: NM_020995.1 | −2.6068 | 2.38009 | −1.19632 | 6.95E-03 |
| collagen, type VI, alpha 1 | −1.418 | 3.85952 | 0.604245 | 1.21E-02 |
| Human (clone 8B1) Br-cadherin mRNA, complete cds./PROD = Br-cadherin/FL = gb: L34057.1 gb: L33477.1 gb: NM_004061.1 | −2.17941 | 2.59894 | −1.02624 | 1.24E-02 |
| ESTs | −1.40092 | 2.57297 | −1.82509 | 1.45E-04 |
| Homo sapiens cystatin SA (CST2), mRNA./PROD = cystatin SA/FL = gb: NM_001322.1 | −0.102178 | 5.21645 | 2.1671 | 2.40E-02 |
| Human mRNA for apolipoprotein Al (apo Al) = ./PROD = preproapolipoprotein Al | 0.215086 | 5.51109 | 2.49684 | 9.57E-03 |
| Homo sapiens MLL septin-like fusion (MSF), mRNA./PROD = MLL septin-like fusion/FL = gb: AF123052.1 gb: NM_006640.1 | −3.29221 | 1.70902 | −1.49951 | 2.25E-03 |
| Homo sapiens cystatin S (CST4), mRNA./PROD = cystatin S/FL = gb: NM_001899.1 | 0.92448 | 6.48842 | 3.87036 | 7.20E-03 |
| Homo sapiens phorbolin-like protein MDS019 (MDS019), mRNA./PROD = phorbolin-like protein MDS019/FL = gb: AF182420.1 gb: NM_021822.1 | −1.11883 | 4.73391 | 2.40782 | 7.86E-03 |
| Homo sapiens apolipoprotein A-II (APOA2), mRNA./PROD = apolipoprotein A-II precursor/FL = gb: M29882.1 gb: NM_001643.1 gb: BC005282.1 | −1.03333 | 5.80468 | 4.46856 | 3.23E-02 |
| ESTs | −1.55475 | 3.48278 | 0.420447 | 2.50E-02 |
| Homo sapiens glutamate decarboxylase 1 (brain, 67 kD) (GAD1), transcript variant GAD67, mRNA./PROD = glutamate decarboxylase 1, isoform GAD67/FL = gb: NM_000817.1 gb: M81883.1 gb: L16888.1 | −3.86752 | 1.56384 | −1.08675 | 2.52E-02 |
| ESTs | −0.731491 | 5.43249 | 3.52168 | 1.60E-02 |
| ESTs | −2.03591 | 3.38924 | 0.760984 | 2.34E-03 |
| Homo sapiens retinoid X receptor, gamma (RXRG), mRNA./PROD = retinoid X receptor, gamma/FL = gb: NM_006917.1 gb: U38480.1 | −2.37496 | 2.62934 | −0.32035 | 8.83E-04 |
| ESTs | −0.648552 | 4.30576 | 1.43266 | 2.19E-03 |
| Homo sapiens cDNA FLJ11550 fis, clone HEMBA1002970 | −1.22228 | 5.37746 | 4.21644 | 1.68E-02 |
| ESTs | −1.782 | 3.50391 | 1.0501 | 1.85E-02 |
| Homo sapiens haptoglobin (HP), mRNA./PROD = haptoglobin/FL = gb: K00422.1 gb: L29394.1 gb: NM_005143.1 | −1.10114 | 3.5449 | 0.477027 | 8.13E-03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* hypothetical protein FLJ10970 (FLJ10970), mRNA./ PROD = hypothetical protein FLJ10970/ FL = gb: NM_018286.1 | −0.431989 | 5.14497 | 3.02045 | 2.62E−02 |
| *Homo sapiens* beta-site APP cleaving enzyme (BACE) mRNA, complete cds./ PROD = beta-site APP cleaving enzyme/ FL = gb: AF200343.1 gb: AF204943.1 gb: AF190725.1 gb: AF201468.1 gb: NM_012104.1 | −2.0354 | 3.70648 | 1.75385 | 8.00E−03 |
| *Homo sapiens* hypothetical protein FLJ22252 similar to SRY-box containing gene 17 (FLJ22252), mRNA./ PROD = hypothetical protein FLJ22252 similar to SRY-boxcontaining gene 17/ FL = gb: NM_022454.1 | 1.36784 | 6.82571 | 4.5979 | 2.10E−02 |
| Cluster Incl. AB028021: *Homo sapiens* HNF-3beta mRNA for hepatocyte nuclear factor-3 beta, complete cds/ cds = (196, 1569)/gb = AB028021/ gi = 4958949/ug = Hs.155651/len = 1944 | −1.5339 | 5.12418 | 4.11704 | 4.47E−02 |
| *Homo sapiens* gastrin-releasing peptide (GRP), mRNA./PROD = gastrin-releasing peptide/FL = gb: NM_002091.1 gb: K02054.1 gb: BC004488.1 | −2.74071 | 2.70077 | 0.509757 | 2.49E−04 |
| *Homo sapiens* sema domain, seven thrombospondin repeats (type 1 and type 1-like), transmembrane domain (TM) and short cytoplasmic domain, (semaphorin) 5A (SEMA5A), mRNA./ PROD = sema domain, seven thrombospondin repeats (type1 and type 1-like), transmem | −1.53335 | 3.78503 | 1.48732 | 4.71E−02 |
| *Homo sapiens* mRNA; cDNA DKFZp586J0624 (from clone DKFZp586J0624); complete cds./ PROD = hypothetical protein/ FL = gb: AF215636.1 gb: NM_014585.1 gb: AF231121.1 gb: AF226614.1 gb: AL136944.1 | −0.835182 | 5.22406 | 3.69882 | 2.08E−02 |
| Human mRNA for alpha-1 type II collagen. | −2.8736 | 2.155 | −0.38021 | 5.70E−03 |
| Rho GDP dissociation inhibitor (GDI) alpha | −1.54385 | 1.7147 | −2.58241 | 1.71E−02 |
| neuropilin 1/FL = gb: AF016050.1 gb: NM_003873.1 gb: AF018956.1 | −1.62253 | 1.95432 | −1.9667 | 8.83E−04 |
| Human DNA sequence from clone RP1-181C24 on chromosome 6p11.1-12.2. Contains the 3 end of the BMP5 gene for bone morphogenetic protein 5, ESTs, STSs and GSSs/FL = gb: M60314.1 gb: NM_021073.1 | −3.72313 | 1.68755 | −0.37308 | 1.38E−03 |
| myristoylated alanine-rich protein kinase C substrate (MARCKS, 80K-L)/ FL = gb: M68956.1 gb: D10522.1 gb: NM_002356.4 | −0.71724 | 3.51728 | 0.335725 | 4.29E−03 |
| hypothetical protein FLJ23403/ FL = gb: NM_022068.1 | −1.45618 | 1.81423 | −2.31327 | 1.20E−02 |
| hepatocyte nuclear factor 4, alpha | −4.26574 | 1.7879 | 0.445241 | 3.25E−02 |
| *Homo sapiens* cell adhesion molecule with homology to L1CAM (close homologue of L1) (CHL1), mRNA./ PROD = cell adhesion molecule with homology to L1CAM(close homologue of L1)/FL = gb: AF002246.1 gb: NM_006614.1 | −0.541188 | 2.1751 | −2.5002 | 1.16E−03 |
| matrix metalloproteinase 14 (membrane-inserted)/FL = gb: U41078.1 gb: NM_004995.2 | −2.05734 | 2.36236 | −0.5185 | 1.66E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* glycophorin B (includes Ss blood group) (GYPB), mRNA./PROD = glycophorin B precursor/FL = gb: J02982.1 gb: NM_002100.2 | −0.947308 | 3.26089 | 0.180293 | 4.83E−04 |
| WAS protein family, member 2/FL = gb: NM_006990.1 gb: AB026542.1 | −2.18746 | 1.99129 | −1.05968 | 4.00E−03 |
| *Homo sapiens* frizzled-related protein (FRZB), mRNA./PROD = frizzled-related protein/FL = gb: U24163.1 gb: U68057.1 gb: NM_001463.1 gb: U91903.1 | 0.56502 | 5.7261 | 3.67629 | 1.75E−02 |
| *Homo sapiens* glutamate decarboxylase 1 (brain, 67 kD) (GAD1), transcript variant GAD25, mRNA./PROD = glutamate decarboxylase 1, isoform GAD25/FL = gb: NM_013445.1 gb: AF178853.1 gb: BC002815.1 | −1.68495 | 2.27067 | −0.96944 | 8.02E−03 |
| ESTs | 0.812766 | 5.93144 | 3.91314 | 4.15E−02 |
| *Homo sapiens* clone 23736 mRNA sequence | −0.047182 | 5.79006 | 4.50744 | 1.74E−02 |
| *Homo sapiens* glycophorin E (GYPE), mRNA./PROD = glycophorin E/FL = gb: NM_002102.1 gb: M29610.1 | −2.01601 | 1.79002 | −1.50134 | 1.97E−02 |
| ESTs | 1.06767 | 5.63319 | 3.12487 | 2.00E−02 |
| ESTs | −1.41162 | 2.5396 | −0.57029 | 1.29E−02 |
| Human Fritz mRNA, complete cds./PROD = Fritz/FL = gb: U24163.1 gb: U68057.1 gb: NM_001463.1 gb: U91903.1 | 0.436589 | 5.69814 | 3.91514 | 1.99E−02 |
| *Homo sapiens*, clone MGC: 4655, mRNA, complete cds./PROD = Unknown (protein for MGC: 4655)/FL = gb: BC004908.1 | 2.3772 | 5.9184 | 2.47596 | 1.20E−02 |
| KIAA0878 protein/FL = gb: NM_014899.1 gb: AB020685.1 | 1.1189 | 6.41747 | 4.78882 | 2.01E−02 |
| *Homo sapiens* sema domain, immunoglobulin domain (Ig), short basic domain, secreted, (semaphorin) 3E (SEMA3E), mRNA./PROD = sema domain, immunoglobulin domain (Ig), shortbasic domain, secreted, (semaphorin) 3E/FL = gb: NM_012431.1 gb: AB002329.1 | −0.785987 | 3.69668 | 1.27624 | 2.10E−02 |
| ESTs | 1.48084 | 6.59709 | 4.81395 | 1.36E−02 |
| noggin/FL = gb: NM_005450.1 | −1.63627 | 3.28161 | 1.32958 | 2.53E−02 |
| *Homo sapiens* hypothetical protein FLJ11316 (FLJ11316), mRNA./PROD = hypothetical protein FLJ11316/FL = gb: NM_018388.1 | −0.904749 | 3.35854 | 0.755319 | 1.12E−04 |
| *Homo sapiens* angiopoietin 2 (ANGPT2), mRNA./PROD = angiopoietin 2/FL = gb: AB009865.1 gb: AF004327.1 gb: NM_001147.1 | −2.93044 | 2.23779 | 0.59685 | 3.43E−02 |
| *Homo sapiens* matrix metalloproteinase 14 (membrane-inserted) (MMP14), mRNA./PROD = matrix metalloproteinase 14 preproprotein/FL = gb: U41078.1 gb: NM_004995.2 | −0.723489 | 2.97262 | −0.09689 | 5.44E−03 |
| G protein-coupled receptor | 1.50709 | 6.65228 | 5.05327 | 2.00E−02 |
| collagen, type IX, alpha 2/FL = gb: NM_001852.1 | 1.27026 | 5.4659 | 2.93507 | 3.19E−03 |
| ESTs | 0.521638 | 3.93176 | 0.620223 | 0.00E+00 |
| KIAA1462 protein | −3.84563 | 1.65452 | 0.437064 | 3.27E−02 |
| *Homo sapiens* cartilage linking protein 1 (CRTL1), mRNA./PROD = cartilage linking protein 1/FL = gb: NM_001884.1 gb: U43328.1 | −1.31515 | 2.27271 | −0.80521 | 2.22E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* solute carrier family 21 (prostaglandin transporter), member 2 (SLC21A2), mRNA./PROD = solute carrier family 21 (prostaglandintransporter), member 2/ FL = gb: U70867.1 gb: NM_005630.1 | 0.711428 | 4.89808 | 2.43304 | 6.84E−03 |
| ESTs | 0.307173 | 4.78515 | 2.65653 | 1.72E−02 |
| 6-phosphofructo-2-kinasefructose-2,6-biphosphatase 4 | −0.242865 | 3.97929 | 1.59985 | 5.28E−03 |
| *Homo sapiens* dual specificity phosphatase 4 (DUSP4), mRNA./PROD = dual specificity phosphatase 4/ FL = gb: NM_001394.2 gb: BC002671.1 gb: U48807.1 gb: U21108.1 | 0.953857 | 5.82811 | 4.12159 | 4.00E−03 |
| ESTs, Weakly similar to T00331 hypothetical protein KIAA0555 (*H. sapiens*) | −1.57372 | 2.70797 | 0.443622 | 6.74E−03 |
| ESTs | −3.57414 | 3.15167 | 3.37198 | 8.82E−03 |
| ESTs, Highly similar to IHH_HUMAN INDIAN HEDGEHOG PROTEIN PRECURSOR (*H. sapiens*) | −0.653989 | 3.22059 | 0.590533 | 5.18E−03 |
| ESTs, Weakly similar to FCE2 MOUSE LOW AFFINITY IMMUNOGLOBULIN EPSILON FC RECEPTOR (*M. musculus*) | 0.494192 | 5.22522 | 3.48031 | 1.97E−02 |
| homeo box HB9/FL = gb: NM_005515.1 | −1.65563 | 3.2238 | 1.63092 | 5.58E−03 |
| *Homo sapiens* arylsulfatase E (chondrodysplasia punctata 1) (ARSE), mRNA./PROD = arylsulfatase E precursor/FL = gb: X83573.1 gb: NM_000047.1 | 0.283004 | 4.95903 | 3.18424 | 9.22E−03 |
| ESTs | −0.05909 | 3.0455 | −0.29817 | 1.47E−02 |
| *Homo sapiens* hypothetical protein FLJ23403 (FLJ23403), mRNA./PROD = hypothetical protein FLJ23403/ FL = gb: NM_022068.1 | −1.48452 | 1.97473 | −1.00431 | 5.72E−03 |
| ESTs | −0.182403 | 3.01548 | −0.18954 | 3.72E−03 |
| hypothetical protein FLJ23091 | 0.323388 | 5.25192 | 3.77987 | 3.57E−02 |
| Human dipeptidyl peptidase IV (CD26) mRNA, complete cds./PROD = dipeptidyl peptidase IV/FL = gb: M74777.1 | −3.61145 | 0.760585 | −1.25595 | 3.07E−02 |
| hypothetical protein FLJ21032 | 0.355672 | 4.67756 | 2.61753 | 4.59E−02 |
| *Homo sapiens* Kell blood group (KEL), mRNA./PROD = Kell blood group antigen/ FL = gb: BC003135.1 gb: NM_000420.1 | −2.20519 | 1.89439 | −0.38393 | 1.91E−02 |
| splicing factor, arginineserine-rich 5 | 0.7481 | 5.68934 | 4.27169 | 2.97E−03 |
| Human prostatic secretory protein 57 mRNA, complete cds./PROD = PSP57/ FL = gb: U22178.1 | −3.01313 | 1.46338 | −0.40767 | 1.97E−02 |
| *Homo sapiens* KIAA0878 protein (KIAA0878), mRNA./PROD = KIAA0878 protein/FL = gb: NM_014899.1 gb: AB020685.1 | 2.0265 | 7.00937 | 5.65368 | 2.85E−02 |
| *Homo sapiens* cryptic mRNA, complete cds./PROD = cryptic/FL = gb: AF312769.1 | 0.104874 | 2.87319 | −0.67353 | 1.61E−03 |
| *Homo sapiens* cDNA FLJ13221 fis, clone NT2RP4002075 | 0.355743 | 3.98782 | 1.30963 | 1.38E−03 |
| phorbolin-like protein MDS019 | −1.11756 | 2.83853 | 0.503523 | 1.59E−02 |
| *Homo sapiens* mRNA for KIAA1409 protein, partial cds./PROD = KIAA1409 protein | 0.368334 | 2.8009 | −1.03191 | 1.78E−02 |
| *Homo sapiens* mRNA; cDNA DKFZp434D0818 (from clone DKFZp434D0818) | −2.63427 | 1.64513 | −0.3056 | 2.52E−02 |
| ESTs | 0.35393 | 5.14775 | 3.74875 | 3.16E−02 |
| *Homo sapiens* TBX3-iso protein (TBX3-iso), mRNA./PROD = TBX3-iso protein/ FL = gb: NM_016569.1 gb: AF216750.1 | −2.34566 | 2.45238 | 1.07038 | 1.31E−02 |
| *Homo sapiens* chromosome 19, cosmid R31181 | −0.258871 | 3.0636 | 0.223926 | 1.58E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* mRNA for GATA-6, complete cds./PROD = GATA-6/ FL = gb: U66075.1 gb: NM_005257.1 gb: D87811.1 | 2.21862 | 6.8609 | 5.34263 | 4.29E−02 |
| *Homo sapiens* ankyrin-like with transmembrane domains 1 (ANKTM1), mRNA | −1.10879 | 3.93484 | 2.81939 | 1.29E−02 |
| G protein-coupled receptor 49 | 0.265509 | 4.46257 | 2.50537 | 2.19E−02 |
| *Homo sapiens* growth differentiation factor 3 (GDF3), mRNA./PROD = growth differentiation factor 3 precursor/ FL = gb: NM_020634.1 gb: AF263538.1 | 1.67253 | 5.34944 | 2.87486 | 8.62E−05 |
| Human (clone HSY3RR) neuropeptide Y receptor (NPYR) mRNA, complete cds./ PROD = neuropeptide Y receptor/ FL = gb: L06797.1 gb: NM_003467.1 gb: AF025375.1 gb: AF147204.1 gb: M99293.1 gb: L01639.1 | 1.77461 | 6.70301 | 5.47995 | 3.00E−02 |
| *Homo sapiens* type VI collagen alpha 2 chain precursor (COL6A2) mRNA, complete cds, alternatively spliced./ PROD = type VI collagen alpha 2 chain precursor/FL = gb: AY029208.1 | 1.7011 | 5.33126 | 2.84458 | 5.91E−03 |
| ESTs | −0.349726 | 3.29119 | 0.824929 | 4.11E−03 |
| ESTs | −0.903317 | 1.89777 | −1.36429 | 6.84E−03 |
| *Homo sapiens* hypothetical protein FLJ10718 (FLJ10718), mRNA./ PROD = hypothetical protein FLJ10718/ FL = gb: NM_018192.1 | 2.60483 | 7.10633 | 5.55242 | 1.41E−02 |
| *Homo sapiens* Rho GTPase activating protein 6 (ARHGAP6), transcript variant 2, mRNA./PROD = Rho GTPase activating protein 6 isoform 2/ FL = gb: AF022212.2 gb: NM_001174.2 | −1.10389 | 1.83053 | −1.28521 | 1.28E−02 |
| stanniocalcin 1/FL = gb: U25997.1 gb: NM_003155.1 gb: U46768.1 | 2.41135 | 7.29563 | 6.14284 | 2.51E−02 |
| Human glycophorin HeP2 mRNA, partial cds./PROD = glycophorin HeP2 | −0.843493 | 2.71108 | 0.233547 | 2.98E−04 |
| *Homo sapiens* cDNA FLJ12993 fis, clone NT2RP3000197 | 0.147259 | 4.12241 | 2.06949 | 6.84E−03 |
| *Homo sapiens* presenilin stabilization factor b (PSF) mRNA, complete cds; alternatively spliced./PROD = presenilin stabilization factor b/FL = gb: AY113699.1 | −0.86173 | 2.85614 | 0.56745 | 6.09E−03 |
| *Homo sapiens* glycophorin Erik STA (GPErik) gene complete cds./ PROD = glycophorin Erik (STA)/ FL = gb: U00178.1 | −1.19362 | 2.17108 | −0.45439 | 1.45E−04 |
| bromodomain and PHD finger containing, 3 | −2.8472 | 1.75573 | 0.369397 | 8.62E−05 |
| ESTs | 0.784344 | 4.74104 | 2.71543 | 7.55E−03 |
| ESTs | −1.26251 | 3.4693 | 2.27614 | 3.80E−03 |
| ESTs | −1.71713 | 1.23763 | −1.71122 | 2.99E−02 |
| *Homo sapiens* microsomal glutathione S-transferase 2 (MGST2), mRNA./ PROD = microsomal glutathione S-transferase 2/FL = gb: NM_002413.1 gb: U77604.1 | 2.06233 | 6.81536 | 5.6918 | 3.79E−02 |
| *Homo sapiens* eomesodermin (*Xenopus laevis*) homolog (EOMES), mRNA./ PROD = eomesodermin (*Xenopus laevis*) homolog/FL = gb: AB031038.1 gb: NM_005442.1 | 2.65926 | 6.71627 | 4.89839 | 2.76E−02 |
| *Homo sapiens* mRNA for MSX-2, complete cds./PROD = MSX-2/ FL = gb: D89377.1 | 0.407211 | 4.11145 | 1.94529 | 1.35E−02 |
| *Homo sapiens* apolipoprotein A-II (APOA2), mRNA./PROD = apolipoprotein A-II precursor/FL = gb: M29882.1 gb: NM_001643.1 gb: BC005282.1 | −1.10237 | 5.10066 | 4.75899 | 1.34E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* adenylate cyclase 8 (brain) (ADCY8), mRNA./PROD = adenylate cyclase 8/ FL = gb: NM_001115.1 | −1.3408 | 1.12773 | −2.26149 | 1.07E−02 |
| *Homo sapiens* glucose-6-phosphate transporter (G6PT) gene, G6PT-Dt allele, complete cds | −0.193516 | 3.03064 | 0.407738 | 1.38E−03 |
| *Homo sapiens* glutathione S-transferase A2 (GSTA2), mRNA./PROD = glutathione S-transferase A2/FL = gb: BC002895.1 gb: M25627.1 gb: M16594.1 gb: M14777.1 gb: M15872.1 gb: M21758.1 gb: NM_000846.1 | −3.10645 | 1.11704 | −0.4221 | 5.37E−04 |
| *Homo sapiens* sodium dependent phosphate transporter isoform NaPi-IIb mRNA, complete cds./PROD = sodium dependent phosphate transporter isoformNaPi-IIb/FL = gb: AF111856.1 gb: NM_006424.1 gb: AF146796.1 | −0.397133 | 2.78341 | 0.231961 | 1.11E−02 |
| ESTs | 2.77413 | 7.19192 | 5.906 | 3.17E−02 |
| *Homo sapiens* partial LHX9 gene for LIM-homeobox 9, 3UTR. | −2.2486 | 1.64952 | −0.13424 | 7.89E−03 |
| *Homo sapiens* LYST-interacting protein LIP3 mRNA, partial cds./PROD = LYST-interacting protein LIP3 | −0.682149 | 2.34271 | −0.31253 | 9.87E−03 |
| putative 47 kDa protein | −0.123937 | 3.2914 | 1.05247 | 3.72E−03 |
| *Homo sapiens* protein S (alpha) (PROS1), mRNA./PROD = protein S (alpha)/FL = gb: M15036.1 gb: NM_000313.1 | 0.577604 | 4.00035 | 1.7883 | 7.89E−03 |
| ESTs | −1.63711 | 0.915477 | −2.15328 | 1.83E−02 |
| protocadherin 10 | 1.76718 | 5.1503 | 2.98569 | 2.52E−02 |
| KIAA1511 protein | 0.620278 | 3.86886 | 1.57543 | 1.86E−03 |
| *Homo sapiens* cDNA FLJ13221 fis, clone NT2RP4002075 | 0.282785 | 3.44178 | 1.08178 | 1.31E−03 |
| *Homo sapiens* fibroblast growth factor receptor 4, soluble-form splice variant (FGFR4) mRNA, complete cds./PROD = fibroblast growth factor receptor 4, soluble-form splice variant/ FL = gb: NM_022963.1 gb: AF202063.1 | −1.72385 | 2.26674 | 0.747239 | 6.86E−03 |
| X75208/FEATURE = cds/ DEFINITION = HSPTKR *H. sapiens* HEK2 mRNA for protein tyrosine kinase receptor | −1.36729 | 2.60456 | 1.08204 | 1.58E−02 |
| *Homo sapiens* chemokine receptor CXCR4 mRNA, complete cds./ PROD = chemokine receptor CXCR4/ FL = gb: AF348491.1 | 2.30557 | 6.72969 | 5.66933 | 3.31E−02 |
| KIAA1415 protein | 0.185854 | 3.70346 | 1.74255 | 7.78E−04 |
| ESTs | −0.048335 | 3.11786 | 0.836448 | 1.29E−02 |
| *Homo sapiens* stanniocalcin 1 (STC1), mRNA./PROD = stanniocalcin 1/ FL = gb: U25997.1 gb: NM_003155.1 gb: U46768.1 | 2.39435 | 6.55737 | 5.28007 | 2.19E−02 |
| *Homo sapiens* high mobility group protein-R mRNA, complete cds./ PROD = high mobility group protein-R/ FL = gb: AF176039.1 | 1.04695 | 3.2786 | 0.095286 | 2.11E−02 |
| ESTs, Moderately similar to ALU4_HUMAN ALU SUBFAMILY SB2 SEQUENCE CONTAMINATION WARNING ENTRY (*H. sapiens*) | −1.10358 | 1.66331 | −0.98371 | 3.37E−02 |
| *Homo sapiens* arrestin, beta 1 (ARRB1), transcript variant 1, mRNA./ PROD = arrestin beta 1, isoform A/ FL = gb: BC003636.1 gb: AF084040.1 gb: NM_004041.2 | −0.158844 | 2.41791 | −0.40915 | 1.12E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | −1.34399 | 1.80279 | −0.44529 | 1.60E−03 |
| Human mRNA for pro-alpha 1 (II) collagen 3end C-term. triple helical and C-terminal non-helical domain./PROD = pro-alpha 1 (II) collagen (313 AA; AA 975-271c)/FL = gb: NM_001844.2 | 0.85982 | 4.1935 | 2.15657 | 1.09E−02 |
| *Homo sapiens* hypothetical protein DKFZp564B052 (DKFZp564B052), mRNA./PROD = hypothetical protein DKFZp564B052/FL = gb: NM_030820.1 | 1.47773 | 4.42479 | 2.00326 | 1.16E−03 |
| testis enhanced gene transcript (BAX inhibitor 1) | −0.695228 | 2.99328 | 1.31679 | 1.17E−03 |
| *Homo sapiens* fasciculation and elongation protein zeta 1 (zygin I) (FEZ1), transcript variant 1, mRNA./PROD = zygin 1, isoform 1/FL = gb: U60060.1 gb: U69139.1 gb: NM_005103.2 | 1.86433 | 4.71354 | 2.20315 | 8.62E−05 |
| *Homo sapiens* matrix metalloproteinase 15 (membrane-inserted) (MMP15), mRNA./PROD = matrix metalloproteinase 15 preproprotein/FL = gb: D86331.1 gb: NM_002428.1 | −0.298504 | 3.44582 | 1.8336 | 4.80E−03 |
| heparan sulfate proteoglycan 2 (perlecan)/FL = gb: M85289.1 gb: NM_005529.2 | −2.53327 | 0.924726 | −0.97212 | 4.31E−02 |
| *Homo sapiens* dickkopf (*Xenopus laevis*) homolog 1 (DKK1), mRNA./PROD = dickkopf (*Xenopus laevis*) homolog 1/FL = gb: AF177394.1 gb: NM_012242.1 gb: AF127563.1 | 0.981469 | 3.70716 | 1.09014 | 1.76E−03 |
| ESTs | −0.801487 | 3.37342 | 2.21393 | 1.22E−02 |
| ESTs | −2.57626 | 1.40231 | 0.050493 | 6.60E−03 |
| ESTs | 0.499579 | 4.10541 | 2.39934 | 4.29E−03 |
| *Homo sapiens* bone morphogenetic protein 2 (BMP2), mRNA./PROD = bone morphogenetic protein 2 precursor/FL = gb: NM_001200.1 | 2.04506 | 6.19114 | 5.02927 | 4.98E−02 |
| Human extracellular matrix protein 1 (ECM1) mRNA, complete cds./PROD = extracellular matrix protein 1/FL = gb: NM_004425.2 gb: U65932.1 gb: U68186.1 | 0.634778 | 3.65829 | 1.37564 | 6.11E−04 |
| *Homo sapiens* nuclear receptor subfamily 0, group B, member 1 (NR0B1), mRNA./PROD = adrenal hypoplasia protein/FL = gb: NM_000475.2 | −1.92783 | 2.32456 | 1.27907 | 2.99E−02 |
| *Homo sapiens* cDNA: FLJ23067 fis, clone LNG04993. | −2.25626 | 1.95987 | 0.882498 | 6.62E−03 |
| *Homo sapiens* ADP-ribosylation factor 4-like (ARF4L), mRNA./PROD = ADP-ribosylation factor 4-like/FL = gb: U25771.1 gb: L38490.1 gb: NM_001661.1 gb: BC000043.1 | 1.63466 | 5.70351 | 4.48037 | 1.90E−02 |
| *Homo sapiens* HT016 mRNA, complete cds./PROD = HT016/FL = gb: AF225426.1 | 0.218762 | 3.97514 | 2.45222 | 3.37E−02 |
| *Homo sapiens*, tropomodulin, clone MGC: 3643, mRNA, complete cds./PROD = tropomodulin/FL = gb: NM_003275.1 gb: M77016.1 gb: BC002660.1 | 0.348796 | 3.54199 | 1.46427 | 1.29E−03 |
| *Homo sapiens* hypothetical protein FLJ22471 (FLJ22471), mRNA./PROD = hypothetical protein FLJ22471/FL = gb: NM_025140.1 | 0.903825 | 4.65366 | 3.1349 | 2.48E−02 |
| ESTs | −0.120583 | 2.94229 | 0.738304 | 7.20E−03 |
| ESTs, Moderately similar to JC4969 pig-c protein (*H. sapiens*) | −2.39713 | 0.906454 | −1.04495 | 1.69E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* LIM homeobox protein 1 (LHX1), mRNA./PROD = LIM homeobox protein 1/FL = gb: NM_005568.1 gb: U14755.1 | −0.77166 | 2.27746 | 0.085559 | 4.26E−02 |
| *Homo sapiens*, hypothetical protein MGC2865, clone MGC: 20246 IMAGE: 4635389, mRNA, complete cds./FL = gb: BC016043.1 | −2.43105 | 0.646883 | −1.50617 | 8.27E−03 |
| ESTs | −2.01523 | 2.16773 | 1.12403 | 1.99E−02 |
| *Homo sapiens* oxoglutarate dehydrogenase (lipoamide) (OGDH), mRNA./PROD = oxoglutarate dehydrogenase (lipoamide)/FL = gb: D10523.1 gb: BC004964.1 gb: NM_002541.1 | −0.032595 | 2.3997 | −0.38533 | 1.45E−02 |
| ESTs, Weakly similar to T32252 hypothetical protein T15B7.2 - *Caenorhabditis elegans* (*C. elegans*) | 2.20966 | 5.35974 | 3.33255 | 1.12E−04 |
| *Homo sapiens*, cleft lip and palate associated transmembrane protein 1, clone MGC: 10593, mRNA, complete cds./PROD = cleft lip and palate associated transmembraneprotein 1/FL = gb: BC004865.1 | 1.31578 | 3.52357 | 0.556735 | 2.92E−03 |
| *Homo sapiens* clone TUA8 Cri-du-chat region mRNA | 0.09218 | 3.37126 | 1.49746 | 6.46E−03 |
| *Homo sapiens* transcriptional activator of the c-fos promoter (CROC4), mRNA./PROD = transcriptional activator of the c-fos promoter/FL = gb: NM_006365.1 gb: U49857.1 | 0.666391 | 4.50481 | 3.22532 | 5.80E−03 |
| *Homo sapiens* hypothetical protein FLJ21195 similar to protein related to DAC and *cerberus* (FLJ21195), mRNA./PROD = hypothetical protein FLJ21195 similar to proteinrelated to DAC and *cerberus*/FL = gb: NM_022469.1 | −1.38519 | 2.23626 | 0.763963 | 7.36E−03 |
| ras homolog gene family, member B/FL = gb: AF498971.1 gb: NM_004040.1 | −0.123101 | 2.52093 | 0.071885 | 1.86E−02 |
| cartilage linking protein 1 | 0.879449 | 3.47789 | 0.987243 | 1.03E−03 |
| *Homo sapiens* BCL2adenovirus E1B 19 kD-interacting protein 3 (BNIP3) mRNA, complete cds./PROD = BCL2adenovirus E1B 19 kD-interacting protein 3/FL = gb: AF002697.1 gb: NM_004052.2 gb: U15174.1 | 3.30506 | 6.91803 | 5.44746 | 1.79E−03 |
| *Homo sapiens* polycythemia rubra vera 1; cell surface receptor (PRV1), mRNA./PROD = polycythemia rubra vera 1; cell surfacereceptor/FL = gb: NM_020406.1 gb: AF146747.1 | −1.19629 | 2.40987 | 0.93741 | 9.40E−03 |
| *Homo sapiens* hypothetical protein FLJ11560 (FLJ11560), mRNA./PROD = hypothetical protein FLJ11560/FL = gb: NM_025182.1 | −0.044112 | 3.42017 | 1.80688 | 3.77E−03 |
| plexin A2 | 0.930527 | 4.36203 | 2.74167 | 1.52E−02 |
| *Homo sapiens* mRNA; cDNA DKFZp547H236 (from clone DKFZp547H236)./PROD = hypothetical protein | 1.37193 | 4.24502 | 2.08129 | 5.37E−04 |
| *Homo sapiens* cystatin C (amyloid angiopathy and cerebral hemorrhage) (CST3), mRNA./PROD = cystatin C (amyloid angiopathy and cerebralhemorrhage)/FL = gb: NM_000099.1 | 2.08601 | 5.30525 | 3.51965 | 2.20E−03 |
| ESTs, Moderately similar to NFY-C (*H. sapiens*) | −0.749407 | 2.00148 | −0.24268 | 2.34E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 2.54243 | 5.75201 | 3.97307 | 2.60E−02 |
| Homo sapiens sialyltransferase (STHM), mRNA./PROD = sialyltransferase/ FL = gb: U14550.1 gb: NM_006456.1 | −0.68709 | 2.89586 | 1.50348 | 3.70E−02 |
| Homo sapiens SG2NA beta isoform mRNA, partial cds./PROD = SG2NA beta isoform | −1.15566 | 1.13989 | −1.53439 | 1.55E−02 |
| Homo sapiens hypothetical protein FLJ12838 (FLJ12838), mRNA./ PROD = hypothetical protein FLJ12838/ FL = gb: NM_024641.1 | 1.49091 | 4.80138 | 3.15205 | 2.63E−02 |
| Homo sapiens solute carrier (SLC25A18) mRNA, complete cds; nuclear gene for mitochondrial product./ PROD = solute carrier/ FL = gb: AY008285.1 | 0.403706 | 2.12385 | −1.10043 | 1.78E−02 |
| KIAA0346 protein | −1.34736 | 2.49605 | 1.41497 | 3.90E−03 |
| Human clone 23826 mRNA sequence | 1.80782 | 4.07112 | 1.44315 | 2.28E−04 |
| Homo sapiens receptor tyrosine kinase-like orphan receptor 2 (ROR2), mRNA./ PROD = receptor tyrosine kinase-like orphan receptor 2/FL = gb: M97639.1 gb: NM_004560.1 | 1.53333 | 4.73839 | 3.05612 | 1.63E−02 |
| Homo sapiens MYC-associated zinc finger protein (purine-binding transcription factor) (MAZ), mRNA./ PROD = MYC-associated zinc finger protein(purine-binding transcription factor)/FL = gb: D85131.1 gb: NM_002383.1 | −0.055569 | 2.67075 | 0.511292 | 2.63E−02 |
| Homo sapiens cDNA FLJ30081 fis, clone BGGI12000693, weakly similar to POLYHOMEOTIC-PROXIMAL CHROMATIN PROTEIN. | 0.677905 | 3.33728 | 1.12499 | 1.12E−04 |
| Homo sapiens elongation of very long chain fatty acids (FEN1Elo2, SUR4Elo3, yeast)-like 2 (ELOVL2), mRNA./ PROD = elongation of very long chain fatty acids(FEN1Elo2, SUR4Elo3, yeast)-like 2/FL = gb: NM_017770.1 | 0.099979 | 3.23372 | 1.50802 | 2.59E−03 |
| Homo sapiens thyrotropin-releasing hormone (TRH), mRNA./ PROD = thyrotropin-releasing hormone/ FL = gb: NM_007117.1 | −1.65672 | 1.46994 | −0.25839 | 3.02E−02 |
| ESTs, Weakly similar to A46302 PTB-associated splicing factor, long form (H. sapiens) | 0.894051 | 4.21835 | 2.69535 | 1.57E−02 |
| Human MLC1emb gene for embryonic myosin alkaline light chain, promoter and exon 1 | 1.3489 | 5.11354 | 4.03961 | 1.61E−02 |
| Homo sapiens microseminoprotein, beta- (MSMB), mRNA./ PROD = microseminoprotein, beta-/ FL = gb: NM_002443.1 | −2.37904 | 1.3101 | 0.169915 | 2.46E−02 |
| Homo sapiens cDNA FLJ11390 fis, clone HEMBA1000561, weakly similar to ZINC FINGER PROTEIN 91. | −1.12944 | 2.02889 | 0.364373 | 0.00E+00 |
| ESTs, Weakly similar to ALU8_HUMAN ALU SUBFAMILY SX SEQUENCE CONTAMINATION WARNING ENTRY (H. sapiens) | 2.76608 | 6.07949 | 4.57766 | 1.93E−02 |
| Homo sapiens cDNA FLJ13810 fis, clone THYRO1000279 | −2.92389 | 0.51764 | −0.85322 | 8.08E−03 |
| Homo sapiens, aminolevulinate, delta-, dehydratase, clone MGC: 5057, mRNA, complete cds./PROD = aminolevulinate, delta-, dehydratase/FL = gb: BC000977.1 gb: M13928.1 gb: NM_000031.1 | 1.3099 | 4.44525 | 2.76918 | 7.69E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* kidney-specific membrane protein NX-17 mRNA, complete cds./PROD = kidney-specific membrane protein NX-17/ FL = gb: AF229179.1 | 1.91929 | 5.08917 | 3.44968 | 6.91E−03 |
| *Homo sapiens* alpha 2,8-sialyltransferase mRNA, complete cds./ PROD = alpha 2,8-sialyltransferase/ FL = gb: L43494.1 gb: D26360.1 gb: L32867.1 gb: NM_003034.1 | −1.10548 | 2.36359 | 1.05469 | 4.63E−03 |
| tyrosine 3-monooxygenasetryptophan 5-monooxygenase activation protein, eta polypeptide | 2.98486 | 6.17918 | 4.60758 | 8.01E−03 |
| *Homo sapiens* cardiac ankyrin repeat protein (CARP), mRNA./PROD = cardiac ankyrin repeat protein/ FL = gb: NM_014391.1 | −0.002291 | 3.35645 | 1.98688 | 3.44E−02 |
| *Homo sapiens* porcupine (MG61), mRNA./PROD = porcupine/ FL = gb: AF317059.1 gb: AF317058.1 gb: NM_022825.1 | 1.51754 | 4.96311 | 3.68103 | 9.86E−03 |
| collagen, type V, alpha 1/ FL = gb: D90279.1 gb: NM_000093.1 gb: M76729.1 | 1.5875 | 3.98844 | 1.66569 | 1.17E−03 |
| *Homo sapiens* forkhead box F2 (FOXF2), mRNA./PROD = forkhead box F2/FL = gb: U13220.1 gb: NM_001452.1 | −1.54469 | 1.02305 | −1.11517 | 6.95E−03 |
| PTPRF interacting protein, binding protein 2 (liprin beta 2) | −1.92021 | 3.74378 | 2.77277 | 2.10E−02 |
| *Homo sapiens* PRO1957 mRNA, complete cds./PROD = PRO1957/ FL = gb: AF116676.1 | 1.68941 | 5.30311 | 4.22705 | 1.43E−02 |
| *Homo sapiens* hypothetical protein FLJ23514 (FLJ23514), mRNA./ PROD = hypothetical protein FLJ23514/ FL = gb: NM_021827.1 | 0.564613 | 5.98527 | 5.24692 | 2.85E−02 |
| *Homo sapiens* mRNA; cDNA DKFZp586G2120 (from clone DKFZp586G2120); complete cds./ PROD = hypothetical protein/ FL = gb: AL136924.1 | −1.80897 | 1.69722 | 0.523009 | 2.47E−02 |
| Cluster Incl. L37033: Human FK-506 binding protein homologue (FKBP38) mRNA, complete cds/cds = (140, 1207)/ gb = L37033/gi = 965469/ug = Hs.173464/ len = 1613 | 0.615619 | 3.478 | 1.66132 | 1.54E−02 |
| ESTs | −0.004009 | 3.63657 | 2.61352 | 4.29E−02 |
| *Homo sapiens* apolipoprotein C-I (APOC1), mRNA./PROD = apolipoprotein C-I precursor/FL = gb: NM_001645.2 | 3.24954 | 6.71073 | 5.50997 | 2.16E−02 |
| ESTs | 1.38635 | 4.93112 | 3.83641 | 1.39E−02 |
| *Homo sapiens* cDNA FLJ34035 fis, clone FCBBF2004788. | −3.58002 | −0.48718 | −2.00751 | 1.46E−02 |
| *Homo sapiens*, clone IMAGE: 3509274, mRNA, partial cds | 0.493686 | 2.94923 | 0.794513 | 1.82E−02 |
| *Homo sapiens* putative sterol reductase SR-1 (TM7SF2) mRNA, complete cds./ PROD = putative sterol reductase SR-1/ FL = gb: AF096304.1 | 1.66857 | 4.3767 | 2.47833 | 5.37E−04 |
| nuclear factor of kappa light polypeptide gene enhancer in B-cells inhibitor, alpha/ FL = gb: NM_020529.1 gb: BC002601.1 gb: BC004983.1 gb: M69043.1 | 2.91463 | 6.48938 | 5.47812 | 1.97E−02 |
| hypothetical protein FLJ12666 | 0.215767 | 3.10249 | 1.40459 | 1.91E−02 |
| *Homo sapiens* ectodermal dysplasia 1, anhidrotic (ED1), mRNA./ PROD = ectodermal dysplasia 1, anhidrotic/FL = gb: AF060999.1 gb: NM_001399.1 gb: AF040628.1 gb: AF061189.1 | 0.796627 | 4.22895 | 3.07833 | 1.01E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
| --- | --- | --- | --- | --- |
| glycoprotein M6A/FL = gb: D49958.1 | 0.274378 | 3.59045 | 2.3278 | 2.64E−02 |
| ESTs | 1.04714 | 3.87608 | 2.12752 | 3.75E−02 |
| ESTs | −1.48489 | 1.371 | −0.35043 | 1.88E−03 |
| ESTs, Weakly similar to KIAA1330 protein (*H. sapiens*) | −0.925232 | 2.41149 | 1.18187 | 2.65E−03 |
| putative 47 kDa protein | 0.156484 | 2.78771 | 0.861726 | 2.60E−02 |
| *Homo sapiens* hypothetical protein FLJ32835 (FLJ32835), mRNA./FL = gb: NM_152506.1 | −0.595622 | 4.84785 | 3.94683 | 3.34E−02 |
| *Homo sapiens* GS1999full mRNA, complete cds./FL = gb: AB048286.1 | 0.137029 | 2.75189 | 0.849942 | 0.00E+00 |
| *Homo sapiens* hexabrachion (tenascin C, cytotactin) (HXB), mRNA./PROD = hexabrachion (tenascin C, cytotactin)/FL = gb: M55618.1 gb: NM_002160.1 | 3.96862 | 5.66572 | 2.85391 | 1.39E−02 |
| *Homo sapiens* Pig10 (PIG10) mRNA, complete cds./PROD = Pig10/FL = gb: AF059611.1 gb: AF010314.1 gb: NM_003633.1 gb: BC000418.1 gb: AF005381.1 | 0.129454 | 2.86013 | 1.09765 | 1.16E−03 |
| *Homo sapiens* annexin A6 (ANXA6), transcript variant 1, mRNA./PROD = annexin VI isoform 1/FL = gb: D00510.1 gb: J03578.1 gb: NM_001155.2 | 3.89026 | 6.43752 | 4.49981 | 8.81E−04 |
| *Homo sapiens* c-mer proto-oncogene tyrosine kinase (MERTK), mRNA./PROD = c-mer proto-oncogene tyrosine kinase/FL = gb: NM_006343.1 gb: U08023.1 | 1.78994 | 4.92901 | 3.61665 | 1.84E−02 |
| *Homo sapiens* caspase-like apoptosis regulatory protein 2 (clarp) mRNA, alternatively spliced, complete cds./PROD = caspase-like apoptosis regulatory protein 2/FL = gb: AF005775.1 | 0.434199 | 5.04863 | 5.2167 | 2.46E−02 |
| Human embryonic myosin alkali light chain (MLC1) mRNA, complete cds./FL = gb: M36172.1 gb: M24121.1 gb: NM_002476.1 | 1.94171 | 5.24959 | 4.11475 | 2.11E−02 |
| *Homo sapiens* phosphatidylinositol-4-phosphate 5-kinase, type I, beta (PIP5K1B), mRNA./PROD = phosphatidylinositol-4-phosphate 5-kinase, typeI, beta/FL = gb: NM_003558.1 | 1.34876 | 4.12788 | 2.46657 | 3.66E−03 |
| *Homo sapiens* mRNA; cDNA DKFZp434E082 (from clone DKFZp434E082) | 1.36443 | 4.34866 | 2.94283 | 2.92E−03 |
| *Homo sapiens* dystrophin (muscular dystrophy, Duchenne and Becker types), includes DXS142, DXS164, DXS206, DXS230, DXS239, DXS268, DXS269, DXS270, DXS272 (DMD), transcript variant Dp427p2, mRNA./PROD = dystrophin Dp427p2 isoform/FL = gb: NM_004010.1 | 1.40427 | 4.41881 | 3.04441 | 1.83E−02 |
| *Homo sapiens*, clone MGC: 14801, mRNA, complete cds./PROD = Unknown (protein for MGC: 14801)/FL = gb: BC005997.1 | 2.03928 | 3.96694 | 1.51059 | 5.65E−04 |
| *Homo sapiens* hypothetical protein BC017868 (LOC159091), mRNA./FL = gb: BC017868.1 gb: NM_138819.1 | −0.290244 | 2.2418 | 0.40157 | 6.04E−03 |
| ESTs, Highly similar to AF229172 1 class III myosin (*H. sapiens*) | −0.475471 | 1.94826 | 0.002417 | 5.28E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* solute carrier family 9 (sodiumhydrogen exchanger), isoform 5 (SLC9A5), mRNA./PROD = solute carrier family 9 (sodiumhydrogenexchanger), isoform 5/FL = gb: AF111173.1 gb: NM_004594.1 | 0.047487 | 2.80601 | 1.19645 | 2.80E−03 |
| *Homo sapiens* F37Esophageal cancer-related gene-coding leucine-zipper motif (FEZ1), mRNA./PROD = F37Esophageal cancer-related gene-codingleucine-zipper motif/FL = gb: AF123659.1 gb: NM_021020.1 | −0.128814 | 3.17069 | 2.10422 | 1.54E−02 |
| *Homo sapiens* deiodinase, iodothyronine, type III (DIO3), mRNA./PROD = thyroxine deiodinase type III/FL = gb: NM_001362.1 gb: S79854.1 | −0.136937 | 5.08366 | 4.22897 | 1.41E−02 |
| *Homo sapiens* insulin-like growth factor binding protein 6 (IGFBP6), mRNA./PROD = insulin-like growth factor binding protein 6/FL = gb: BC005007.1 gb: M62402.1 gb: BC003507.1 gb: NM_002178.1 | 2.6126 | 5.13945 | 3.30402 | 9.72E−04 |
| *Homo sapiens* U2 small nuclear ribonucleoprotein auxiliary factor (65 kD) (U2AF65), mRNA./PROD = U2 small nuclear ribonucleoprotein auxiliaryfactor (65 kD)/FL = gb: NM_007279.1 | −0.821533 | 1.81533 | 0.096512 | 4.72E−02 |
| *Homo sapiens* hypothetical protein DKFZp434F0318 (DKFZP434F0318), mRNA./PROD = hypothetical protein DKFZp434F0318/FL = gb: NM_030817.1 | −1.11464 | 1.81375 | 0.394686 | 9.09E−03 |
| *Homo sapiens* BACE mRNA for beta-site APP cleaving enzyme I-476, complete cds./PROD = beta-site APP cleaving enzyme I-476/FL = gb: AB050436.1 | 0.48553 | 3.13284 | 1.44588 | 4.99E−04 |
| ESTs, Weakly similar to ALUC_HUMAN!!!! ALU CLASS C WARNING ENTRY!!! (*H. sapiens*) | 1.07951 | 4.06134 | 2.7193 | 2.11E−02 |
| *Homo sapiens* mRNA for KIAA0876 protein, partial cds./PROD = KIAA0876 protein | −0.432037 | 1.97736 | 0.073246 | 3.37E−02 |
| *Homo sapiens* mRNA for protein-tyrosine kinase, complete cds./PROD = protein-tyrosine kinase/FL = gb: U05682.1 gb: D17517.1 gb: D50479.1 | 0.160986 | 2.75713 | 1.04172 | 2.11E−02 |
| KIAA0418 gene product | −0.677643 | 1.83134 | 0.034385 | 1.45E−04 |
| *Homo sapiens* phosphofructokinase, liver (PFKL), mRNA./PROD = phosphofructokinase, liver/FL = gb: NM_002626.1 gb: BC004920.1 gb: X15573.1 | 2.039 | 4.51747 | 2.70388 | 1.28E−03 |
| *Homo sapiens* enolase 2, (gamma, neuronal) (ENO2), mRNA./PROD = enolase 2, (gamma, neuronal)/FL = gb: NM_001975.1 gb: BC002745.1 gb: M22349.1 | 2.60624 | 5.37458 | 3.92621 | 3.17E−03 |
| *Homo sapiens* AD036 mRNA, complete cds./PROD = AD036/FL = gb: AF260333.1 | −0.503334 | 2.65787 | 1.60278 | 3.61E−02 |
| ESTs | −2.07933 | 1.00157 | −0.1307 | 2.39E−02 |
| *Homo sapiens* keratin 19 (KRT19), mRNA./PROD = keratin 19/FL = gb: NM_002276.1 gb: BC002539.1 | 3.80582 | 6.96535 | 5.91937 | 2.11E−02 |
| pleiomorphic adenoma gene-like 1/FL = gb: U72621.3 | −0.646793 | 1.88692 | 0.221481 | 4.21E−03 |
| *Homo sapiens*, Similar to lipase protein, clone MGC: 2843, mRNA, complete cds./PROD = Similar to lipase protein/FL = gb: NM_020676.1 gb: BC001698.1 | −1.16073 | 1.9994 | 0.961706 | 1.89E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Cluster Incl. AB002344: Human mRNA for KIAA0346 gene, partial cds/ cds = (0, 4852)/gb = AB002344/ gi = 2280479/ug = Hs.103915/len = 6121 | 2.15679 | 4.91332 | 3.47797 | 7.39E−03 |
| Cluster Incl. N80935: zb07g06.s1 *Homo sapiens* cDNA, 3 end/clone = IMAGE-301402/clone_end = 3/gb = N80935/ gi = 1243636/ug = Hs.22483/len = 527 | 2.12419 | 4.48236 | 2.66555 | 1.50E−02 |
| tryptase, alpha | 2.99108 | 5.46095 | 3.76442 | 1.31E−03 |
| ESTs, Weakly similar to Z132_HUMAN ZINC FINGER PROTEIN 13 (*H. sapiens*) | 1.04865 | 3.65906 | 2.12166 | 2.43E−02 |
| *Homo sapiens* core histone macroH2A2.2 (MACROH2A2), mRNA./ PROD = core histone macroH2A2.2/ FL = gb: AF151534.1 gb: NM_018649.1 | 1.67293 | 4.73906 | 3.66212 | 3.62E−02 |
| ESTs | −0.146413 | 2.69334 | 1.39451 | 1.02E−02 |
| Human rho GDI mRNA, complete cds./ PROD = human rho GDI/ FL = gb: M97579.1 gb: D13989.1 gb: NM_004309.1 | 0.019358 | 1.75075 | −0.65155 | 1.85E−02 |
| heat shock 90 kD protein 1, alpha | 1.69225 | 4.20576 | 2.60887 | 2.10E−02 |
| *Homo sapiens* BTB (POZ) domain containing 2 (BTBD2), mRNA./ PROD = BTB (POZ) domain containing 2/ FL = gb: NM_017797.1 | 1.10085 | 3.7628 | 2.32464 | 1.85E−02 |
| *Homo sapiens* mandaselin long form mRNA, complete cds./ PROD = mandaselin long form/ FL = gb: AY048775.1 | −0.148053 | 2.58361 | 1.2296 | 1.57E−02 |
| signal transducer and activator of transcription 3 (acute-phase response factor) | −0.837261 | 1.90254 | 0.560225 | 8.83E−04 |
| *Homo sapiens* lymphocyte antigen 6 complex, locus E (LY6E), mRNA./ PROD = lymphocyte antigen 6 complex, locus E/FL = gb: U42376.1 gb: NM_002346.1 gb: U56145.1 | 0.866364 | 4.91832 | 4.92642 | 2.78E−02 |
| ESTs | −1.24632 | 1.09042 | −0.61316 | 4.05E−02 |
| *Homo sapiens*, clone IMAGE: 4047715, mRNA. | −2.50816 | 1.81 | 1.52693 | 2.63E−02 |
| Cluster Incl. AB002344: Human mRNA for KIAA0346 gene, partial cds/ cds = (0, 4852)/gb = AB002344/ gi = 2280479/ug = Hs.103915/len = 6121 | 1.89578 | 4.61333 | 3.31717 | 1.12E−02 |
| *Homo sapiens* singed (*Drosophila*)-like (sea urchin fascin homolog like) (SNL), mRNA./PROD = singed (*Drosophila*)-like (sea urchin fascinhomolog like)/ FL = gb: BC000521.1 gb: NM_003088.1 gb: U03057.1 gb: U09873.1 | 4.23317 | 6.74774 | 5.25403 | 5.12E−03 |
| *Homo sapiens* mRNA; cDNA DKFZp586L0120 (from clone DKFZp586L0120). | −2.72593 | 1.58998 | 1.27994 | 4.54E−02 |
| *Homo sapiens* mitogen-activated protein kinase 10 (MAPK10), mRNA./ PROD = mitogen-activated protein kinase 10/FL = gb: U07620.1 gb: U34819.1 gb: U34820.1 gb: NM_002753.1 | 0.647994 | 3.46459 | 2.28644 | 6.65E−03 |
| *Homo sapiens* transmembrane tyrosine kinase mRNA, complete cds./ PROD = tyrosine kinase/ FL = gb: L08961.1 | −0.006089 | 2.96035 | 1.93237 | 7.69E−03 |
| *Homo sapiens* mRNA; cDNA DKFZp762H185 (from clone DKFZp762H185) | 2.83663 | 5.30784 | 3.79206 | 6.22E−03 |
| tyrosine 3-monooxygenasetryptophan 5-monooxygenase activation protein, eta polypeptide | 3.48271 | 6.19368 | 4.92556 | 2.11E−02 |
| *Homo sapiens* mRNA; cDNA DKFZp434K0621 (from clone DKFZp434K0621); partial cds | 0.581419 | 3.38088 | 2.21428 | 3.89E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs, Weakly similar to ALUF_HUMAN!!!! ALU CLASS F WARNING ENTRY!!! (*H. sapiens*) | −1.03247 | 1.75349 | 0.587598 | 2.11E−02 |
| tudor repeat associator with PCTAIRE 2 | 2.15771 | 4.69127 | 3.27451 | 2.63E−02 |
| *Homo sapiens* mRNA; cDNA DKFZp564K1672 (from clone DKFZp564K1672); partial cds./PROD = hypothetical protein | 4.49405 | 7.38448 | 6.33474 | 1.39E−02 |
| ESTs | −0.184212 | 2.15367 | 0.554696 | 1.15E−02 |
| *Homo sapiens* bHLH factor Hes4 (LOC57801), mRNA./PROD = bHLH factor Hes4/FL = gb: NM_021170.1 gb: AB048791.1 | 0.47816 | 3.40725 | 2.40001 | 3.16E−02 |
| *Homo sapiens* guanylate cyclase activator 1B (retina) (GUCA1B), mRNA./PROD = guanylate cyclase activator 1B (retina)/FL = gb: M95174.1 gb: NM_002098.1 gb: M97496.1 | −0.714216 | 1.95339 | 0.684983 | 3.38E−03 |
| KIAA0918 protein | −1.39708 | 0.961939 | −0.57499 | 1.40E−02 |
| *Homo sapiens* mRNA for KIAA1161 protein, partial cds./PROD = KIAA1161 protein | 0.781796 | 3.32846 | 1.98143 | 6.60E−03 |
| *Homo sapiens*, Similar to B9 protein, clone MGC: 11339, mRNA, complete cds./PROD = Similar to B9 protein/FL = gb: BC002944.1 | 1.43881 | 3.80457 | 2.29205 | 8.62E−05 |
| hypothetical protein FLJ12666 | 2.34087 | 5.11201 | 4.02837 | 1.97E−02 |
| *Homo sapiens* FLICE-like inhibitory protein short form mRNA, complete cds./PROD = FLICE-like inhibitory protein short form/FL = gb: U97075.1 | 0.135783 | 4.45631 | 4.92758 | 1.96E−02 |
| *Homo sapiens* olfactory receptor, family 52, subfamily A, member 1 (OR52A1), mRNA./PROD = olfactory receptor, family 52, subfamily A, member 1/FL = gb: NM_012375.1 | −0.309574 | 2.08723 | 0.636487 | 4.36E−03 |
| Human DNA sequence from clone RP4-781L3 on chromosome 1p34.3-36.11 Contains a pseudogene similar to IFITM3 (interferon inducedntransmembrane protein 3 (1-8U)), STSs and GSSs | 2.82768 | 5.54517 | 4.43909 | 2.04E−03 |
| *Homo sapiens* KIAA0127 gene product (KIAA0127), mRNA./PROD = KIAA0127 gene product/FL = gb: D50917.1 gb: NM_014755.1 | 2.05236 | 4.43794 | 3.00216 | 3.12E−02 |
| *Homo sapiens* clone HB-2 mRNA sequence | −0.503949 | 2.27896 | 1.25171 | 3.01E−02 |
| hypothetical protein FLJ23091 | −0.76092 | 3.70916 | 3.04154 | 2.45E−02 |
| ESTs | −0.403665 | 2.01868 | 0.643615 | 5.11E−04 |
| ESTs | 2.14401 | 4.70353 | 3.47114 | 3.15E−03 |
| *Homo sapiens* regulator of G protein signalling 5 (RGS5) mRNA, complete cds./PROD = regulator of G protein signalling 5/FL = gb: AF493929.1 | 3.0091 | 5.37511 | 3.95132 | 1.29E−03 |
| endothelin receptor type A/FL = gb: NM_001957.1 gb: L06622.1 | −1.83423 | 2.54948 | 1.95432 | 1.51E−02 |
| *H. sapiens* skeletal embryonic myosin light chain 1 (MLC1) mRNA./PROD = myosin light chain 1 | 0.690058 | 3.3896 | 2.36018 | 3.27E−02 |
| *Homo sapiens* Kruppel-like factor 8 (KLF8), mRNA./PROD = Kruppel-like factor 8/FL = gb: U28282.1 gb: NM_007250.1 | 0.326119 | 2.825 | 1.63929 | 3.92E−02 |
| hypothetical protein DKFZp434F2322 | 0.070576 | 2.58185 | 1.42121 | 5.81E−03 |
| *Homo sapiens* transcription factor 2, hepatic; LF-B3; variant hepatic nuclear factor (TCF2), transcript variant a, mRNA./PROD = transcription factor 2, isoform a/FL = gb: NM_000458.1 | −1.12537 | 3.45355 | 2.54347 | 1.15E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| H2A histone family, member X | 1.37085 | 2.48515 | −0.04057 | 1.34E−02 |
| Homo sapiens H1 histone family, member X (H1FX), mRNA./PROD = H1 histone family, member X/ FL = gb: D64142.1 gb: BC000426.1 gb: NM_006026.1 | 3.21701 | 5.68105 | 4.50969 | 4.29E−03 |
| ESTs, Weakly similar to KIAA1399 protein (H. sapiens) | −0.831241 | 2.82364 | 2.79997 | 4.18E−02 |
| Homo sapiens PNAS-145 mRNA, complete cds./PROD = PNAS-145/ FL = gb: U03105.1 gb: NM_006813.1 gb: AF279899.1 | 2.84962 | 5.38084 | 4.2868 | 8.61E−03 |
| Homo sapiens erythrocyte membrane protein band 4.9 (dematin) (EPB49), mRNA./PROD = erythrocyte membrane protein band 4.9 (dematin)/ FL = gb: NM_001978.1 gb: U28389.1 | −0.306603 | 2.11391 | 0.923806 | 4.81E−03 |
| ESTs | 0.783545 | 3.23146 | 2.07738 | 2.13E−02 |
| ESTs | 1.17515 | 3.61815 | 2.46265 | 1.56E−03 |
| nudix (nucleoside diphosphate linked moiety X)-type motif 4 | 2.09472 | 5.82355 | 5.68859 | 3.63E−02 |
| Novel human mRNA from chromosome 22./PROD = hypothetical protein | −0.533665 | 3.44679 | 3.05803 | 3.99E−02 |
| Homo sapiens partial mRNA for putative nuclear factor./PROD = putative nuclear factor/FL = gb: NM_017688.1 | 1.55224 | 3.89366 | 2.67866 | 1.53E−03 |
| Homo sapiens BCL2adenovirus E1B 19 kD-interacting protein 3 (BNIP3), nuclear gene encoding mitochondrial protein, mRNA./ PROD = BCL2adenovirus E1B 19 kD-interacting protein 3/FL = gb: AF002697.1 gb: NM_004052.2 gb: U15174.1 | 4.51142 | 6.99506 | 5.92755 | 2.25E−03 |
| Homo sapiens bone morphogenetic protein 5 (BMP5), mRNA./PROD = bone morphogenetic protein 5/ FL = gb: M60314.1 gb: NM_021073.1 | −0.6099 | 1.76351 | 0.614791 | 6.46E−03 |
| Homo sapiens nuclear receptor subfamily 0, group B, member 1 (NR0B1), mRNA./PROD = adrenal hypoplasia protein/FL = gb: NM_000475.2 | −0.213822 | 4.14059 | 3.29782 | 3.42E−02 |
| Homo sapiens mRNA; cDNA DKFZp434P228 (from clone DKFZp434P228) | 1.76846 | 4.196 | 3.11284 | 1.23E−02 |
| Homo sapiens pilin-like transcription factor (PILB), mRNA./PROD = pilin-like transcription factor/FL = gb: AF122004.1 gb: NM_012228.1 | 3.14467 | 5.51066 | 4.38212 | 3.80E−03 |
| Homo sapiens complement component 5 (C5), mRNA./PROD = complement component 5/FL = gb: M57729.1 gb: NM_001735.1 | −1.89639 | 1.65637 | 1.59643 | 1.74E−02 |
| Homo sapiens adaptor-related protein complex 3, beta 2 subunit (AP3B2), mRNA./PROD = adaptor-related protein complex 3, beta 2subunit/ FL = gb: AF022152.1 gb: NM_004644.1 gb: U37673.1 | −0.208283 | 2.17404 | 1.07398 | 1.39E−02 |
| Homo sapiens dynein, axonemal, light polypeptide 4 (DNAL4), mRNA./ PROD = dynein, axonemal, light polypeptide 4/FL = gb: BC002968.1 gb: NM_005740.1 | 0.458271 | 2.88755 | 1.8494 | 3.66E−03 |
| Homo sapiens, Similar to RIKEN cDNA C330013D18 gene, clone MGC: 11226, mRNA, complete cds | 0.087468 | 2.45867 | 1.42701 | 3.35E−03 |
| Homo sapiens cDNA: FLJ22731 fis, clone HSI15841. | −2.30948 | 1.62817 | 2.24143 | 4.15E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 0.532996 | 4.6172 | 3.79228 | 2.76E−02 |
| Homo sapiens CXCR4 gene encoding receptor CXCR4 | 3.11086 | 7.24917 | 6.36084 | 3.13E−02 |
| stanniocalcin 1 | 2.48686 | 6.20245 | 5.70081 | 4.94E−02 |
| KIAA0761 protein | −2.09591 | 1.57935 | 1.05907 | 1.86E−02 |
| ESTs | −1.16374 | 2.24964 | 2.52108 | 3.83E−02 |
| Homo sapiens cDNA FLJ36116 fis, clone TESTI2022338. | 3.02587 | 6.7146 | 6.15456 | 3.88E−02 |
| Homo sapiens, clone MGC: 24252 IMAGE: 3932604, mRNA, complete cds./PROD = Unknown (protein for MGC: 24252)/FL = gb: BC014364.1 | −1.53346 | 2.53854 | 1.59251 | 3.91E−03 |
| Homo sapiens cDNA FLJ13392 fis, clone PLACE1001280 | −1.90184 | 1.76129 | 1.16856 | 1.47E−02 |
| Homo sapiens hypothetical protein FLJ12538 similar to ras-related protein RAB17 (FLJ12538), mRNA./PROD = hypothetical protein FLJ12538 similar toras-related protein RAB17/FL = gb: AL136645.1 gb: NM_022449.1 | 1.70617 | 5.11419 | 4.73391 | 2.71E−02 |
| Human DNA sequence from clone RP11-446H13 on chromosome 10. Contains the 3 end of the gene for a novel protein similar to KIAA1059 (ortholog of mouse VPS10 domain receptor protein SORCS), an RPL23A (60S ribosmal protein 23A) pseudogene, ESTs, STSs an | −0.889422 | 2.90076 | 2.11955 | 3.52E−02 |
| Homo sapiens calmegin (CLGN), mRNA./PROD = calmegin/FL = gb: NM_004362.1 gb: D86322.1 | −0.104278 | 2.97817 | 3.11092 | 1.89E−02 |
| Homo sapiens testican 3 (HSAJ1454), mRNA./PROD = testican 3/FL = gb: NM_016950.1 gb: BC000460.1 gb: BC003017.1 | −2.81226 | 0.7939 | 1.55068 | 3.99E−02 |
| Homo sapiens gelsolin (amyloidosis, Finnish type) (GSN), mRNA./PROD = gelsolin (amyloidosis, Finnish type)/FL = gb: NM_000177.1 | 1.6198 | 4.54047 | 4.45008 | 1.07E−02 |
| Homo sapiens endothelin receptor type A (EDNRA), mRNA./PROD = endothelin receptor type A/FL = gb: NM_001957.1 gb: L06622.1 | 0.763007 | 4.05983 | 3.55203 | 3.99E−02 |
| Homo sapiens cDNA: FLJ22808 fis, clone KAIA2925. | −0.367449 | 2.7584 | 2.41394 | 4.31E−02 |
| Homo sapiens hypothetical protein FLJ10312 (FLJ10312), mRNA./PROD = hypothetical protein FLJ10312/FL = gb: NM_030672.1 | 1.59498 | 4.6335 | 4.89157 | 4.85E−02 |
| Homo sapiens lipase mRNA, complete cds./PROD = lipase/FL = gb: AF225418.1 | −2.2131 | 1.0208 | 0.55849 | 3.57E−02 |
| Homo sapiens clone FLC1492 PRO3121 mRNA, complete cds./PROD = PRO3121/FL = gb: AF130082.1 | −0.300037 | −0.46894 | −3.39203 | 1.80E−02 |
| protease, serine, 4 (trypsin 4, brain) | −0.345569 | 2.86256 | 3.35886 | 4.65E−02 |
| Homo sapiens ret finger protein-like 2 (RFPL2), mRNA./PROD = ret finger protein-like 2/FL = gb: NM_006605.1 | −2.15511 | 1.1797 | 0.503917 | 1.94E−02 |
| Homo sapiens beta3GalNAcT-1 mRNA for globoside synthase, complete cds, clone: type 2./PROD = globoside synthase/FL = gb: AB050856.1 | −2.73257 | 0.21269 | −0.0984 | 2.48E−02 |
| Homo sapiens hypothetical protein FLJ11155 (FLJ11155), mRNA./PROD = hypothetical protein FLJ11155/FL = gb: NM_018342.1 | −3.34565 | −0.42738 | −0.71255 | 3.07E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens*, dual specificity phosphatase 4, clone MGC: 3713, mRNA, complete cds./PROD = dual specificity phosphatase 4/ FL = gb: NM_001394.2 gb: BC002671.1 gb: U48807.1 gb: U21108.1 | 2.11487 | 5.16681 | 5.60057 | 3.11E−02 |
| *Homo sapiens* MAD (mothers against decapentaplegic, *Drosophila*) homolog 6 (MADH6), mRNA./PROD = MAD (mothers against decapentaplegic, *Drosophila*) homolog 6/ FL = gb: U59914.1 gb: NM_005585.1 | 0.917516 | 4.29847 | 3.5309 | 2.44E−02 |
| secreted frizzled-related protein 1/ FL = gb: AF056087.1 gb: NM_003012.2 gb: AF017987.1 gb: AF001900.1 | 1.64933 | 4.41286 | 4.21799 | 4.12E−02 |
| *Homo sapiens* secreted apoptosis related protein 2 (SARP2) mRNA, complete cds./PROD = secreted apoptosis related protein 2/ FL = gb: AF056087.1 gb: NM_003012.2 gb: AF017987.1 gb: AF001900.1 | 3.18446 | 5.9316 | 5.74251 | 3.31E−02 |
| KIAA0882 protein | 2.05587 | 4.63577 | 4.67451 | 4.89E−02 |
| *Homo sapiens* nudix (nucleoside diphosphate linked moiety X)-type motif 4 (NUDT4), mRNA./PROD = nudix (nucleoside diphosphate linked moietyX)-type motif 4/ FL = gb: NM_019094.1 gb: AF191653.1 gb: AF191649.1 gb: AF191650.1 | 3.91519 | 6.54632 | 6.42767 | 4.63E−02 |
| *Homo sapiens* cDNA FLJ31061 fis, clone HSYRA2000927. | −1.30452 | 2.06218 | 1.20749 | 1.72E−02 |
| *Homo sapiens* diphosphoinositol polyphosphate phosphohydrolase type 2 beta (NUDT4) mRNA, complete cds./ PROD = diphosphoinositol polyphosphate phosphohydrolasetype 2 beta/FL = gb: NM_019094.1 gb: AF191653.1 gb: AF191649.1 gb: AF191650.1 | 2.62612 | 5.53515 | 5.12935 | 3.96E−02 |
| *Homo sapiens* titin (TTN), mRNA./ PROD = titin/FL = gb: NM_003319.1 | −0.466154 | 2.46856 | 2.00309 | 4.18E−03 |
| carboxypeptidase E/ FL = gb: NM_001873.1 | 2.72316 | 5.80072 | 5.15668 | 2.99E−02 |
| ESTs | −1.80443 | 0.692933 | 0.613229 | 1.46E−03 |
| *Homo sapiens* hypothetical protein FLJ39502 (FLJ39502), mRNA./ FL = gb: NM_173648.1 | −1.60435 | 1.6149 | 2.4204 | 2.10E−02 |
| *Homo sapiens* renal tumor antigen (RAGE), mRNA./PROD = renal tumor antigen/FL = gb: NM_014226.1 gb: AB022694.1 | −0.305406 | 2.4556 | 2.09136 | 3.30E−02 |
| T-box 3 (ulnar mammary syndrome) | −1.70952 | 1.31576 | 0.679584 | 1.29E−02 |
| *Homo sapiens* mitogen-activated protein kinase kinase kinase 8 (MAP3K8), mRNA./PROD = mitogen-activated protein kinase kinase kinase8/ FL = gb: NM_005204.1 gb: D14497.1 | −1.14241 | 1.82177 | 1.23928 | 2.48E−02 |
| *Homo sapiens* enoyl-Coenzyme A, hydratase3-hydroxyacyl Coenzyme A dehydrogenase (EHHADH), nuclear gene encoding mitochondrial protein, mRNA./PROD = enoyl-Coenzyme A, hydratase3-hydroxyacylCoenzyme A dehydrogenase/FL = gb: NM_001966.1 gb: L07077.1 | 0.226733 | 3.18231 | 2.59938 | 6.22E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 1.65525 | 3.9984 | 3.98375 | 1.97E−02 |
| *Homo sapiens* secreted frizzled-related protein 1 (SFRP1), mRNA./PROD = secreted frizzled-related protein 1/FL = gb: AF056087.1 gb: NM_003012.2 gb: AF017987.1 gb: AF001900.1 | 3.91678 | 7.18429 | 6.24313 | 2.35E−02 |
| ESTs | 2.28659 | 5.21675 | 4.59884 | 3.11E−02 |
| *Homo sapiens* selenoprotein P, plasma, 1 (SEPP1), mRNA./PROD = selenoprotein P precursor/FL = gb: NM_005410.1 | 2.73332 | 5.13625 | 5.04138 | 1.75E−02 |
| hypothetical protein FLJ12838/FL = gb: NM_024641.1 | 2.21522 | 5.4785 | 4.50835 | 4.55E−02 |
| *Homo sapiens* mRNA; cDNA DKFZp761M1216 (from clone DKFZp761M1216) | −2.59761 | 0.092924 | −0.31569 | 4.19E−02 |
| *Homo sapiens* KPL1 (KPL1) mRNA, complete cds./PROD = KPL1/FL = gb: AF081583.1 gb: U89715.1 gb: NM_021200.1 | −0.08886 | 2.51294 | 2.15967 | 1.97E−02 |
| *Homo sapiens*, synovial sarcoma, X breakpoint 1, clone MGC: 5162, mRNA, complete cds./PROD = synovial sarcoma, X breakpoint 1/FL = gb: BC001003.2 gb: NM_005635.1 | −1.57209 | 1.39869 | 2.12662 | 6.84E−03 |
| *Homo sapiens*, Similar to testican 3, clone MGC: 8506, mRNA, complete cds./PROD = Similar to testican 3/FL = gb: NM_016950.1 gb: BC000460.1 gb: BC003017.1 | −2.778 | 0.563149 | 1.66935 | 1.87E−02 |
| ESTs | 0.502949 | 3.0682 | 2.72874 | 2.02E−02 |
| *Homo sapiens* cDNA FLJ32963 fis, clone TESTI2008405. | 1.49644 | 3.87336 | 3.68478 | 6.89E−03 |
| triadin/FL = gb: U18985.1 gb: NM_006073.1 | −1.61408 | 0.713083 | 0.566175 | 1.87E−02 |
| *Homo sapiens* adlican mRNA, complete cds./PROD = adlican/FL = gb: AF245505.1 | 0.872786 | 3.20404 | 3.02406 | 4.21E−02 |
| Human midkine mRNA, complete cds./PROD = midkine/FL = gb: NM_002391.1 gb: M69148.1 | 3.55275 | 5.93819 | 5.68363 | 1.89E−02 |
| *Homo sapiens*, synovial sarcoma, X breakpoint 4, clone MGC: 12411, mRNA, complete cds./PROD = synovial sarcoma, X breakpoint 4/FL = gb: BC005325.1 | −0.806785 | 1.90972 | 2.5215 | 4.17E−02 |
| ESTs | −3.61193 | −0.9408 | −1.53439 | 2.43E−03 |
| ESTs | −0.619714 | 1.93617 | 1.44843 | 4.14E−02 |
| ESTs | 0.446983 | 3.14315 | 2.48676 | 1.98E−02 |
| *Homo sapiens* flavin containing monooxygenase 5 (FMO5) mRNA./PROD = flavin containing monooxygenase 5/FL = gb: L37080.1 gb: NM_001461.1 | −0.476203 | 1.99948 | 1.55491 | 3.73E−02 |
| *Homo sapiens* aminopeptidase A mRNA, complete cds./PROD = aminopeptidase A/FL = gb: L12468.1 gb: NM_001977.1 gb: L14721.1 | −0.758987 | 2.07596 | 1.20831 | 3.00E−02 |
| *Homo sapiens* hypothetical protein DKFZp761H1710 (DKFZP761H1710), mRNA./PROD = hypothetical protein DKFZp761H1710/FL = gb: NM_031297.1 | −0.713164 | 2.03145 | 1.24823 | 2.17E−03 |
| ESTs | −1.94194 | 0.608912 | 0.013238 | 1.72E−02 |
| *Homo sapiens* sialyltransferase 8 (alpha-2,8-polysialyltransferase) D (SIAT8D), mRNA./PROD = sialyltransferase 8 (alpha-2,8-polysialyltransferase) D/FL = gb: NM_005668.1 gb: L41680.1 | −1.07243 | 1.83889 | 0.855205 | 2.16E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Homo sapiens, clone IMAGE: 5194204, mRNA. | −2.13256 | 0.383746 | 1.02639 | 4.55E−02 |
| hypothetical protein MGC4342/ FL = gb: NM_024329.1 gb: BC003033.1 | −0.403018 | 2.01722 | 1.41263 | 1.97E−02 |
| Homo sapiens PHD finger protein 1 (PHF1), transcript variant 2, mRNA./ PROD = PHD finger protein 1, isoform b/ FL = gb: NM_024165.1 gb: AF052205.1 | 0.620171 | 2.95191 | 2.42296 | 2.32E−02 |
| actinin, alpha 4 | 0.436893 | 3.11051 | 2.23625 | 5.44E−03 |
| Homo sapiens PCTAIRE protein kinase 1 (PCTK1), mRNA./PROD = PCTAIRE protein kinase 1/FL = gb: NM_006201.1 | 2.38171 | 4.87071 | 4.16957 | 2.90E−03 |
| Human DNA sequence from clone RP11-165F24 on chromosome 9. Contains the 3 end of the gene for a novel protein (similar to Drosophila CG6630 and CG11376, KIAA1058, rat TRG), an RPL12 (60S ribosomal protein L12) pseudogene, ESTs, STSs, GSSs and a C . . . | 0.167347 | 2.56439 | 1.93736 | 3.93E−02 |
| insulin-like growth factor binding protein 3/FL = gb: NM_000598.1 | 0.921068 | 3.60279 | 2.67905 | 4.80E−02 |
| Homo sapiens, clone IMAGE: 3840937, mRNA, partial cds./PROD = Unknown (protein for IMAGE: 3840937) | 3.59778 | 6.12936 | 6.92649 | 8.62E−05 |
| Homo sapiens phosphoglucomutase 1 (PGM1), mRNA./ PROD = phosphoglucomutase 1/ FL = gb: NM_002633.1 gb: BC001756.1 gb: M83088.1 | 4.74364 | 7.09524 | 6.43056 | 2.21E−02 |
| apolipoprotein C-I | 2.77701 | 5.23054 | 4.44049 | 3.39E−02 |
| Homo sapiens insulin induced gene 1 (INSIG1), mRNA./PROD = insulin induced gene 1/FL = gb: NM_005542.1 | 2.11462 | 4.44128 | 3.77765 | 3.21E−02 |
| Human a6(IV) collagen (COL4A6) mRNA, complete cds./PROD = A type IV collagen/FL = gb: U04845.1 | 0.798849 | 3.23623 | 2.41372 | 1.38E−03 |
| Homo sapiens mRNA for alpha 1,6-fucosyltransferase, complete cds./ PROD = alpha 1,6-fucosyltransferase/ FL = gb: AB049740.2 | 1.31479 | 3.6699 | 2.90742 | 3.48E−02 |
| ESTs, Moderately similar to Six5 (M. musculus) | 0.434259 | 2.81512 | 1.9556 | 1.23E−02 |
| solute carrier family 2 (facilitated glucose transporter), member 3/ FL = gb: NM_006931.1 gb: M20681.1 | 5.23156 | 7.63734 | 6.74444 | 1.99E−02 |
| Human acid sphingomyelinase (ASM) mRNA, complete cds./PROD = acid sphingomyelinase/FL = gb: NM_000543.1 gb: M59916.1 | 1.03965 | 3.45689 | 2.52125 | 2.62E−02 |
| ESTs, Weakly similar to unnamed protein product (H. sapiens) | 3.0131 | 5.41021 | 4.46614 | 4.79E−03 |
| Homo sapiens cDNA FLJ33178 fis, clone ADRGL2002753. | 0.137476 | −1.9718 | −4.73502 | 2.23E−03 |
| Homo sapiens, parathyroid hormone-like hormone, clone MGC: 14611, mRNA, complete cds./PROD = parathyroid hormone-like hormone/ FL = gb: BC005961.1 | 2.46289 | −0.34647 | −1.96791 | 3.05E−02 |
| Homo sapiens colon carcinoma related protein (LOC51159), mRNA./ PROD = colon carcinoma related protein/ FL = gb: NM_016206.1 gb: AF099505.1 | 2.50614 | −0.01889 | −1.04926 | 2.52E−02 |
| KIAA0036 gene product | 3.05174 | −0.66523 | −2.2068 | 2.62E−02 |
| Homo sapiens cDNA FLJ13536 fis, clone PLACE1006521 | 4.27968 | 1.86625 | 1.70965 | 1.11E−02 |
| Homo sapiens cDNA: FLJ22463 fis, clone HRC10126 | 3.68063 | 1.24806 | 1.39728 | 1.42E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* UDP-N-acetylglucosamine: a-1,3-D-mannoside beta-1,4-N-acetylglucosaminyltransferase IV-homolog (HGNT-IV-H), mRNA./PROD = UDP-N-acetylglucosamine: a-1,3-D-mannosidebeta-1,4-N-acetylglucosaminyltransferase IV-homolog/FL = gb: AB024729.1 gb: NM__0 | 2.71164 | 0.270906 | 0.433883 | 1.98E−02 |
| tissue factor pathway inhibitor 2/ FL = gb: D29992.1 gb: L27624.1 gb: NM__006528.1 gb: BC005330.1 | 4.19529 | 1.63281 | 1.58393 | 7.53E−03 |
| ESTs | 2.8924 | 0.521234 | 0.762594 | 2.82E−02 |
| putative gene product | −0.518738 | −0.66615 | 1.82038 | 4.91E−02 |
| *Homo sapiens* mRNA for KIAA1758 protein, partial cds./PROD = KIAA1758 protein | 2.42082 | −0.03923 | 0.213473 | 1.25E−02 |
| prostaglandin E receptor 4 (subtype EP4)/FL = gb: L25124.1 gb: D28472.1 gb: NM__000958.1 gb: L28175.1 | 2.58497 | 0.196846 | 0.527172 | 1.42E−02 |
| *Homo sapiens* cDNA: FLJ22463 fis, clone HRC10126 | 2.85068 | 0.473875 | 0.830447 | 1.97E−02 |
| *Homo sapiens* heparan sulfate (glucosamine) 3-O-sulfotransferase 2 (HS3ST2), mRNA./PROD = heparan sulfate D-glucosaminyl3-O-sulfotransferase 2/FL = gb: AF105375.1 gb: AF105374.1 gb: NM__006043.1 | 3.18462 | 0.571052 | 0.709206 | 4.54E−02 |
| *Homo sapiens* schwannomin interacting protein 1 (SCHIP-1), mRNA./PROD = schwannomin interacting protein 1/FL = gb: AF145713.1 gb: NM__014575.1 | 5.5957 | 3.21054 | 3.57915 | 2.11E−02 |
| Human lysyl oxidase (LOX) gene, exon 7 | 2.11886 | −0.24936 | 0.138069 | 2.55E−03 |
| Human nephropontin mRNA, complete cds./PROD = nephropontin/ FL = gb: M83248.1 | 7.82555 | 5.27856 | 5.06542 | 4.61E−02 |
| Human mRNA for KIAA0386 gene, complete cds./FL = gb: AB002384.1 | 3.9213 | 1.56305 | 1.13663 | 1.93E−02 |
| ESTs | 3.22146 | 0.851355 | 0.404487 | 3.41E−03 |
| Human glioma pathogenesis-related protein (GliPR) mRNA, complete cds./ PROD = glioma pathogenesis-related protein/FL = gb: NM__006851.1 gb: U16307.1 | 3.20187 | 0.502872 | 0.348681 | 1.34E−02 |
| ESTs | 2.96697 | 0.440894 | 0.773495 | 1.97E−02 |
| *Homo sapiens* cDNA FLJ13384 fis, clone PLACE1001062, highly similar to *Homo sapiens* mRNA for lysine-ketoglutarate reductasesaccharopine dehydrogenase. | 5.9221 | 3.48419 | 3.9531 | 3.38E−02 |
| *Homo sapiens* mRNA; cDNA DKFZp761I1912 (from clone DKFZp761I1912) | 6.06894 | 3.31919 | 3.4798 | 4.97E−02 |
| ESTs | 4.12419 | 1.53997 | 1.88239 | 5.68E−03 |
| *Homo sapiens* fibroblast growth factor 2 (basic) (FGF2), mRNA./ PROD = fibroblast growth factor 2 (basic)/ FL = gb: NM__002006.1 gb: M27968.1 | 5.49297 | 2.64534 | 2.76054 | 4.71E−02 |
| ribosomal protein L34 pseudogene 1 | 3.45116 | 2.78236 | 5.10812 | 2.42E−02 |
| HIV-1 rev binding protein 2 | 4.4245 | 1.47599 | 1.52824 | 2.10E−02 |
| *H. sapiens* FGF gene, exon 3/ FL = gb: NM__000800.1 gb: M13361.1 | 2.04849 | −0.34703 | −0.95745 | 3.33E−02 |
| ESTs | 2.03304 | −0.9164 | −0.83676 | 4.19E−02 |
| ESTs | 2.87393 | 0.428858 | 1.02011 | 9.72E−04 |
| *Homo sapiens* clone 23700 mRNA sequence | 4.60148 | 1.64243 | 1.72052 | 4.74E−02 |
| ESTs, Highly similar to S21424 nestin (*H. sapiens*) | 3.08579 | 0.725853 | 1.40345 | 1.99E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Homo sapiens actin, gamma 2, smooth muscle, enteric (ACTG2), mRNA./PROD = actin, gamma 2 propeptide/FL = gb: NM_001615.2 | 7.17155 | 4.15208 | 4.18551 | 4.72E−02 |
| hypothetical protein FLJ22833 | 2.80785 | 0.480636 | 1.25154 | 2.43E−02 |
| Homo sapiens LIM homeobox protein 6 (LHX6), mRNA./PROD = LIM homeobox protein 6/FL = gb: AB031041.1 gb: NM_014368.1 gb: AL136570.1 | 2.52571 | −0.06036 | 0.459727 | 4.37E−02 |
| Homo sapiens, clone IMAGE: 5271039, mRNA. | 3.05576 | 0.189935 | 0.452681 | 4.05E−02 |
| Homo sapiens cAMP response element-binding protein CRE-BPa (H_GS165L15.1), mRNA./PROD = cAMP response element-binding protein CRE-BPa/FL = gb: NM_004904.1 gb: L05911.1 | 2.90971 | 0.487264 | 1.21334 | 4.24E−02 |
| G protein-coupled receptor 1/FL = gb: NM_005279.1 | 1.15804 | −1.24345 | −0.49352 | 2.28E−03 |
| Homo sapiens neuropilin (NRP) and tolloid (TLL)-like 1 (NETO1), transcript variant 3, mRNA./PROD = neuropilin-and tolloid-like protein 1 isoform 3precursor/FL = gb: AF448838.1 gb: NM_138966.2 | 3.25525 | 0.20233 | 0.301354 | 2.83E−02 |
| Homo sapiens mRNA for KIAA0559 protein, partial cds./PROD = KIAA0559 protein | 2.37088 | −0.29358 | 0.199028 | 2.81E−02 |
| Human 65-kilodalton phosphoprotein (p65) mRNA, complete cds./PROD = phosphoprotein p65/FL = gb: M22300.1 gb: NM_002298.2 gb: J02923.1 | 3.25522 | 0.620942 | 1.15317 | 2.88E−02 |
| Human DNA sequence from clone RP11-31K16 on chromosome 9. Contains a snoRNA binding domain pseudogene, the ELAVL2 gene for ELAV (embryonic lethal, abnormal vision, Drosophila)-like 2, ESTs, STSs, GSSs and a CpG island | 4.77522 | 2.18971 | 2.77459 | 4.04E−02 |
| hypothetical protein FLJ11006 | 1.75389 | −0.66646 | 0.100591 | 7.78E−04 |
| Homo sapiens mRNA; cDNA DKFZp566A1046 (from clone DKFZp566A1046) | 3.97344 | 1.32598 | 1.8683 | 3.19E−02 |
| ESTs | 4.13356 | 1.60769 | 2.27415 | 1.85E−02 |
| H. sapiens gene from PAC 106H8. | 3.05906 | −0.08711 | −0.13845 | 4.34E−02 |
| Human T-cell receptor rearranged beta-chain V-region (V-D-J) mRNA, complete cds./FL = gb: M15564.1 | 3.43862 | 0.94127 | 1.64514 | 5.31E−03 |
| peptidylprolyl isomerase A (cyclophilin A) | 1.76352 | 0.908832 | 3.26124 | 2.19E−02 |
| Homo sapiens mRNA for KIAA1597 protein, partial cds./PROD = KIAA1597 protein | 6.20675 | 3.06104 | 3.12403 | 1.78E−02 |
| HIV-1 rev binding protein 2 | 3.54001 | 0.617783 | 0.325316 | 3.52E−02 |
| Homo sapiens nidogen 2 (NID2), mRNA./PROD = nidogen 2/FL = gb: NM_007361.1 gb: D86425.1 | 3.39549 | 0.915898 | 1.65422 | 4.70E−03 |
| Homo sapiens mRNA; cDNA DKFZp566A1046 (from clone DKFZp566A1046) | 3.49826 | 0.859233 | 1.46022 | 3.01E−02 |
| Homo sapiens muscleblind (Drosophila)-like (MBNL), mRNA./PROD = muscleblind (Drosophila)-like/FL = gb: NM_021038.1 gb: AB007888.1 | 3.53962 | 0.508166 | 0.298438 | 3.90E−02 |
| hypothetical protein FLJ20163 | 5.26708 | 2.17148 | 2.01643 | 3.33E−02 |
| KIAA0455 gene product | 3.25374 | 0.057742 | −0.01612 | 2.66E−02 |
| hypothetical protein FLJ22833/FL = gb: NM_022837.1 | 2.93229 | 0.533105 | 1.40606 | 3.19E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 2.19313 | −0.32822 | 0.427128 | 1.87E−02 |
| Homo sapiens NADPH oxidase 4 (NOX4), mRNA./PROD = NADPH oxidase 4/FL = gb: AF261943.1 gb: NM_016931.1 gb: AF254621.1 gb: AB041035.1 | 5.57794 | 2.61602 | 2.28462 | 4.04E−02 |
| ESTs | 3.3266 | 0.840887 | 1.69605 | 0.00E+00 |
| ESTs | 1.99635 | −0.56359 | 0.236236 | 1.39E−02 |
| Homo sapiens serumglucocorticoid regulated kinase (SGK), mRNA./PROD = serumglucocorticoid regulated kinase/FL = gb: BC001263.1 gb: NM_005627.1 gb: AF153609.1 | 4.81433 | 2.46478 | 3.47797 | 2.02E−02 |
| A kinase (PRKA) anchor protein 2 | 6.03149 | 3.65135 | 4.63469 | 1.17E−02 |
| ESTs | 3.8522 | 1.17894 | 0.483367 | 3.08E−02 |
| Homo sapiens similar to rat tricarboxylate carrier-like protein (BA108L7.2), mRNA./PROD = similar to rat tricarboxylate carrier-likeprotein/ FL = gb: NM_030971.1 | 1.74077 | −1.45032 | −1.24979 | 5.69E−04 |
| Homo sapiens, lectin, galactoside-binding, soluble, 3 (galectin 3), clone MGC: 2058, mRNA, complete cds./ PROD = lectin, galactoside-binding, soluble, 3(galectin 3)/ FL = gb: NM_002306.1 gb: M35368.1 gb: BC001120.1 gb: M36682.1 gb: M57710.1 gb: AB006780.1 | 4.53668 | 1.85893 | 2.59596 | 3.84E−03 |
| ESTs | 1.06738 | −1.51321 | −0.67814 | 7.68E−03 |
| Homo sapiens heptacellular carcinoma novel gene-3 protein (LOC51339), mRNA./PROD = heptacellular carcinoma novel gene-3 protein/ FL = gb: NM_016651.2 gb: AF251079.2 | 5.55437 | 3.02649 | 3.91576 | 2.22E−02 |
| Homo sapiens, Similar to transforming growth factor beta 1 induced transcript 1, clone MGC: 4078, mRNA, complete cds./ PROD = Similar to transforming growth factor beta 1 induced transcript 1/ FL = gb: NM_015927.1 gb: BC001830.1 gb: AF116343.1 | 4.82642 | 2.07249 | 2.74019 | 1.03E−02 |
| ESTs, Highly similar to FXD3_HUMAN FORKHEAD BOX PROTEIN D3 (H. sapiens) | 3.81523 | 1.18624 | 1.98102 | 4.17E−02 |
| ESTs | 4.52094 | 1.70664 | 2.3196 | 2.78E−02 |
| Homo sapiens potassium intermediatesmall conductance calcium-activated channel, subfamily N, member 2 (KCNN2), mRNA./PROD = potassium intermediatesmall conductancecalcium-activated channel, subfamily N, member 2/FL = gb: NM_021614.1 gb: AF239613.1 | 3.68048 | 0.897369 | 1.5433 | 1.32E−02 |
| Homo sapiens transporter similar to yeast MRS2 (MRS2L), mRNA./ PROD = transporter similar to yeast MRS2/FL = gb: AF288288.1 gb: NM_020662.1 | 5.68324 | 3.35483 | 4.46553 | 3.00E−03 |
| Homo sapiens a disintegrin-like and metalloprotease (reprolysin type) with thrombospondin type 1 motif, 5 (aggrecanase-2) (ADAMTS5), mRNA./ PROD = a disintegrin and metalloprotease withthrombospondin motifs-5 preproprotein/ FL = gb: NM_007038.1 gb: AF14209 | 4.54713 | 2.07152 | 1.10726 | 5.91E−03 |
| HIV-1 rev binding protein 2 | 3.85003 | 0.823769 | 0.407316 | 3.76E−02 |
| Human, parathyroid-like protein (associated with humoral hypercalcemia of malignancy) mRNA, complete cds./ FL = gb: J03580.1 | 1.73564 | −1.5631 | −1.41799 | 4.04E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 5.27633 | 2.76577 | 3.71542 | 1.39E−02 |
| ESTs | 1.7022 | −1.29085 | −0.81236 | 1.72E−02 |
| pyruvate dehydrogenase phosphatase/ FL = gb: NM_018444.1 gb: AF155661.1 | 6.62966 | 4.26189 | 5.37384 | 1.04E−03 |
| ESTs | 3.90566 | 1.11378 | 1.80307 | 1.57E−02 |
| Homo sapiens DRM (DRM) mRNA, complete cds./PROD = DRM/ FL = gb: NM_013372.1 gb: AF110137.2 gb: AF045800.1 gb: AF154054.1 | 6.16645 | 3.12369 | 3.57831 | 1.59E−02 |
| Homo sapiens cDNA: FLJ22769 fis, clone KAIA1316 | 2.36483 | −0.5543 | 0.025213 | 1.45E−04 |
| ESTs | 4.31647 | 1.44801 | 2.11226 | 2.19E−02 |
| ESTs | 1.24891 | −1.42983 | −0.57145 | 1.29E−02 |
| Homo sapiens mRNA; cDNA DKFZp586N012 (from clone DKFZp586N012) | 2.85031 | 0.231102 | 1.16439 | 1.08E−02 |
| jagged 1 (Alagille syndrome) | 2.54951 | 0.151382 | 1.31733 | 4.46E−03 |
| ESTs, Weakly similar to I38588 reverse transcriptase homolog (H. sapiens) | 1.16209 | −1.26828 | −0.1187 | 3.40E−02 |
| KIAA1339 protein | 4.41803 | 2.09451 | 3.35786 | 3.90E−02 |
| ESTs | 3.83407 | 0.892884 | 1.56759 | 8.98E−03 |
| DKFZP434D156 protein | 4.42983 | 2.05154 | 3.28988 | 1.60E−02 |
| Homo sapiens mRNA expressed only in placental villi, clone SMAP41. | 3.84408 | 0.705031 | 1.20856 | 2.25E−02 |
| RAS guanyl releasing protein 2 (calcium and DAG-regulated) | 2.7724 | 0.235409 | 1.34452 | 1.96E−02 |
| KIAA0164 gene product/ FL = gb: NM_014739.1 gb: D79986.1 | 4.99867 | 2.5327 | 3.72535 | 2.85E−02 |
| Homo sapiens mRNA; cDNA DKFZp761M0111 (from clone DKFZp761M0111) | 5.14752 | 2.61217 | 3.76652 | 3.78E−02 |
| Homo sapiens NPD009 mRNA, complete cds./PROD = NPD009/ FL = gb: NM_020686.1 gb: AF237813.1 | 2.15383 | −0.27664 | 0.990295 | 2.09E−03 |
| muscleblind (Drosophila)-like/ FL = gb: NM_021038.1 gb: AB007888.1 | 3.23823 | 0.467215 | 1.39628 | 7.60E−03 |
| ESTs | 4.49318 | 1.35004 | 1.91395 | 3.79E−02 |
| muscleblind (Drosophila)-like/ FL = gb: NM_021038.1 gb: AB007888.1 | 1.84877 | −0.57315 | 0.732468 | 8.06E−03 |
| ESTs | 6.068 | 3.42334 | 4.51189 | 1.89E−02 |
| ESTs, Weakly similar to unnamed protein product (H. sapiens) | 3.24528 | 0.740266 | 1.98306 | 3.89E−04 |
| Human complement cytolysis inhibitor (CLI) mRNA, complete cds./ FL = gb: J02908.1 gb: NM_001831.1 gb: M64722.1 gb: M25915.1 | 6.50766 | 4.03647 | 5.33533 | 1.77E−02 |
| ESTs | 5.36759 | 2.42249 | 3.24765 | 3.23E−03 |
| ESTs | 0.957239 | −1.43055 | −0.04796 | 5.55E−04 |
| transporter similar to yeast MRS2 | 3.77395 | 1.18311 | 2.36844 | 1.83E−02 |
| Homo sapiens, Similar to regulator for ribosome resistance homolog (S. cerevisiae), clone MGC: 2755, mRNA, complete cds./ PROD = Similar to regulator for ribosome resistancehomolog (S. cerevisiae)/ FL = gb: BC001811.1 | 5.09957 | 2.72179 | 4.14116 | 2.72E−02 |
| SWISNF related, matrix associated, actin dependent regulator of chromatin, subfamily a, member 2/ FL = gb: NM_003070.1 gb: D26155.1 | 2.54229 | −0.29226 | 0.695255 | 1.89E−02 |
| Homo sapiens mRNA; cDNA DKFZp586L2424 (from clone DKFZp586L2424) | 3.34446 | 0.795373 | 2.07147 | 1.03E−02 |
| ESTs | 4.63117 | 2.08252 | 3.36946 | 2.25E−03 |
| Homo sapiens bicarbonate transporter-related protein BTR1 mRNA, complete cds./PROD = bicarbonate transporter-related protein BTR1/ FL = gb: AF336127.1 | 3.17407 | 0.745852 | 2.17046 | 1.71E−03 |
| ESTs | 1.08377 | −1.27197 | 0.228305 | 4.76E−02 |
| ESTs | 2.94657 | 0.127188 | 1.20032 | 1.43E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* mRNA; cDNA DKFZp434B2016 (from clone DKFZp434B2016). | 2.47798 | −0.26439 | 0.894731 | 4.51E−03 |
| ESTs | 2.39983 | −1.04089 | −0.57976 | 3.37E−02 |
| *Homo sapiens* synaptotagmin interacting protein STIP1 mRNA, partial cds./PROD = synaptotagmin interacting protein STIP1 | 2.11009 | −0.57109 | 0.653181 | 1.78E−02 |
| *Homo sapiens* connexin 26 (GJB2) mRNA, complete cds./PROD = connexin 26/FL = gb: NM_004004.1 gb: M86849.2 | 2.86049 | −0.57377 | −0.09328 | 4.27E−04 |
| *Homo sapiens* brain-derived neurotrophic factor (BDNF), mRNA./PROD = brain-derived neurotrophic factor/FL = gb: NM_001709.1 | 1.71599 | −0.79412 | 0.616733 | 3.09E−02 |
| ESTs, Weakly similar to unknown (*H. sapiens*) | 2.33677 | −0.04066 | 1.5217 | 1.87E−03 |
| ESTs | 2.57265 | 0.177794 | 1.74876 | 2.74E−04 |
| ESTs | 2.6809 | 0.209095 | 1.70624 | 1.21E−02 |
| *Homo sapiens* DKC1 gene, exons 1 to 11 | 4.18307 | 1.70283 | 3.20863 | 2.00E−02 |
| *Homo sapiens* T cell receptor beta chain (TCRBV13S1-TCRBJ2S1) mRNA, complete cds./PROD = T cell receptor beta chain/FL = gb: AF043179.1 | 4.45228 | 1.38318 | 2.30031 | 3.27E−03 |
| *Homo sapiens* PRO0066 mRNA, complete cds./PROD = PRO0066/FL = gb: AF113007.1 | 0.466715 | −1.87679 | −0.22665 | 4.25E−03 |
| axonal transport of synaptic vesicles | 5.20385 | 2.74124 | 4.27648 | 3.33E−03 |
| *Homo sapiens*, Similar to cyclin M2, clone MGC: 12933 IMAGE: 4308662, mRNA, complete cds./PROD = Similar to cyclin M2/FL = gb: BC021222.1 | 0.139313 | −2.31405 | −0.76333 | 1.46E−02 |
| *Homo sapiens* clone CDABP0095 mRNA sequence | 3.87201 | 2.7936 | 5.73958 | 9.63E−03 |
| *H. sapiens* mRNA for ribosomal protein L18a homologue./PROD = ribosomal protein L18a homologue | 2.00401 | 0.354674 | 2.73013 | 4.70E−04 |
| ESTs, Weakly similar to ALU7_HUMAN ALU SUBFAMILY SQ SEQUENCE CONTAMINATION WARNING ENTRY (*H. sapiens*) | 3.43639 | 0.843826 | 2.28468 | 3.37E−02 |
| *Homo sapiens*, clone IMAGE: 5242616, mRNA. | −0.525567 | −2.07832 | 0.406964 | 2.23E−02 |
| *Homo sapiens* C1orf24 mRNA, complete cds./PROD = C1orf24/FL = gb: AF288391.1 gb: AB050477.1 gb: NM_022083.1 | 5.17968 | 2.58724 | 4.04213 | 1.98E−04 |
| *Homo sapiens* clone IMAGE: 451939, mRNA sequence | 5.15776 | 2.22786 | 3.40438 | 2.60E−02 |
| *Homo sapiens* cDNA FLJ14942 fis, clone PLACE1011185, highly similar to INSERTION ELEMENT IS1 PROTEIN INSB. | 0.682724 | −2.08716 | −0.74074 | 1.45E−02 |
| hypothetical protein FLJ20425/FL = gb: NM_017816.1 gb: AL136750.1 | 4.23689 | 1.90847 | 3.69988 | 1.15E−02 |
| *Homo sapiens* matrix metalloproteinase 10 (stromelysin 2) (MMP10), mRNA./PROD = matrix metalloproteinase 10 preproprotein/FL = gb: BC002591.1 gb: NM_002425.1 | 2.28308 | −0.65903 | 0.521586 | 8.87E−03 |
| ESTs | 3.67167 | 2.20619 | 4.86553 | 3.16E−03 |
| *Homo sapiens* prominin (mouse)-like 1 (PROML1), mRNA./PROD = prominin (mouse)-like 1/FL = gb: NM_006017.1 gb: AF027208.1 | 5.46002 | 2.79737 | 4.29571 | 1.38E−03 |
| *Homo sapiens* mRNA; cDNA DKFZp434M2415 (from clone DKFZp434M2415). | 2.40278 | −0.68409 | 0.399469 | 1.48E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens* hypothetical protein FLJ20701 (FLJ20701), mRNA./PROD = hypothetical protein FLJ20701/FL = gb: NM_017933.1 | 2.1471 | 0.312211 | 2.65409 | 2.28E−04 |
| *Homo sapiens* cDNA FLJ35259 fis, clone PROST2004251. | 6.79033 | 3.86627 | 5.12737 | 1.23E−03 |
| *Homo sapiens* hypothetical protein FLJ39553 (FLJ39553), mRNA./FL = gb: NM_173549.1 | 4.0369 | 1.34318 | 2.84336 | 7.69E−03 |
| Human microfibril-associated glycoprotein-2 MAGP-2 mRNA, complete cds./PROD = microfibril-associated glycoprotein-2 MAGP-2/FL = gb: NM_003480.1 gb: U37283.1 | 3.89326 | 0.527618 | 1.35764 | 1.81E−03 |
| *Homo sapiens* proprotein convertase subtilisinkexin type 5 (PCSK5), mRNA./PROD = proprotein convertase subtilisinkexin type 5/FL = gb: U56387.2 gb: NM_006200.1 | 3.76897 | 0.368734 | 1.17396 | 1.38E−02 |
| Cluster Incl. AI735391: at10e09.x1 *Homo sapiens* cDNA, 3 end/clone = IMAGE-2354728/clone_end = 3/gb = AI735391/gi = 5056915/ug = Hs.20137/len = 567 | 2.59941 | 0.203564 | 2.03637 | 1.12E−04 |
| ESTs | 2.30031 | −1.01596 | −0.08964 | 1.46E−02 |
| Kruppel-like factor 4 (gut) | 3.50041 | 1.09954 | 2.95915 | 1.22E−02 |
| *Homo sapiens* full length insert cDNA YI25A03 | −1.40946 | −3.04877 | −0.39378 | 3.32E−02 |
| ESTs | 0.806666 | −2.01081 | −0.53076 | 1.91E−02 |
| *Homo sapiens* mRNA; cDNA DKFZp761G02121 (from clone DKFZp761G02121); partial cds | 3.1892 | 0.012768 | 1.13562 | 1.35E−03 |
| *Homo sapiens* TMEFF2 mRNA, complete cds./FL = gb: AB017269.1 gb: NM_016192.2 gb: AF179274.2 gb: AF242222.1 | 2.28638 | −0.89508 | 0.225546 | 1.21E−03 |
| *Homo sapiens*, clone MGC: 3328, mRNA, complete cds./PROD = Unknown (protein for MGC: 3328)/FL = gb: BC001745.1 gb: NM_014392.1 | 3.54625 | 0.772486 | 2.30168 | 4.16E−02 |
| ESTs | 2.18149 | −0.58303 | 0.984522 | 2.68E−02 |
| synaptojanin 2 | 4.166 | 1.83143 | 3.84199 | 0.00E+00 |
| KIAA0367 protein | 1.5999 | −1.50555 | −0.26286 | 1.58E−02 |
| ESTs, Moderately similar to ALU8_HUMAN ALU SUBFAMILY SX SEQUENCE CONTAMINATION WARNING ENTRY (*H. sapiens*) | 0.868185 | −1.46804 | 0.573078 | 1.69E−02 |
| bromodomain adjacent to zinc finger domain, 1B | 1.60872 | −1.12544 | 0.518361 | 2.11E−02 |
| Human complement cytolysis inhibitor (CLI) mRNA, complete cds./FL = gb: J02908.1 gb: NM_001831.1 gb: M64722.1 gb: M25915.1 | 6.61592 | 3.91665 | 5.596 | 1.66E−02 |
| forkhead box O1A (rhabdomyosarcoma)/FL = gb: NM_002015.2 gb: AF032885.1 gb: U02310.1 | 5.04975 | 2.59802 | 4.53545 | 1.60E−03 |
| *Homo sapiens* cDNA: FLJ22727 fis, clone HSI15054 | 4.88391 | 2.09093 | 3.68875 | 1.91E−02 |
| cadherin 6, type 2, K-cadherin (fetal kidney)/FL = gb: D31784.1 gb: NM_004932.1 | 3.27371 | 0.243335 | 1.61199 | 2.74E−04 |
| ESTs | 3.97749 | 0.786845 | 1.99803 | 1.73E−02 |
| endonuclease G-like 1/FL = gb: AB020523.1 gb: NM_005107.1 | 1.11519 | −2.09018 | −0.88324 | 1.69E−02 |
| *Homo sapiens* cDNA FLJ13034 fis, clone NT2RP3001232 | 4.59641 | 0.64328 | 1.1121 | 1.66E−02 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Human DNA sequence from clone RP4-614O4 on chromosome 20q11.1-12 Contains the 3 part of the MMP24 (matrix metalloproteinase 24 (membrane-inserted)) gene, the ITGB4BP (integrin beta 4 binding protein) gene, the 3 end of a novel gene, the 3 end o . . . | 2.91607 | 0.209555 | 1.92644 | 1.93E−02 |
| Homo sapiens, collapsin response mediator protein-5; CRMP3-associated molecule, clone MGC: 11247, mRNA, complete cds./PROD = collapsin response mediator protein-5; CRMP3-associated molecule/ FL = gb: BC002874.1 | 0.672753 | −1.75265 | 0.250803 | 8.65E−03 |
| ESTs, Moderately similar to ALU7_HUMAN ALU SUBFAMILY SQ SEQUENCE CONTAMINATION WARNING ENTRY (*H. sapiens*) | 2.91576 | 0.289656 | 2.10334 | 2.57E−03 |
| ESTs, Moderately similar to CA1C RAT COLLAGEN ALPHA 1(XII) CHAIN (*R. norvegicus*) | 6.2681 | 1.94518 | 1.82747 | 4.12E−02 |
| Homo sapiens alpha-aminoadipate semialdehyde synthase mRNA, complete cds./PROD = alpha-aminoadipate semialdehyde synthase/ FL = gb: AF229180.1 | 5.2604 | 2.72549 | 4.6685 | 4.33E−03 |
| Homo sapiens Wnt inhibitory factor-1 (WIF-1), mRNA./PROD = Wnt inhibitory factor-1/FL = gb: AF122922.1 gb: NM_007191.1 | 1.03265 | −1.51207 | 0.433159 | 8.62E−05 |
| ribosomal protein S11 | 4.95358 | 2.25158 | 4.04683 | 2.98E−04 |
| Homo sapiens tumor necrosis factor, alpha-induced protein 6 (TNFAIP6), mRNA./PROD = tumor necrosis factor, alpha-induced protein 6/ FL = gb: NM_007115.1 | 2.42729 | −0.73843 | 0.613222 | 1.93E−02 |
| Homo sapiens hairyenhancer-of-split related with YRPW motif 2 (HEY2), mRNA./PROD = hairyenhancer-of-split related with YRPW motif2/ FL = gb: NM_012259.1 gb: AF311884.1 gb: AB044755.1 gb: AF232238.1 gb: AF237949.1 gb: AF173901.1 | 2.3848 | −0.44154 | 1.27956 | 3.16E−03 |
| Homo sapiens semenogelin I (SEMG1), mRNA./PROD = semenogelin I/ FL = gb: J04440.1 gb: NM_003007.1 | 0.585816 | −2.46893 | −0.95223 | 3.05E−02 |
| Homo sapiens, Similar to cadherin 6, type 2, K-cadherin (fetal kidney), clone MGC: 1470, mRNA, complete cds./ PROD = Similar to cadherin 6, type 2, K-cadherin (fetalkidney)/ FL = gb: BC000019.1 | 2.38648 | −0.02212 | 2.14359 | 2.59E−03 |
| Homo sapiens mRNA; cDNA DKFZp434H0350 (from clone DKFZp434H0350); partial cds./ PROD = hypothetical protein | 2.16899 | −0.56794 | 1.27546 | 3.16E−03 |
| Homo sapiens growth factor receptor-bound protein 14 (GRB14), mRNA./ PROD = growth factor receptor-bound protein 14/FL = gb: L76687.1 gb: NM_004490.1 | 4.2346 | 1.17569 | 2.73613 | 4.80E−03 |
| Homo sapiens, Similar to TAF5-like RNA polymerase II, p300CBP-associated factor (PCAF)-associated factor, 65 kDa, clone MGC: 46101 IMAGE: 5551246, mRNA, complete cds./PROD = Similar to TAF5-like RNA polymerase II, p300CBP-associated factor (PCAF)-associat | 2.10954 | −0.1313 | 2.24853 | 8.24E−04 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| Homo sapiens mRNA; cDNA DKFZp761J1324 (from clone DKFZp761J1324) | 1.42404 | −1.99222 | −0.77126 | 3.21E−02 |
| solute carrier family 30 (zinc transporter), member 1 | 2.82535 | 0.288493 | 2.38889 | 0.00E+00 |
| antizyme inhibitor | 3.65887 | 0.37346 | 1.74912 | 1.86E−02 |
| Homo sapiens GRO1 oncogene (melanoma growth stimulating activity, alpha) (GRO1), mRNA./PROD = GRO1 oncogene (melanoma growth stimulatingactivity, alpha)/FL = gb: NM_001511.1 | 2.51473 | 0.107263 | 2.38874 | 7.16E−04 |
| Homo sapiens proprotein convertase subtilisinkexin type 5 (PCSK5), mRNA./PROD = proprotein convertase subtilisinkexin type 5/FL = gb: U56387.2 gb: NM_006200.1 | 4.90999 | 0.871309 | 1.52441 | 1.71E−02 |
| ESTs | 0.254736 | −1.96122 | 0.51777 | 4.00E−02 |
| G-protein gamma-12 subunit/FL = gb: NM_018841.1 gb: AF119663.1 | 3.93653 | 1.06178 | 2.88889 | 5.11E−04 |
| platelet-derived growth factor alpha polypeptide | 3.50343 | 0.651246 | 2.50207 | 3.99E−03 |
| clusterin (complement lysis inhibitor, SP-40,40, sulfated glycoprotein 2, testosterone-repressed prostate message 2, apolipoprotein J) | 2.88196 | −0.42677 | 0.9712 | 8.48E−03 |
| ESTs | 2.82081 | −1.69816 | −1.89985 | 4.10E−02 |
| Homo sapiens insulinoma-associated 1 (INSM1), mRNA./PROD = insulinoma-associated 1/FL = gb: NM_002196.1 gb: M93119.1 | 2.94347 | 0.120494 | 2.02248 | 1.43E−03 |
| LBP protein 32/FL = gb: NM_014552.1 gb: AF198489.1 | 2.68546 | −0.16678 | 1.70626 | 1.87E−03 |
| ESTs, Highly similar to T42654 hypothetical protein DKFZp434G1115.1 (H. sapiens) | 2.84504 | 0.515703 | 2.95379 | 7.92E−04 |
| Homo sapiens Friend leukemia virus integration 1 (FLI1), mRNA./PROD = Friend leukemia virus integration 1/FL = gb: BC001670.1 gb: NM_002017.2 gb: M98833.3 | 1.7744 | −2.28064 | −1.56765 | 3.14E−02 |
| ESTs | 0.846429 | −2.42046 | −0.91891 | 1.57E−02 |
| Homo sapiens oxidative 3 alpha hydroxysteroid dehydrogenase; retinol dehydrogenase; 3-hydroxysteroid epimerase (RODH), mRNA./PROD = oxidative 3 alpha hydroxysteroid dehydrogenase; retinol dehydrogenase; 3-hydroxysteroid epimerase/FL = gb: AF016509.1 gb: A | 1.30153 | −1.64227 | 0.196394 | 3.20E−03 |
| minor histocompatibility antigen HA-1 | 1.89498 | −0.37136 | 2.15157 | 4.61E−02 |
| UDP-glucose pyrophosphorylase 2 | 4.26327 | 0.968939 | 2.4776 | 6.20E−03 |
| Homo sapiens regulator of G-protein signalling 2, 24 kD (RGS2), mRNA./PROD = regulator of G-protein signalling 2, 24 kD/FL = gb: L13463.1 gb: NM_002923.1 | 5.42952 | 3.05504 | 5.49711 | 1.21E−03 |
| ESTs | 4.49987 | 1.01623 | 2.35659 | 1.86E−03 |
| ESTs | 0.623422 | −1.94907 | 0.317138 | 8.95E−04 |
| ESTs | 0.326084 | −1.69499 | 1.13586 | 1.10E−02 |
| ESTs | 3.82952 | 0.673296 | 2.37112 | 3.92E−02 |
| Homo sapiens cDNA FLJ10160 fis, clone HEMBA1003545, highly similar to INSULIN GENE ENHANCER PROTEIN ISL-2. | 2.80876 | −0.24405 | 1.56853 | 1.39E−02 |
| thyroid hormone receptor-associated protein, 150 kDa subunit/FL = gb: NM_005119.1 gb: AF117756.1 | 4.66717 | 2.01883 | 4.2391 | 4.63E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 2.4548 | −0.3811 | 1.65212 | 4.08E−03 |
| *Homo sapiens* mRNA; cDNA DKFZp667D095 (from clone DKFZp667D095) | 3.13835 | 0.605922 | 2.95511 | 1.53E−03 |
| *Homo sapiens* synaptojanin 2 mRNA, complete cds./PROD = synaptojanin 2/ FL = gb: AF318616.1 | 2.94452 | 0.23595 | 2.4148 | 3.63E−04 |
| *Homo sapiens* procollagen C-endopeptidase enhancer (PCOLCE), mRNA./PROD = procollagen C-endopeptidase enhancer/ FL = gb: BC000574.1 gb: NM_002593.2 gb: AB008549.1 gb: L33799.1 | 3.37999 | 0.343624 | 2.21149 | 1.46E−02 |
| ESTs | 3.24495 | 0.925809 | 3.52818 | 1.70E−04 |
| *Homo sapiens* mRNA for KIAA0930 protein, partial cds./PROD = KIAA0930 protein | 3.65772 | 0.911608 | 3.09513 | 8.62E−05 |
| *Homo sapiens* forkhead transcription factor FOXL2 (BPES), mRNA./ PROD = forkhead transcription factor FOXL2/FL = gb: AF301906.1 gb: NM_023067.1 | 1.51993 | −2.14186 | −0.86243 | 3.75E−02 |
| ESTs | 1.9867 | −1.5948 | −0.2171 | 2.81E−03 |
| ESTs, Highly similar to AF174600 1 F-box protein Fbx20 (*H. sapiens*) | 3.06175 | 0.202953 | 2.35691 | 2.45E−02 |
| *Homo sapiens* ankyrin 3, node of Ranvier (ankyrin G) (ANK3), transcript variant 2, mRNA./PROD = ankyrin 3, isoform 2/FL = gb: NM_001149.1 gb: U43965.1 | 3.11644 | 0.101116 | 2.09865 | 2.90E−03 |
| *Homo sapiens* tumor necrosis factor receptor superfamily, member 6 (TNFRSF6), mRNA./PROD = apoptosis (APO-1) antigen 1/FL = gb: NM_000043.1 gb: M67454.1 | 2.39086 | −1.04254 | 0.558779 | 1.62E−02 |
| *Homo sapiens* thyrotropin-releasing hormone degrading ectoenzyme (TRHDE), mRNA./PROD = thyrotropin-releasing hormone degradingectoenzyme/ FL = gb: AF126372.1 gb: NM_013381.1 | 1.30849 | −1.50688 | 0.822517 | 4.91E−02 |
| ESTs | 4.65711 | 0.915563 | 2.32327 | 6.29E−03 |
| *Homo sapiens* mRNA; cDNA DKFZp564N1116 (from clone DKFZp564N1116) | 2.36072 | −2.02594 | −1.25286 | 1.50E−02 |
| *Homo sapiens* placental protein 13-like protein (LOC56891), mRNA./ PROD = placental protein 13-like protein/ FL = gb: NM_020129.1 gb: AF267852.1 | 3.55894 | 0.434263 | 2.47085 | 3.48E−03 |
| *Homo sapiens*, Similar to receptor tyrosine kinase-like orphan receptor 1, clone MGC: 12687, mRNA, complete cds./PROD = Similar to receptor tyrosine kinase-like orphanreceptor 1/ FL = gb: BC006374.1 | 2.05578 | 0.178992 | 3.5007 | 4.46E−04 |
| ESTs | 0.159066 | −2.96514 | −0.84976 | 3.25E−02 |
| *Homo sapiens*, Similar to v-ets avian erythroblastosis virus E26 oncogene homolog 1, clone MGC: 29755 IMAGE: 3946751, mRNA, complete cds./ PROD = Similar to v-ets avian erythroblastosis virusE26 oncogene homolog 1/FL = gb: BC017314.1 | 2.22285 | −1.58562 | −0.1074 | 2.63E−02 |
| ESTs, Highly similar to dedicator of cyto-kinesis 1 (*H. sapiens*) | 0.83871 | −2.29829 | −0.12951 | 1.85E−02 |
| ESTs | 1.1465 | −1.7403 | 0.682768 | 3.99E−02 |
| ESTs | 1.7466 | −1.67509 | 0.283174 | 2.97E−03 |
| ESTs, Weakly similar to PMXB_HUMAN PAIRED MESODERM HOMEOBOX PROTEIN 2B (*H. sapiens*) | 1.03192 | −2.44485 | −0.51457 | 1.87E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | 3.22222 | −0.29339 | 1.59904 | 7.36E−03 |
| Homo sapiens cDNA FLJ10561 fis, clone NT2RP2002672 | 2.295 | −1.60823 | −0.08369 | 3.93E−03 |
| Homo sapiens, Similar to KIAA0441 gene product, clone MGC: 45124 IMAGE: 5578893, mRNA, complete cds./PROD = Similar to KIAA0441 gene product/FL = gb: BC036731.1 | 1.38545 | −1.60426 | 0.86909 | 2.33E−03 |
| Homo sapiens, clone IMAGE: 4067166, mRNA | 0.195869 | −2.50507 | 0.276993 | 1.16E−03 |
| ESTs | 1.5857 | −2.61787 | −1.30022 | 1.12E−02 |
| Homo sapiens methyl-CpG binding protein MBD2 (MBD2) mRNA, complete cds./PROD = methyl-CpG binding protein MBD2/FL = gb: NM_003927.2 gb: AF072242.1 | 0.490598 | −3.45465 | −1.70163 | 3.90E−03 |
| KIAA1151 protein | 0.642527 | −2.04288 | 1.00885 | 4.09E−03 |
| H. sapiens mRNA for B-HLH DNA binding protein./PROD = B-HLH DNA binding protein/FL = gb: NM_000474.1 | 5.43034 | 1.56039 | 3.45122 | 1.12E−04 |
| Homo sapiens, Similar to hypothetical protein FLJ32001, clone MGC: 39559 IMAGE: 4828136, mRNA, complete cds./PROD = Similar to hypothetical protein FLJ32001/FL = gb: BC036200.1 | 0.520711 | −1.99011 | 1.26899 | 2.63E−02 |
| Homo sapiens Wilms tumor 1 (WT1), transcript variant D, mRNA./PROD = Wilms tumor 1 isoform D/FL = gb: NM_024424.1 gb: NM_024426.1 | 2.40462 | −2.96375 | −2.43546 | 1.41E−02 |
| ESTs | 1.53104 | −1.54553 | 1.37309 | 8.14E−03 |
| Homo sapiens, Similar to cadherin 6, type 2, K-cadherin (fetal kidney), clone MGC: 1470, mRNA, complete cds./PROD = Similar to cadherin 6, type 2, K-cadherin (fetalkidney)/FL = gb: BC000019.1 | 2.54746 | −0.69811 | 2.13419 | 1.45E−04 |
| ESTs | 0.133612 | −3.77953 | −1.56636 | 1.40E−02 |
| paternally expressed 3 | 2.87581 | −1.67669 | −0.0118 | 2.17E−02 |
| Homo sapiens Charot-Leyden crystal protein (CLC), mRNA./PROD = Charot-Leyden crystal protein/FL = gb: NM_001828.3 gb: L01664.1 | 3.30086 | −0.41644 | 2.1096 | 2.08E−02 |
| ESTs | 3.26198 | −0.72777 | 1.5682 | 3.16E−03 |
| Homo sapiens tachykinin, precursor 1 (substance K, substance P, neurokinin 1, neurokinin 2, neuromedin L, neurokinin alpha, neuropeptide K, neuropeptide gamma) (TAC1), transcript variant beta, mRNA./PROD = tachykinin 2 precursor, isoform beta/FL = gb: U3 | 2.77265 | −1.02081 | 1.48319 | 4.07E−04 |
| Homo sapiens PNAS-123 mRNA, complete cds | 1.59659 | −1.46656 | 1.84663 | 3.90E−03 |
| Homo sapiens hypothetical protein FLJ20075 (FLJ20075), mRNA./PROD = hypothetical protein FLJ20075/FL = gb: NM_017655.1 | −0.359245 | −3.46654 | −0.06528 | 2.55E−03 |
| Human platelet-derived growth factor alpha-receptor (PDGFRA) mRNA, exons 13-16 | 2.44464 | −0.5846 | 2.90484 | 3.63E−04 |
| Homo sapiens cDNA: FLJ22547 fis, clone HSI00356 | 4.29365 | −0.10882 | 2.09548 | 1.54E−02 |
| Homo sapiens HSPC156 protein (HSPC156), mRNA./PROD = HSPC156 protein/FL = gb: NM_014178.1 gb: AF161505.1 | 0.786188 | −2.32161 | 1.29619 | 8.62E−05 |
| Homo sapiens mRNA; cDNA DKFZp586P1124 (from clone DKFZp586P1124) | 0.485642 | −4.8524 | −3.09356 | 2.02E−02 |
| caldesmon 1/FL = gb: M64110.1 gb: NM_004342.2 | 7.09236 | 2.67863 | 5.63436 | 7.47E−03 |

TABLE VI-continued

MEAN NORMALIZED INTENSITY VALUES (IN LOG FORMAT) OF GENES
FOR H9 EMBRYONIC STEM CELLS DERIVED DEFINITIVE ENDODERM STAGE
CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| *Homo sapiens*, Similar to hypothetical protein FLJ10058, clone MGC: 34305 IMAGE: 5167647, mRNA, complete cds./PROD = Similar to hypothetical protein FLJ10058/FL = gb: BC034293.1 | 1.69808 | −2.74939 | 0.215566 | 1.92E−02 |
| *Homo sapiens*, Similar to LIM homeobox protein 8, clone IMAGE: 4839343, mRNA. | −0.062884 | −4.30121 | −1.10961 | 1.16E−02 |
| *Homo sapiens* chorionic somatomammotropin hormone 2 (CSH2), transcript variant 4, mRNA./PROD = chorionic somatomammotropin hormone 2, isoform4/FL = gb: NM_022646.1 | 0.812166 | −2.21846 | 2.21843 | 3.60E−03 |
| *Homo sapiens* HES-related repressor protein 1 HERP1 mRNA, complete cds./PROD = HES-related repressor protein 1 HERP1/FL = gb: NM_012259.1 gb: AF311884.1 gb: AB044755.1 gb: AF232238.1 gb: AF237949.1 gb: AF173901.1 | 2.80599 | −1.19396 | 2.40562 | 2.44E−03 |
| *Homo sapiens* cadherin 6, type 2, K-cadherin (fetal kidney) (CDH6), mRNA./PROD = cadherin 6, type 2, K-cadherin (fetal kidney)/FL = gb: D31784.1 gb: NM_004932.1 | 0.824752 | −3.83509 | −0.87634 | 2.49E−02 |
| paternally expressed 3 | 2.87398 | −4.12925 | −3.49232 | 2.19E−02 |
| *Homo sapiens* cDNA FLJ11398 fis, clone HEMBA1000637. | 2.5268 | −1.71619 | 1.84868 | 4.46E−04 |
| *Homo sapiens* BCL2-interacting killer (apoptosis-inducing) (BIK), mRNA./PROD = BCL2-interacting killer/FL = gb: NM_001197.2 gb: BC001599.1 gb: U34584.1 gb: U49730.1 | 4.30042 | 0.023414 | 3.56237 | 1.94E−03 |
| *Homo sapiens* testis expressed sequence 14 (TEX14), mRNA./PROD = testis expressed sequence 14/FL = gb: NM_031272.1 | 3.51154 | −2.84891 | −1.3824 | 2.18E−02 |
| *Homo sapiens* growth hormone 2 (GH2), transcript variant 2, mRNA./PROD = growth hormone 2, isoform 2 precursor/FL = gb: J03756.1 gb: NM_022557.1 | 0.922569 | −2.77587 | 1.4679 | 1.60E−03 |
| *Homo sapiens*, clone IMAGE: 4828836, mRNA. | 0.972907 | −4.24111 | −1.48398 | 1.63E−02 |
| *Homo sapiens* galanin receptor 1 (GALR1), mRNA./PROD = galanin receptor 1/FL = gb: NM_001480.2 gb: U23854.1 gb: L34339.1 gb: U53511.1 | 2.50745 | −3.13141 | −0.33802 | 3.38E−03 |
| *Homo sapiens*, serine (or cysteine) proteinase inhibitor, clade B (ovalbumin), member 3, clone MGC: 12244, mRNA, complete cds./PROD = serine (or cysteine) proteinase inhibitor, cladeB (ovalbumin), member 3/FL = gb: NM_006919.1 gb: U19556.1 gb: BC005224.1 | 1.96851 | −4.13943 | −1.56568 | 3.06E−02 |
| DKFZP566K1924 protein | 2.88225 | −2.59632 | 1.39062 | 0.00E+00 |
| ESTs, Moderately similar to ALU2_HUMAN ALU SUBFAMILY SB SEQUENCE CONTAMINATION WARNING ENTRY (*H. sapiens*) | 4.24074 | −0.69782 | 3.87444 | 1.12E−04 |
| Human mRNA upregulated during camptothecin-induced apoptosis of U937 cells. | 0.494505 | −4.62912 | −0.18915 | 4.38E−02 |
| nuclear receptor subfamily 1, group I, member 3 | 1.77902 | −4.02806 | −0.19682 | 4.34E−02 |

TABLE VI-continued

MEAN NORMALIZED INTENSITY VALUES (IN LOG FORMAT) OF GENES FOR H9 EMBRYONIC STEM CELLS DERIVED DEFINITIVE ENDODERM STAGE CELLS CULTURED ON EITHER MATRIGEL ™ OR MEFS +/− WNT-3A.

| Gene Title | DE treatment in low serum + AA on MATRIGEL | DE treatment in low serum + AA + Wnt-3A on MATRIGEL | DE treatment in low serum + AA on MEFS | Benjamini and Hochberg-P-value |
|---|---|---|---|---|
| ESTs | −1.3795 | −6.08172 | −0.94606 | 6.91E-04 |
| Homo sapiens chorionic somatomammotropin hormone 2 (CSH2), transcript variant 1, mRNA./PROD = chorionic somatomammotropin hormone 2, isoform 1precursor/ FL = gb: NM_020991.2 gb: BC002717.1 | 1.12437 | −3.12138 | 2.61605 | 1.12E-04 |
| Homo sapiens mRNA for SCCA2b, complete cds./PROD = SCCA2b/ FL = gb: AB046400.1 | 3.32911 | −3.16288 | 0.568045 | 1.93E-02 |
| Homo sapiens KIAA0469 gene product (KIAA0469), mRNA./PROD = KIAA0469 gene product/FL = gb: AB007938.1 gb: NM_014851.1 | 4.03097 | −1.94826 | 2.56518 | 2.49E-04 |
| ESTs | 4.45389 | −2.40636 | 5.33359 | 5.65E-04 |

TABLE VII

THE EFFECT OF WNT-3A TREAMENT ON CYTOKINE EXPRESSION IN POPULATIONS OF CELLS FROM THE HUMAN EMBRYONIC STEM CELL LINE H9.

| | Cell lysate | | | | Cell conditioned media | | | |
|---|---|---|---|---|---|---|---|---|
| | w/o wnt 1 | w/o wnt 2 | w/wnt 1 | w/wnt 2 | w/o wnt 1 | w/o wnt 2 | w/wnt 1 | w/wnt 2 |
| POS | 62,842.33 | 67,606.06 | 49,758.34 | 50,702.57 | 96,585.15 | 109,721.82 | 199,709.04 | 195,889.94 |
| NEG | 23.38 | 34.49 | 370.82 | 400.66 | 58.06 | 34.45 | 216.90 | 105.20 |
| Angiogenin | 38.50 | 132.91 | 619.40 | 750.85 | 13,726.35 | 11,749.55 | 57,442.48 | 54,969.04 |
| BDNF | 167.50 | 167.82 | 763.51 | 951.45 | 689.22 | 563.39 | 770.08 | 715.86 |
| BLC | 2.00 | 48.99 | 742.24 | 476.36 | 107.69 | 512.77 | 337.12 | 249.80 |
| BMP-4 | 247.00 | 273.70 | 348.44 | 304.48 | 583.40 | 541.83 | 1,158.54 | 771.19 |
| BMP-6 | 8.50 | 141.92 | 571.23 | 641.05 | 354.91 | 355.28 | 985.70 | 670.60 |
| CK beta 8-1 | 1.00 | 1.13 | 22.48 | 21.54 | 17.79 | 25.31 | 42.78 | 75.44 |
| CNTF | 1.00 | 55.19 | 1,382.51 | 1,060.82 | 282.81 | 211.86 | 787.19 | 541.51 |
| EGF | 32.50 | 82.22 | 742.24 | 984.39 | 1,681.85 | 1,406.12 | 23,331.57 | 22,768.53 |
| Eotaxin | 1.00 | 7.32 | 301.87 | 253.80 | 207.89 | 199.67 | 622.91 | 291.71 |
| Eotaxin-2 | 262.00 | 336.77 | 1,155.31 | 960.31 | 890.56 | 744.31 | 2,156.21 | 1,445.14 |
| Eotaxin-3 | 184.50 | 284.96 | 934.12 | 847.56 | 975.77 | 665.56 | 2,140.81 | 1,480.35 |
| FGF-6 | 629.00 | 379.57 | 1,327.92 | 964.54 | 1,239.85 | 947.73 | 3,283.94 | 2,519.78 |
| FGF-7 | 31.00 | 222.45 | 1,075.02 | 941.73 | 449.49 | 352.47 | 1,086.66 | 861.72 |
| Flt-3 Ligand | 44.00 | 180.21 | 857.45 | 795.19 | 315.58 | 277.47 | 511.67 | 792.98 |
| Fractalkine | 23.50 | 62.51 | 792.02 | 456.51 | 120.80 | 145.30 | 359.37 | 367.15 |
| GCP-2 | 1.00 | 45.05 | 593.71 | 538.86 | 203.21 | 166.86 | 451.78 | 362.12 |
| GDNF | 84.00 | 292.84 | 436.75 | 444.68 | 176.99 | 194.98 | 443.22 | 509.66 |
| GM-CSF | 433.00 | 636.37 | 1,343.17 | 1,161.75 | 777.25 | 722.75 | 1,808.82 | 1,446.82 |
| I-309 | 152.50 | 246.10 | 708.52 | 743.25 | 1,828.87 | 179.05 | 318.30 | 288.36 |
| IFN-gamma | 349.00 | 441.52 | 1,202.67 | 1,037.60 | 283.74 | 559.64 | 1,238.97 | 1,435.08 |
| IGFBP-1 | 1.50 | 3.38 | 59.41 | 85.73 | 33.71 | 24.37 | 227.60 | 155.91 |
| IGFBP-2 | 3,785.50 | 5,554.45 | 2,671.90 | 2,414.72 | 27,656.85 | 28,473.95 | 42,215.53 | 43,934.33 |
| IGFBP-4 | 5,553.00 | 6,043.27 | 4,459.85 | 4,173.19 | 10,091.09 | 6,029.45 | 18,988.34 | 13,380.14 |
| IGF-I | 1.00 | 2.25 | 558.38 | 208.19 | 88.96 | 148.11 | 254.98 | 187.77 |
| IL-10 | 158.00 | 422.93 | 1,222.75 | 1,096.30 | 722.93 | 564.32 | 1,625.71 | 1,129.96 |
| IL-13 | 428.50 | 555.84 | 1,486.89 | 1,407.96 | 1,114.36 | 786.49 | 2,522.42 | 1,807.27 |
| IL-15 | 599.50 | 808.13 | 1,677.16 | 1,601.79 | 1,140.59 | 858.67 | 2,495.04 | 1,981.62 |
| IL-16 | 2.00 | 137.97 | 651.11 | 668.50 | 259.39 | 214.67 | 436.38 | 405.71 |
| IL-1alpha | 1,236.00 | 1,216.99 | 1,612.93 | 1,421.89 | 10,155.70 | 5,842.90 | 3,999.26 | 3,545.79 |
| IL-1beta | 1.00 | 1.13 | 352.05 | 312.08 | 117.99 | 75.93 | 316.59 | 278.30 |
| IL-1ra | 33.00 | 25.91 | 302.68 | 198.48 | 142.34 | 93.74 | 354.23 | 581.75 |
| IL-2 | 210.50 | 681.99 | 966.23 | 1,133.88 | 188.22 | 363.72 | 758.10 | 881.84 |
| IL-3 | 3,146.50 | 1,976.13 | 2,119.94 | 1,497.48 | 4,598.86 | 5,260.77 | 11,345.78 | 12,174.73 |
| IL-4 | 17.50 | 74.34 | 625.42 | 638.94 | 357.72 | 239.04 | 804.30 | 673.95 |
| IL-5 | 400.50 | 555.84 | 1,245.23 | 1,167.24 | 1,056.31 | 791.18 | 2,120.27 | 1,713.38 |
| IL-6 | 828.50 | 516.98 | 1,121.19 | 842.07 | 7,377.28 | 9,527.88 | 9,774.82 | 9,991.93 |
| IL-7 | 190.00 | 313.12 | 1,212.31 | 531.68 | 456.98 | 430.27 | 681.09 | 1,017.63 |
| Leptin | 900.50 | 617.79 | 1,234.39 | 1,091.65 | 2,999.42 | 2,016.38 | 7,238.71 | 4,886.99 |
| LIGHT | 10.50 | 232.02 | 1,081.04 | 888.10 | 619.92 | 453.71 | 1,346.78 | 1,108.17 |

TABLE VII-continued

THE EFFECT OF WNT-3A TREAMENT ON CYTOKINE EXPRESSION IN POPULATIONS OF CELLS FROM THE HUMAN EMBRYONIC STEM CELL LINE H9.

| | Cell lysate | | | | Cell conditioned media | | | |
|---|---|---|---|---|---|---|---|---|
| | w/o wnt 1 | w/o wnt 2 | w/wnt 1 | w/wnt 2 | w/o wnt 1 | w/o wnt 2 | w/wnt 1 | w/wnt 2 |
| MCP-1 | 242.50 | 282.71 | 1,022.03 | 1,076.03 | 572.17 | 500.58 | 2,015.89 | 1,567.53 |
| MCP-2 | 24.00 | 109.25 | 909.63 | 1,152.46 | 129.23 | 351.53 | 694.78 | 694.07 |
| MCP-3 | 1.00 | 168.38 | 1,184.61 | 1,255.50 | 401.73 | 169.67 | 701.62 | 583.42 |
| MCP-4 | 7.50 | 46.74 | 1,380.51 | 1,606.86 | 123.61 | 61.87 | 231.02 | 276.62 |
| M-CSF | 1.00 | 63.64 | 852.63 | 867.83 | 529.09 | 269.04 | 740.98 | 684.01 |
| MDC | 1.00 | 2.25 | 269.36 | 280.41 | 157.32 | 52.50 | 280.65 | 132.44 |
| MIG | 291.00 | 226.39 | 1,113.16 | 1,137.26 | 272.50 | 486.52 | 617.77 | 1,222.17 |
| MIP-1-delta | 1.50 | 1.13 | 491.75 | 322.22 | 144.21 | 66.56 | 474.02 | 291.71 |
| MIP-3-alpha | 1.00 | 5.63 | 1,602.09 | 1,399.93 | 55.25 | 0.00 | 208.78 | 184.41 |
| NAP-2 | 1.00 | 6.19 | 465.66 | 177.37 | 97.39 | 110.61 | 371.35 | 343.68 |
| NT-3 | 1.00 | 1.13 | 316.73 | 275.76 | 97.39 | 171.55 | 571.57 | 427.51 |
| PARC | 1.00 | 2.25 | 352.85 | 353.04 | 170.43 | 81.56 | 474.02 | 363.80 |
| PDGF-BB | 437.00 | 1,644.99 | 517.84 | 597.56 | 4,729.96 | 8,521.09 | 2,635.37 | 2,005.09 |
| RANTES | 1.00 | 89.54 | 724.98 | 637.25 | 393.31 | 347.78 | 682.80 | 855.01 |
| SCF | 74.50 | 148.67 | 1,152.50 | 1,021.13 | 691.09 | 487.46 | 1,394.69 | 2,155.98 |
| SDF-1 | 23.50 | 51.25 | 940.14 | 1,294.78 | 382.07 | 123.74 | 326.85 | 616.65 |
| TARC | 1.50 | 5.07 | 372.93 | 343.33 | 206.95 | 71.24 | 277.23 | 1,642.97 |
| TGF-beta 1 | 362.00 | 230.33 | 1,426.67 | 1,240.30 | 752.90 | 740.56 | 1,827.65 | 1,849.18 |
| TGF-beta 3 | 3.00 | 25.91 | 377.74 | 1,130.93 | 111.44 | 115.30 | 294.34 | 343.68 |
| TNF-alpha | 431.00 | 579.49 | 2,851.74 | 1,285.91 | 1,205.20 | 929.91 | 2,609.70 | 2,167.71 |
| TNF-beta | 241.00 | 342.40 | 1,049.33 | 1,026.62 | 675.17 | 671.19 | 1,701.01 | 1,637.94 |
| Internal Control | 18,642.67 | 18,642.67 | 18,642.67 | 18,642.67 | 18,642.67 | 18,642.67 | 18,642.67 | 18,642.67 |
| POS | 60,794.83 | 48,106.85 | 35,652.42 | 47,391.58 | 94,013.71 | 90,889.16 | 141,321.30 | 149,125.43 |
| NEG | 11.13 | 5.53 | 11.22 | 30.45 | 24.93 | 17.75 | 36.22 | 33.27 |
| Acrp30 | 1,036.00 | 744.50 | 601.61 | 690.66 | 1,797.52 | 1,319.88 | 2,795.71 | 2,302.99 |
| AgRP | 11.00 | 153.99 | 77.82 | 89.00 | 378.17 | 195.90 | 651.26 | 482.21 |
| Angiopoietin-2 | 28.50 | 10.43 | 357.97 | 771.04 | 655.82 | 632.60 | 65,959.24 | 71,664.21 |
| Amphiregulin | 17.50 | 15.44 | 73.63 | 154.62 | 250.52 | 151.01 | 619.07 | 782.60 |
| Axl | 637.50 | 795.83 | 88.59 | 139.03 | 401.31 | 324.05 | 610.40 | 748.34 |
| bFGF | 59,820.50 | 54,057.29 | 11,722.95 | 21,398.52 | 7,948.03 | 4,993.83 | 1,226.99 | 1,241.09 |

TABLE VIII

CHANGES IN THE PERCENTAGE OF INSULIN-EXPRESSING CELLS AND SYNAPTOPHYSIN-EXPRESSING CELLS DERIVED FROM HUMAN EMBRYONIC STEM CELLS WITH DIFFERENT CONCENTRATION OF GLUCOSE.

| | 5 mM | 10 mM | 20 mM |
|---|---|---|---|
| Insulin | 8.9% | 10.9% | 16% |
| Synaptophysin | 19.2% | 21% | 36% |

---

What is claimed is:

1. A method for generating human pancreatic endocrine cells, comprising differentiating pancreatic endoderm cells into pancreatic endocrine cells by culturing the pancreatic endoderm cells with a medium supplemented with Exendin-4, then removing the medium supplemented with Exendin-4 and subsequently culturing the cells in medium supplemented with hepatocyte growth factor (HGF), Exendin-1 and insulin growth factor (IGF)-1.

2. The method of claim 1, wherein the pancreatic endoderm cells are differentiated from human pluripotent stem cells.

3. The method of claim 1, wherein the pancreatic endoderm cells are derived from definitive endoderm cells.

4. The method of claim 1, wherein the pancreatic endoderm cells are treated with a gamma secretase inhibitor, or Exendin-4, or Exendin-4 and HGF for about 2 days to about 30 days.

5. The method of claim 1, wherein the method comprises treating the pancreatic endoderm cells with a medium supplemented with a gamma secretase inhibitor.

6. The method of claim 1, wherein the method comprises treating the pancreatic endoderm cells with a medium supplemented with Exendin-4.

7. The method of claim 1, wherein the method comprises treating the pancreatic endoderm cells with a medium supplemented with Exendin-4 and HGF.

8. A method for differentiating pluripotent stem cells into pancreatic endocrine cells, comprising the steps of:
   a. Differentiating human pluripotent stem cells into definitive endoderm cells by treating the pluripotent cells with activin A;
   b. Differentiating the definitive endoderm cells into pancreatic endoderm cells by treating the definitive endoderm cells with at least one fibroblast growth factor, or with retinoic acid and at least one fibroblast growth factor (FGF); and
   c. Differentiating the pancreatic endoderm cells into pancreatic endocrine cells by treating the pancreatic endoderm cells with Exendin-4, then removing the medium supplemented with Exendin-4 and subsequently culturing the cells in medium supplemented with hepatocyte growth factor (HGF), Exendin-1 and insulin growth factor (IGF)-1.

9. The method of claim 8, wherein the method comprises treating the pluripotent cells with activin A and a GSK-3B inhibitor.

10. The method of claim 8, wherein the FGF is FGF-2 or FGF-4.

11. The method of claim 8, wherein the method comprises treating the definitive endoderm cells with FGF-2 and retinoic acid or FGF-4 and retinoic acid.

12. The method of claim 8, wherein the pancreatic endoderm cells are treated with a gamma secretase inhibitor, or Exendin-4, or 4 and HGF for about 2 days to about 30 days.

13. The method of claim 11, wherein the method comprises treating the pancreatic endoderm cells with a medium supplemented with a gamma secretase inhibitor.

14. The method of claim 11, wherein the method comprises treating the pancreatic endoderm cells with a medium supplemented with Exendin-4.

15. The method of claim 11, wherein the method comprises treating the pancreatic endoderm cells with a medium supplemented with Exendin-4 and HGF.

* * * * *

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Synthetic Construct

<400> SEQUENCE: 1
tggcgcagca gatacca                                                    17

<210> SEQ ID NO 2
<211> LENGTH: 18
<212> TYPE: DNA
<213> ORGANISM: Artificial Sequence
```

```
<220> FEATURE:
<223> OTHER INFORMATION: Synthetic Construct

<400> SEQUENCE: 2
agcgccttcc acgacttg                                            18

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
ccagcatctt gctcaactcg gcg                                      23
```